(12) United States Patent
Eckhardt

(10) Patent No.: US 8,592,217 B2
(45) Date of Patent: Nov. 26, 2013

(54) METHOD OF CONDUCTING AN ASSAY

(71) Applicant: Advanced Liquid Logic, Inc., Research Triangle Park, NC (US)

(72) Inventor: Allen E. Eckhardt, Durham, NC (US)

(73) Assignee: Advanced Liquid Logic, Inc., Research Triangle Park, NC (US)

(*) Notice: Subject to any disclaimer, the term of this patent is extended or adjusted under 35 U.S.C. 154(b) by 0 days.

(21) Appl. No.: 13/738,259

(22) Filed: Jan. 10, 2013

(65) Prior Publication Data

US 2013/0130936 A1 May 23, 2013

Related U.S. Application Data

(63) Continuation of application No. 13/305,820, filed on Nov. 29, 2011, now Pat. No. 8,394,641, which is a continuation-in-part of application No. 12/531,844, filed as application No. PCT/US2008/057959 on Mar. 23, 2008, said application No. 13/305,820 is a continuation of application No. 13/012,831, filed on Jan. 25, 2011, now Pat. No. 8,093,062, which is a continuation of application No. PCT/US2010/061118, filed on Dec. 10, 2010.

(60) Provisional application No. 60/896,341, filed on Mar. 22, 2007, provisional application No. 61/288,633, filed on Dec. 21, 2009, provisional application No. 61/290,296, filed on Dec. 28, 2009, provisional application No. 61/325,580, filed on Apr. 19, 2010, provisional application No. 61/334,376, filed on May 13, 2010, provisional application No. 61/359,943, filed on Jun. 30, 2010, provisional application No. 61/378,705, filed on Aug. 31, 2010, provisional application No. 61/382,564, filed on Sep. 14, 2010, provisional application No. 61/392,633, filed on Oct. 13, 2010, provisional application No. 61/406,380, filed on Oct. 25, 2010.

(51) Int. Cl.
*G01N 33/00* (2006.01)

(52) U.S. Cl.
USPC .......................................................... 436/86

(58) Field of Classification Search
USPC .......................................................... 436/86
See application file for complete search history.

(56) References Cited

U.S. PATENT DOCUMENTS

| 5,559,134 A | 9/1996 | Buchmann et al. |
| 5,753,186 A | 5/1998 | Hanley et al. |

(Continued)

FOREIGN PATENT DOCUMENTS

| JP | 05025159 A | 1/1993 |
| WO | 9111172 A1 | 8/1991 |

(Continued)

OTHER PUBLICATIONS

Barbulovic-Nad, et al., "A microfluidic platform for complete mammalian cell culture", Lab on a chip, vol. 10, Apr. 2010, 1536-1542.

(Continued)

*Primary Examiner* — Monique Cole
(74) *Attorney, Agent, or Firm* — William A. Barrett; Ward and Smith, P.A.

(57) ABSTRACT

The invention is directed to droplet actuator devices and assay methods. The invention includes assay methods of conducting an assay comprising combining a sample with an umbelliferyl derivative, wherein the sample potentially comprises an enzyme capable of cleaving the umbelliferyl derivative and where the umbelliferyl derivative comprises an umbelliferyl core modified with one or more modifying moieties.

11 Claims, 53 Drawing Sheets

100

(56) References Cited

U.S. PATENT DOCUMENTS

| | | | |
|---|---|---|---|
| 6,171,810 | B1* | 1/2001 | Zhu .................................. 435/18 |
| 6,294,063 | B1 | 9/2001 | Becker et al. |
| 6,406,667 | B1 | 6/2002 | Singh et al. |
| 6,565,727 | B1 | 5/2003 | Shenderov |
| 6,911,132 | B2 | 6/2005 | Pamula et al. |
| 6,989,234 | B2 | 1/2006 | Kohlar et al. |
| 7,108,354 | B2 | 9/2006 | Gulvin et al. |
| 7,109,222 | B2 | 9/2006 | Cheng et al. |
| 7,413,706 | B2 | 8/2008 | Peeters et al. |
| 7,569,129 | B2 | 8/2009 | Pamula et al. |
| 7,632,388 | B2 | 12/2009 | Rikihisa et al. |
| 7,939,021 | B2 | 5/2011 | Smith et al. |
| 2002/0102737 | A1 | 8/2002 | Millington et al. |
| 2003/0148538 | A1 | 8/2003 | Ng |
| 2003/0170698 | A1 | 9/2003 | Gascoyne et al. |
| 2004/0055891 | A1 | 3/2004 | Pamula et al. |
| 2005/0031657 | A1 | 2/2005 | Gilson et al. |
| 2005/0158845 | A1 | 7/2005 | Wikswo et al. |
| 2006/0078893 | A1 | 4/2006 | Griffiths et al. |
| 2006/0254933 | A1 | 11/2006 | Adachi et al. |
| 2007/0023292 | A1 | 2/2007 | Kim et al. |
| 2008/0018709 | A1 | 1/2008 | Takenaka et al. |
| 2008/0039636 | A1 | 2/2008 | Harichian et al. |
| 2008/0089005 | A1 | 4/2008 | Choi et al. |
| 2009/0127123 | A1 | 5/2009 | Raccurt et al. |
| 2010/0041086 | A1 | 2/2010 | Pamula et al. |
| 2011/0104725 | A1 | 5/2011 | Pamula et al. |

FOREIGN PATENT DOCUMENTS

| | | |
|---|---|---|
| WO | 0218539 A2 | 3/2002 |
| WO | 2007120241 A2 | 10/2007 |
| WO | 2008098236 A2 | 8/2008 |
| WO | 2008116209 A1 | 9/2008 |
| WO | 2009021173 A1 | 2/2009 |

OTHER PUBLICATIONS

Barbulovic-Nad, et al., "Digital microfluidics for cell-based assays", Lab on a chip, vol. 8, Apr. 2008, 519-526.

Batchelder, et al., "Dielectrophoretic manipulator", Review of Scientific Instruments, vol. 54 ., 1983, 300-302.

Baviere, et al., "Dynamics of droplet transport induced by electrowetting actuation", Microfluidics and Nanofluidics, vol. 4, May 2007, 287-294.

Becker, , "Mind the gap!", Lab on a chip, vol. 10, Feb. 2010, 271-273.

Besley, et al., "Studies on sphingomyelinase and ◆-glucosidase activities in Niemann-Pick disease variants. Phosphodiesterase activities measured with natural and artificial substrates", Biochimica et Biophysica Acta—Lipids and Lipid M, 1983, 54-64.

Boggs, , "Detection of Inborn Errors of Metabolism", Critical Reviews in Clinical Laboratory Sciences, vol. 2, No. 4, 1971, 529-572.

Brassard, et al., "Water-oil core-shell droplets for electrowetting-based digital microfluidic devices", Lab on a chip, vol. 8, 2008, 1342-1349.

Broadhead, et al., "The diagnosis of gaucher's disease in liver using 4-methylumbelliferyl-B-d-glucopyranoside", Clinica Chemica Acta, vol. 75, Issue 1, Feb. 15, 1977, 155-161.

Chatterjee, et al., "Droplet-based microfluidics with nonaqueous solvents and solutions", Lab on a Chip, vol. 6., Feb. 2006, 199-206.

Chin, et al., "Lab-on-a-chip devices for global health past studies and future opportunities", Lab on a Chip, vol. 7, Jan. 2007, 41-57.

Chiou, et al., "Light actuation of liquid by optoelectwetting", Sensors and Actuators A: Physical, vol. 104, May 2003, 222-228.

Coltro, et al., "Toner and paper-based fabrication techniques for microfluidic applications", Electrophoresis, vol. 31, Jul. 2010, 2487-2498.

Cooney, et al., "Electrowetting droplet microfluidics on a single planar surface", Microfluidics and Nanofluidics, vol. 2., Mar. 2006, 435-446.

Ding, , "System level architectural optimization of semi-reconfigurable micro fluidic system", M.S. Thesis, Duke University Dept of Electrical Engineering, 2000.

Dubois, et al., "Ionic Liquid Droplet as e-Microreactor", Analytical Chemistry, vol. 78, 2006, 4909-4917.

Fair, et al., "Integrated chemical/biochemical sample collection, pre-concentration, and analysis on a digital microfluidic lab-on-a-chip platform", Lab-on-a-Chip: Platforms, Devices, and Applications, Conf. 5591, SPIE Optics East, Philadelphia, Oct. 25-28, 2004.

Fouillet, et al., "Design and Validation of a Complex Generic Fluidic Microprocessor Based on EWOD Droplet for Biological Applications", 9th International Conference on Miniaturized Systems for Chem and Life Sciences, Boston, MA, Oct. 9-13, 2005, 58-60.

Fouillet, et al., "Digital microfluidic design and optimization of classic and new fluidic functions for lab on a chip systems", Microfluid Nanofluid, vol. 4, 2008, 159-165.

Garrell, et al., "Preventing Biomolecular Absorption in Electrowetting-Based Biofluidic Chips", Analytical Chemistry, vol. 75, Oct. 2003, 5097-5102.

Gong, et al., "Direct-referencing two-dimensional-array digital microfluidics using multi-layer printed circuit board", Journal of Microelectromechanical Systems, vol. 17, Apr. 2008, 257-264.

Guttenberg, et al., "Planar chip devices for PCR and hybridization with surface acoustic wave pump", Lab on a chip, vol. 5, Mar. 2005, 12617-22.

Haeberle, et al., "Microfluidic lab-on-a-chip platform: requirements, characteristics and applications", Chemical Society reviews, vol. 39,, Mar. 2010, 1153-1182.

Hopwood, et al., "A fluorometric assay using 4-methylumbelliferyl alpha-L-iduronide for the estimation of alpha-Liduronidase activity and the detection of Hurler and Scheie syndromes", Clin Chim Acta. vol. 92(2), 1979, 257-265.

Hoshiyama, et al., "Complexation and proton dissociation behavior of 7-hydroxy-4-methylcoumarin and related compounds in the presence of β-cyclodextrin", Journal of Photochemistry and Photobiology A: Chemistry vol. 138, 2001, 227-233.

Hua, et al., "Multiplexed real-time polymerase chain reaction on a digital microfluidic platform", Analytical Chemistry, vol. 82, No. 6, Mar. 15, 2010, Published on Web, Feb. 12, 2010, 2310-2316.

Huebner, et al., "Microdroplets:a sea of applications?", Lab on a Chip, vol. 8, Aug. 2008, 1244-1254.

Jebrail, et al., "Lets get digital: digitizing chemical biology with microfluidics", Current Opinion in Chemical Biology, vol. 14, Oct. 2010, 574-581.

Kim, et al., "Electrowetting on paper for electronic paper display", ACS Applied Materials & Interfaces, vol. 2, Nov. 2010, 3318-3323.

Kolossvary, et al., "Molecular Dynamics Simulation of Cyclodextrin Inclusion Complexes in Enzymatic Lipid Hydrolysis", Biotechnology Letters, vol. 18, No. 4, Apr. 1996, pp. 440-444.

Langelier, et al., "Acoustically driven programmable liquid motion using resonance cavities", Proceedings of the National Academy of Sciences of the USA, vol. 106, Aug. 2009, 12617-12622.

Locascio, et al., "Polymer microfluidic devices", Talanta, vol. 56, Feb. 2002, 267-287.

Luan, et al., "Integrated Optical Sensor in a Digital Microfluidic Platform", IEEE Sensors Journal, vol. 8, May 2008, 628-635.

Luk, et al., "Pluronic additives: a solution to sticky problems in digital microfluidics", Langmuir: The ACS journal of surfaces ans colloids, vol. 24, Jun. 2008, 6382-6389.

Madou, et al., "Lab on a CD", Annual Review of Biomedical Engineering, vol. 8, 2006, 601-628.

Malic, et al., "Biochip fuctionalization using electrowetting-on-dielectric digital microfluidics for surface plasmon resonance imaging detection of DNA hybridization", Biosensors & Bioelectronics, vol. 24, Mar. 2009, 2218-2224.

Malic, et al., "Integration and detection of biochemical assays in digital microfluidic LOC devices", Lab on a chip, vol. 10, Feb. 2010, 418-431.

Manz, et al., "Miniaturized Total Chemical Analysis Systems: a Novel Concept for Chemical Sensing", Sensors and Actuators B: Chemical, 1990, 244-248.

(56) References Cited

OTHER PUBLICATIONS

Mariella, et al., "Sample preparation: The weak link in microfluidics-based biodetection", Biomedical Microdevices, vol. 10, Dec. 2008, 777-784.

McDonald, et al., "Fabrication of Microfluidic systems in poly (dimethylsiloxane)", Electrophoresis, vol. 21, 2000, 27-40.

Miller, et al., "A Digital Microfluidic Approach to Homogeneous Enzyme Assays", Analytical Chemistry, vol. 80, 2008, 1614-1619.

Millington, et al., "Digital microfluidics: a future technology in the newborn screening laboratory", Seminars in Perinatology, vol. 34, Apr. 2010, 163-169.

Moon, "Electrowetting-on-dielectric microfluidics: Modeling, physics, and MALDI application", Dissertation, University of California, Los Angeles, 2005.

Moon, et al., "Low voltage electrowetting-on-dielectric", Journal of Applied Physics, vol. 92 (7), Oct. 1, 2002, 4080-4087.

Mousa, et al., "Droplet-scale estrogen assays in breast tissue, blood, and serum", Science Translational Medicine, vol. 1, Issue 1, 1ra2, Oct. 7, 2009, 1-6.

Mukhopadhyay, R et al., "Microfluidic: on the slope of enlightement", Analytical Chemstry, vol. 81, Jun. 2009, 4169-4173.

Murphey, et al., "Screening testing for argininosuccinic aciduria, orotic aciduria, and other inherited enzyme deficiencies using dried blood specimens", Biochemical Genetics, vol. 6, No. 1, DOI: 10.1007/ BF00485965, 1972, 51-59.

Paik, et al., "A digital-microfluidic approach to chip cooling", IEEE Design & Test of Computers, vol. 25, Jul. 2008, 372-381.

Park, et al., "Single-sided continuous optoelectrowetting (SCOEW) droplet manipulation with light patterns", Lab on a chip, vol. 10, Jul. 2010, 1655-1661.

Pollack, et al., "Electrowetting-Based Actuation of Droplets for Integrated Microfluidics", Lab on a Chip (LOC), vol. 2, 2002, 96-101.

Poulos, et al., "Electrowetting on dielectric-based microfluidics for integrated lipid bilayer formation and measurement", Applied Physics Letters, vol. 95, 2009, 013706.

Shah, et al., "EWOD-driven droplet microfluidic device integrated with optoelectronic tweezers as an automated platform for cellular isolation and analysis", Lab on a Chip, vol. 9, Jun. 2009, 1732-1739.

Shin, et al., "Machine vision for digital microfluidics", Review of Scientific Instruments, vol. 81, 2010, 014302.

Sista, , "Development of a Digital Microfluidic Lab-on-a-Chip for Automated Immunoassays with Magnetically Responsive Beads", PhD Thesis, Department of Chemical Engineering, Florida State University, 2007.

Sista, et al., "Heterogeneous immunoassays using magnetic beads on a digital microfluidic platform", Lab on a Chip, vol. 8, Dec. 2008, First published as an Advance Article on the web, Oct. 14, 2008, 2188-2196.

Squires, et al., "Microfluidics:Fluid physics at the nanoliter scale", Reviews of Modern Physics, vol. 77, 2005, 977-1-26.

Srinivasan, et al., "An integrated digital microfluidic lab-on-a-chip for clinical diagnostics on human physiological fluids", Lab on a Chip, vol. 4, 2004, 310-315.

Srinivasan, et al., "Protein Stamping for MALDI Mass Spectrometry Using an Electrowetting-based Microfluidic Platform", Lab-on-a-Chip: Platforms, Devices, and Applications, Conf. 5591, SPIE Optics East, Philadelphia, Oct. 25-28, 2004.

Svennerholm, et al., "Assay of the B-glucosidase activity with natural labelled and artificial substrates in leukocytes from homozygotes and heterozygotes with norrbottnian type (type 3) of Gaucher disease", Clinica Chimica Acta, vol. 106, Issue 2, Sep. 25, 1980, 183-193.

Teh, et al., "Droplet microfluidics", Lab on a chip, vol. 8, Feb. 2008, 198-220.

Terry, et al., "A Gas Chromatographic Air Analyzer Fabricated on a Silicon Wafer", IEEE Transactions on Electron Devices, vol. ED-26, 1979, 1880-1886.

Tuckerman, et al., "High-Performance Heat Sinking for VLSI", IEEE Electron Device Letters, 1981, 126-129.

Vaitkus, et al., "Inhibition of cyclodextrin acid hydrolysis by some inclusion complexes", J. Ind Phenom Macrocycl Chem, 2010.

Wagner, , "The Effects of Cyclodextrins on Guest Fluorescence", Chapter 2, Cyclodextrin Materials Photochemistry, Photophysics, and Photobiology, 2006.

Wagner, Brian D. , "The Use of Coumarins as Environmentally-Sensitive Fluorescent Probes of Heterogeneous Inclusion Systems", Molecules, vol. 14, No. 1,, Jan. 6, 2009, pp. 210-237.

Wang, et al., "Efficient in-droplet separation of magnetic particles for digital microfluidics", Journal of Micromechanics and Microengineering, vol. 17, 2007, 2148-2156.

Wego, et al., "Fluidic microsystems based on printed circuit board technology", Journal of Micromechanics and Microengineering, vol. 11, No. 5, Sep. 2001, 528-531.

Welters, et al., "Fast Electrically Switchable Capillary Effects", Langmuir, vol. 14, Mar. 1998, 1535-1538.

Whitesides, , "The origins and future of microfluidics", Nature, vol. 442, 2006, 368-373.

Wiederschain, et al., "Characterization of 6-hexadecanoylamino-4-methylumbelliferyl-B-D-galactopyranoside as fluorogenic substrate of balactocerebrosidase for the diagnosis of Krabbe disease", Clinica Chimica Acta, vol. 205 (1-2), 1992, 87-96.

Wulff-Burchfield, et al., "Microfluidic platform versus conventional real-time polymerase chain reaction for the detection of *Mycoplasma pneumoniae* in respiratory specimens", Diagnostic Microbiology and Infectious Disease, vol. 67, 2010, 22-29.

Yager, et al., "Microfluidic diagnostic technologies for global public health", Nature, vol. 442, 2006, 412-418.

Yang, et al., "Manipulation of droplets in microfluidic systems", Trends in Analytical Chemistry, vol. 29, Feb. 2010, 141-157.

Yi, et al., "Characterization of electrowetting actuation on addressable single-side coplanar electrodes", Journal of Micromechanics and Microengineering, vol. 16.,Oct. 2006 http://dx.doi.org/10.1088/0960-1317/16/10/018, published online at stacks.iop.org/JMM/16/2053, Aug. 25, 2006, 2053-2059.

* cited by examiner

| AS# | BE RFU (1.5xCMC) |
|---|---|
| AS93 | 6,653 |
| AS91 | 9,784 |
| AS1 | 10,658 |
| AS90 | 14,366 |
| AS70 | 14,720 |
| AS69 | 16,329 |
| AS66 | 19,376 |
| AS68 | 20,125 |
| AS89 | 20,343 |
| AS67 | 21,318 |
| AS88 | 22,206 |
| AS83 | 23,164 |
| AS7 | 24,421 |
| AS9 | 26,683 |
| AS92 | 27,587 |
| AS62 | 28,413 |
| AS86 | 28,745 |
| AS94 | 29,581 |
| AS77 | 29,777 |
| AS80 | 30,270 |
| AS58 | 30,368 |
| AS87 | 30,515 |
| AS85 | 31,341 |
| AS78 | 31,376 |
| AS64 | 31,385 |
| AS63 | 33,080 |
| AS84 | 33,141 |
| AS81 | 34,523 |
| AS95 | 34,786 |
| AS2 | 35,464 |
| AS79 | 35,866 |
| AS82 | 37,128 |
| AS60 | 38,401 |
| AS25 | 38,436 |
| AS54 | 38,702 |
| AS53 | 39,616 |
| AS55 | 39,782 |
| AS29 | 40,077 |
| AS17 | 40,095 |
| AS56 | 40,277 |
| AS96 | 40,405 |
| AS59 | 41,659 |
| AS57 | 41,773 |
| AS31 | 42,019 |
| AS74 | 42,923 |
| AS12 | 43,257 |
| AS17 | 43,585 |
| AS34 | 43,661 |
| AS19 | 43,937 |

| Structure | Name |
|---|---|
| 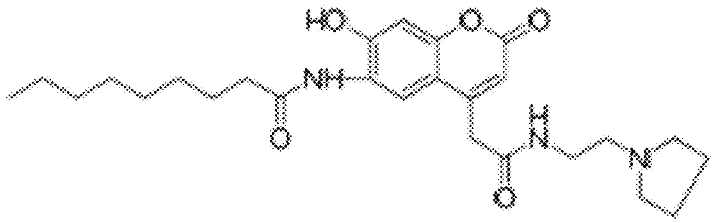 | 4-HMU-6 |
| 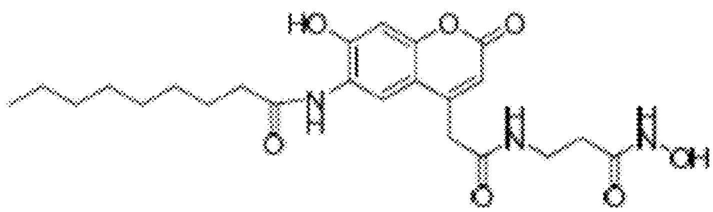 | 4-HMU-7 |
| 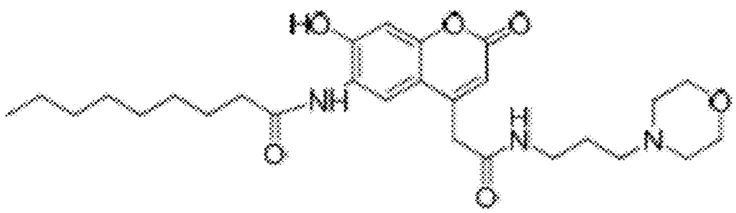 | 4-HMU-8 |
| 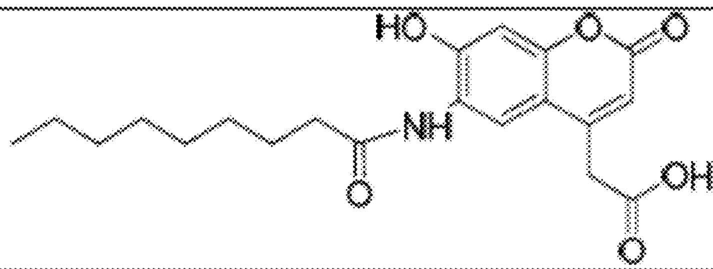 | 4-HMU-9 |
| 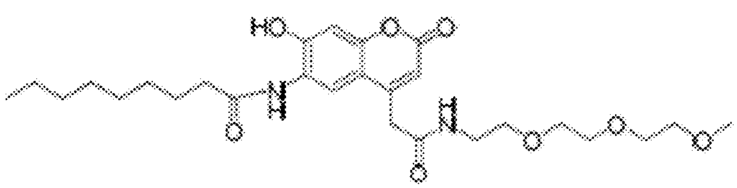 | 4-HMU-10 |
| 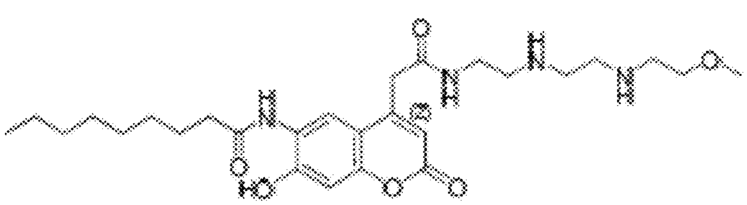 | 4-HMU-11 |

| Structure | Name |
|---|---|
| 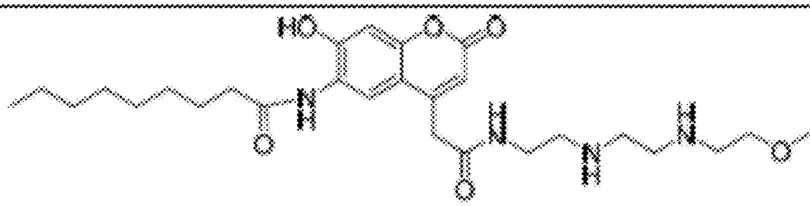 | 4-HMU-12 |
| 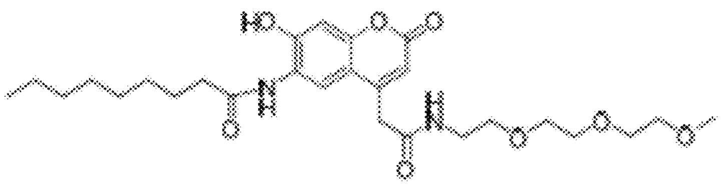 | 4-HMU-13 |
| 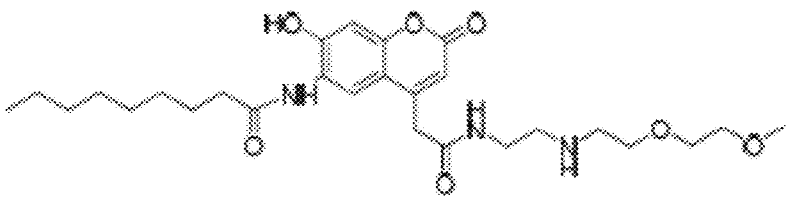 | 4-HMU-14 |
| 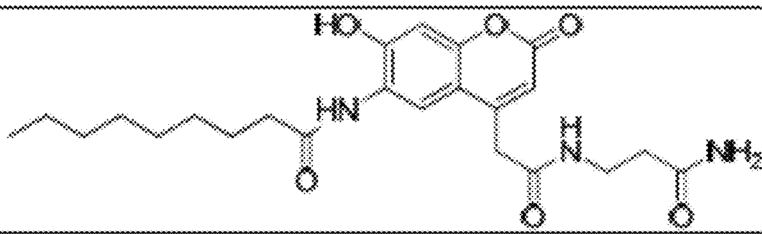 | 4-HMU-15 |
| 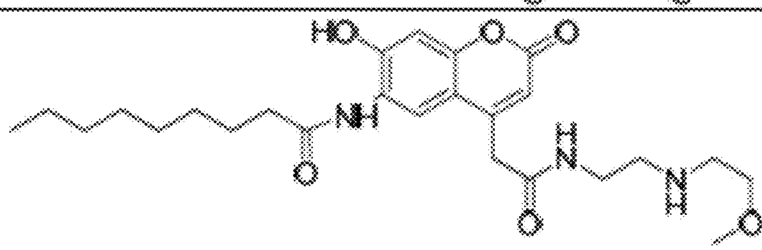 | 4-HMU-16 |
| 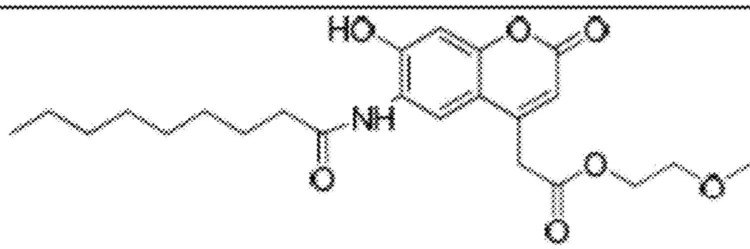 | 4-HMU-17 |

Figure 35C

| Structure | Name |
|---|---|
| 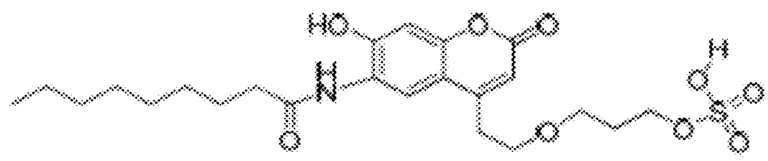 | 4-HMU-18 |
| 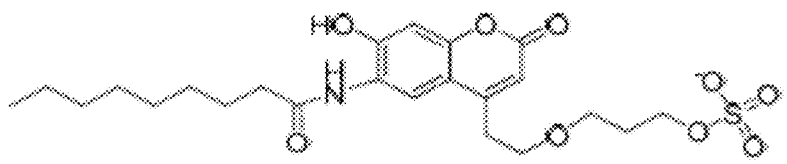 | 4-HMU-19 |
| 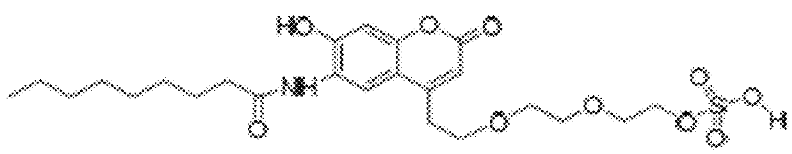 | 4-HMU-20 |
| 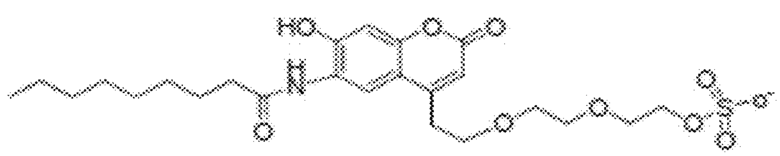 | 4-HMU-21 |
| 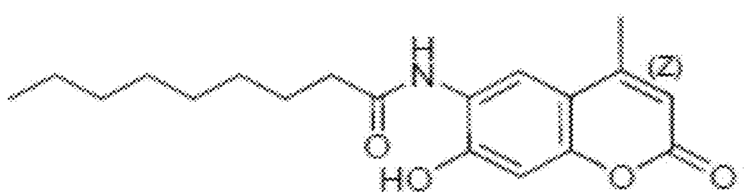 | 4-HMU-22 |
| 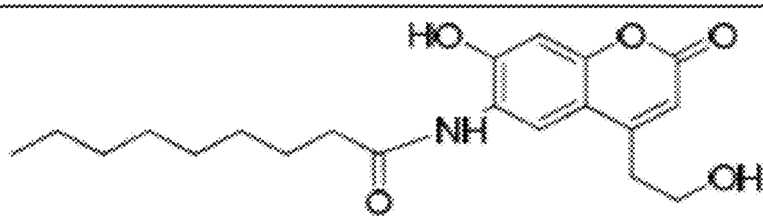 | 4-HMU-23 |

| Structure | Name |
|---|---|
| 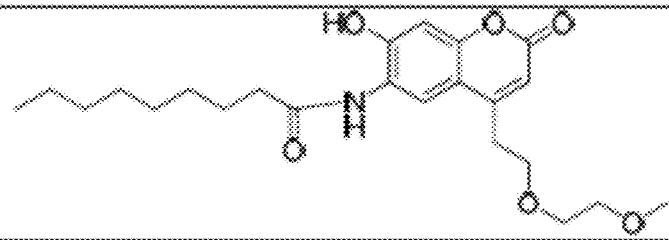 | 4-HMU-30 |
| 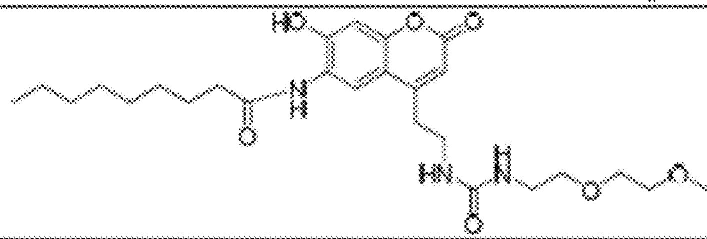 | 4-HMU-31 |
| 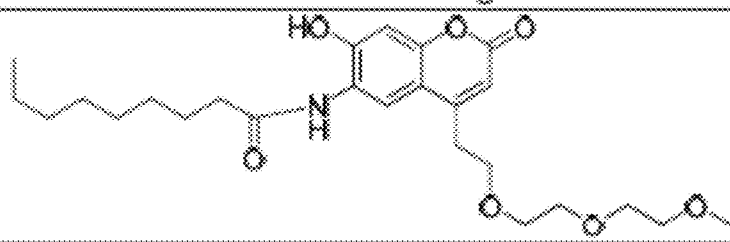 | 4-HMU-32 |
| 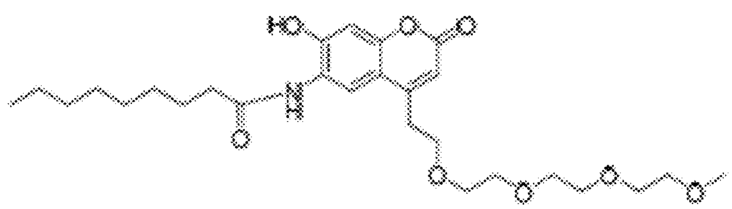 | 4-HMU-33 |
| 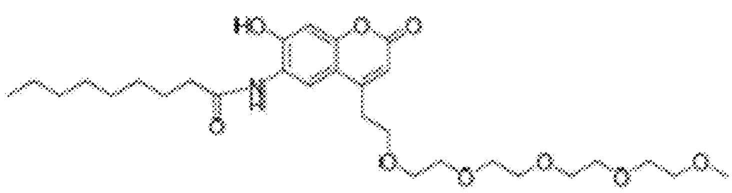 | 4-HMU-34 |
| 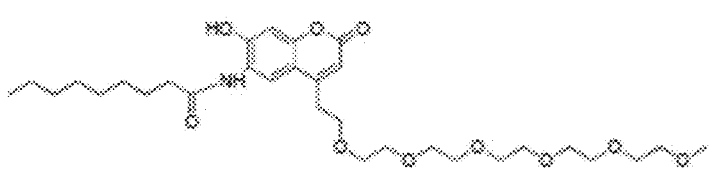 | 4-HMU-35 |

Figure 35F

| Structure | Name |
|---|---|
| (structure) | 4-HMU-41 |
| (structure) | 4-HMU-42 |

Figure 35H

| Structure | Name |
|---|---|
| 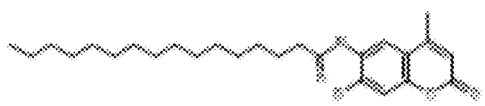 | 6HMU |
| 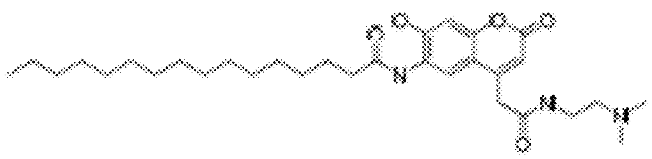 | 6HMU-1 |
| 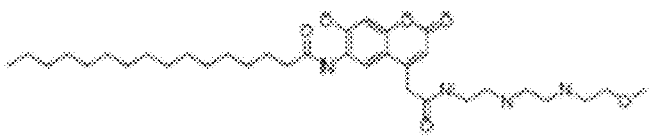 | 6HMU-2 |
| 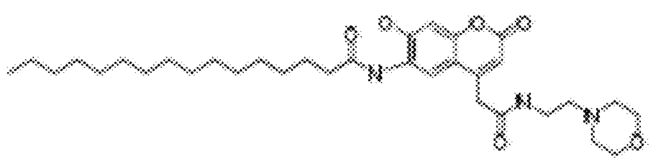 | 6HMU-3 |
| 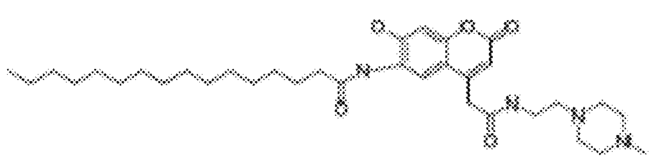 | 6HMU-4 |
| 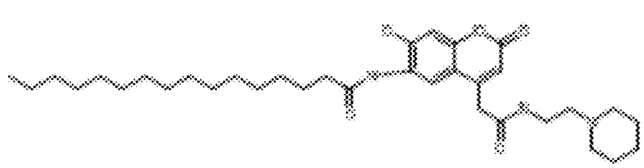 | 6HMU-5 |

| Structure | Name |
|---|---|
| 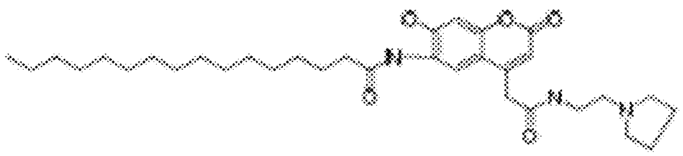 | 6HMU-6 |
| 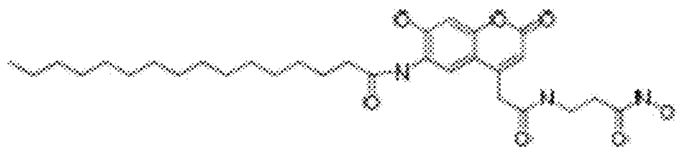 | 6HMU-7 |
| 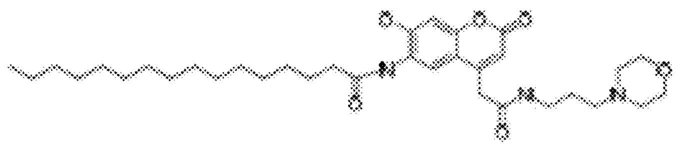 | 6HMU-8 |
| 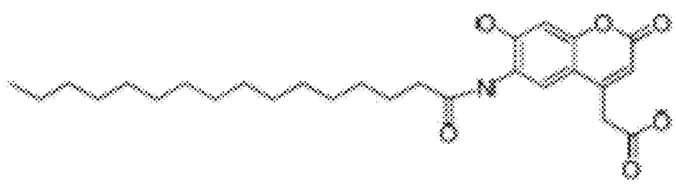 | 6HMU-9 |
| 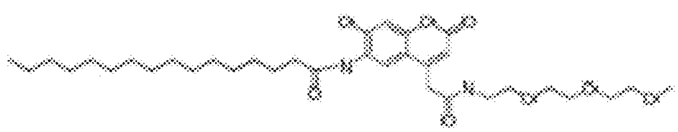 | 6HMU-10 |
| 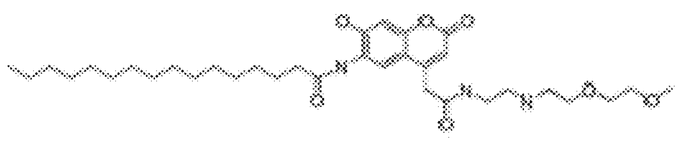 | 6HMU-11 |

Figure 36B

| Structure | Name |
|---|---|
| 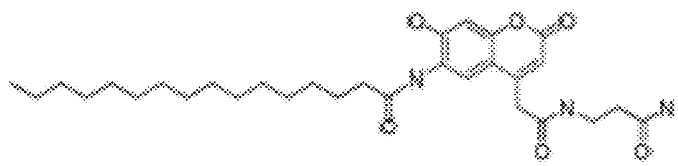 | 6HMU-12 |
| 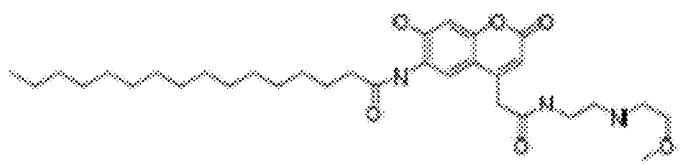 | 6HMU-13 |
| 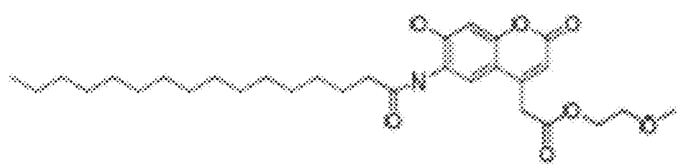 | 6HMU-14 |
| 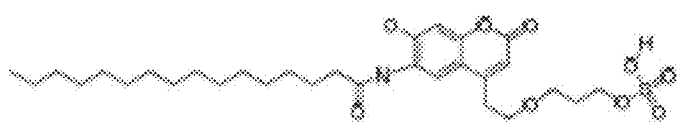 | 6HMU-15 |
| 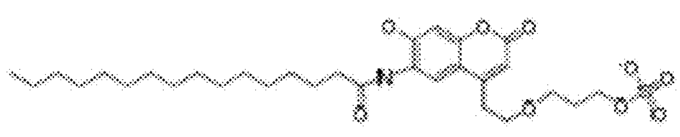 | 6HMU-16 |

| Structure | Name |
|---|---|
| 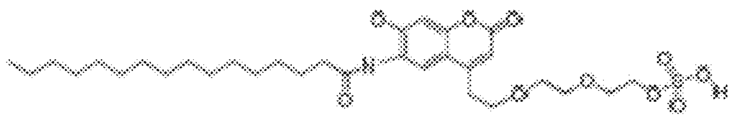 | 6HMU-17 |
| 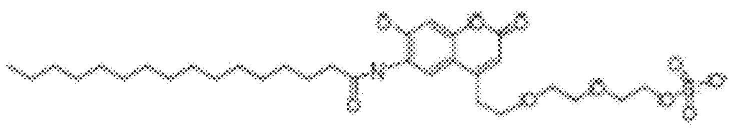 | 6HMU-18 |
| 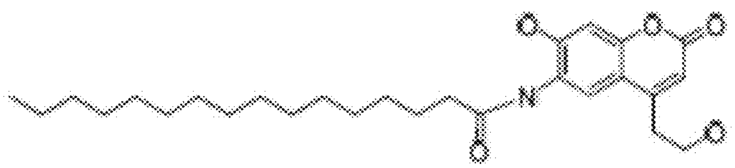 | 6HMU-19 |
| 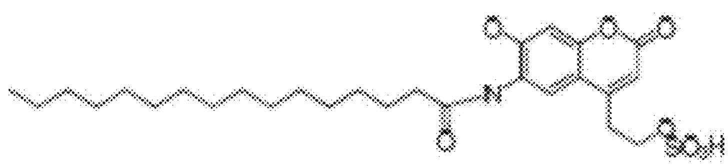 | 6HMU-20 |
| 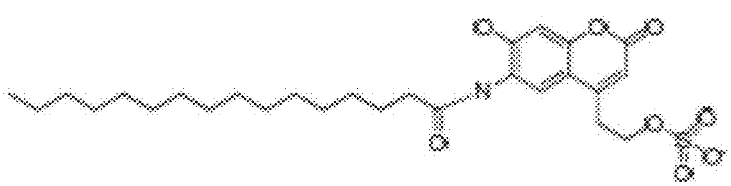 | 6HMU-21 |

| Structure | Name |
|---|---|
| 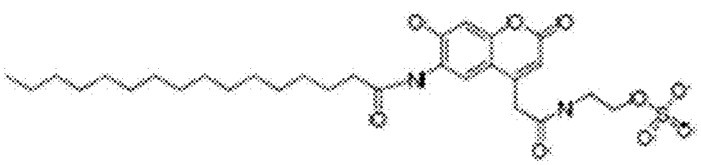 | 6HMU-22 |
| 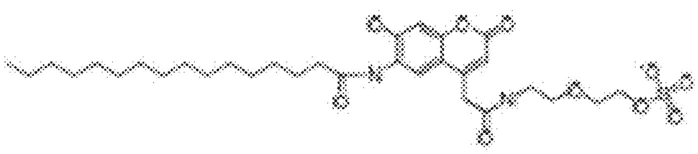 | 6HMU-23 |
| 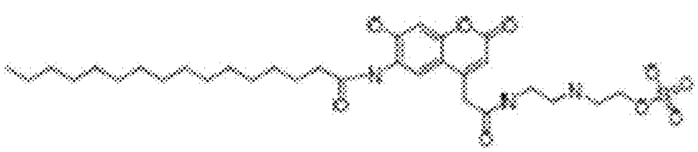 | 6HMU-24 |
| 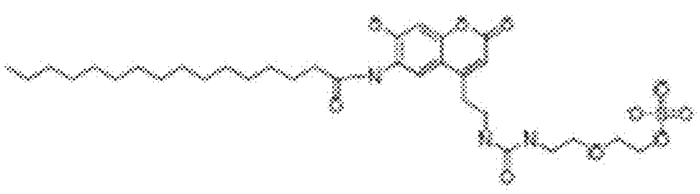 | 6HMU-25 |

| Structure | Name |
|---|---|
| 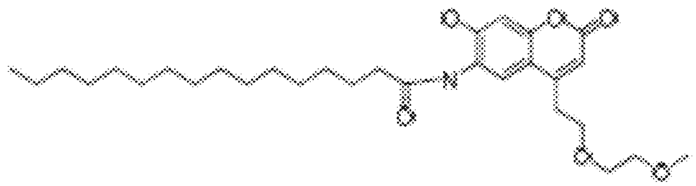 | 6HMU-26 |
| 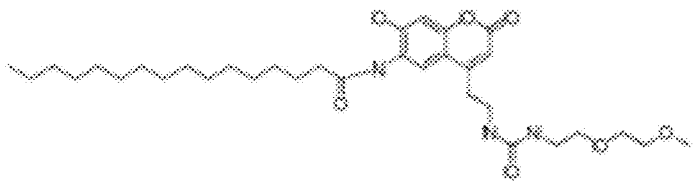 | 6HMU-27 |
| 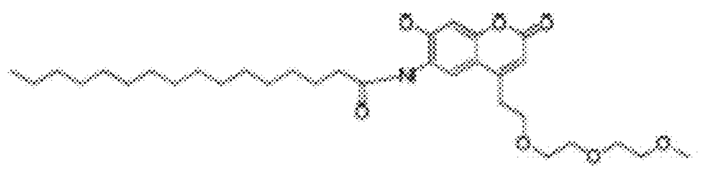 | 6HMU-28 |
| 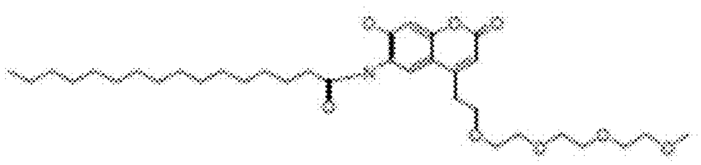 | 6HMU-29 |
| 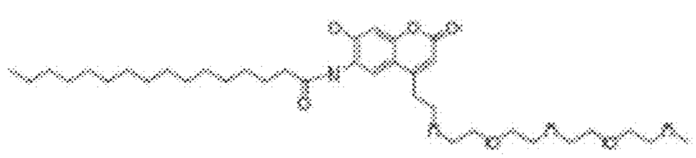 | 6HMU-30 |

| Structure | Name |
|---|---|
| 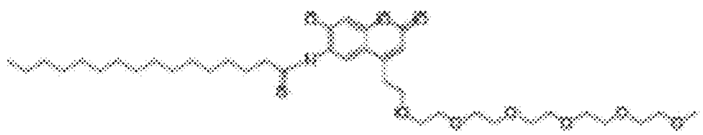 | 6HMU-31 |
| 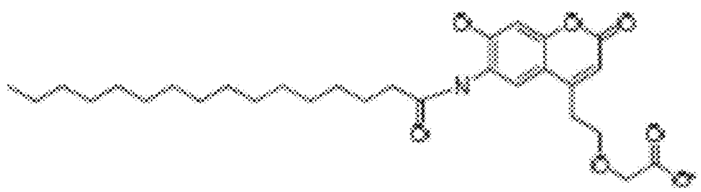 | 6HMU-32 |
| 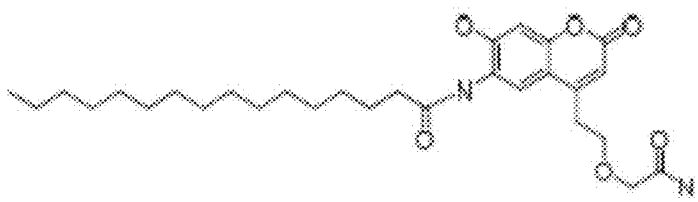 | 6HMU-33 |
| 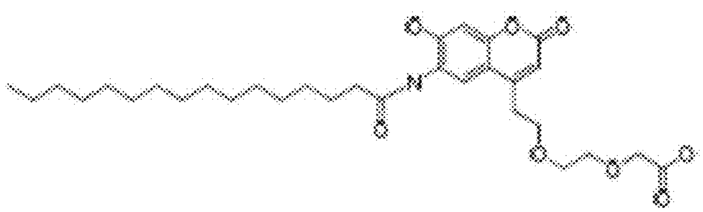 | 6HMU-34 |

| Structure | Name |
|---|---|
| 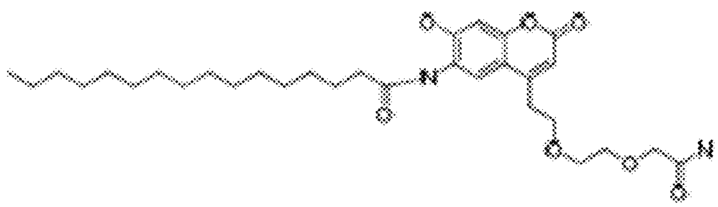 | 6HMU-35 |
| 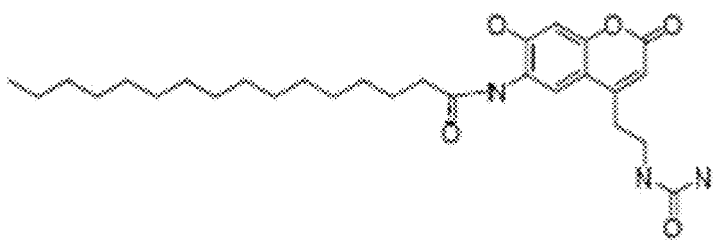 | 6HMU-36 |
| 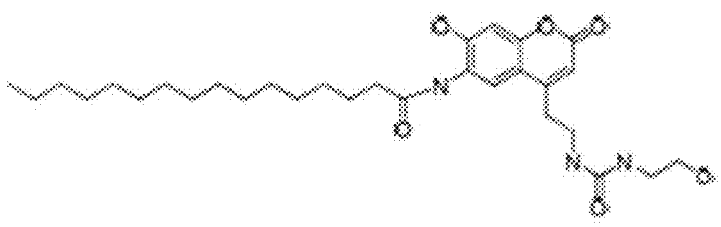 | 6HMU-37 |
| 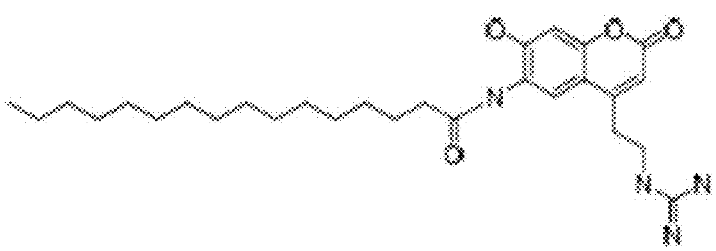 | 6HMU-38 |

METHOD OF CONDUCTING AN ASSAY

1 RELATED APPLICATIONS

This application is a continuation of and incorporates by reference U.S. patent application Ser. No. 13/305,820, entitled "Method of Hydrolyzing an Enzymatic Substrate" having a filing date of Nov. 29, 2011, the application of which is a continuation-in-part of and incorporates by reference U.S. patent application Ser. No. 12/531,844, entitled "Enzymatic Assays for a Droplet Actuator" filed on Feb. 26, 2010, the application of which claims priority to and incorporates by reference International Patent Application No. PCT/US2008/057959, entitled "Enzymatic Assays for a Droplet Actuator" International filing date of Mar. 23, 2008, the application of which claims priority to and incorporates by reference related provisional U.S. Patent Application No. 60/896,341, entitled "Enzymatic Assays for a Droplet Microactuator" filed on Mar. 22, 2007; U.S. patent application Ser. No. 13/305,820 is also a continuation of U.S. patent application Ser. No. 13/012,831, entitled "Enzymatic Assays Using Umbelliferone Substrates with Cyclodextrins in Droplets in Oil," filed Jan. 25, 2011, which is a continuation of and incorporates by reference International Patent App. No. PCT/US2010/061118, entitled "Enzyme Assays on a Droplet Actuator" filed Dec. 10, 2010, the application of which claims priority to and incorporates by reference related provisional U.S. Patent Applications: 61/288,633, entitled "MPS II Assay on a Droplet Actuator" filed on Dec. 21, 2009; 61/290,296, entitled "Enzyme Assays on a Droplet Actuator" filed on Dec. 28, 2009; 61/325,580, entitled "Enzyme Assays on a Droplet Actuator" filed on Apr. 19, 2010; 61/334,376, entitled "Enzyme Assays on a Droplet Actuator" filed on May 13, 2010; 61/359,943, entitled "Enzyme Assays on a Droplet Actuator" filed on Jun. 30, 2010; 61/378,705, entitled "Enzyme Assays on a Droplet Actuator" filed on Aug. 31, 2010; 61/382,564, entitled "Enzyme Assays on a Droplet Actuator" filed on Sep. 14, 2010; 61/392,633, entitled "Enzyme Assays on a Droplet Actuator" filed on Oct. 13, 2010; and 61/406,380, entitled "Enzyme Assays on a Droplet Actuator" filed on Oct. 25, 2010. The disclosures of the aforementioned applications are specifically incorporated by reference herein in their entireties.

2 GOVERNMENT INTEREST

This invention was made with government support under HD062316 awarded by the National Institutes of Health. The government has certain rights in the invention.

The foregoing statement with respect to government support under HD062316 applies only to those aspects of the invention described and claimed in this application arising out of U.S. Provisional Patent Application Nos. 61/406,380, entitled "Enzyme Assays on a Droplet Actuator," filed Oct. 25, 2010.

3 FIELD OF THE INVENTION

The invention generally relates to droplet actuator devices and assay methods. In particular, the invention relates to droplet actuator devices and enzymatic assays using umbelliferone substrates with cyclodextrins in droplets in oil.

4 BACKGROUND

A droplet actuator may include one or more substrates configured to form a surface or gap for conducting droplet operations. The one or more substrates establish a droplet operations surface or gap for conducting droplet operations and may also include electrodes arrange to conduct the droplet operations. The droplet operations substrate or the gap between the substrates may be coated or filled with a filler fluid that is immiscible with the liquid that forms the droplets.

Droplet actuators are used in a variety of applications, including molecular diagnostic assays, such as enzymatic assays and immunoassays. In one application, enzymatic assays and immunoassays are used as part of a routine testing process to test newborn infants for various genetic disorders. For example, enzymatic assays may be used to test for various lysosomal storage diseases (LSD), galactosemia and biotinidase deficiency (BIOT). Immunoassays may be used to test for congenital hypothyroidism (CH), congenital adrenal hyperplasia (CAH) and cystic fibrosis (CF). Current enzymatic assay and immunoassay technologies used in newborn testing are based on 96-well microtiter plate compatible systems. Specimens are punched automatically from a neonatal dried blood spot (DBS) sample into several plates (i.e., one punch for each test to be performed) and each plate is manipulated according to a specific assay protocol. Each assay may require a separate laboratory section with a manager, one or more technologists, and equipment dedicated to the assay. Overall, the system is labor intensive (although one or more steps are at least partially automated) and reagent and equipment costs can be high. Because the current system is labor intensive and costly, testing is generally restricted to centralized laboratories and often unavailable in developing countries. Therefore, there is a need for new approaches to newborn testing.

5 SUMMARY OF THE INVENTION

The invention provides droplet actuator devices and assay methods for multiplexed newborn testing for metabolic disorders. The methods include, among other things, droplet-based enzymatic assays and immunoassays for testing for metabolic disorders. The invention includes methods and devices for conducting multiple assays for different metabolic disorders on a single droplet actuator, as well as multiple assays for the same metabolic disorder using samples from different subjects and/or multiple samples from the same subject on a single droplet actuator. In various embodiments, the invention includes methods for conducting enzymatic activity assays and/or immunoassays in a single fresh blood and/or plasma samples and dried blood and/or plasma samples.

The invention provides assay methods for detection of one or more (i.e., multiplex detection) lysosomal storage diseases (LSDs) on a droplet actuator. In one embodiment, the invention provides assay methods for detection of MSP II (Hunter's syndrome) on a droplet actuator. The methods include, among other things, droplet-based enzymatic assays for iduronate-2-sulfate sulphatase (IDS) enzyme activity. In certain embodiments, the Hunter's assay may be performed at room temperature or at an alternate temperature, such as 37° C. In other embodiments the Hunter's assay may be performed for 8 hours or less. The Hunter's assay is a single-step homogenous assay that is performed at a single pH (i.e., pH 5.0) with a time to result of 8 hours or less.

In yet another embodiment, the invention provides an integrated droplet actuator device and methods for performing multiplexed enzymatic assays and immunoassays on a single droplet actuator using a single dried blood spot (DBS) sample. In one example, the integrated droplet actuator device and methods of the invention may be used for multiplexed detection of congenital adrenal hyperplasia (CAH), congenital hypothyroidism (CH), cystic fibrosis (CF), galactosemia and biotinidase deficiency (BIOT).

Using digital microfluidics technology, sub-microliter-sized droplets may be manipulated using high-speed transport of droplets, reliable dispensing, rapid mixing, dilution, and disposal to provide rapid sample-to-result testing. Because substantially all of the steps in a sample testing protocol are performed on-chip (automated), the risk of operator error is substantially reduced. The flexibility, programmability and modular format of the microfluidic platform, additional assay protocols (i.e., for other disorders) may be readily added to an on-chip testing panel.

The droplet actuator devices and methods of the invention complement tandem mass spectrometry (MS/MS) testing by multiplexing testing of metabolic disorders that are not suited for MS/MS.

In yet another embodiment, the invention provides bench-based methods for enzymatic detection of Hunter's syndrome and Fabry disease.

In yet another embodiment, the invention provides a digital microfluidic platform and methods for multiplexed testing for hyperbilirubinemia, glucose-6-phosphate dehydrogenase (G6PD) deficiency, and congenital hypothyroidism (CH).

6 DEFINITIONS

As used herein, the following terms have the meanings indicated.

"Activate," with reference to one or more electrodes, means affecting a change in the electrical state of the one or more electrodes which, in the presence of a droplet, results in a droplet operation. Activation of an electrode can be accomplished using alternating or direct current. Any suitable voltage may be used. For example, an electrode may be activated using a voltage which is greater than about 150 V, or greater than about 200 V, or greater than about 250 V, or from about 275 V to about 375 V, or about 300 V. Where alternating current is used, any suitable frequency may be employed. For example, an electrode may be activated using alternating current having a frequency from about 1 Hz to about 100 Hz, or from about 10 Hz to about 60 Hz, or from about 20 Hz to about 40 Hz, or about 30 Hz.

"Bead," with respect to beads on a droplet actuator, means any bead or particle that is capable of interacting with a droplet on or in proximity with a droplet actuator. Beads may be any of a wide variety of shapes, such as spherical, generally spherical, egg shaped, disc shaped, cubical, amorphous and other three dimensional shapes. The bead may, for example, be capable of being subjected to a droplet operation in a droplet on a droplet actuator or otherwise configured with respect to a droplet actuator in a manner which permits a droplet on the droplet actuator to be brought into contact with the bead on the droplet actuator and/or off the droplet actuator. Beads may be provided in a droplet, in a droplet operations gap, or on a droplet operations surface. Beads may be provided in a reservoir that is external to a droplet operations gap or situated apart from a droplet operations surface, and the reservoir may be associated with a fluid path that permits a droplet including the beads to be brought into a droplet operations gap or into contact with a droplet operations surface. Beads may be manufactured using a wide variety of materials, including for example, resins, and polymers. The beads may be any suitable size, including for example, microbeads, microparticles, nanobeads and nanoparticles. In some cases, beads are magnetically responsive; in other cases beads are not significantly magnetically responsive. For magnetically responsive beads, the magnetically responsive material may constitute substantially all of a bead, a portion of a bead, or only one component of a bead. The remainder of the bead may include, among other things, polymeric material, coatings, and moieties which permit attachment of an assay reagent. Examples of suitable beads include flow cytometry microbeads, polystyrene microparticles and nanoparticles, functionalized polystyrene microparticles and nanoparticles, coated polystyrene microparticles and nanoparticles, silica microbeads, fluorescent microspheres and nanospheres, functionalized fluorescent microspheres and nanospheres, coated fluorescent microspheres and nanospheres, color dyed microparticles and nanoparticles, magnetic microparticles and nanoparticles, superparamagnetic microparticles and nanoparticles (e.g., DYNABEADS® particles, available from Invitrogen Group, Carlsbad, Calif.), fluorescent microparticles and nanoparticles, coated magnetic microparticles and nanoparticles, ferromagnetic microparticles and nanoparticles, coated ferromagnetic microparticles and nanoparticles, and those described in U.S. Patent Publication Nos. 20050260686, entitled "Multiplex flow assays preferably with magnetic particles as solid phase," published on Nov. 24, 2005; 20030132538, entitled "Encapsulation of discrete quanta of fluorescent particles," published on Jul. 17, 2003; 20050118574, entitled "Multiplexed Analysis of Clinical Specimens Apparatus and Method," published on Jun. 2, 2005; 20050277197. Entitled "Microparticles with Multiple Fluorescent Signals and Methods of Using Same," published on Dec. 15, 2005; 20060159962, entitled "Magnetic Microspheres for use in Fluorescence-based Applications," published on Jul. 20, 2006; the entire disclosures of which are incorporated herein by reference for their teaching concerning beads and magnetically responsive materials and beads. Beads may be pre-coupled with a biomolecule or other substance that is able to bind to and form a complex with a biomolecule. Beads may be pre-coupled with an antibody, protein or antigen, DNA/RNA probe or any other molecule with an affinity for a desired target. Examples of droplet actuator techniques for immobilizing magnetically responsive beads and/or non-magnetically responsive beads and/or conducting droplet operations protocols using beads are described in U.S. patent application Ser. No. 11/639,566, entitled "Droplet-Based Particle Sorting," filed on Dec. 15, 2006; U.S. Patent Application No. 61/039,183, entitled "Multiplexing Bead Detection in a Single Droplet," filed on Mar. 25, 2008; U.S. Patent Application No. 61/047,789, entitled "Droplet Actuator Devices and Droplet Operations Using Beads," filed on Apr. 25, 2008; U.S. Patent Application No. 61/086,183, entitled "Droplet Actuator Devices and Methods for Manipulating Beads," filed on Aug. 5, 2008; International Patent Application No. PCT/US2008/053545, entitled "Droplet Actuator Devices and Methods Employing Magnetic Beads," filed on Feb. 11, 2008; International Patent Application No. PCT/US2008/058018, entitled "Bead-based Multiplexed Analytical Methods and Instrumentation," filed on Mar. 24, 2008; International Patent Application No. PCT/US2008/058047, "Bead Sorting on a Droplet Actuator," filed on Mar. 23, 2008; and International Patent Application No. PCT/US2006/047486, entitled "Droplet-based Biochemistry," filed on Dec. 11, 2006; the entire disclosures of which are incorporated herein by reference. Bead characteristics may be employed in the multiplexing aspects of the invention. Examples of beads having characteristics suitable for multiplexing, as well as methods of detecting and analyzing signals emitted from such beads, may be found in U.S. Patent Publication No. 20080305481, entitled "Systems and Methods for Multiplex Analysis of PCR in Real Time," published on Dec. 11, 2008; U.S. Patent Publication No. 20080151240, "Methods and Systems for Dynamic Range Expansion," published on Jun. 26, 2008; U.S. Patent Publication No. 20070207513, entitled "Methods, Products, and Kits for Identifying an Analyte in a Sample," published on Sep. 6, 2007; U.S. Patent Publication No. 20070064990, entitled "Methods and Systems for Image Data Processing," published on Mar. 22, 2007; U.S. Patent Publication No. 20060159962, entitled "Magnetic Microspheres for use in Fluorescence-based Applications," published on Jul. 20, 2006; U.S. Patent Publication No. 20050277197, entitled "Microparticles with Multiple Fluorescent Signals and Methods of Using Same," published on Dec. 15, 2005; and U.S. Patent Publication No. 20050118574, entitled "Multiplexed Analysis of Clinical Specimens Apparatus and Method," published on Jun. 2, 2005.

"Blood Sample" includes whole blood, whole blood constituents, such as serum or plasma, and dried blood spot extracts. The dried blood can be on tissue paper or standard blood collection card or any other suitable substrate that does not eliminate the usefulness of the blood as a sample for the target of interest. The blood may be from the subject, and the subject may be a human subject of any age, such as an adult, infant or a fetus. In the case of a fetus, the blood may be from the mother.

"Droplet" means a volume of liquid on a droplet actuator. A droplet may be at least partially bounded by a filler fluid. For example, a droplet may be completely surrounded by a filler fluid or may be bounded by filler fluid and one or more surfaces of the droplet actuator. As another example, a droplet may be bounded by filler fluid, one or more surfaces of the droplet actuator, and/or the atmosphere. As yet another example, a droplet may be bounded by filler fluid and the atmosphere. Droplets may, for example, be aqueous or non-aqueous or may be mixtures or emulsions including aqueous and non-aqueous components. A 1× droplet may be about 300 nl. Droplets may take a wide variety of shapes; non-limiting examples include generally disc shaped, slug shaped, truncated sphere, ellipsoid, spherical, partially compressed sphere, hemispherical, ovoid, cylindrical, combinations of such shapes, and various shapes formed during droplet operations, such as merging or splitting or formed as a result of contact of such shapes with one or more surfaces of a droplet actuator. For examples of droplet fluids that may be subjected to droplet operations using the approach of the invention, see International Patent Application No. PCT/US 06/47486, entitled, "Droplet-Based Biochemistry," filed on Dec. 11, 2006. In various embodiments, a droplet may include a biological sample, such as whole blood, lymphatic fluid, serum, plasma, sweat, tear, saliva, sputum, cerebrospinal fluid, amniotic fluid, seminal fluid, vaginal excretion, serous fluid, synovial fluid, pericardial fluid, peritoneal fluid, pleural fluid, transudates, exudates, cystic fluid, bile, urine, gastric fluid, intestinal fluid, fecal samples, liquids containing single or multiple cells, liquids containing organelles, fluidized tissues, fluidized organisms, liquids containing multi-celled organisms, biological swabs and biological washes. Moreover, a droplet may include a reagent, such as water, deionized water, saline solutions, acidic solutions, basic solutions, detergent solutions and/or buffers. Other examples of droplet contents include reagents, such as a reagent for a biochemical protocol, such as a nucleic acid amplification protocol, an affinity-based assay protocol, an enzymatic assay protocol, a sequencing protocol, and/or a protocol for analyses of biological fluids. In various embodiments the droplets may include surfactants to improve droplet operations. It will be appreciated that where specific surfactants are mentioned, these may readily be supplemented or replaced with other similar surfactants, such as surfactants having similar HLB profile.

"Droplet Actuator" means a device for manipulating droplets. For examples of droplet actuators, see Pamula et al., U.S. Pat. No. 6,911,132, entitled "Apparatus for Manipulating Droplets by Electrowetting-Based Techniques," issued on Jun. 28, 2005; Pamula et al., U.S. patent application Ser. No. 11/343,284, entitled "Apparatuses and Methods for Manipulating Droplets on a Printed Circuit Board," filed on filed on Jan. 30, 2006; Pollack et al., International Patent Application No. PCT/US2006/047486, entitled "Droplet-Based Biochemistry," filed on Dec. 11, 2006; Shenderov, U.S. Pat. Nos. 6,773,566, entitled "Electrostatic Actuators for Microfluidics and Methods for Using Same," issued on Aug. 10, 2004 and 6,565,727, entitled "Actuators for Microfluidics Without Moving Parts," issued on Jan. 24, 2000; Kim and/or Shah et al., U.S. patent application Ser. Nos. 10/343,261, entitled "Electrowetting-driven Micropumping," filed on Jan. 27, 2003, 11/275,668, entitled "Method and Apparatus for Promoting the Complete Transfer of Liquid Drops from a Nozzle," filed on Jan. 23, 2006, 11/460,188, entitled "Small Object Moving on Printed Circuit Board," filed on Jan. 23, 2006, 12/465,935, entitled "Method for Using Magnetic Particles in Droplet Microfluidics," filed on May 14, 2009, and 12/513,157, entitled "Method and Apparatus for Real-time Feedback Control of Electrical Manipulation of Droplets on Chip," filed on Apr. 30, 2009; Velev, U.S. Pat. No. 7,547,380, entitled "Droplet Transportation Devices and Methods Having a Fluid Surface," issued on Jun. 16, 2009; Sterling et al., U.S. Pat. No. 7,163,612, entitled "Method, Apparatus and Article for Microfluidic Control via Electrowetting, for Chemical, Biochemical and Biological Assays and the Like," issued on Jan. 16, 2007; Becker and Gascoyne et al., U.S. Pat. Nos. 7,641,779, entitled "Method and Apparatus for Programmable fluidic Processing," issued on Jan. 5, 2010, and 6,977,033, entitled "Method and Apparatus for Programmable fluidic Processing," issued on Dec. 20, 2005; Decre et al., U.S. Pat. No. 7,328,979, entitled "System for Manipulation of a Body of Fluid," issued on Feb. 12, 2008; Yamakawa et al., U.S. Patent Pub. No. 20060039823, entitled "Chemical Analysis Apparatus," published on Feb. 23, 2006; Wu, International Patent Pub. No. WO/2009/003184, entitled "Digital Microfluidics Based Apparatus for Heat-exchanging Chemical Processes," published on Dec. 31, 2008; Fouillet et al., U.S. Patent Pub. No. 20090192044, entitled "Electrode Addressing Method," published on Jul. 30, 2009; Fouillet et al., U.S. Pat. No. 7,052,244, entitled "Device for Displacement of Small Liquid Volumes Along a Micro-catenary Line by Electrostatic Forces," issued on May 30, 2006; Marchand et al., U.S. Patent Pub. No. 20080124252, entitled "Droplet Microreactor," published on May 29, 2008; Adachi et al., U.S. Patent Pub. No. 20090321262, entitled "Liquid Transfer Device," published on Dec. 31, 2009; Roux et al., U.S. Patent Pub. No. 20050179746, entitled "Device for Controlling the Displacement of a Drop Between two or Several Solid Substrates," published on Aug. 18, 2005; Dhindsa et al., "Virtual Electrowetting Channels: Electronic Liquid Transport with Continuous Channel Functionality," *Lab Chip,* 10:832-836 (2010); the entire disclosures of which are incorporated herein by reference, along with their priority documents. Certain droplet actuators will include one or more substrates arranged with a gap therebetween and electrodes associated with (e.g., layered on, attached to, and/or embedded in) the one or more substrates and arranged to conduct one or more droplet operations. For example, certain droplet actuators will include a base (or bottom) substrate, droplet operations electrodes associated with the substrate, one or more dielectric layers atop the substrate and/or electrodes, and optionally one or more hydrophobic layers atop the substrate, dielectric layers and/or the electrodes forming a droplet operations surface. A top substrate may also be provided, which is separated from the droplet operations surface by a gap, commonly referred to as a droplet operations gap. Various electrode arrangements on the top and/or bottom substrates are discussed in the above-referenced patents and applications and certain novel electrode arrangements are discussed in the description of the invention. During droplet operations it is preferred that droplets remain in continuous contact or frequent contact with a ground or reference electrode. A ground or reference electrode may be associated with the top substrate facing the gap, the bottom substrate facing the gap, in the gap. Where electrodes are provided on both substrates, electrical contacts for coupling the electrodes to a droplet actuator instrument for controlling or monitoring the electrodes may be associated with one or both plates. In some cases, electrodes on one substrate are electrically coupled to the other substrate so that only one substrate is in contact with the droplet actuator. In one embodiment, a conductive material (e.g., an epoxy, such as MASTER BOND™ Polymer System EP79, available from Master Bond, Inc., Hackensack, N.J.) provides the electrical connection between electrodes on one substrate and electrical paths on the other substrates, e.g., a ground electrode on a top substrate may be coupled to an electrical path on a bottom substrate by such a conductive material. Where multiple substrates are used, a spacer may be provided between the substrates to determine the height of the gap therebetween and define dispensing reservoirs. The spacer height may, for example, be from about 5 µm to about 600 µm, or about 100 µm to about 400 µm, or about 200 µm to about 350 µm, or about 250 µm to about 300 µm, or about 275 µm. The spacer may, for example, be formed of a layer of projections form the top or bottom substrates, and/or a material inserted between the top and bottom substrates. One or more openings may be provided in the one or more substrates for forming a fluid path through which liquid may be delivered into the droplet operations gap. The one or more openings may in some cases be aligned for interaction with one or more electrodes, e.g., aligned such that liquid flowed through the opening will come into sufficient proximity with one or more droplet operations electrodes to permit a droplet operation to be effected by the droplet operations electrodes using the liquid. The base (or bottom) and top substrates may in some cases be formed as one integral component. One or more reference electrodes may be provided on the base (or bottom) and/or top substrates and/or in the gap. Examples of reference electrode arrangements are provided in the above referenced patents and patent applications. In various embodiments, the manipulation of droplets by a droplet actuator may be electrode mediated, e.g., electrowetting mediated or dielectrophoresis mediated or Coulombic force mediated. Examples of other techniques for controlling droplet operations that may be used in the droplet actuators of the invention include using devices that induce hydrodynamic fluidic pressure, such as those that operate on the basis of mechanical principles (e.g. external syringe pumps, pneumatic membrane pumps, vibrating membrane pumps, vacuum devices, centrifugal forces, piezoelectric/ultrasonic pumps and acoustic forces); electrical or magnetic principles (e.g. electroosmotic flow, electrokinetic pumps, ferrofluidic plugs, electrohydrodynamic pumps, attraction or repulsion using magnetic forces and magnetohydrodynamic pumps); thermodynamic principles (e.g. gas bubble generation/phase-change-induced volume expansion); other kinds of surface-wetting principles (e.g. electrowetting, and optoelectrowetting, as well as chemically, thermally, structurally and radioactively induced surface-tension gradients); gravity; surface tension (e.g., capillary action); electrostatic forces (e.g., electroosmotic flow); centrifugal flow (substrate disposed on a compact disc and rotated); magnetic forces (e.g., oscillating ions causes flow); magnetohydrodynamic forces; and vacuum or pressure differential. In certain embodiments, combinations of two or more of the foregoing techniques may be employed to conduct a droplet operation in a droplet actuator of the invention. Similarly, one or more of the foregoing may be used to deliver liquid into a droplet operations gap, e.g., from a reservoir in another device or from an external reservoir of the droplet actuator (e.g., a reservoir associated with a droplet actuator substrate and a fluid path from the reservoir into the droplet operations gap). Droplet operations surfaces of certain droplet actuators of the invention may be made from hydrophobic materials or may be coated or treated to make them hydrophobic. For example, in some cases some portion or all of the droplet operations surfaces may be derivatized with low surface-energy materials or chemistries, e.g., by deposition or using in situ synthesis using compounds such as poly- or per-fluorinated compounds in solution or polymerizable monomers. Examples include TEFLON® AF (available from DuPont, Wilmington, Del.), members of the cytop family of materials, coatings in the FLUOROPEL® family of hydrophobic and superhydrophobic coatings (available from Cytonix Corporation, Beltsville, Md.), silane coatings, fluorosilane coatings, hydrophobic phosphonate derivatives (e.g., those sold by Aculon, Inc), and NOVEC™ electronic coatings (available from 3M Company, St. Paul, Minn.), and other fluorinated monomers for plasma-enhanced chemical vapor deposition (PECVD). In some cases, the droplet operations surface may include a hydrophobic coating having a thickness ranging from about 10 nm to about 1,000 nm. Moreover, in some embodiments, the top substrate of the droplet actuator includes an electrically conducting organic polymer, which is then coated with a hydrophobic coating or otherwise treated to make the droplet operations surface hydrophobic. For example, the electrically conducting organic polymer that is deposited onto a plastic substrate may be poly(3,4-ethylenedioxythiophene) poly(styrenesulfonate) (PEDOT:PSS). Other examples of electrically conducting organic polymers and alternative conductive layers are described in Pollack et al., International Patent Application No. PCT/US2010/040705, entitled "Droplet Actuator Devices and Methods," the entire disclosure of which is incorporated herein by reference. One or both substrates may be fabricated using a printed circuit board (PCB), glass, indium tin oxide (ITO)-coated glass or polymer, and/or semiconductor materials as the substrate. When the substrate is ITO-coated glass, the ITO coating is preferably a thickness in the range of about 20 to about 200 nm, preferably about 50 to about 150 nm, or about 75 to about 125 nm, or about 100 nm. In some cases, the top and/or bottom substrate includes a PCB substrate that is coated with a dielectric, such as a polyimide dielectric, which may in some cases also be coated or otherwise treated to make the droplet operations surface hydrophobic. When the substrate includes a PCB, the following materials are examples of suitable materials: MITSUI™ BN-300 (available from MITSUI Chemicals America, Inc., San Jose Calif.); ARLON™ 11N (available from Arlon, Inc, Santa Ana, Calif.); NELCO® N4000-6 and N5000-30/32 (available from Park Electrochemical Corp., Melville, N.Y.); ISOLA™ FR406 (available from Isola Group, Chandler, Ariz.), especially IS620; fluoropolymer family (suitable for fluorescence detection since it has low background fluorescence); polyimide family; polyester; polyethylene naphthalate; polycarbonate; polyetheretherketone; liquid crystal polymer; cyclo-olefin copolymer (COC); cyclo-olefin polymer (COP); aramid; THERMOUNT® nonwoven aramid reinforcement (available from DuPont, Wilmington, Del.); NOMEX® brand fiber (available from DuPont, Wilmington, Del.); and paper. Various materials are also suitable for use as the dielectric component of the substrate. Examples include: vapor deposited dielectric, such as PARYLENE™ C (especially on glass) and PARYLENE™ N (available from Parylene Coating Services, Inc., Katy, Tex.); TEFLON® AF coatings; cytop; soldermasks, such as liquid photoimageable soldermasks (e.g., on PCB) like TAIYO™ PSR4000 series, TAIYO™ PSR and AUS series (available from Taiyo America, Inc. Carson City, Nev.) (good thermal characteristics for applications involving thermal control), and PRO-BIMER™ 8165 (good thermal characteristics for applications involving thermal control (available from Huntsman Advanced Materials Americas Inc., Los Angeles, Calif.); dry film soldermask, such as those in the VACREL® dry film soldermask line (available from DuPont, Wilmington, Del.); film dielectrics, such as polyimide film (e.g., KAPTON® polyimide film, available from DuPont, Wilmington, Del.), polyethylene, and fluoropolymers (e.g., FEP), polytetrafluoroethylene; polyester; polyethylene naphthalate; cyclo-olefin copolymer (COC); cyclo-olefin polymer (COP); any other PCB substrate material listed above; black matrix resin; and polypropylene. Droplet transport voltage and frequency may be selected for performance with reagents used in specific assay protocols. Design parameters may be varied, e.g., number and placement of on-chip reservoirs, number of independent electrode connections, size (volume) of different reservoirs, placement of magnets/bead washing zones, electrode size, inter-electrode pitch, and gap height (between top and bottom substrates) may be varied for use with specific reagents, protocols, droplet volumes, etc. In some cases, a substrate of the invention may derivatized with low surface-energy materials or chemistries, e.g., using deposition or in situ synthesis using poly- or per-fluorinated compounds in solution or polymerizable monomers. Examples include TEFLON® AF coatings and FLUOROPEL® coatings for dip or spray coating, and other fluorinated monomers for plasma-enhanced chemical vapor deposition (PECVD). Additionally, in some cases, some portion or all of the droplet operations surface may be coated with a substance for reducing background noise, such as background fluorescence from a PCB substrate. For example, the noise-reducing coating may include a black matrix resin, such as the black matrix resins available from Toray industries, Inc., Japan. Electrodes of a droplet actuator may be controlled by a controller or a processor, which is itself provided as part of a system, which may include processing functions as well as data and software storage and input and output capabilities.

"Droplet operation" means any manipulation of a droplet on a droplet actuator. A droplet operation may, for example, include: loading a droplet into the droplet actuator; dispensing one or more droplets from a source droplet; splitting, separating or dividing a droplet into two or more droplets; transporting a droplet from one location to another in any direction; merging or combining two or more droplets into a single droplet; diluting a droplet; mixing a droplet; agitating a droplet; deforming a droplet; retaining a droplet in position; incubating a droplet; heating a droplet; vaporizing a droplet; cooling a droplet; disposing of a droplet; transporting a droplet out of a droplet actuator; other droplet operations described herein; and/or any combination of the foregoing. The terms "merge," "merging," "combine," "combining" and the like are used to describe the creation of one droplet from two or more droplets. It should be understood that when such a term is used in reference to two or more droplets, any combination of droplet operations that are sufficient to result in the combination of the two or more droplets into one droplet may be used. For example, "merging droplet A with droplet B," can be achieved by transporting droplet A into contact with a stationary droplet B, transporting droplet B into contact with a stationary droplet A, or transporting droplets A and B into contact with each other. The terms "splitting," "separating" and "dividing" are not intended to imply any particular outcome with respect to volume of the resulting droplets (i.e., the volume of the resulting droplets can be the same or different) or number of resulting droplets (the number of resulting droplets may be 2, 3, 4, 5 or more). The term "mixing" refers to droplet operations which result in more homogenous distribution of one or more components within a droplet. Examples of "loading" droplet operations include microdialysis loading, pressure assisted loading, robotic loading, passive loading, and pipette loading. Droplet operations may be electrode-mediated. In some cases, droplet operations are further facilitated by the use of hydrophilic and/or hydrophobic regions on surfaces and/or by physical obstacles. For examples of droplet operations, see the patents and patent applications cited above under the definition of "droplet actuator." Impedance or capacitance sensing or imaging techniques may sometimes be used to determine or confirm the outcome of a droplet operation. Examples of such techniques are described in Sturmer et al., International Patent Pub. No. WO/2008/101194, entitled "Capacitance Detection in a Droplet Actuator," published on Aug. 21, 2008, the entire disclosure of which is incorporated herein by reference. Generally speaking, the sensing or imaging techniques may be used to confirm the presence or absence of a droplet at a specific electrode. For example, the presence of a dispensed droplet at the destination electrode following a droplet dispensing operation confirms that the droplet dispensing operation was effective. Similarly, the presence of a droplet at a detection spot at an appropriate step in an assay protocol may confirm that a previous set of droplet operations has successfully produced a droplet for detection. Droplet transport time can be quite fast. For example, in various embodiments, transport of a droplet from one electrode to the next may exceed about 1 sec, or about 0.1 sec, or about 0.01 sec, or about 0.001 sec. In one embodiment, the electrode is operated in AC mode but is switched to DC mode for imaging. It is helpful for conducting droplet operations for the footprint area of droplet to be similar to electrowetting area; in other words, 1×-, 2×-3×-droplets are usefully controlled operated using 1, 2, and 3 electrodes, respectively. If the droplet footprint is greater than the number of electrodes available for conducting a droplet operation at a given time, the difference between the droplet size and the number of electrodes should typically not be greater than 1; in other words, a 2× droplet is usefully controlled using 1 electrode and a 3× droplet is usefully controlled using 2 electrodes. When droplets include beads, it is useful for droplet size to be equal to the number of electrodes controlling the droplet, e.g., transporting the droplet.

"Filler fluid" means a fluid associated with a droplet operations substrate of a droplet actuator, which fluid is sufficiently immiscible with a droplet phase to render the droplet phase subject to electrode-mediated droplet operations. For example, the gap of a droplet actuator may be filled with a filler fluid. The filler fluid may, for example, be a low-viscosity oil, such as silicone oil or an alkane filler fluid, such as hexadecane filler fluid. The filler fluid may fill the entire gap of the droplet actuator or may coat one or more surfaces of the droplet actuator. Filler fluids may be conductive or non-conductive. Filler fluids may, for example, be doped with surfactants or other additives. For example, additives may be selected to improve droplet operations and/or reduce loss of reagent or target substances from droplets, formation of microdroplets, cross contamination between droplets, contamination of droplet actuator surfaces, degradation of droplet actuator materials, etc. Composition of the filler fluid, including surfactant doping, may be selected for performance with reagents used in the specific assay protocols and effective interaction or non-interaction with droplet actuator materials. Examples of filler fluids and filler fluid formulations suitable for use with the invention are provided in Srinivasan et al, International Patent Pub. Nos. WO/2010/027894, entitled "Droplet Actuators, Modified Fluids and Methods," published on Mar. 11, 2010, and WO/2009/021173, entitled "Use of Additives for Enhancing Droplet Operations," published on Feb. 12, 2009; Sista et al., International Patent Pub. No. WO/2008/098236, entitled "Droplet Actuator Devices and Methods Employing Magnetic Beads," published on Aug. 14, 2008; and Monroe et al., U.S. Patent Publication No. 20080283414, entitled "Electrowetting Devices," filed on May 17, 2007; the entire disclosures of which are incorporated herein by reference, as well as the other patents and patent applications cited herein.

"Immobilize" with respect to magnetically responsive beads, means that the beads are substantially restrained in position in a droplet or in filler fluid on a droplet actuator. For example, in one embodiment, immobilized beads are sufficiently restrained in position in a droplet to permit execution of a droplet splitting operation, yielding one droplet with substantially all of the beads and one droplet substantially lacking in the beads.

"Magnetically responsive" means responsive to a magnetic field. "Magnetically responsive beads" include or are composed of magnetically responsive materials. Examples of magnetically responsive materials include paramagnetic materials, ferromagnetic materials, ferrimagnetic materials, and metamagnetic materials. Examples of suitable paramagnetic materials include iron, nickel, and cobalt, as well as metal oxides, such as $Fe_3O_4$, $BaFe_{12}O_{19}$, $CoO$, $NiO$, $Mn_2O_3$, $Cr_2O_3$, and $CoMnP$.

"Washing" with respect to washing a bead means reducing the amount and/or concentration of one or more substances in contact with the bead or exposed to the bead from a droplet in contact with the bead. The reduction in the amount and/or concentration of the substance may be partial, substantially complete, or even complete. The substance may be any of a wide variety of substances; examples include target substances for further analysis, and unwanted substances, such as components of a sample, contaminants, and/or excess reagent. In some embodiments, a washing operation begins with a starting droplet in contact with a magnetically responsive bead, where the droplet includes an initial amount and initial concentration of a substance. The washing operation may proceed using a variety of droplet operations. The washing operation may yield a droplet including the magnetically responsive bead, where the droplet has a total amount and/or concentration of the substance which is less than the initial amount and/or concentration of the substance. Examples of suitable washing techniques are described in Pamula et al., U.S. Pat. No. 7,439,014, entitled "Droplet-Based Surface Modification and Washing," granted on Oct. 21, 2008, the entire disclosure of which is incorporated herein by reference.

The terms "top," "bottom," "over," "under," and "on" are used throughout the description with reference to the relative positions of components of the droplet actuator, such as relative positions of top and bottom substrates of the droplet actuator. It will be appreciated that the droplet actuator is functional regardless of its orientation in space.

When a liquid in any form (e.g., a droplet or a continuous body, whether moving or stationary) is described as being "on", "at", or "over" an electrode, array, matrix or surface, such liquid could be either in direct contact with the electrode/array/matrix/surface, or could be in contact with one or more layers or films that are interposed between the liquid and the electrode/array/matrix/surface.

When a droplet is described as being "on" or "loaded on" a droplet actuator, it should be understood that the droplet is arranged on the droplet actuator in a manner which facilitates using the droplet actuator to conduct one or more droplet operations on the droplet, the droplet is arranged on the droplet actuator in a manner which facilitates sensing of a property of or a signal from the droplet, and/or the droplet has been subjected to a droplet operation on the droplet actuator.

7 BRIEF DESCRIPTION OF THE DRAWINGS

FIGS. 16A through 16G show screenshots of an example of an experiment designed to evaluate the effect of cyclodextrins, pH and ionic strength on aqueous containment of 4-MU;

FIGS. 17A and 17B show data tables of fluorescence readings for forward transfer and backward transfer, respectively, of the 4-MU partitioning assay of Tables 5 and 6;

FIGS. 18A and 18B show data tables of another example of a 4-MU partitioning assay;

FIG. 19 shows a data table of relative fluorescence readings for backward transfer partitioning (backward extraction; BE) of a 4-MU partitioning assay used to evaluate the effect of aqueous phase surfactants on 4-MU containment;

Figure 1:
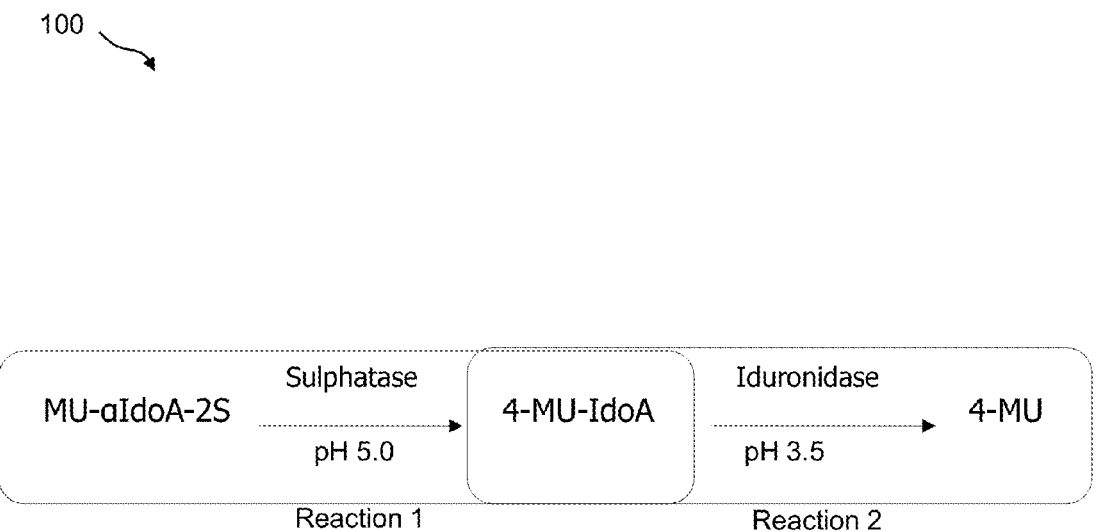
FIG. 1 shows a flow diagram of an enzymatic assay protocol for Hunter's syndrome.

FIG. 35 A-H illustrates examples of individual 4-HMU analog structures.

FIG. 36 A-H illustrates examples of individual 6-HMU analog structures.

8 DESCRIPTION

The invention provides droplet actuator devices and methods of conducting testing. For example, the methods of testing include methods of testing samples for activity of certain enzymes. In one embodiment, the enzymes tested are enzymes associated with metabolic disorders. The testing may be associated with screening programs (e.g., screening newborn infants for metabolic disorders), diagnostics, monitoring, screening of modified enzymes, or for any other useful purpose.

The invention includes methods and devices for conducting multiple assays for different metabolic disorders on a single droplet actuator, as well as multiple assays for the same metabolic disorder using samples from different subjects and/or multiple samples from the same subject on a single droplet actuator.

The invention provides modified assays for detecting altered enzymatic activity. Among the enzyme assays which may be conducted according to the methods of the invention are those methods useful in the diagnosis of defects in glycosidases, such as lysosomal storage diseases. Enzymatic indicators of lysosomal storage diseases can be identified using droplet based assays on a droplet actuator. Assays of the appropriate glycosidase activity can be used to detect altered activity of a particular glycosidase, which may be an indicator of a particular lysosomal storage disease. A deficiency in .alpha.-glucosidase activity, for example, is a diagnostic indicator of Pompe disease. Similarly, a deficiency in .alpha.-galactosidase activity is a diagnostic indicator of Fabry disease. Multiple diseases and/or multiple samples can be tested simultaneously on a single droplet actuator.

In some embodiments, the invention provides diagnostic techniques for metabolic disorders that result from defects in lysosomal function. Examples include, without limitation: activator deficiency/GM2 gangliosidosis; alpha-mannosidosis; aspartylglucosaminuria; cholesteryl ester storage disease; chronic hexosaminidase a deficiency; cystinosis; Danon disease; Fabry disease; Farber disease; fucosidosis; galactosialidosis; Gaucher disease (Type I, Type II, Type III); GM1 gangliosidosis (infantile, late infantile/juvenile, adult/chronic); I-cell disease/mucolipidosis II; infantile free sialic acid storage disease/ISSD; juvenile hexosaminidase A deficiency; Krabbe disease (infantile onset, late onset); metachromatic leukodystrophy; mucopolysaccharidoses disorders (pseudo-hurler polydystrophy/mucolipidosis IIIA, PSI Hurler syndrome, MPSI Scheie syndrome, MPS I Hurler-Scheie syndrome, MPS II Hunter syndrome, Sanfilippo syndrome Type A/MPS III A, Sanfilippo syndrome Type B/MPS III B, Sanfilippo syndrome Type C/MPS III C, Sanfilippo syndrome Type D/MPS III D, Morquio type A/MPS IVA, morquio Type B/MPS IVB, MPS IX hyaluronidase deficiency, MPS VI Maroteaux-Lamy, MPS VII Sly syndrome, mucolipidosis I/Sialidosis, mucolipidosis IIIC, mucolipidosis type IV); Maroteaux-Lamy; multiple sulfatase deficiency; Niemann-Pick disease (Type A, Type B, Type C); Neuronal ceroid lipofuscinoses (CLN6 disease—Atypical late infantile, late onset variant, early juvenile, Batten-Spielmeyer-Vogt/juvenile NCL/CLN3 disease, Finnish variant late infantile CLN5, Jansky-Bielschowsky disease/late infantile CLN2/TPP1 disease, Kufs/adult-onset NCL/CLN4 disease, northern epilepsy/variant late infantile CLN8, Santavuori-Haltia/infantile CLN1/PPT disease, beta-mannosidosis); Pompe disease/glycogen storage disease type II; Pycnodysostosis; Sandhoff disease/GM2 gangliosidosis (Adult Onset, Infantile, Juvenile); Schindler disease; Salla disease/sialic acid storage disease; Tay-Sachs/GM2 gangliosidosis; and Wolman disease. Various enzyme-related conditions, including without limitation lysosomal storage diseases, are described in the Merck Manual, 18 ed., Apr. 7, 2006, the entire disclosure of which is incorporated herein by reference.

In one embodiment, the invention provides assay methods for detection of MSP II (Hunter's syndrome) on a droplet actuator. The methods include, among other things, droplet-based enzymatic assays for iduronate-2-sulfate sulphatase (IDS) enzyme activity. In certain embodiments, the Hunter's assay may be performed at room temperature or at an alternate temperature, such as 37° C. In other embodiments the Hunter's assay may be performed for 8 hours or less. The Hunter's assay is a single-step homogenous assay that is performed at a single pH (i.e., pH 5.0) with a time to result of 8 hours or less.

In an embodiment the invention provides assay methods for detection of one or more diseases related to insufficient quantity or activity of a specific enzyme or enzymes, such as Hunter's, Gaucher and Niemann-Pick diseases, Pompe and Fabry diseases, and Morquio B syndrome on a droplet actuator.

In yet another embodiment, the invention provides an integrated droplet actuator device and methods for performing multiplexed enzymatic assays and immunoassays on a single droplet actuator using a single dried blood spot (DBS) sample. In one example, the integrated droplet actuator device and methods of the invention may be used for one or more of congenital adrenal hyperplasia (CAH), congenital hypothyroidism (CH), cystic fibrosis (CF), galactosemia and biotinidase deficiency (BIOT).

It will be appreciated that while the methods of the invention are primarily directed at droplet-based testing using microfluidic devices or droplet actuators, the invention also provides novel chemistries that may be conducted using manual techniques, pipetting, robotics, or other devices or techniques.

The invention also provides techniques for conducting enzymatic screening in droplets associated with, surrounded by, or otherwise in contact with, an immiscible phase, such as an oil phase, such as a silicone oil phase. For example, the invention provides for the use of relatively lipophilic signal molecules, such as 4-MU and its analogs, in solution with molecules that associate with and increase retention of the signal molecules in the aqueous phase. Examples include cyclodextrins, cyclic peptides, cyclic oligonucleotides, crown ethers, cyclic polymers, and various conjugates and combinations of the foregoing. Suitable signal retaining molecules can be selected by screening for molecules that result in greater retention of signal in their presence than in their absence.

The invention also provides novel substrates for conducting enzymatic assays that exhibit improved aqueous solubility. Such molecules are particularly useful in conducting enzymatic screening in droplets surrounded by or in contact with an immiscible phase, such as an oil phase, such as a silicone oil phase, because less signal is lost to the oil phase. Examples of modified substrates described herein are 4-MU and HMU molecules modified to add moieties that improve their aqueous solubility without significantly diminishing their fluorescence or eliminating their suitability as an enzyme substrate. Preferred modified substrates are those which retain sufficient fluorescence and exhibit sufficient water solubility to provide greater signal under the same assay conditions relative to the corresponding 4-MU or HMU substrates, in particular where the assay is conducted in a droplet surrounded by or in contact with, an immiscible phase, such as an oil phase, such as a silicone oil phase.

8.1 Enzymatic Assay for Hunter's Syndrome

The invention provides a two-step enzymatic assay. The assay may be performed in a standard laboratory setting. In one embodiment it may have about a 24 hour turn-around time. In another embodiment it may have a turn-around time of less than or about 12 hours. In yet another embodiment it may have a turn-around time of less than or about 6 hours. Blood samples are obtained from a subject and spotted onto a solid medium such as filter paper, dried and sent to a central laboratory. Because the blood samples are spotted onto a solid medium and dried, they must be reconstituted before analysis, a step that requires dilution of the sample into a suitable liquid medium. There is a need for an improved Hunter's assay that provides for a rapid, single-step protocol that may be used on fresh and/or dried blood samples (i.e., whole blood samples, plasma samples). Hunter's syndrome is caused by a reduction (or absence) of the enzyme iduronate-2-sulfate sulphatase (IDS). FIG. 1 shows a flow diagram of an enzymatic assay protocol 100 for Hunter's syndrome. The assay may be performed using a microtiter-plate based assay and microtiter plate reader (e.g., Biotek KC4 plate reader). The assay for Hunter's syndrome uses 4-methylumbelliferyl-α-L-iduronide-2-sulfate (MU-αIdoA-2S) as a substrate. The assay is a two enzyme, two step assay where IDS first acts on the MU-αIdoA-2S substrate fluid to hydrolyze the sulfates yielding a 4-MU-IdoA intermediate (Reaction 1). A secondary enzyme α-L-iduronidase acts on the sulfate free intermediate (4-MU-IdoA) to release the 4-methylumbelliferone (4-MU), generating a fluorescent signal (Reaction 2). In the absence of active IDS, the 4-MU-IdoA intermediate is not formed and no fluorescent signal is produced. Reactions 1 and 2 are performed at different pHs, pH 5.0 and pH 3.5, respectively.

The α-L-iduronidase (or any active iduronidase) may, for example, be partially purified from bovine testis or rabbit liver and may introduce significant concentrations of contaminating sulphatases into the reaction. To inactivate contaminating sulphatases in the L-iduronidase extracts, a bolus of phosphate/citric acid buffer (McIlvain's buffer) is added to the reaction prior to the second enzymatic reaction. Purified or synthetically produced α-L-iduronidase or analogues or derivatives with similar activity may be used as alternatives to purified α-L-iduronidase.

In one example, the assay protocol includes the following steps:
1. A 5× diluted plasma sample (10 μL) is incubated with 20 μL of 1.25 mM MU-αIdoA-2S (0.1M Na acetate, 0.1M acetic acid buffer, pH 5.0 containing 10 mM Pb-Acetate) at 37° C. for 4 h (Reaction 1);
2. Add 20 μL McIlvains' phosphate/citric acid buffer (Pi/Ci buffer) to all samples (including substrate blank) and mix (Pi/Ci buffer is added to all samples to quench the activity of all sulphatases in the sample and in the added LEBT solution (step 3));
3. Add 10 μL LEBT solution, pH 3.5 (partially purified lysosomal extract bovine testis) to plasma samples and mix;
4. Incubate 24 h at 37° C. (Reaction 2); and Add 200 μL stop buffer (sodium carbonate pH 10.1, 0.01% Tween® 20 solution available from Promega Corporation, Madison, Wis.) to all samples and read fluorescence of 4-MU.

4MU fluid substrates may be replaced or supplemented with 4-trifluoromethylumbelliferyl substrates. For example, 4-trifluoromethylumbelliferyl glycosides may be used as substrates for the assay of LSD hydrolyases (sulfatases, etc.). The 4-trifluoromethylumbelliferone leaving group exhibits a greater signal and the signal is shifted more to the red when compared to 4-methylumbelliferone.

8.2 Enzyme Assay for Hunter's Syndrome on a Droplet Actuator

In another embodiment, the invention provides a droplet actuator-based assay for Hunter's syndrome. The assay may be a homogeneous assay that uses purified recombinant iduronidase. Because purified recombinant iduronidase is used, contaminating sulphatases from partially purified lysosomal iduronidase from bovine testis (i.e., LEBT solution) are not present and the addition of McIlvains' phosphate/citric acid buffer (Pi/Ci buffer) is not required. The Hunter's assay is adapted for pH, sample concentration and iduronidase enzyme activity. The substrate MU-αIdoA-2S and the recombinant iduronidase are added to the diluted plasma sample at the same time and incubated together for the entire reaction at, for example, 25° C. (room temperature). The droplet actuator-based Hunter's assay is a homogeneous, single step assay that is performed without requiring a substrate change in pH.

Sample droplets and reagent droplets for use in conducting the enzymatic assays may be dispensed and/or combined according to appropriate assay protocols using droplet operations on a droplet actuator. Incubation of assay droplets, including temperature adjustments as needed, may also be performed on a droplet actuator. Further, detection of signals from assay droplets, such as detection of fluorescence may be conducted while the droplet is present on the droplet actuator. Further, each of these processes may be conducted while the droplet is partially or completely surrounded by a filler fluid on the droplet actuator.

In some embodiments, certain assay steps may be conducted outside of a droplet actuator and certain assay steps may be conducted on a droplet actuator. For example, in some embodiments, sample and reagents may be prepared outside the droplet actuator and combined, incubated and detected on the droplet actuator.

8.2.1 Effect of Plasma Dilution

Anions, such as chloride, sulfate, and phosphate, inherently present in a plasma sample are inhibitors of sulphatase activity (e.g., iduronate-2-sulfate sulphatase (IDS)). For example, at 30 mM chloride, IDS activity is inhibited by 50% and at 250 mM chloride IDS activity is completely inhibited. A plasma sample may have a chloride concentration of 150 mM, a concentration that may reduce the signal output in a Hunter's assay. The amount of chloride present in a plasma sample may, for example, be reduced by dilution of the sample with a suitable liquid, such as water. Anions (e.g., chloride, sulfate, and phosphate) present in a plasma sample may also be reduced by precipitation with lead-acetate (Pb-acetate).

Figure 2:
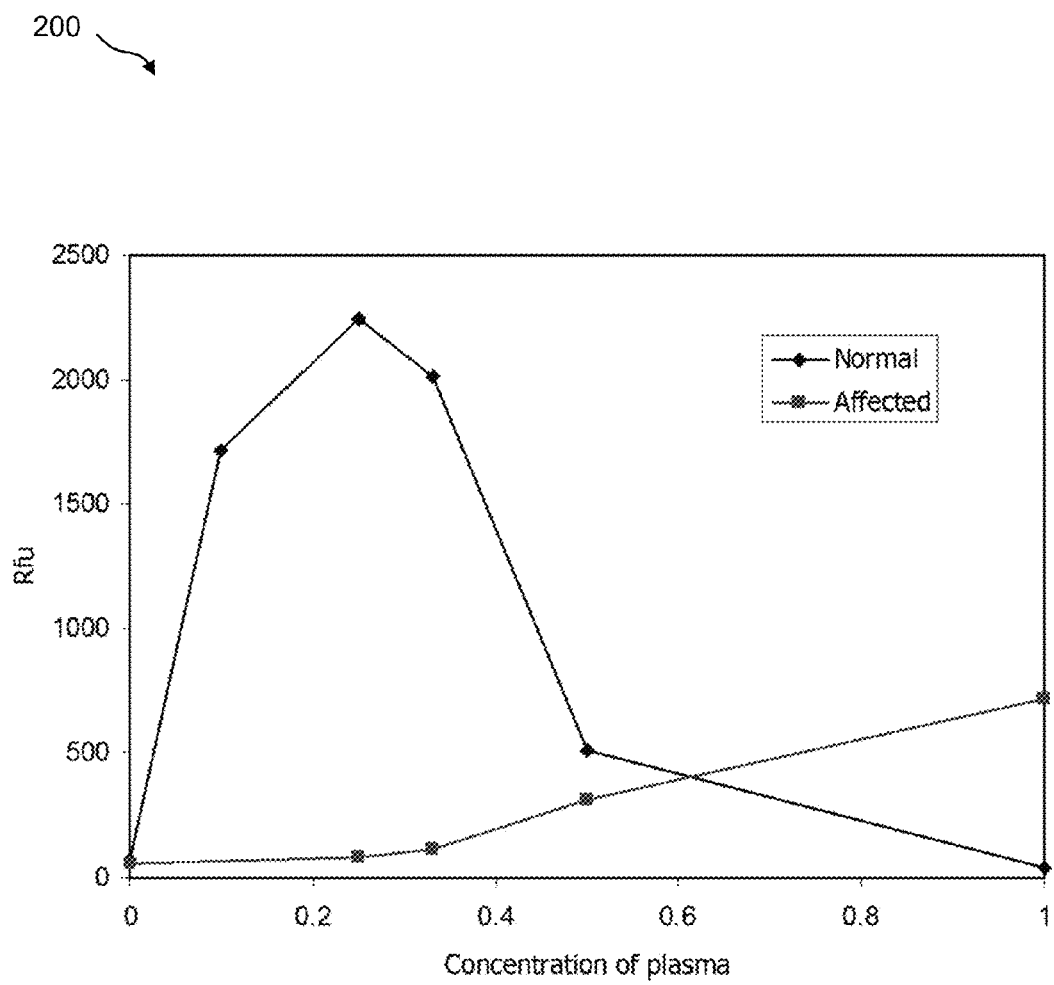
FIG. 2 shows a plot of the effect of plasma dilution on a modified Hunter's assay.

FIG. 2 shows a plot 200 of the effect of plasma dilution on a modified Hunter's assay. Reagent solutions were prepared on-bench, and the experiment was performed on a droplet actuator using a digital microfluidic protocol. Different dilutions (1/10×, 1/4×, 1/3×, 1/2× and 1×) of plasma samples from normal (n=1) and affected (n=1) subjects were prepared using molecular grade water. A blank sample was prepared using 1 µg/mL of recombinant iduronidase in 0.05 M Na-Acetate/0.05 M Acetic acid buffer pH 5.0. A working stock of 10 µg/mL recombinant iduronidase in 0.05 M Na-Acetate/0.05 M Acetic acid buffer pH 5.0 was prepared from a stock of 0.5 mg/mL iduronidase (supplied in 0.05 M Na-Acetate with 150 mM NaCl, 0.02% Brij-35 (w/v) pH 3.5). A working stock of 1.25 mM MU-αIdoA-S substrate fluid was prepared in 0.1 M Na-Acetate, 0.1M Acetic Acid buffer pH 5.0 containing 10 mM Pb-Acetate. A substrate fluid was prepared by mixing 1 µL of 10 µg/mL recombinant iduronidase and 9 µL of 1.25 mM MU-αIdoA-S.

In one example, the digital microfluidic protocol for testing plasma sample dilutions included the following steps:
1. Dispense eleven 1× droplets of the substrate fluid from a reagent reservoir onto 11 reaction lanes of a droplet actuator;
2. Dispense 1× droplets of plasma samples from the respective sample reservoirs;
3. Merge the plasma sample droplets with the substrate fluid droplets to yield 2× reaction droplets;
4. Split each 2× reaction droplet into two 1× reaction droplets;
5. Dispense 11 droplets of stop buffer (sodium carbonate pH 10.1, 0.01% Tween® 20) and merge them using droplet operations with the first set of 1× reaction droplets;
6. Detect fluorescence at 364 nm (t=0 h);
7. Incubate the second set of 1× reaction droplets for 8 h at room temperature;
8. After 8 h, dispense 11 droplets of stop buffer and combine them with the second set of 1× reaction droplets; and
9. Detect fluorescence at 364 nm (t=8 h).

Referring to FIG. 2, the maximum separation of fluorescence signal between the normal and affected plasma samples was observed at a dilution of 1:4. Because one droplet of plasma sample was mixed with one droplet of the substrate fluid, the final effective dilution of the plasma sample is 1:8. The chloride concentration at this dilution has a minimal impact on the iduraonate-2-sulfate sulphatase activity.

In various embodiments, the plasma blood sample is diluted from about 1:2 to about 1:15 plasma:buffer, or from any of about 1:2, 1:3, 1:4, 1:5, 1:6 or 1:7 to any of about 1:8, 1:9, 1:10, 1:11, 1:12, 1:13, 1:14 or 1:15 plasma:buffer. In other embodiments, the plasma blood sample is diluted to at least 1:2 plasma:buffer, to at least 1:3 plasma:buffer, to at least 1:4 plasma:buffer, to at least 1:5 plasma:buffer, to at least 1:6 plasma:buffer, to at least 1:7 plasma:buffer, to at least 1:8 plasma:buffer.

8.2.2 Concentration of Recombinant Iduronidase

Figure 3:
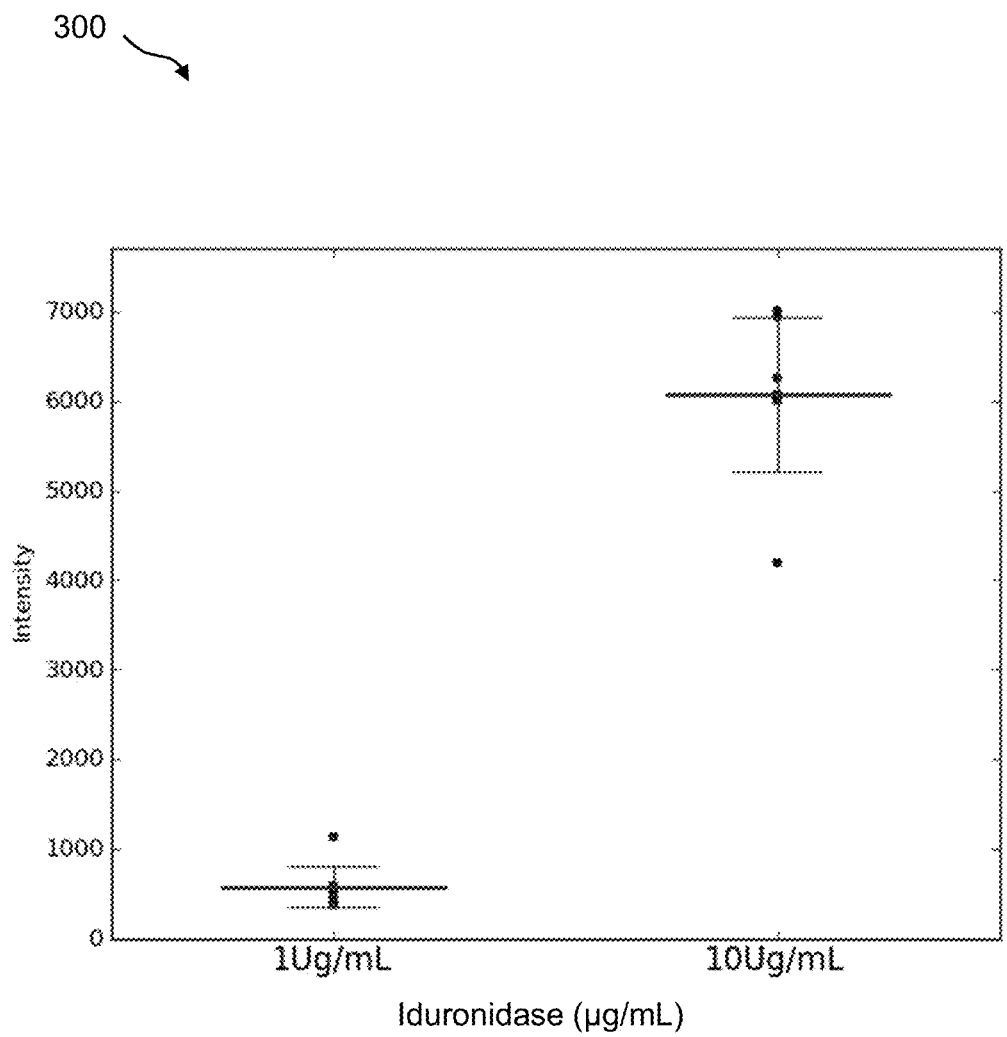
FIG. 3 shows a plot of the concentration dependence of recombinant iduronidase on the modified Hunter's assay.

FIG. 3 shows a plot 300 of the concentration dependence of recombinant iduronidase on the modified Hunter's assay. Eight different normal plasma samples were analyzed using two concentrations of recombinant iduronidase (i.e., 1 µg/mL and 10 µg/mL) in the modified Hunter's assay. The activity of the Hunter's assay shows a significant concentration dependence on the amount of recombinant iduronidase used (i.e., higher activity at 10 µg/mL). In plot 300, the thick solid line represents the mean of all the readings. In plot 300, the error bars represent the standard deviation among the readings. Because of the concentration dependence on the amount of recombinant iduronidase used in the modified Hunter's assay, an even higher concentration (>10 µg/mL) of recombinant iduronidase may be used.

8.2.3 Effect of Carrier Protein on Recombinant Iduronidase Activity

Reagent solutions were prepared outside a droplet actuator (i.e., on-bench) and the experiments were performed on a droplet actuator using a digital microfluidic protocol, such as the protocol of FIG. 2.

Figure 4A:
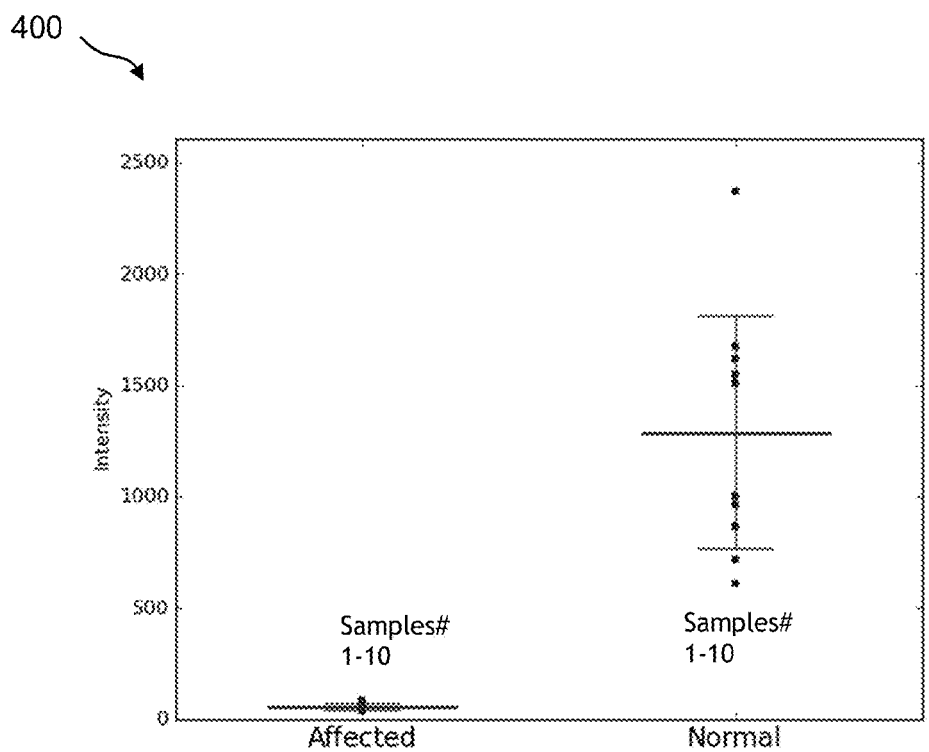
FIGS. 4A and 4B show plots of affected and normal plasma samples screened for MSPII using the modified Hunter's assay of FIG. 2.
Figure 4B:
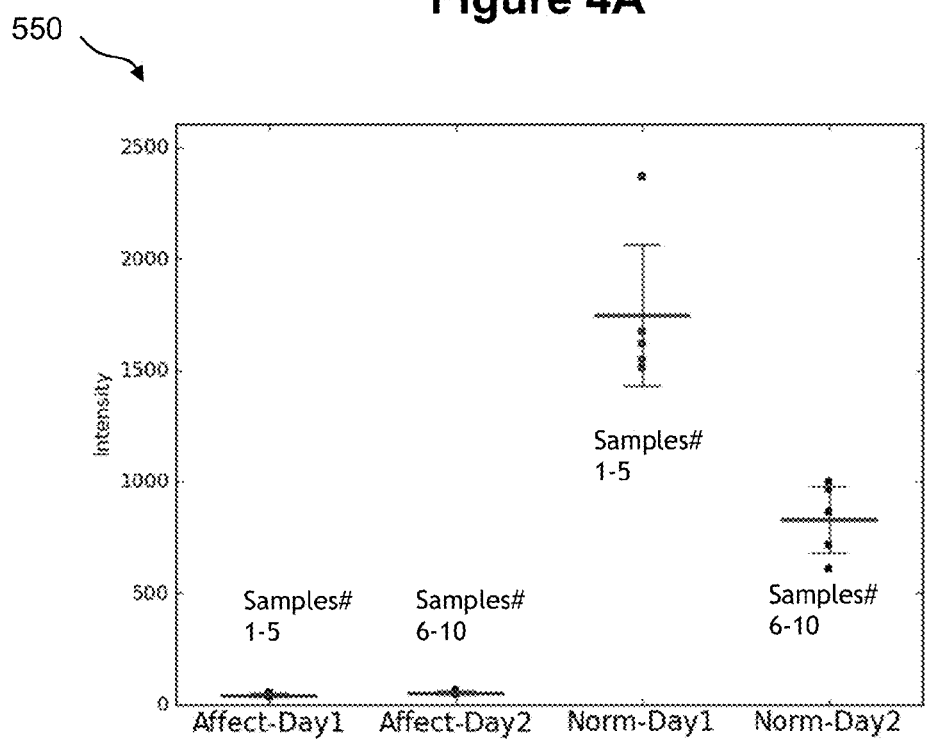

FIGS. 4A and 4B show plots 400 and 450 of affected and normal plasma samples screened for MSPII using the modified Hunter's assay of FIG. 2. Affected (n=10) and normal (n=10) plasma samples were diluted 1:4 and analyzed on two separate days on the same droplet actuator. Samples 1 through 5 of both affected and normal samples were analyzed on day 1. Samples 6 through 10 of both affected and normal samples were analyzed on day 2. Plot 400 of FIG. 4A shows the distribution of all 10 affected and 10 normal samples (i.e., days 1 and 2). Plot 450 of FIG. 4B shows the distribution of samples at day 1 (1-5 affected, 1-5 normal) and day 2 (6-10 affected, 6-10 normal). Referring to plot 450 of FIG. 4B, the signal for normal samples was decreased between days 1 and 2. The decrease in signal for normal plasma samples at day 2 may be due to loss of iduronidase activity with time. The thick solid line represents the mean of all the readings. The error bars represent the standard deviation among the readings.

The stability of recombinant iduronidase activity may be sufficiently increased by incorporation of a carrier protein, such as bovine serum albumin (BSA), into the substrate fluid.

Figure 5:
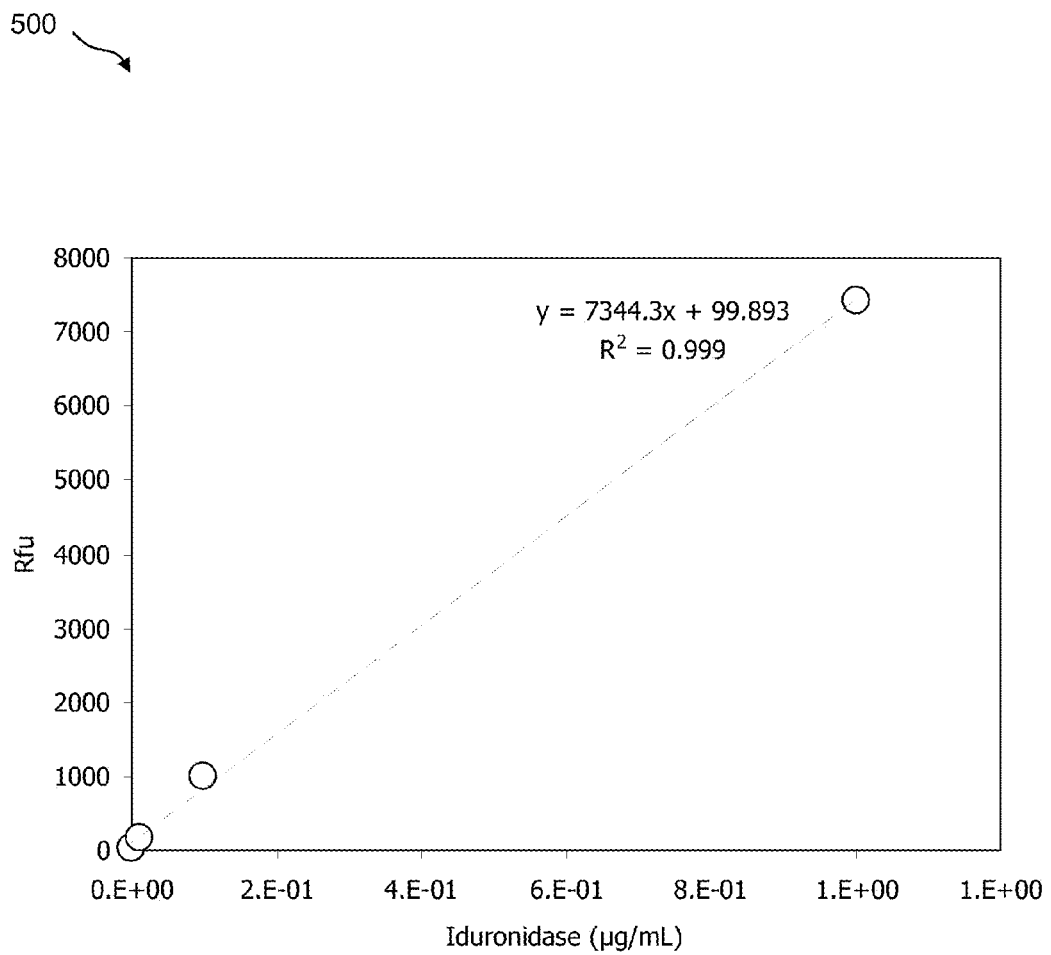
FIG. 5 shows a plot of a standard curve for recombinant iduronidase activity in the presence of BSA.

FIG. 5 shows a plot 500 of a standard curve for recombinant iduronidase activity in the presence of BSA. Serial dilutions of recombinant iduronidase were prepared in 0.05 M Na-Acetate/0.05 M Acetic acid buffer, pH 5.0 from a stock of 0.5 mg/mL recombinant iduronidase containing 1 mg/mL molecular biology grade bovine serum albumin (BSA). A substrate fluid was prepared in 0.05 M Na Acetate, pH 5.0 containing 1 mM 4-methylumbelliferyl-α-L-idopyranosiduronic acid (4-MUI) and 100 μM D-saccharic acid 1,4-lactone.

The digital microfluidic protocol for the iduronidase standard curve included the following steps:
1. Mix one 1× droplet of iduronidase and one 1× droplet of substrate fluid to yield a 2× reaction droplet;
2. Split the 2× reaction droplet into two 1× reaction droplets;
3. Dispense 11 droplets of stop buffer (sodium carbonate pH 10.1, 0.01% Tween® 20) and combine them with the first set of 1× reaction droplets;
4. Detect end point fluorescence at 365 nm (t=0);
5. Incubate the second set of 1× reaction droplets for 1 h at room temperature;
6. After 1 h of incubation, dispense 11 droplets of stop buffer and combine with the reaction droplets; and
7. Detect end point fluorescence at 365 nm (t=1 h).

Table 1 shows the relative fluorescence of the iduronidase standard curve at t=1 h incubation after the addition of stop buffer.

TABLE 1

Relative fluorescence at t = 1 hrs incubation

| Idu (μg/mL) | Rfu |
|---|---|
| 0 | 17.99915 |
| 0.001 | 34.6948 |
| 0.01 | 179.1927 |
| 0.1 | 999.3997 |
| 1 | 7427.665 |

Figure 6A:
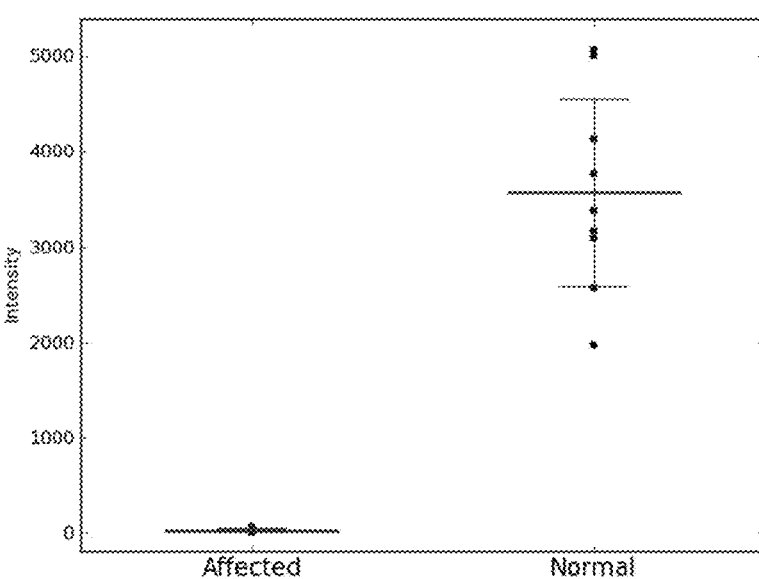
FIGS. 6A and 6B show plots of a Hunter's assay using recombinant iduronidase formulated with BSA.
Figure 6B:
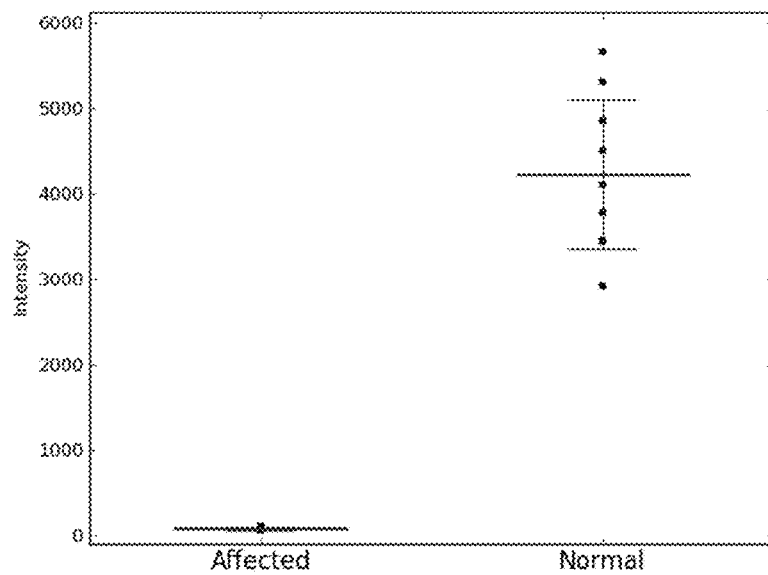

FIGS. 6A and 6B show plots 600 and 650, respectively, of a Hunter's assay using recombinant iduronidase formulated with BSA. Plasma samples from normal (n=9; samples 2-10) and affected (n=9; samples 2-10) subjects were diluted 1:4 using molecular grade water. A blank sample was prepared using 1 μg/mL of recombinant iduronidase in 0.05 M Na-Acetate/0.05 M Acetic acid buffer pH 5.0. A working stock of 10 μg/mL recombinant iduronidase in 0.05 M Na-Acetate/0.05 M Acetic acid buffer pH 5.0 containing 1 mg/mL of molecular grade BSA was prepared from a stock of 0.5 mg/mL iduronidase (supplied in 0.05 M Na-Acetate with 150 mM NaCl, 0.02% Brij-33 (w/v) pH 3.5). A stock of 1.25 mM MU-IdoA-S substrate fluid was supplied in 0.1 M Na-Acetate, 0.1 M Acetic Acid buffer pH 5.0 containing 10 mM Pb-Acetate. A substrate fluid was prepared by mixing 1 μL of 10 μg/mL recombinant iduronidase and 9 μL of 1.25 mM MU-αIdoA-S. Final concentrations of recombinant iduronidase and MU-αIdoA-S in the reaction mixture in the droplet are 0.5 μg/mL and 0.5625 mM respectively.

Plasma samples (#2-10 normal and #2-10 Hunter) were analyzed on two different days. Referring to plot 600 of FIG. 6A, on day 1 a first aliquot of normal and Hunter patient samples were analyzed on a first droplet actuator and instrument. Referring to plot 650 of FIG. 6B, on day 2, a second aliquot of normal and Hunter patient samples were analyzed on a second droplet actuator and instrument. The assays on day 1 and day 2 were performed by different operators.

The digital microfluidic protocol for testing plasma samples included the following steps:
1. Dispense eleven 1× droplets of the substrate fluid from a reagent reservoir onto 11 reaction lanes of a droplet actuator;
2. Dispense 1× droplets of plasma samples from the respective sample reservoirs;
3. Merge the plasma sample droplets with the substrate fluid droplet to yield a 2× reaction droplet;
4. Split the 2× reaction droplet into two 1× reaction droplets;
5. Dispense 11 droplets of stop buffer (0.1 M sodium bicarbonate pH 10.1, 0.01% Tween® 20) and merge them using droplet operations with the first set of 1× reaction droplets;
6. Detect fluorescence at 365 nm (t=0 h);
7. Incubate the second set of 1× reaction droplets for 8 h at room temperature;
8. After 8 h, dispense 11 droplets of stop buffer and combine them with the 1× reaction droplets; and
9. Detect fluorescence at 365 nm (t=8 h).

Referring again to plot 600 of FIG. 6A and plot 650 of FIG. 6B, at an incubation time of t=8 h there is a significant separation in the fluorescence signal between a Hunter patient's plasma sample and a normal plasma sample. The fluorescence signals for normal samples analyzed on day 1 and day 2 are consistent indicating stability in the assay protocol. In plots 600 and 650 the thick solid line represents the mean of all the readings. In plots 600 and 650 the error bars represent the standard deviation among the readings. All data points for the Hunter affected samples overlapped one another.

Because there is about a 20-100 fold separation in the fluorescence signal between a Hunter patient's plasma sample and a normal plasma sample, the time to result and throughput of the modified Hunter's assay may be significantly increased further. In one embodiment, the overall incubation time for the assay may be significantly reduced to less than about 12, 8, 6, 4, or 2 hours. In another embodiment, the time to result of the Hunter assay may be reduced by performing the reaction at 37° C.

8.3 Hunter's Assay on DBS and DPS

Hunter's assays may be performed in a central laboratory on a dried blood spot (DBS) sample. To evaluate to efficacy of the droplet actuator-based Hunter assay on dried samples, plasma samples, fresh blood and plasma from fresh blood were spotted on ⅛" diameter filter paper and air dried.

Frozen plasma samples (n=10 affected and n=10 normal) were thawed and 1.4 μL of the sample was spotted onto filter paper and air dried for about 3 hours. Each DBS was placed in a separate centrifuge tube and stored at −20° C.

Fresh whole blood was collected in a lithium heparin tube. Whole blood (3.1 μL) was spotted onto filter paper and air dried for about 3 hours. Plasma was prepared from the blood sample by centrifugation and spotted onto filter paper and air dried for about 3 hours. Each DBS and DPS was placed in a separate centrifuge tube.

Samples were extracted from the filter paper using water containing extraction buffer, which may include a surfactant, such as 0.1% Tween® 20. Dried plasma spots from frozen plasma samples (n=10 affected and n=10 normal) and plasma obtained from fresh blood samples were extracted in 40 μL and 100 μL water containing 0.1% Tween® 20. DBS prepared from fresh blood were extracted in 100 μL and 150 μL water containing 0.1% Tween® 20. All samples were incubated for 30 minutes with agitation. The tubes were centrifuged to deposit the filter paper at the bottom of the tube and the sample extracts were transferred into sample reservoirs on a droplet actuator. All the extracts were assayed for MPS II (Hunter's syndrome) along with fresh plasma obtained from whole blood. The digital microfluidic protocol for testing DBS and DPS samples was as described in reference to FIGS. 6A and 6B. The data is shown in Table 2.

TABLE 2

Hunter Assay on DPS and DBS

| # | Sample | t = 0 | t = 8 hrs | Difference |
|---|---|---|---|---|
| 1 | Blank | 58 | 89 | 31 |
| 2 | Hunter Affected#10 DPS extracted in 40 μL | 58 | 178 | 119 |
| 3 | Hunter Affected#10 DPS extracted in 100 μL | 59 | 103 | 44 |
| 4 | Hunter Normal#10 DPS extracted in 40 μL | 58 | 303 | 244 |
| 5 | Hunter Normal#10 DPS extracted in 100 μL | 56 | 341 | 284 |
| 6 | Fresh DPS extracted in 40 μL | 52 | 1938 | 1886 |
| 7 | Fresh DPS extracted in 100 μL | 53 | 704 | 650 |
| 8 | Fresh DBS extracted in 100 μL | 49 | 744 | 694 |
| 9 | Fresh DBS extracted in 150 μL | 51 | 739 | 688 |
| 10 | Fresh Plasma diluted ¼x | 56 | 6023 | 5967 |
| 11 | Fresh Plasma diluted ¼x | 56 | 8471 | 8415 |

The data from Table 2 clearly shows that there is separation between a Hunter patient DPS and a normal DPS. The extracts from DPS and DBS prepared from fresh whole blood gave similar fluorescence values using 100 μL extraction volumes. Assay on fresh plasma prepared from whole blood and diluted 1:4 using water was used as a positive control. The fluorescence signal obtained from fresh plasma was within the range as the fluorescence signals obtained from plasma samples in FIGS. 6A and 6B.

8.3.1 Effect of Temperature on Hunter Assay

To examine the effect of temperature on the Hunter assay, the assay (referring to the protocol of FIGS. 6A and 6B) was performed at 37° C. with an incubation time of 8 hours. Plasma samples were diluted 1:4 as described in reference to FIGS. 6A and 6B. Archived DBS samples were extracted in 150 μL of water containing 0.1% Tween® 20 as described in reference to Table 2. The data is shown in Table 3. A clear separation in fluorescence signal is observed between Hunter affected plasma samples and normal plasma samples. The fluorescence signal from archived DBS are also increased compared to Hunter affected samples and are comparable to the signal from fresh DBS.

TABLE 3

Effect of Temperature On Hunter Assay

| | |
|---|---|
| Blank | 31 |
| Hunter Affected Plasma sample#2 diluted ¼x | 45 |
| Hunter Affected Plasma sample#3 diluted ¼x | 34 |
| Hunter Affected Plasma sample#4 diluted ¼x | 108 |
| Hunter Normal Plasma sample#2 diluted ¼x | 2136 |
| Hunter Normal Plasma sample#3 diluted ¼x | 3761 |
| Hunter Normal Plasma sample#4 diluted ¼x | 6878 |
| Archived DBS (1230N) extracted in 150 μL | 1084 |
| Archived DBS (1240N) extracted in 150 μL | 570 |
| Archived DBS (1299N) extracted in 150 μL | 481 |
| Fresh DBS extracted in 150 μL | 658 |

8.3.2 Effect of Extraction Volume on Hunter Assay Using Dried Blood Spot Extracts To examine the effect of extraction volume on the Hunter assay, archived normal DBS (1264N, 1265N) and fresh normal DBS were extracted in 50, 100, or 150 μL of water containing 0.1% Tween® 20. The samples were analyzed on a droplet actuator using a digital microfluidic protocol, such as the protocol of FIGS. 6A and 6B.

Figure 7:
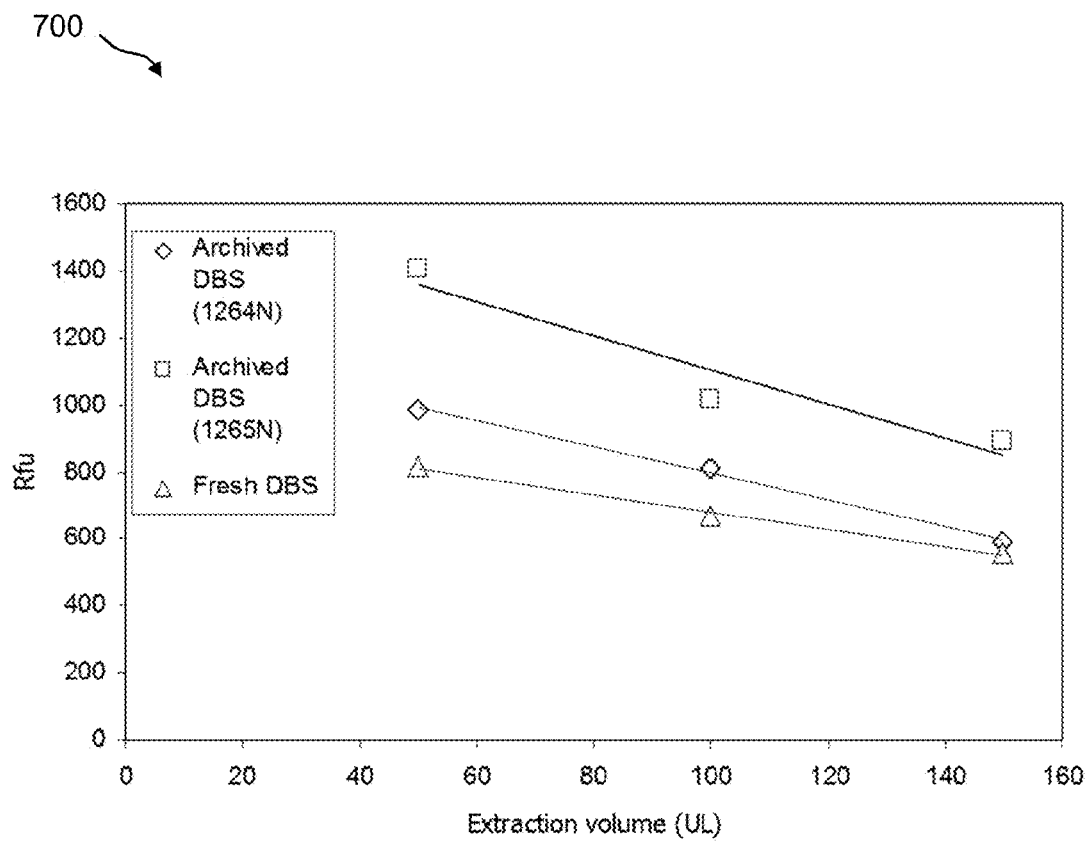
FIG. 7 shows a plot of the effect of extraction volume on Hunter's assay using DBS extracts.

FIG. 7 shows a plot 700 of the effect of extraction volume on Hunter assay using DBS extracts. The data is shown in Table 4. The data show that as the extraction volume is decreased (i.e., from 150 to 50 μL) the relative fluorescence signal of the sample increases. The increase in signal intensity may be due to an increase in the concentration of iduronate-2-sulfate sulphatase (IDS) in the samples at lower extraction volumes. In a preferred embodiment, about 100 μL extraction volume may be used to prepare DBS extracts.

TABLE 4

Effect of DBS Extraction Volume on Hunter Assay

| Volume (μL) | 1264N | 1265N | Fresh DBS |
|---|---|---|---|
| 150 | 590 | 892 | 553 |
| 100 | 807 | 1018 | 668 |
| 50 | 988 | 1403 | 815 |

8.4 Enzyme Assays for Gaucher and Niemann-Pick Diseases

The invention provides assay methods for detection of Gaucher and Niemann-Pick diseases on a droplet actuator. Gaucher's disease and Niemann-Pick's disease are caused by deficient activity of the lysosomal enzymes acid β-D-glucosidase and acid sphingomyelinase, respectively. In one embodiment, the invention provides methods for a droplet-based enzymatic assay for acid β-D-glucosidase activity. For example, a multrifluoroethylumbelliferyl-β-D-glucoside, such as a 4-pentafluoroethylumbelliferyl-β-D-glucoside, may be used as a substrate fluid in a droplet-based enzymatic assay for acid β-D-glucosidase enzyme activity. The increased number of fluorines makes the substrate fluid more labile to hydrolysis. The excitation/emission wavelengths for 4-pentafluoroethylumbelliferyl-β-D-glucoside are 385/495 nm. When testing for Gaucher's disease in a droplet actuator, the enzymatic activity may, for example, be as much as eight-fold greater when using the 4-pentafluoroethylumbelliferyl-B-D-glucoside substrate fluid compared with using the 4-methylumbelliferyl-β-D-glucoside substrate fluid.

4MU fluid substrates may be replaced or supplemented with 4-trifluoromethylumbelliferyl substrates. For example, 4-trifluoromethylumbelliferyl glycosides may be used as substrates for the assay of LSD hydrolyases (glycosidases, etc.). The 4-trifluoromethylumbelliferone leaving group exhibits a greater signal and the signal is shifted more to the red when compared to 4-methylumbelliferone. In addition, the 4-trifluoromethylumbelliferyl glycosides may be cleaved more readily than the 4-methylumbelliferyl glycosides leading to a larger signal.

In another embodiment, the invention provides methods for droplet-based enzymatic assays for chitotriosidase activity. Chitotriosidase is significantly increased in the plasma of patients with certain conditions, such as Gaucher's disease. In one example, chitotriosidase activity may be used as a surrogate plasma marker for a condition in which chitotriosidase activity is altered, such as Gaucher's disease. In another example, chitotriosidase activity may be used as a surrogate plasma marker for Niemann-Pick's disease. The substrate fluid for chitotriosidase in an enzymatic assay may, for example, be the fluorogenic substrate 4-trifluoromethylumbelliferylchitroside. The sample for the enzymatic assay may, for example, be a plasma droplet or a dried blood extract droplet. Because chitotriosidase is increased in the plasma of patients with Gaucher and Niemann-Pick diseases, there may be a significant separation in the fluorescence signal between a patient's plasma sample and a normal plasma sample. The use of chitotriosidase in may also reduce the number of tests that need to be performed in a testing panel for lysosomal storage diseases.

An example of a testing assay for chitotriosidase activity may involve, but is not limited to, the following: A sample droplet (e.g., a dried blood extract droplet) is combined using droplet operations with a substrate droplet (e.g., fluorogenic substrate 4-trifluoromethylumbelliferylchitroside) droplet to form a 2× droplet. The 2× droplet is split using droplet operations to form two 1× reaction droplets. One 1× reaction droplet is combined using droplet operations with a stop buffer droplet. Fluorescence of the combined droplet is measured (t–0 hrs). The second 1× reaction droplet is incubated for a predetermined time and then the reaction droplet is combined with a stop buffer droplet. End point fluorescence is measured (t–END hrs). In this example, a single sample droplet is dispensed and analyzed. However, any number of sample droplets may be dispensed and analyzed.

In another embodiment, droplet-based enzymatic assays for chitotriosidase activity may be combined with other droplet-based enzymatic assays in a panel of tests used for a testing panel for lysosomal storage diseases.

Other embodiments may make use of the modified umbelliferyl substrates described herein.

8.5 Enzyme Assay for Morquio B Syndrome

The invention provides assay methods for detection of the lysosomal storage disorder Morquio B syndrome (mucopolysaccharidosis IV) on a droplet actuator. Morquio B syndrome is caused by deficient activity of the lysosomal enzyme β-galactosidase. The substrate fluid for β-galactosidase in an enzymatic assay may, for example, be the fluorogenic substrate 4-methylumbelliferyl-β-galactose (4-MU-β-galactose; excitation 360 nm, emission 460 nm). The sample for the enzymatic assay may, for example, be a plasma droplet or a dried blood extract droplet. Because β-galactosidase is deficient in patients with Morquio B syndrome, there may be a significant separation in the fluorescence signal between a patient's blood sample and a normal blood sample. A second enzyme that may be present in a blood sample, β-galactocerebrosidase, may also cleave the 4-MU-β-galactose substrate. However, levels of β-galactocerebrosidase are significantly lower (e.g., about 200× lower) than levels of β-galactosidase.

On-bench assays for β-galactosidase activity in a blood sample may be adapted and described as discrete droplet-based protocols. One example of an on-bench assay for β-galactosidase activity includes the following steps:

1. A 250 mM stock solution of substrate (4-MU-β-galactose) was diluted 10× in buffer (0.1 M citrate/0.2 M phosphate pH 4.6);
2. Add 4 µL 10× diluted substrate to 196 µL of buffer (0.1 M citrate/0.2 M phosphate pH 4.6); Make a 25 mM stock in DMSO. Final concentration: 0.5 mM.
3. Add 10 µL of the substrate to 10 µL of dried blood extract and incubate at 37° C. for 21 hrs; and
4. Measure fluorescence at 360/460 nm at a gain of 50.

An example of a digital microfluidic testing assay for β-galactosidase activity may include, but is not limited to, the following: A sample droplet (e.g., a dried blood extract droplet) is combined and mixed using droplet operations with a Morquio B reagent (e.g., 4-MU-B-galactose) droplet to form a 2× reaction droplet. The 2× reaction droplet is split using droplet operations to form two 1× reaction droplets. One 1× reaction droplet is combined using droplet operations with a stop buffer droplet. Fluorescence of the combined droplet is measured (t–0 hrs). The second 1× reaction droplet is incubated at a certain temperature (e.g., 37° C.) for a predetermined time and then the reaction droplet is combined with a stop buffer droplet. End point fluorescence is measured (t–END hrs). In this example, a single sample droplet is dispensed and analyzed. However, any number of sample droplets may be dispensed and analyzed. B-galactosidase activity is calculated from the difference of t–0 hrs from t–END hrs.

In another embodiment, droplet-based enzymatic assays for β-galactosidase activity may be combined with other droplet-based enzymatic assays in a panel of tests used for a testing panel for lysosomal storage diseases.

Other embodiments may make use of the modified umbelliferyl substrates described herein.

8.6 Multiplexed Enzyme Assays on a Droplet Actuator

Figure 8:
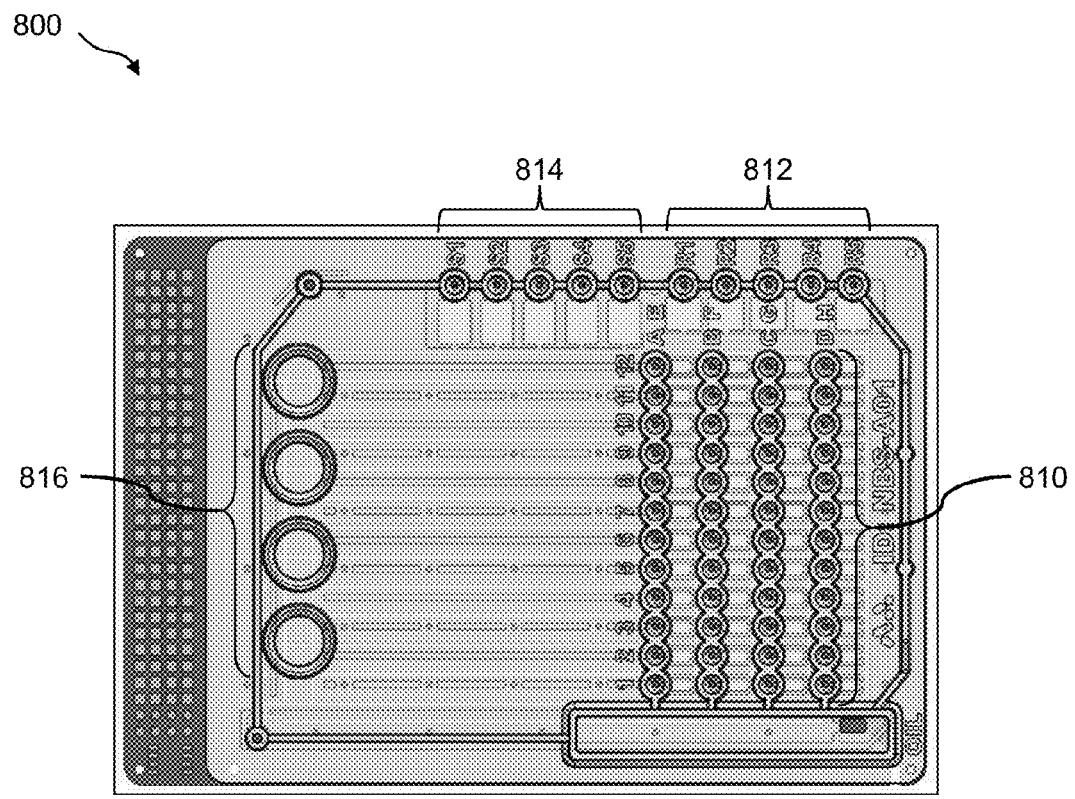
FIG. 8 illustrates a top view of an example of a droplet actuator that is suitable for use in conducting multiplexed enzymatic assays in a newborn testing protocol.

FIG. 8 illustrates a top view of an example of a droplet actuator 800 that is suitable for use in conducting multiplexed enzymatic assays in a newborn testing protocol. Droplet actuator 800 includes multiple dispensing reservoirs, which may, for example, be allocated as sample dispensing reservoirs 810 (e.g., 48 sample dispensing reservoirs 810) for dispensing sample fluids (e.g., dried blood spot extracts); one or more reagent dispensing reservoirs 812 for dispensing different reagent fluids; one or more substrate fluid dispensing reservoirs 814 for dispensing substrate fluids; and one or more waste collection reservoirs 816 for receiving waste droplets. Droplet actuator 800 is configured to perform 5-plex enzymatic assays on each sample, i.e., 5 enzymatic assays on each of 48 samples for a total of 240 assays.

Figure 9:
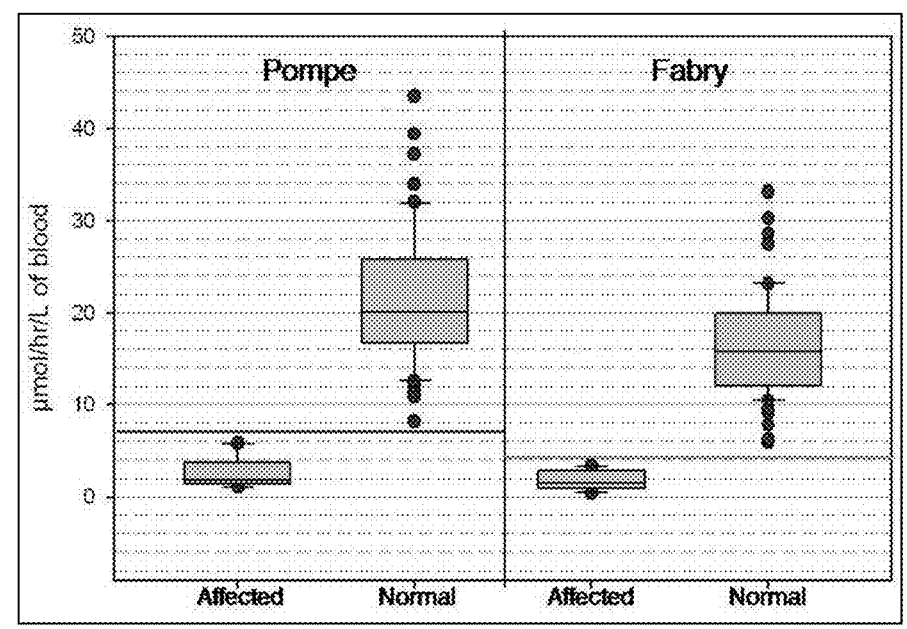
FIG. 9 shows an example of a plot of multiplexed testing for Pompe and Fabry diseases using extracts from single DBS punch.

Any of the enzymatic assay protocols described herein may be adapted for use on a droplet actuator, e.g., for use in testing newborns for enzymatic disorders. In one example, enzymatic assays for Pompe and Fabry diseases may be adapted and performed on a droplet actuator. FIG. 9 shows an example of a plot 900 of multiplexed testing for Pompe and Fabry diseases using extracts from single DBS punch. FIG. 9 shows clear separation between the affected (enzyme deficient) and normal samples for both the Pompe assay and the Fabry assay. The assays were reproducibly performed on over 100 normal neonatal DBS samples and 20 affected neonatal samples.

Other embodiments may make use of the modified umbelliferyl substrates described herein.

8.7 Enzyme Assays for Biotinidase (BIOT) and Galactosemia

Assays for biotinidase and total galactose, for BIOT and galactosemia testing, respectively, are currently available and performed by many newborn testing (NBS) laboratories world-wide. The assay for biotinidase may be the colorimetric Wolf's assay (absorbance detection assay). The assay for total galactose is a fluorometric assay (365 nm excitation/465 nm emission). The colorimetric assay for biotinidase and the fluorometric assay for total galactose may be adapted for use on a droplet actuator. In one embodiment, the invention provides on-chip enzyme assay protocols for newborn testing for BIOT and galactosemia using a single punch from a DBS sample. DBS extracts may be prepared using a single extraction buffer and exclusive components required for each assay may be included in the reagent formulation. The on-chip enzyme assays are adapted for each enzymatic reaction and are reproducible. For example, different concentrations of analyte (e.g., DBS punch extracted in about 50 µL or about 100 µL or about 150 µL or about 200 µL of extraction buffer) may be selected such that a minimal amount of DBS extract provides a detectable signal. Because a minimal amount of DBS extract is used, multiple NBS assays may be performed. The concentrations of the different reagents, buffering capacity, and pH may be adapted for use in a digital microfluidics protocol. Incubation times for each enzymatic reaction may be selected based on kinetic data. The relatively large reaction volumes in the on-bench protocol may be reduced, i.e., unitized to droplet volumes that are compatible with a digital microfluidic format.

Other embodiments may make use of the modified umbelliferyl substrates described herein.

8.8 Immunoassays for CH, CAH, and CF Testing

The invention provides on-chip immunoassay protocols for newborn testing for congenital hypothyroidism (CH), congenital adrenal hyperplasia (CH), and cystic fibrosis (CF) using a single punch from a DBS sample. DBS extracts may be prepared using a single extraction buffer and exclusive components required for each assay may be included in the reagent formulation.

In one embodiment, the invention provides on-chip immunoassay protocols for immunoreactive trysinogen (IRT) for CF. In another embodiment, the invention provides on-chip immunoassay protocols for thyroid stimulating hormone (TSH) and free thryroxine (T4) for CH. In yet another embodiment, the invention provides on-chip immunoassay protocols for 17α-hydroxy progesterone (17-OHP) for CAH. The immunoassays for IRT and TSH are sandwich immunoassays. The immunoassays for 17-OHP and T4 are competitive assays.

In one embodiment, the enzyme label (labeled secondary antibody) for all on-chip immunoassays may be alkaline phosphatase (ALP). Detection may, for example, be fluorescence-based. The substrate fluid for ALP may, for example, be 4-methylumbeliferrone phosphate (4-MUPi) with excitation/emission wavelength of 365/460 nm. The on-chip immunoassays may be adapted for each enzymatic reaction. For example, different concentrations of analyte (e.g., DBS punch extracted in about 50 µL or about 100 µL or about 150 µL of extraction buffer) may be selected such that a minimal amount of DBS extract provides a detectable signal. Because a minimal amount of DBS extract is used, multiple NBS assays may be performed. The concentrations of the different reagents (e.g., primary and secondary antibodies-labeled with ALP) may be adapted for use in a digital microfluidics protocol. In one example, concentrations of primary and secondary antibodies required for sufficient sensitivity may be determined using antigen standards. Incubation times for each immunoassay may be selected based on binding kinetic data. Binding incubations may, for example, be determined using a droplet mixing protocol wherein the droplet mixture of reagents and the sample are continuously mixed on-chip to ensure substantially complete resuspension of magnetically responsive beads with bound immune-complex thereon. In another example, fluorescence kinetic data for the reaction of 4-MUPi with the washed magnetically responsive beads with bound immune-complex thereon may be used to select an incubation time sufficient for required sensitivity. Adsorption of proteins and other contaminating materials from the DBS extract onto the magnetically responsive immunocapture beads may be substantially eliminated by using suitable blocking solutions and/or surfactants in the wash buffer. Exemplary protocols for droplet-based immunoassays are set forth in Pamula, et al., U.S. Pat. No. 7,815,871, issued on Oct. 19, 2010, the entire disclosure of which is incorporated herein by reference.

Figure 10:
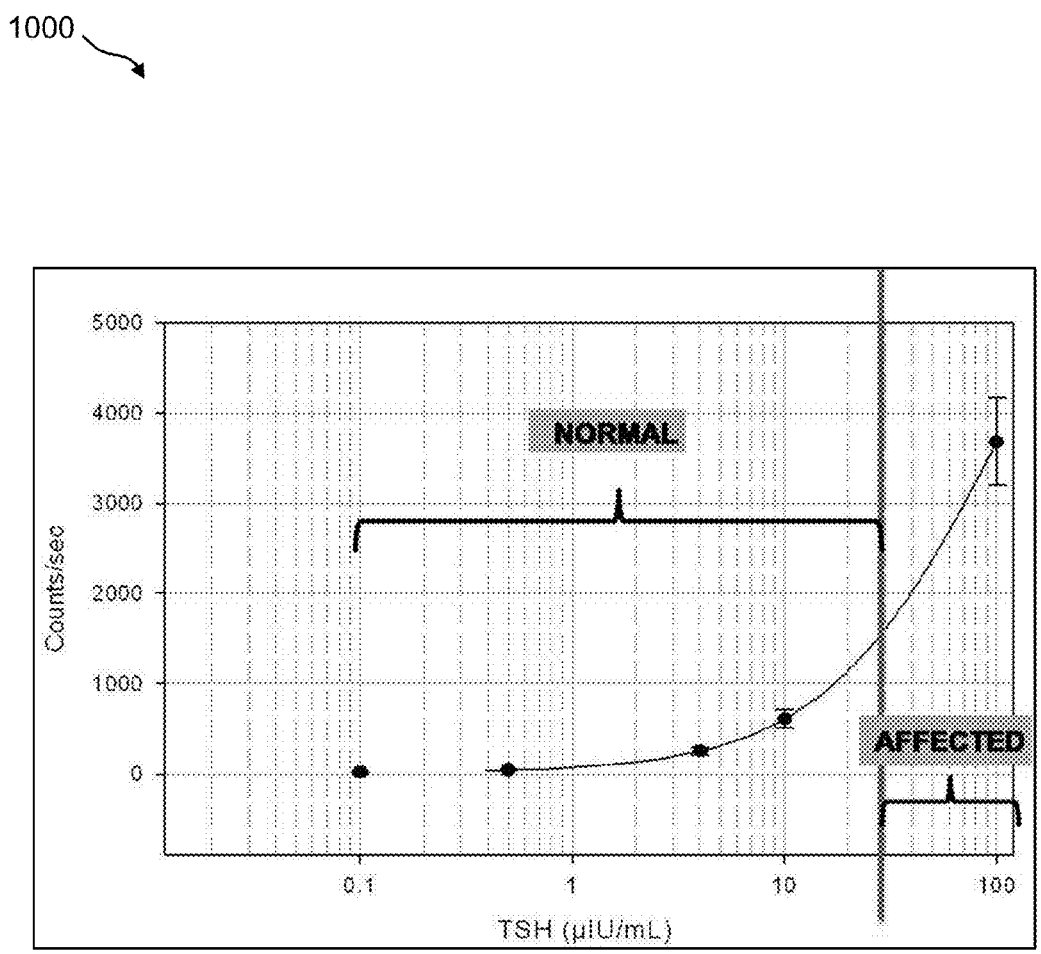
FIG. 10 shows an example of a plot of a standard curve for thyroid stimulating hormone (TSH)

FIG. 10 shows an example of a plot 1000 of a standard curve for thyroid stimulating hormone (TSH). A reagent mixture that contains equal volumes of primary antibody that are bound to magnetically responsive beads (immunocapture beads), blocking solution, and secondary antibody labeled with ALP was prepared on-bench. TSH standards were prepared on-bench. The digital microfluidic protocol associated with the TSH standard curve shown in plot 1000 included the following steps: One droplet of reagent mixture was mixed with two droplets of different concentrations of TSH standards to form a reaction droplet. The reaction droplet was incubated for 4 minutes. Magnetically responsive beads with bound immunocomplexes thereon were washed using a bead washing protocol to remove any unbound secondary antibody. One droplet of chemiluminescent substrate fluid was combined using droplet operations with the reaction droplet and incubated for 2 minutes. End point chemiluminscence was measured using a photon counting photomultiplier tube. A 4-parameter logistic fit was used to fit the data. The error bars represent standard deviation from four different assays. Cut-off concentration for TSH that is used by most newborn testing laboratories in the US is 20 µIU/mL.

Other embodiments may make use of the modified umbelliferyl substrates described herein.

8.9 Integrated Droplet Actuator Device

Newborn testing may be performed in centralized laboratories and often requires different types of assays for different conditions. For example, immunoassays may be used to test for congenital hypothyroidism (CH), congenital adrenal hyperplasia (CAH) and cystic fibrosis (CF) and enzymatic assays are used to test for biotinidase deficiency (BIOT) and galactosemia. Current technologies used in testing for these conditions use separate instrumentation. For example, most newborn testing laboratories use Perkin Elmer's Autodelfia immunoanalyzer to test for CF, CH, and CAH and Astoria Pacific's Spotcheck (fluorescence based analyzer) to test for galactosemia. Other laboratories may use a manual fluorometric method to test for galactosemia. To test for BIOT, most newborn testing laboratories use a manual colorimetric assay (e.g., Wolf's assay) in a 96-well format. Because separate assays and instrumentation are used, precious neonatal sample volume is not conserved.

The invention provides an integrated droplet actuator device and methods for performing enzymatic assays and immunoassays on a single droplet actuator. In one example, the integrated droplet actuator device and methods of the invention may be used for multiplexed detection of CAH, CH, CF, galactosemia, and BIOT using, for example, extract from a single dried blood spot sample.

Figure 11:
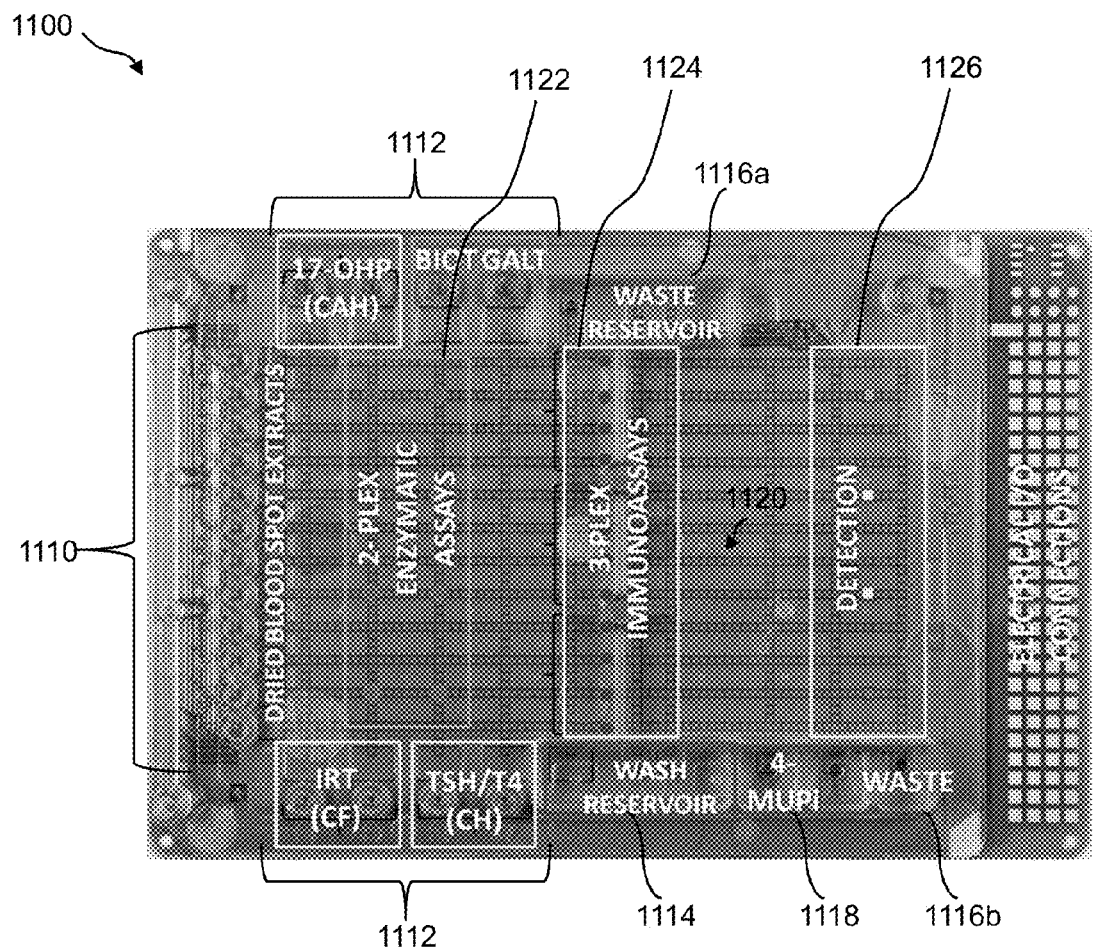
FIG. 11 illustrates a top view of an example of a droplet actuator that is suitable for use in conducting an integrated enzymatic assay and immunoassay newborn testing protocol.

FIG. 11 illustrates a top view of an example of a droplet actuator 1100 that is suitable for use in conducting an integrated enzyme assay and immunoassay newborn testing protocol. Droplet actuator 1100 includes multiple dispensing reservoirs, which may, for example, be allocated as sample dispensing reservoirs 1110 (e.g., 12 sample dispensing reservoirs 1110) for dispensing sample fluids (e.g., dried blood spot extracts); reagent dispensing reservoirs 1112 (e.g., 8 reagent dispensing reservoirs 1112) for dispensing different reagent fluids; a wash buffer dispensing reservoir 1114 for dispensing wash buffer fluids; one or more waste collection reservoirs 1116 (e.g., waste collection reservoirs 1116a and 1116b) for receiving waste droplets; and a substrate fluid dispensing reservoir 1118 for dispensing substrate fluids. In one example, two reagent dispensing reservoirs 1112 may be used to dispense reagents for a CAH immunoassay (e.g., 17-OHP); one reagent dispensing reservoir 1112 may be used to dispense reagents for a BIOT enzyme assay; one reagent dispensing reservoir 1112 may be used to dispense reagents for a galactosemia enzymatic assay; two reagent dispensing reservoirs 1112 may be used to dispense reagents for a CR immunoassay (e.g., IRT); and two reagent dispensing reservoirs 1112 may be used to dispense reagents for a CH immunoassay (e.g., TSH/T4). Substrate fluid dispensing reservoir 1118 may be used to dispense a fluorogenic substrate fluid, such as 4-MUPi, for fluorescence-based immunoassays. Sample dispensing reservoirs 1110, reagent dispensing reservoirs 1112, wash buffer dispensing reservoir 1114, waste collection reservoirs 1116, and substrate fluid dispensing reservoir 1118 are aligned with dispensing electrodes and interconnected through an arrangement, such as a path or array, of droplet operations electrodes 1120 (e.g., electrowetting electrodes). Droplet operations are conducted atop droplet operations electrodes 1120 on a droplet operations surface.

Droplet actuator 1100 may include an enzymatic assay zone 1122 (e.g., a 2-plex enzymatic assay zone) for performing enzymatic assays such as enzymatic assays for BIOT and galactosemia. Droplet actuator 1100 may further include an immunoassay zone 1124 (e.g., a 3-plex immunoassay zone) for performing immunoassays such as immunoassays for CH, CAH and CF. Droplet actuator 1100 may further include a detection zone 1126. Detection zone 1126 may include certain areas for detection of a fluorescent signal and certain areas for absorbance detection as described in reference to FIG. 12.

Figure 12:
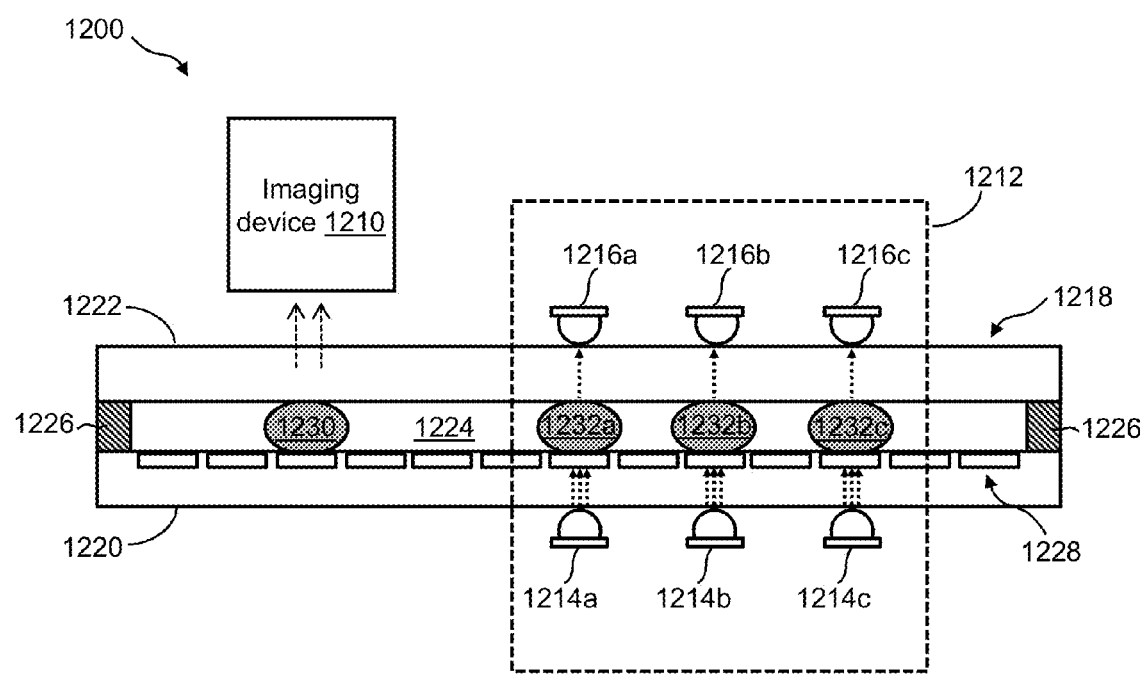
FIG. 12 illustrates a side view of an example of a detection system for simultaneous fluorescence and absorbance detection of multiple droplets on a single droplet actuator.

FIG. 12 illustrates a side view of an example of a detection system 1200 for simultaneous fluorescence and absorbance detection of multiple droplets on a single droplet actuator. The detection system of the invention includes a detector to measure absorbance for colorimetric assays and a sensitive fluorimeter for low level (e.g., about 0.55 nM of 4-MU) fluorescence detection.

Detection system 1200 may include an imaging device 1210 and a detector 1212. Imaging device 1210 may, for example, be a sensitive fluorimeter. Detector 1212 may include an arrangement of light emitting diodes (LEDs) 1214, e.g., three LEDs 1214a, 1214b and 1214c, and an arrangement of photodetectors 1216, e.g., three photodetectors 1216a, 1216b, and 1216c. Photodetectors 1216 may, for example, be photodiodes. The arrangement of LEDs 1214 and photodetectors 1216 is such that photodetectors 1216 are substantially aligned with LEDs 1214. Detection system 1200 is part of an instrument (not shown) used for operation of a droplet actuator.

A droplet actuator may be used in combination with detection system 1200. For example, a droplet actuator 1218 may be positioned in an instrument deck (not shown) such that a certain region of droplet actuator 1218 is aligned with detection system 1200. Droplet actuator 1218 may include a bottom substrate 1220 and a top substrate 1222 that are separated by a gap 1224. A gasket 1226 may be used to set the size of gap 1224. Bottom substrate 1220 may include an arrangement of droplet operations electrodes 1228 (e.g., electrowetting electrodes). Droplet operations are conducted atop droplet operations electrodes 1228 on a droplet operations surface.

Droplet actuator 1218 is positioned in an instrument deck (not shown) such that imaging device 1210 and detector 1212 are aligned with certain droplet operations electrodes 1228. In particular, LEDs 1214 and photodetectors 1216 are substantially aligned with certain droplet operations electrodes 1228.

Droplet actuator 1218 may include a droplet 1230. Droplet 1230 may, for example, be a droplet of sample fluid to be evaluated. Droplet 1230 may, for example, have a volume of about 300 nL. In one example, droplet 1230 may contain a quantity of beads (not shown). For example, the beads may be immunocapture beads for targeting a certain substance (e.g., protein, DNA, and/or antigens) during the assay operations (i.e., immunoassay) of droplet actuator 1218. Upon interacting with a reagent, droplet 1230 may be evaluated for target substances that have an affinity for the immunocapture beads therein. One example method of evaluation may be by digital imaging for identifying, for example, a fluorescent signal. In another example, droplet 1230 may contain a quantity of fluorescent reaction product generated during an enzymatic assay, such as an assay used to test for galactosemia.

In operation, imaging device 1210 is substantially aligned with a certain droplet operations electrode 1228, such that the certain droplet operations electrode 1228 is within the imaging field of imagining device 1210. Imaging device 1210 may be used to capture images (e.g., fluorescent signal) that may be emitted from droplet 1230. Imaging device 1210 may capture images through top substrate 1222, which may, for example, be a glass plate that is substantially transparent. Further, the thickness of top substrate 1222 may be optimized to provide effective imaging of droplet 1230.

Droplet actuator 1218 may further include one or more droplets 1232 (e.g., droplets 1232a, 1232b, and 1232c) to be evaluated. Each droplet 1232 may, for example, have a volume of about 300 nL. Droplets 1232 may, for example, contain a quantity of reaction product generated during an enzymatic assay, such as a colorimetric assay used to test for BIOT. One example method of evaluation may be by absorbance detection of a colored reaction product.

All operations to multiplex enzymatic assays and immunoassays on a droplet actuator may be programmed in the software for controlling the droplet actuator. In one example, software that converts complex assay protocols into simple flow charts may be used to provide input commands for the electronics of the droplet actuator.

An example of multiplex testing assay protocol may include, but is not limited to, the following: Dispense five sample droplets (e.g., extracted from a single DBS punch) and transport the droplets using droplet operations to the appropriate reaction zones (e.g., enzymatic assay zone or immunoassay zone). For an enzymatic assay (e.g., galactosemia, BIOT), dispense one droplet of reagent and combine it using droplet operations with one sample droplet to form a reaction droplet. Incubate the reaction droplet for a period of time sufficient for generation of a reaction product. Dispense one droplet of stop/quench buffer and combine it using droplet operations with the reaction droplet. Detect fluorescence (e.g., galactosemia assay) or absorbance (e.g., BIOT assay). For sandwich immunoassays (e.g., CF, CH), dispense one droplet each of magnetically responsive immunocapture beads, blocking solution and secondary antibody labeled with ALP. Merge all the droplets (reagent droplets and sample droplet) using droplet operations and incubate for a period of time sufficient for formation of immunocomplexes. Magnetically responsive beads with bound immunocomplexes thereon are washed using a bead washing protocol to remove any unbound secondary antibody. Dispense one droplet of substrate fluid, e.g., 4-MUPi, and combine it using droplet operations with the washed bead droplet. Detect fluorescence. For competitive immunoassays (e.g., CH and CAH), dispense on droplet of magnetically responsive immunocapture beads and combine it using droplet operations with one sample droplet and one droplet of ALP-labeled analyte to form a reaction droplet. Incubate the reaction droplet for a period of time sufficient for antigen-antibody binding Magnetically responsive beads are washed using a bead washing protocol to remove excess material. Dispense one droplet of substrate fluid, e.g., 4-MUPi, and combine it using droplet operations with the washed bead droplet. Detect fluorescence.

8.10 Reducing Contamination

In newborn testing assays, contamination may be caused by liquid handling failures, such as droplet splitting, or pinning of previous droplets on the same electrode pathway.

Contamination may cause false negatives for one or more droplets on the contaminated pathway. In one embodiment, contamination is avoided by using stop buffer droplets to wash the previous lane. Examples of stop buffers are those often used in enzymatic assays, such as newborn testing assays for metabolic disorders. Examples of lane or pathway washing protocols are described in International Patent Application No. PCT/US09/43774, entitled Droplet Actuator Devices, Systems, and Methods, filed on May 13, 2009, the entire disclosure of which is incorporated herein by reference.

As an example, wash droplets may be transported along a common pathway between each potentially contaminating droplet. The potentially contaminating droplet may include a reagent droplet, a sample droplet, and/or a reaction droplet that includes a potentially contaminating substance, such as a target enzyme. The wash droplets may, for example, include a wash buffer, such as a stop buffer. Wash droplets may include compounds that degrade contaminants. Wash droplets may include components that bind to contaminants Wash droplets may be transported along the common pathway in the same direction or in an opposite, or transverse direction relative to the potentially contaminating droplets. In some cases, multiple wash droplets are interposed on paths between potentially contaminating droplets. In some cases, the wash droplets are larger than the potentially contaminating droplets, e.g., 2×, 3×, 4× or larger droplets may be used as wash droplets.

8.10.1 Immobilization of 4-Methylumbelliferone (4-MU)

4-MU-containing substrates (a.k.a 7-hydroxy 4-methylcoumarin) are used in a number of bioassays, including assays for the detection of lysosomal storage disorders in newborns. The fluorometric enzyme assays are based on the hydrolysis of a 4-MU-containing substrate by a specific enzyme to yield the fluorescent molecule 4-MU. In the droplet operations environment of a droplet actuator, partitioning of 4-MU between the aqueous phase (i.e., droplet) and the organic phase (filler fluid) may potentially contaminate an electrode pathway. The enzymatic turnover of the 4-MU substrate requires a low-pH environment (acidic environment). At low pH (pK of 4-MU=7.9), 4-MU is non-ionic and hydrophobic and partitions preferentially from the aqueous droplet phase into the oil filler phase (100:1). Droplets subsequently prepared for the detection step of the bioassay are at a high pH. Fluorescence of 4-MU is optimal at elevated pH (pH>10). A high pH (pH>10) facilitates reverse partitioning of 4-MU from the oil phase back into an aqueous phase droplet. The potential for droplet cross-contamination is problematic when an acidic droplet with elevated enzyme concentration (producing significant amounts of 4-MU product) is in proximity of a basic droplet with substantially lower 4-MU concentrations.

The invention provides methods to substantially eliminate cross-contamination between droplets or loss of signal from droplets in 4-MU-based bioassays (e.g., newborn testing assays) on a droplet actuator. The method provides significantly improved discrimination between a positive signal and a negative signal in 4-MU-based bioassays. In one embodiment, the enzymatic 4-MU-containing substrate may be immobilized onto a solid support. In another example the enzymatic 4-MU-containing substrate may be immobilized on magnetically responsive beads. In yet another example, the enzymatic 4-MU-containing substrate may be immobilized on hydrogel beads. The 4-MU-containing substrate may, for example, be immobilized onto a solid support via the 4-MU component of the substrate molecule. The solid support (e.g., magnetically responsive beads or hydrogel beads) may be selected such that the beads remain suspended in an aqueous droplet and move with the aqueous droplet during droplet operations. Immobilization of the 4-MU onto a solid support (e.g., magnetically responsive beads or hydrogel beads) provides for retention of the enzymatic 4-MU substrate within the aqueous droplet and substantially eliminates partitioning of 4-MU into the oil filler phase at any pH Immobilization of 4-MU may also occur onto macromolecules, such as cellulose.

In another embodiment, enzymatic substrates, such as 4-MU-containing substrates, may be retained within an aqueous phase (e.g., an aqueous droplet) by formation of an "inclusion complex." In one example, cyclodextrins may be used to form an inclusion complex containing 4-MU. Cyclodextrins are donut-shaped cyclic glucose molecules with a hydrophobic inner cavity and a hydrophilic outer surface. Cyclodextrins are commercially available in various sizes. For example, alpha-cyclodextrins have 6 glucose units, β-cyclodextrins have 7 glucose units and gamma-cyclodextrins have 8 glucose units. The size of the inner cavity increases from alpha-cyclodextrin to gamma-cyclodextrin. Alternatives to cyclodextrins may include crown ethers, cryptands, and cyclic peptides, as well as derivatives, conjugates, and combinations of the foregoing, and may be used in other embodiments described herein.

Figure 13:
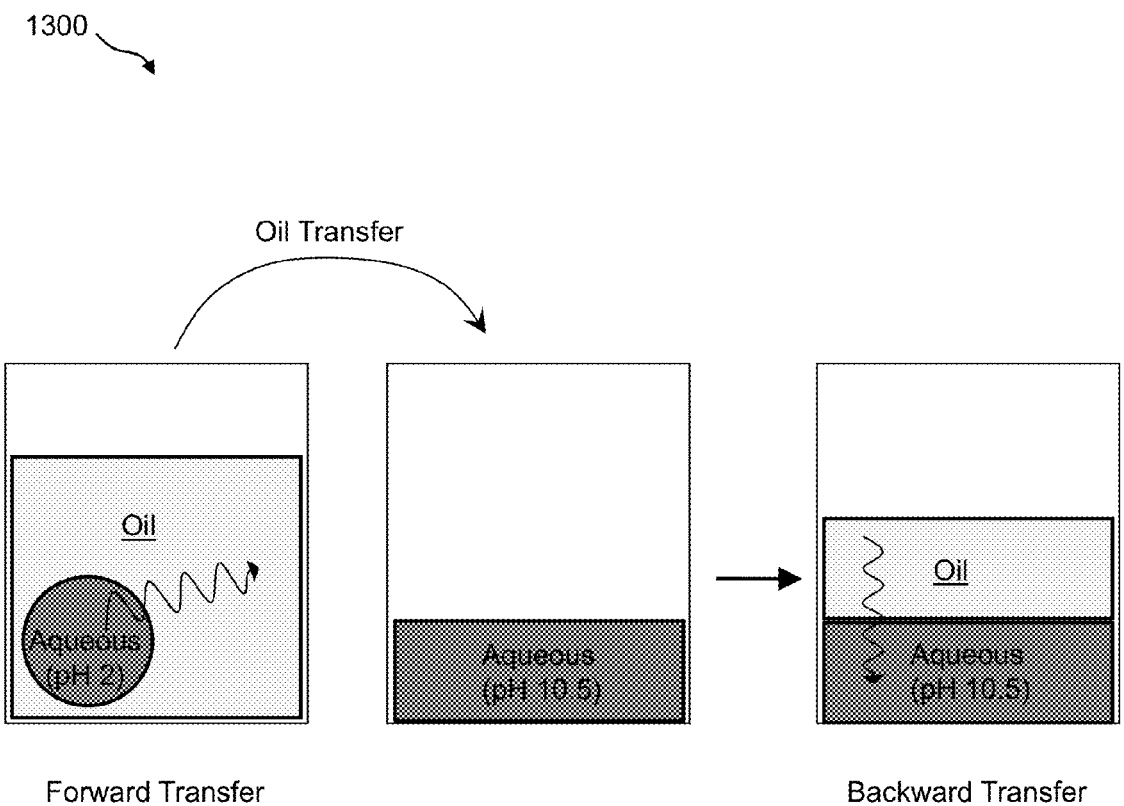
FIG. 13 shows a diagram of an assay protocol for evaluating the effect of β-cyclodextrins on 4-MU partitioning.

FIG. 13 shows a diagram of an on-bench assay protocol 1300 for evaluating the effect of additives (e.g., β-cyclodextrins, surfactants) on 4-MU partitioning. The assay format includes forward transfer partitioning (forward extraction; FE) of 4-MU from an aqueous phase to an oil phase and backward transfer partitioning (backward extraction; BE) of 4-MU from an oil phase to an aqueous phase. The assay is performed in 96-well microtiter substrates; clear 96-well substrates (e.g., Costar 3631) for evaluation of forward transfer partitioning with bottom probe fluorescence detection and solid black 96-well substrates (e.g., Costar 3915) for evaluation of backward transfer partitioning with top probe fluorescence detection. A BioTek Synergy HT instrument with 3 mm top probe and 5 mm bottom probe, may, for example, be used for fluorescence measurements. In one example, parameters that may be varied in the assay for evaluation of cyclodextrins in aqueous containment of 4-MU include, but are not limited to, ionic strength of the aqueous phase solution, pH of the aqueous phase solution (e.g., pH 2 or pH 5), and the molar ratio of cyclodextrins to 4-MU.

An example of an assay format used for testing the effect of cyclodextrins on contamination through 4-MU partitioning includes, but is not limited to, the following steps: Pipette an aliquot (20 µL) of an aqueous phase solution (e.g., at pH 2, pH5 or pH 10.5) containing a surfactant, such as 0.01% Tween® 20 in a well of a 96-well clear microtiter plate. The aqueous phase solution may also include 4-MU (e.g., 100 µM), NaCl (e.g., 50 mM), and β-cylcodextrin (e.g., 100 µM, 1 mM, 10 mM, or 100 mM). Add 130 µL of silicone oil (5 cSt, 0.1% Triton X-15) to each well that contains an aqueous phase droplet. Seal the plate with aluminum foil and shake using a bench top shaker (e.g., Thermofisher shaker at speed setting 5) for 30 min at room temperature. Carefully remove the aluminum foil and observe each well to note and record any defects in droplet quality (minimize light exposure during this step). Measure the fluorescence of each well using a bottom probe at gains 40, 45, and 50. Transfer, without disturbing the aqueous droplet, 50 μL of the oil phase (FE oil) from each well into the respective well of a solid black microtiter plate that contains 50 μL of 200 mM $NaHCO_3$ in each well. Seal the plate with aluminum foil and shake using, for example, a Thermofisher bench top shaker (e.g., speed setting 5) for 30 min at room temperature. Remove the aluminum foil and measure the fluorescence of each well using a top probe at gains 50, 60, 70, and 80.

Figure 14A:
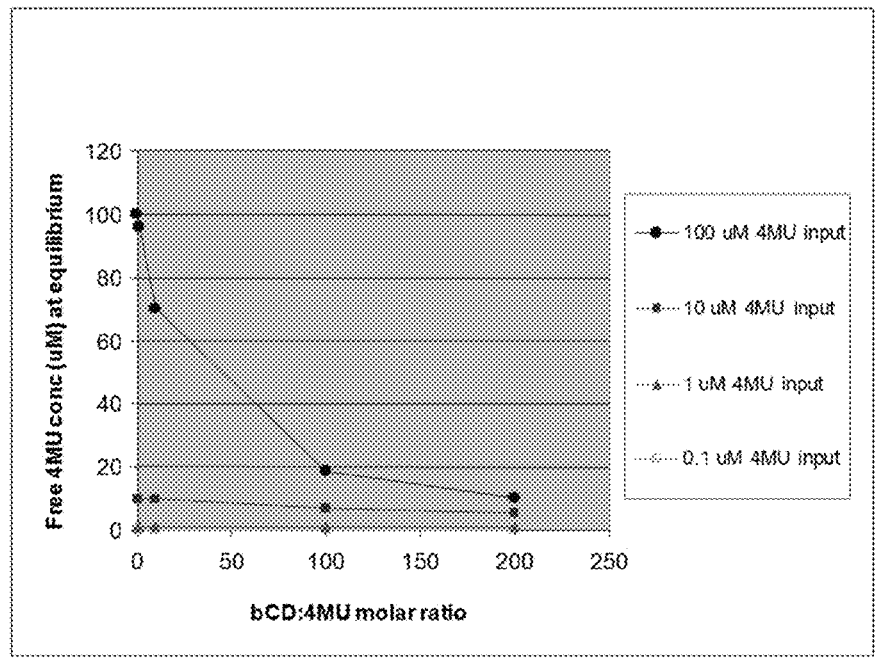
FIGS. 14A and 14B show plots of the concentration free 4-MU as a function of β-cyclodextrin:4-MU molar ratio.
Figure 14B:
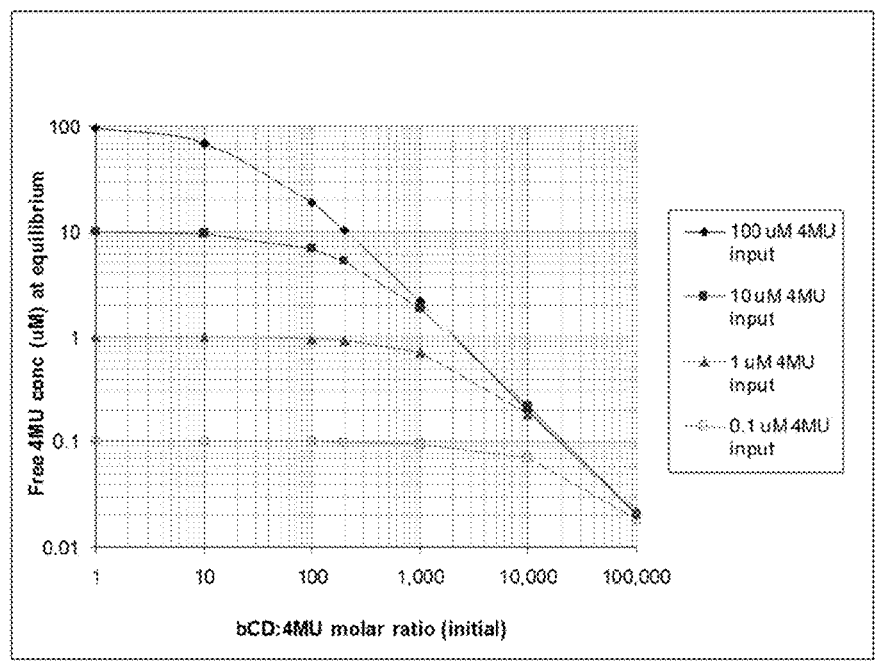

Aqueous containment of 4-MU may be examined as a function of the molar ratio of β-cyclodextrin to 4-MU. FIGS. 14A and 14B show a plot 1400 (linear-linear scale) and a plot 1450 (log-log scale), respectively, of concentration free 4-MU as a function of β-cyclodextrin:4-MU molar ratio. The data was generated at pH 2 in 100 mM KCl, MeOH/water 2/98 v/v.

Figure 15:
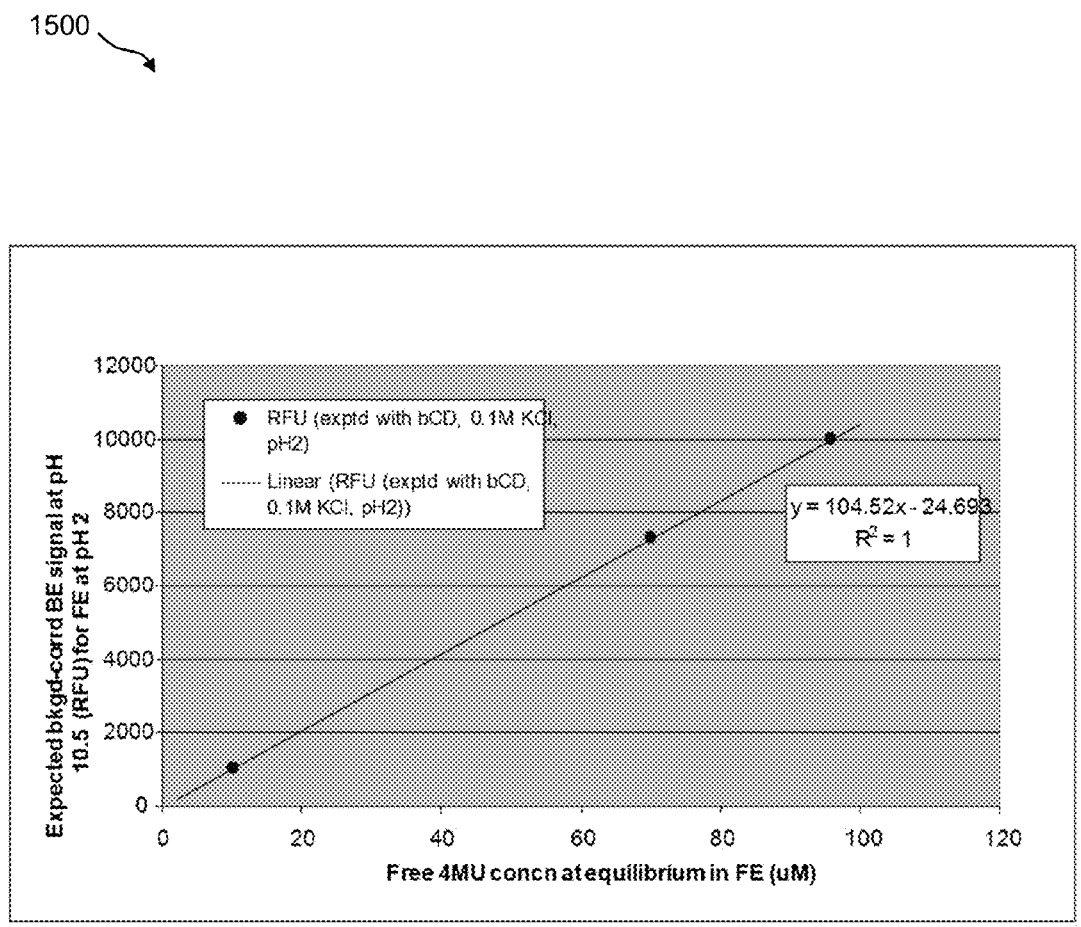
FIG. 15 shows a plot of an expected BE signal (back extraction) as a function of free 4-MU concentration at equilibrium in FE (forward extraction)

FIG. 15 shows a plot 1500 of an expected BE signal (back extraction) as a function of free 4-MU concentration at equilibrium in FE (forward extraction). Relative fluorescence was measured at gain 70. The molar ratio of β-cyclodextrin to 4-MU was 0:1 to 200:1.

Figures 16A, 16B:
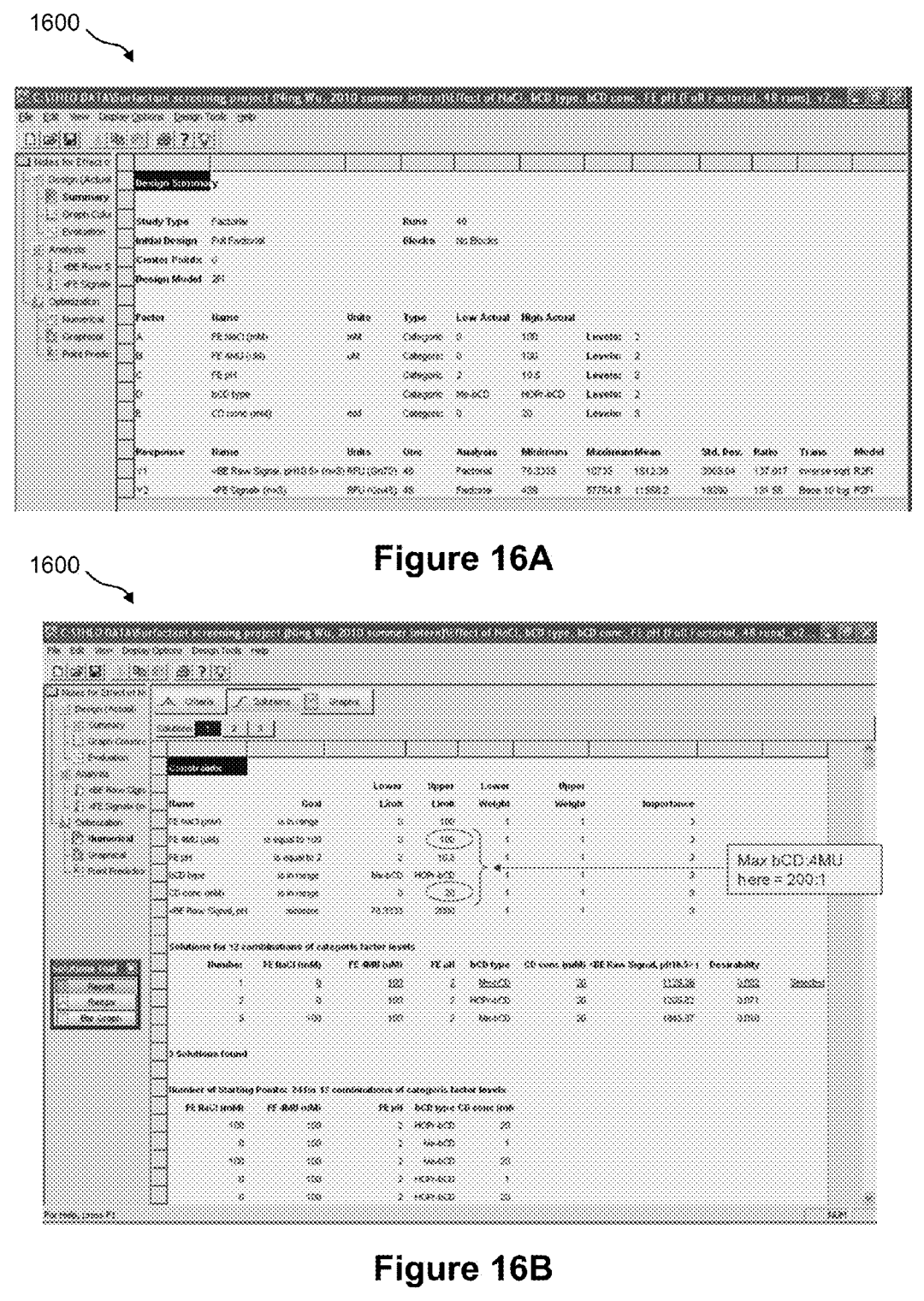
Figure 16C:
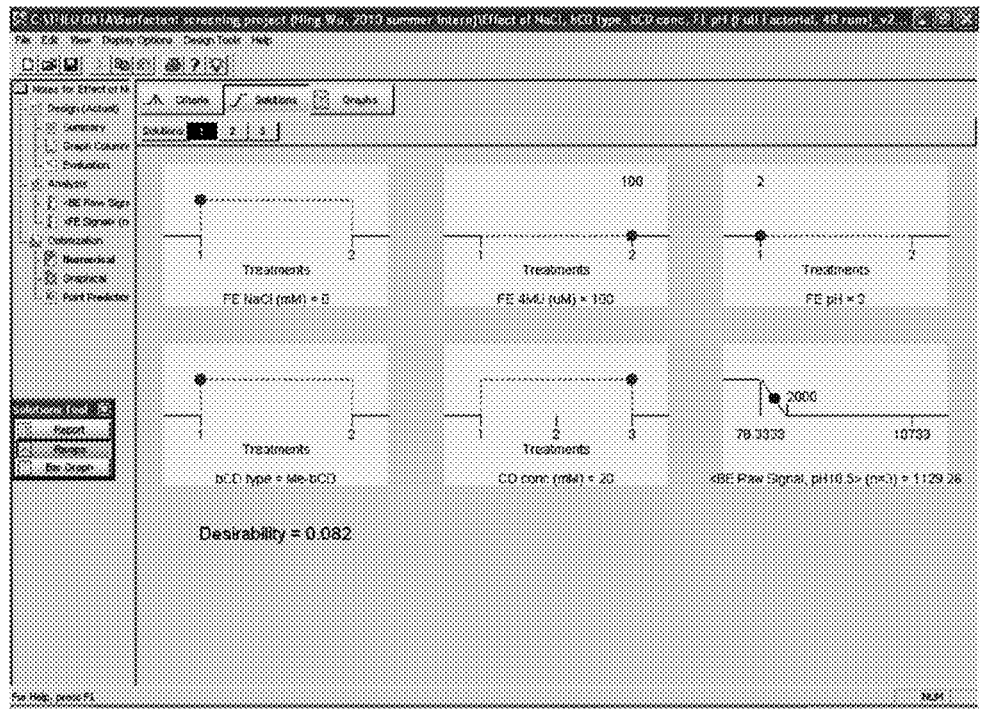
Figure 16D:
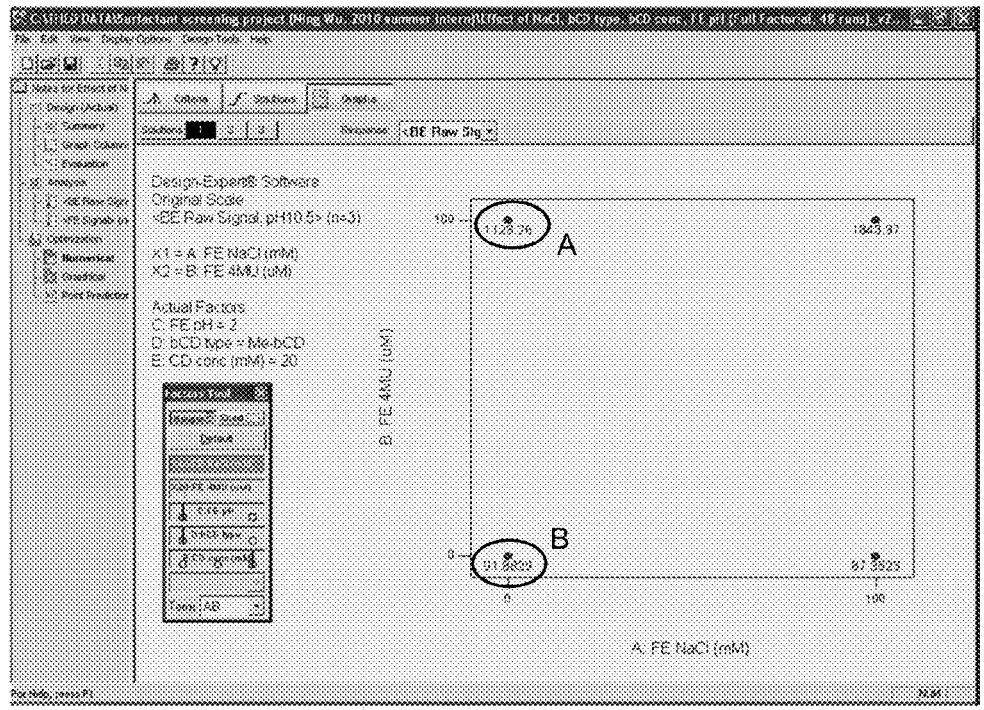
Figure 16E:
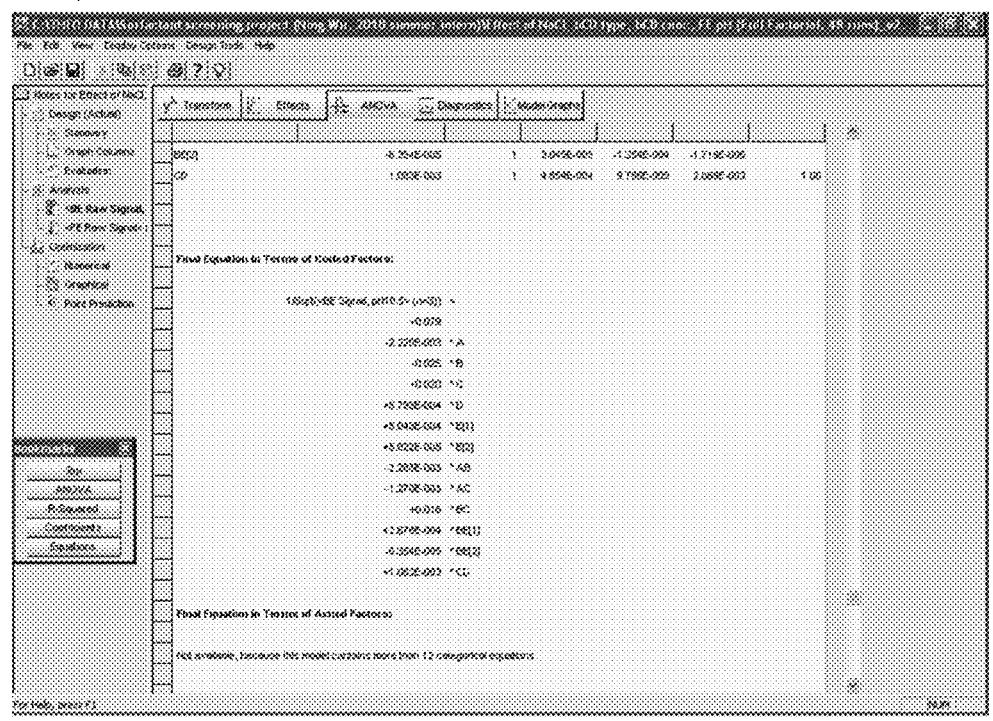
Figure 16F:
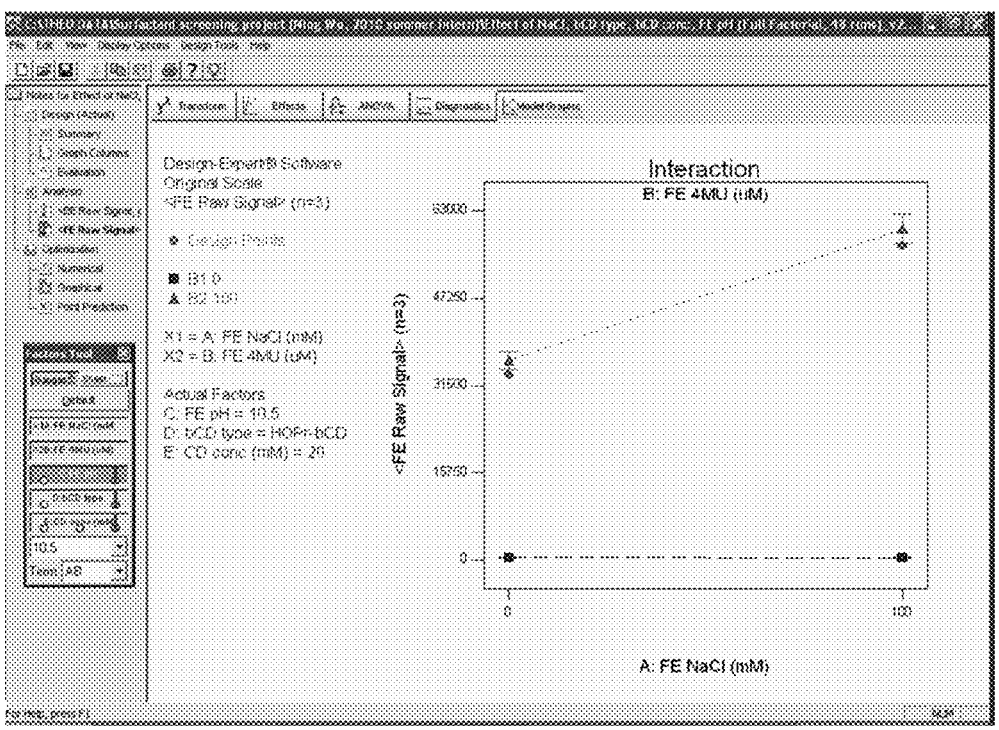
Figure 16G:
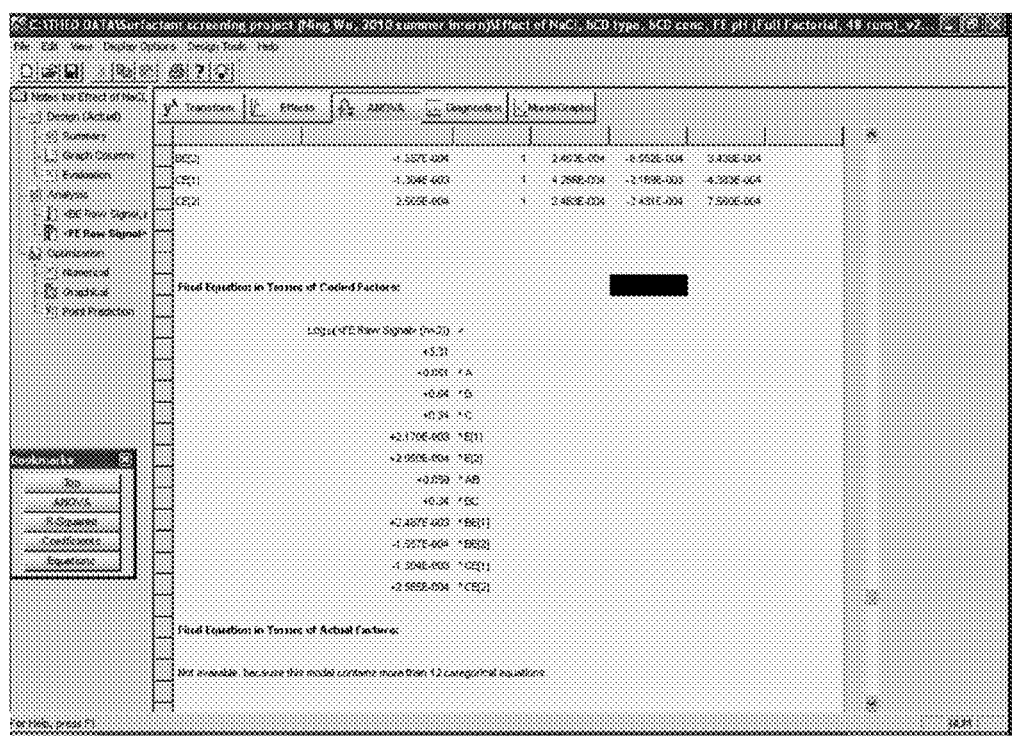

FIGS. 16A through 16G show screenshots of an example of an experiment designed to evaluate the effect of cyclodextrins, pH and ionic strength on aqueous containment of 4-MU. Referring to FIG. 16D, the lowest contamination signal (A) was achieved at a molar ratio of Me-bCD to 4-MU of 200:1 compared to the corresponding background signal (B). The experiment demonstrates that β-cyclodextrins (methyl-β-cyclodextrin, hydroxypropyl-β-cyclodextrin) are effective in aqueous containment of 4-MU. The effect of β-cyclodextrin on the aqueous containment of 4-MU is independent of pH. A large molar excess of β-cyclodextrin to 4-MU (e.g., >1,000:1) may be required for favorable equilibrium shift particularly when the initial 4-MU concentration is low.

Tables 5 and 6 show an example of a microtiter plate layout used to evaluate the effect of cyclodextrins (CD) on aqueous containment of 4-MU. The plate layout for forward transfer partitioning is shown in Table 5. In this example, the pH of the aqueous phase was pH 2 or pH 5. The concentrations of β-cyclodextrins were 100 μM, 10 mM, or 100 mM. The concentration of 4-MU is either 0 μM or 100 μM.

TABLE 5

Plate layout (n = 4 reps) for forward transfer

| | 1 | 2 | 3 | 4 | 5 | 6 | 7 | 8 | 9 | 10 | 11 | 12 |
|---|---|---|---|---|---|---|---|---|---|---|---|---|
| A | 20 μL__0 μM@pH 2__CD1<br>130 μL oil (5 cSt, 0.1% Tx15) | | | | 20 μL__0 μM@pH 5__CD1<br>130 μL oil (5 cSt, 0.1% Tx15) | | | | 20 μL__0 μM@pH 2__CD2<br>130 μL oil (5 cSt, 0.1% Tx15) | | | |
| B | 20 μL__100 μM@pH 2__CD1<br>130 μL oil (5 cSt, 0.1% Tx15) | | | | 20 μL__100 μM@pH 5__CD1<br>130 μL oil (5 cSt, 0.1% Tx15) | | | | 20 μL__100 μM@pH 2__CD2<br>130 μL oil (5 cSt, 0.1% Tx15) | | | |
| C | 20 μL__0 μM@pH 5__CD2<br>130 μL oil (5 cSt, 0.1% Tx15) | | | | 20 μL__0 μM@pH 2__CD3<br>130 μL oil (5 cSt, 0.1% Tx15) | | | | 20 μL__0 μM@pH 5__CD3<br>130 μL oil (5 cSt, 0.1% Tx15) | | | |
| D | 20 μL__100 μM@pH 5__CD2<br>130 μL oil (5 cSt, 0.1% Tx15) | | | | 20 μL__100 μM@pH 2__CD3<br>130 μL oil (5 cSt, 0.1% Tx15) | | | | 20 μL__100 μM@pH 5__CD3<br>130 μL oil (5 cSt, 0.1% Tx15) | | | |
| E | 20 μL__0 μM@pH 2__CD4<br>130 μL oil (5 cSt, 0.1% Tx15) | | | | 20 μL__0 μM@pH 5__CD4<br>130 μL oil (5 cSt, 0.1% Tx15) | | | | 20 μL__0 μM@pH 2__CD5<br>130 μL oil (5 cSt, 0.1% Tx15) | | | |
| F | 20 μL__100 μM@pH 2__CD4<br>130 μL oil (5 cSt, 0.1% Tx15) | | | | 20 μL__100 μM@pH 5__CD4<br>130 μL oil (5 cSt, 0.1% Tx15) | | | | 20 μL__100 μM@pH 2__CD5<br>130 μL oil (5 cSt, 0.1% Tx15) | | | |
| G | 20 μL__0 μM@pH 5__CD5<br>130 μL oil (5 cSt, 0.1% Tx15) | | | | EMPTY | | | | EMPTY | | | |
| H | 20 μL__100 μM@pH 5__CD5<br>130 μL oil (5 cSt, 0.1% Tx15) | | | | EMPTY | | | | EMPTY | | | |

*CD1 = 100 μM methyl-β-cyclodextrin; CD2 = 10 mM methyl-β-cyclodextrin; CD3 = 100 mM methyl-β-cyclodextrin; CD4 = 100 μM hydroxylpropyl-β-cyclodextrin; CD5 = 100 mM hydroxylpropyl-β-cyclodextrin The corresponding microtiter plate layout for the backward transfer (backward extraction) is shown in Table 6. Each well of the second microtiter plate (i.e., a solid black microtiter plate) contains 50 μL of an aqueous solution (200 mM NaHCO$_3$) at pH 10.5. Each well also contains an aliquot (50 μL) of oil (i.e., FE oil) from the corresponding well of the forward transfer reaction described in reference to Table 5. For fluorescence calibration, an aqueous solution containing 4-MU (0, 0.01, 0.1, or 1 μM) was added to the corresponding "empty" wells of Table 5 and overlaid with a 50 μL aliquot of fresh oil.

corresponds to cell F9,10,11,12 of Table 5, and value V4 corresponds to cell H1,2,3,4. The data show that at higher concentrations of CD, i.e., 100 mM (b-cyclodextrin:4-MU molar ratio>>200:1), forward transfer of 4-MU from the aqueous phase to the oil phase is significantly reduced.

Figures 18A, 18B:
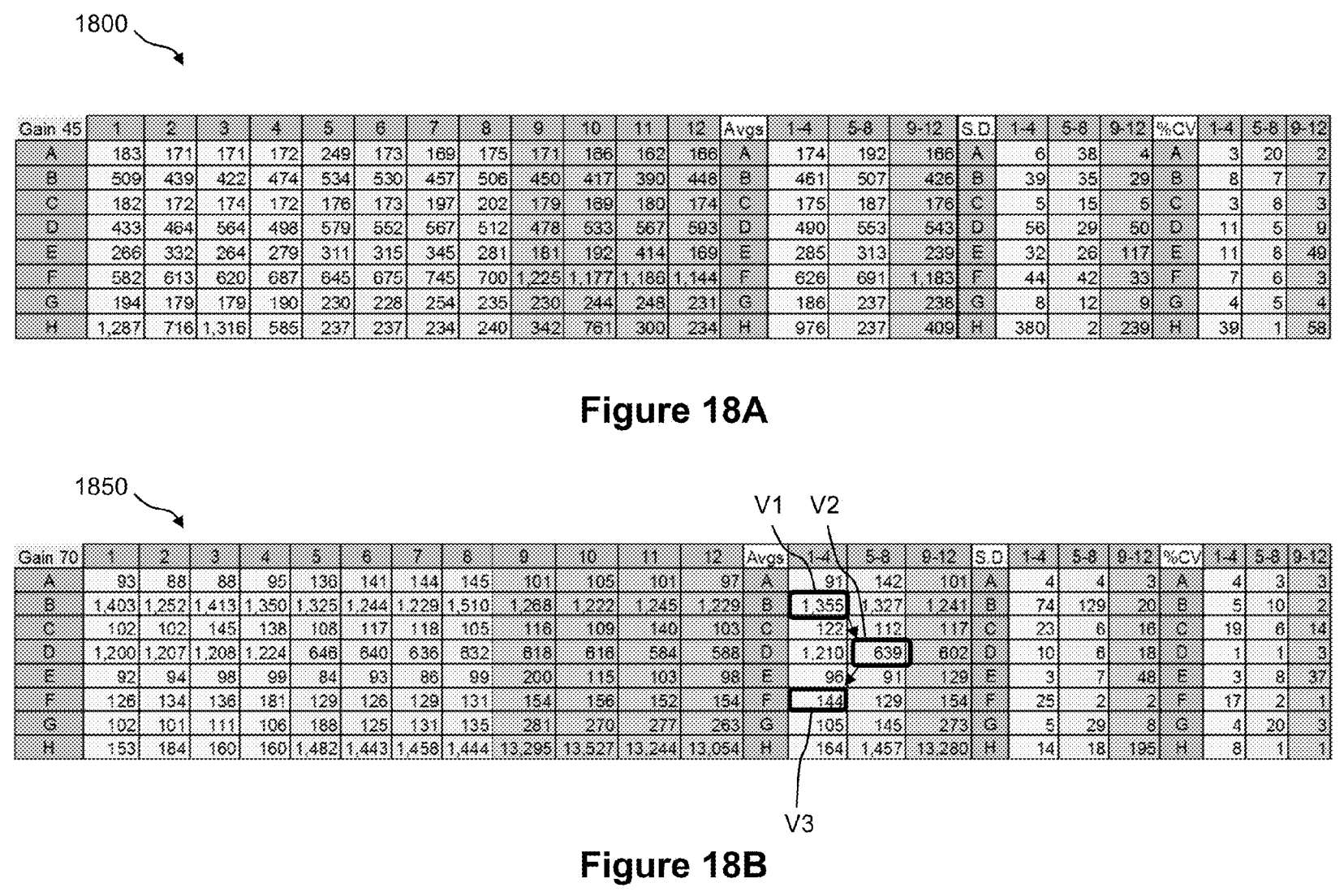

FIGS. 18A and 18B show data tables 1800 and 1850, respectively, of another example of a 4-MU partitioning assay. The microtiter plate layouts for forward and backward transfer are shown in Tables 7 and 8, respectively, which are below. In this example, the concentration of 4-MU was 10

TABLE 6

| Plate layout (n = 4 reps) for backward transfer | | | | | | | | | | | |
|---|---|---|---|---|---|---|---|---|---|---|---|
| 1 | 2 | 3 | 4 | 5 | 6 | 7 | 8 | 9 | 10 | 11 | 12 |

| Row | Columns 1–4 | Columns 5–8 | Columns 9–12 |
|---|---|---|---|
| A | 50 μL_0 μM@pH 10.5_no S or CD<br>50 μL FE oil (5 cSt, 0.1% Tx15) | 50 μL_0 μM@pH 10.5_no S or CD<br>50 μL FE oil (5 cSt, 0.1% Tx15) | 50 μL_0 μM@pH 10.5_no S or CD<br>50 μL FE oil (5 cSt, 0.1% Tx15) |
| B | 50 μL_0 μM@pH 10.5_no S or CD<br>50 μL FE oil (5 cSt, 0.1% Tx15) | 50 μL_0 μM@pH 10.5_no S or CD<br>50 μL FE oil (5 cSt, 0.1% Tx15) | 50 μL_0 μM@pH 10.5_no S or CD<br>50 μL FE oil (5 cSt, 0.1% Tx15) |
| C | 50 μL_0 μM@pH 10.5_no S or CD<br>50 μL FE oil (5 cSt, 0.1% Tx15) | 50 μL_0 μM@pH 10.5_no S or CD<br>50 μL FE oil (5 cSt, 0.1% Tx15) | 50 μL_0 μM@pH 10.5_no S or CD<br>50 μL FE oil (5 cSt, 0.1% Tx15) |
| D | 50 μL_0 μM@pH 10.5_no S or CD<br>50 μL FE oil (5 cSt, 0.1% Tx15) | 50 μL_0 μM@pH 10.5_no S or CD<br>50 μL FE oil (5 cSt, 0.1% Tx15) | 50 μL_0 μM@pH 10.5_no S or CD<br>50 μL FE oil (5 cSt, 0.1% Tx15) |
| E | 50 μL_0 μM@pH 10.5_no S or CD<br>50 μL FE oil (5 cSt, 0.1% Tx15) | 50 μL_0 μM@pH 10.5_no S or CD<br>50 μL FE oil (5 cSt, 0.1% Tx15) | 50 μL_0 μM@pH 10.5_no S or CD<br>50 μL FE oil (5 cSt, 0.1% Tx15) |
| F | 50 μL_0 μM@pH 10.5_no S or CD<br>50 μL FE oil (5 cSt, 0.1% Tx15) | 50 μL_0 μM@pH 10.5_no S or CD<br>50 μL FE oil (5 cSt, 0.1% Tx15) | 50 μL_0 μM@pH 10.5_no S or CD<br>50 μL FE oil (5 cSt, 0.1% Tx15) |
| G | 50 μL_0 μM@pH 10.5_no S or CD<br>50 μL FE oil (5 cSt, 0.1% Tx15) | 50 μL_0 μM@pH 10.5_no S or CD<br>50 μL fresh oil (5 cSt, 0.1% Tx15) | 50 μL_0.01 μM@pH 10.5_no S or CD<br>50 μL fresh oil (5 cSt, 0.1% Tx15) |
| H | 50 μL_0 μM@pH 10.5_no S or CD<br>50 μL FE oil (5 cSt, 0.1% Tx15) | 50 μL_0.1 μM@pH 10.5_no S or CD<br>50 μL fresh oil (5 cSt, 0.1% Tx15) | 50 μL_1 μM@pH 10.5_no S or CD<br>50 μL fresh oil (5 cSt, 0.1% Tx15) |

"no S or CD" means no surfactant or β-cyclodextrin

Figures 17A, 17B:
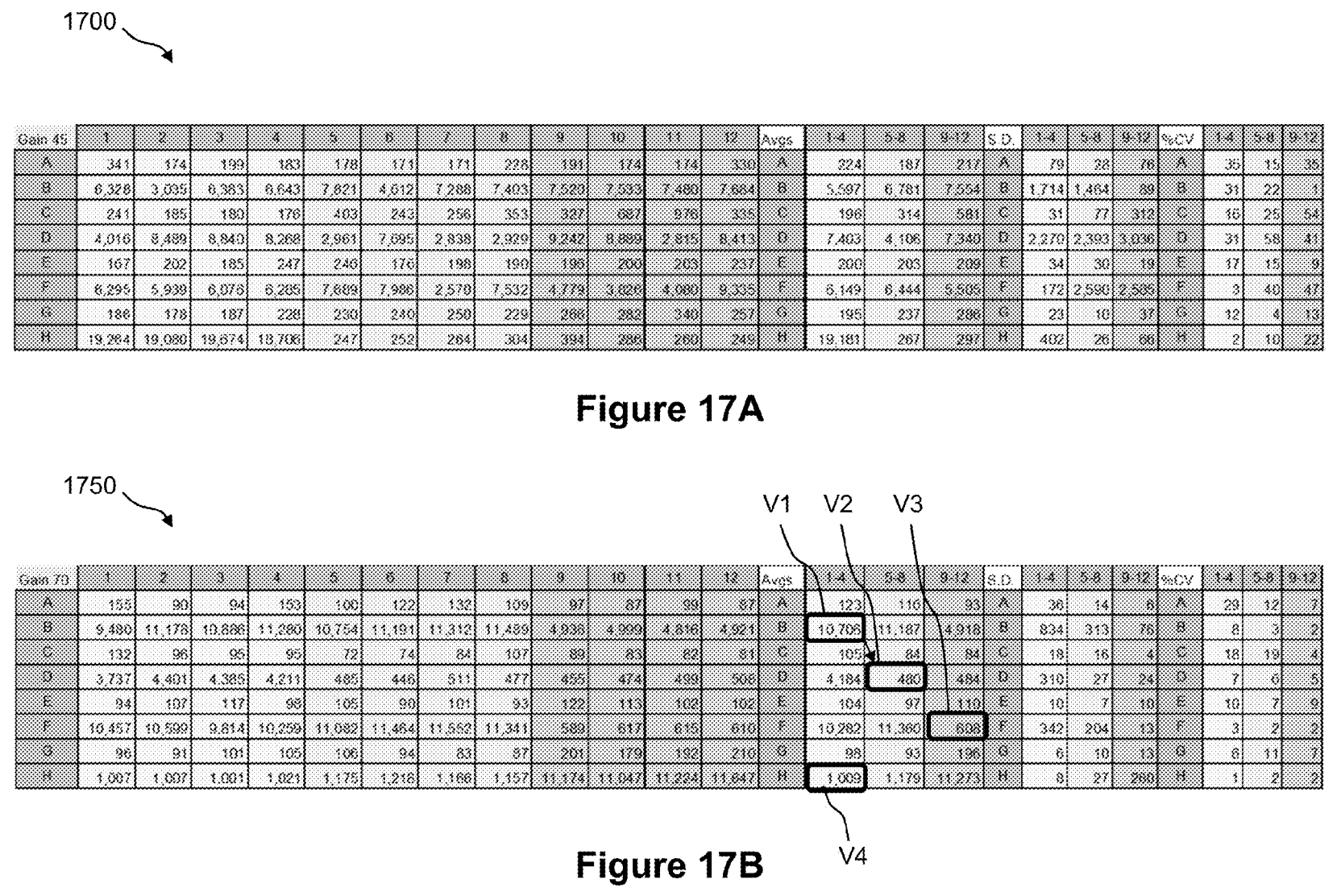

FIGS. 17A and 17B show data tables 1700 and 1750, respectively, of fluorescence readings for forward transfer and backward transfer, respectively, of the 4-MU partitioning assay of Tables 5 and 6. The forward transfer fluorescence (FIG. 17A) was read at a gain of 45 and the backward transfer fluorescence (FIG. 17B) was read at a gain of 70. Referring to FIG. 17B, value V1 corresponds to cell B1,2,3,4 of Table 5, value V2 corresponds to cell D5,6,7,8 of Table 5, value V3

μM. Forward transfer (FIG. 18A) was read at a gain of 45 and the backward transfer (FIG. 18B) was read at a gain of 70. Referring to FIG. 18B, value V1 corresponds to cell B1,2,3,4 of Table 7, value V2 corresponds to cell D5,6,7,8 of Table 7, and value V3 corresponds to cell F1,2,3,4 of Table 7. The data show that at higher concentrations of cyclodextrin, i.e., 100 mM (b-cyclodextrin:4-MU molar ratio>>200:1), forward transfer of 4-MU from the aqueous phase to the oil phase is significantly reduced.

TABLE 7

Plate layout (n = 4 reps) for forward transfer

| | 1 | 2 | 3 | 4 | 5 | 6 | 7 | 8 | 9 | 10 | 11 | 12 |
|---|---|---|---|---|---|---|---|---|---|---|---|---|
| A | 20 μL_0 μM@pH 2_CD1 130 μL oil (5 cSt, 0.1% Tx15) | | | | 20 μL_0 μM@pH 5_CD1 130 μL oil (5 cSt, 0.1% Tx15) | | | | 20 μL_0 μM@pH 2_CD2 130 μL oil (5 cSt, 0.1% Tx15) | | | |
| B | 20 μL_10 μM@pH 2_CD1 130 μL oil (5 cSt, 0.1% Tx15) | | | | 20 μL_10 μM@pH 5_CD1 130 μL oil (5 cSt, 0.1% Tx15) | | | | 20 μL_10 μM@pH 2_CD2 130 μL oil (5 cSt, 0.1% Tx15) | | | |
| C | 20 μL_0 μM@pH 5_CD2 130 μL oil (5 cSt, 0.1% Tx15) | | | | 20 μL_0 μM@pH 2_CD3 130 μL oil (5 cSt, 0.1% Tx15) | | | | 20 μL_0 μM@pH 5_CD3 130 μL oil (5 cSt, 0.1% Tx15) | | | |
| D | 20 μL_10 μM@pH 5_CD2 130 μL oil (5 cSt, 0.1% Tx15) | | | | 20 μL_10 μM@pH 2_CD3 130 μL oil (5 cSt, 0.1% Tx15) | | | | 20 μL_10 μM@pH 5_CD3 130 μL oil (5 cSt, 0.1% Tx15) | | | |
| E | 20 μL_0 μM@pH 2_CD4 130 μL oil (5 cSt, 0.1% Tx15) | | | | 20 μL_0 μM@pH 5_CD4 130 μL oil (5 cSt, 0.1% Tx15) | | | | 20 μL_0 μM@pH 2_CD5 130 μL oil (5 cSt, 0.1% Tx15) | | | |
| F | 20 μL_10 μM@pH 2_CD4 130 μL oil (5 cSt, 0.1% Tx15) | | | | 20 μL_10 μM@pH 5_CD4 130 μL oil (5 cSt, 0.1% Tx15) | | | | 20 μL_10 μM@pH 2_CD5 130 μL oil (5 cSt, 0.1% Tx15) | | | |
| G | 20 μL_0 μM@pH 5_CD5 130 μL oil (5 cSt, 0.1% Tx15) | | | | EMPTY | | | | EMPTY | | | |
| H | 20 μL_10 μM@pH 5_CD5 130 μL oil (5 cSt, 0.1% Tx15) | | | | EMPTY | | | | EMPTY | | | |

*CD1 = 10 μM methyl-β-cyclodextrin; CD2 = 1 mM methyl-β-cyclodextrin; CD3 = 10 mM methyl-β-cyclodextrin; CD4 = 100 mM methyl-β-cyclodextrin; CD5 = 100 mM hydroxylpropyl-β-cyclodextrin

TABLE 8

Plate layout (n = 4 reps) for backward transfer

| | 1 | 2 | 3 | 4 | 5 | 6 | 7 | 8 | 9 | 10 | 11 | 12 |
|---|---|---|---|---|---|---|---|---|---|---|---|---|
| A | 50 μL_0 μM@pH 10.5_no S or CD 50 μL FE oil (5 cSt, 0.1% Tx15) | | | | 50 μL_0 μM@pH 10.5_no S or CD 50 μL FE oil (5 cSt, 0.1% Tx15) | | | | 50 μL_0 μM@pH 10.5_no S or CD 50 μL FE oil (5 cSt, 0.1% Tx15) | | | |
| B | 50 μL_0 μM@pH 10.5_no S or CD 50 μL FE oil (5 cSt, 0.1% Tx15) | | | | 50 μL_0 μM@pH 10.5_no S or CD 50 μL FE oil (5 cSt, 0.1% Tx15) | | | | 50 μL_0 μM@pH 10.5_no S or CD 50 μL FE oil (5 cSt, 0.1% Tx15) | | | |
| C | 50 μL_0 μM@pH 10.5_no S or CD 50 μL FE oil (5 cSt, 0.1% Tx15) | | | | 50 μL_0 μM@pH 10.5_no S or CD 50 μL FE oil (5 cSt, 0.1% Tx15) | | | | 50 μL_0 μM@pH 10.5_no S or CD 50 μL FE oil (5 cSt, 0.1% Tx15) | | | |
| D | 50 μL_0 μM@pH 10.5_no S or CD 50 μL FE oil (5 cSt, 0.1% Tx15) | | | | 50 μL_0 μM@pH 10.5_no S or CD 50 μL FE oil (5 cSt, 0.1% Tx15) | | | | 50 μL_0 μM@pH 10.5_no S or CD 50 μL FE oil (5 cSt, 0.1% Tx15) | | | |
| E | 50 μL_0 μM@pH 10.5_no S or CD 50 μL FE oil (5 cSt, 0.1% Tx15) | | | | 50 μL_0 μM@pH 10.5_no S or CD 50 μL FE oil (5 cSt, 0.1% Tx15) | | | | 50 μL_0 μM@pH 10.5_no S or CD 50 μL FE oil (5 cSt, 0.1% Tx15) | | | |
| F | 50 μL_0 μM@pH 10.5_no S or CD 50 μL FE oil (5 cSt, 0.1% Tx15) | | | | 50 μL_0 μM@pH 10.5_no S or CD 50 μL FE oil (5 cSt, 0.1% Tx15) | | | | 50 μL_0 μM@pH 10.5_no S or CD 50 μL FE oil (5 cSt, 0.1% Tx15) | | | |
| G | 50 μL_0 μM@pH 10.5_no S or CD 50 μL FE oil (5 cSt, 0.1% Tx15) | | | | 50 μL_0 μM@pH 10.5_no S or CD 50 μL fresh oil (5 cSt, 0.1% Tx15) | | | | 50 μL_0.01 μM@pH 10.5_no S or CD 50 μL fresh oil (5 cSt, 0.1% Tx15) | | | |
| H | 50 μL_0 μM@pH 10.5_no S or CD 50 μL FE oil (5 cSt, 0.1% Tx15) | | | | 50 μL_0.1 μM@pH 10.5_no S or CD 50 μL fresh oil (5 cSt, 0.1% Tx15) | | | | 50 μL_1 μM@pH 10.5_no S or CD 50 μL fresh oil (5 cSt, 0.1% Tx15) | | | |

"no S or CD" means no surfactant or β-cyclodextrin

In the droplet operations environment of a droplet actuator, formation of an inclusion complex between 4-MU and cyclodextrins may be used to substantially minimize droplet cross-contamination by preventing 4-MU from leaking from the aqueous phase into the filler fluid (e.g., silicone oil) phase at low pH. In one example, cyclodextrin may be used as an additive to a reagent droplet that includes the 4-MU-containing substrate. A sample droplet (e.g., a dried blood extract droplet) is combined and mixed using droplet operations with the reagent droplet. Because cyclodextrin is included in the reagent droplet, the enzymatic product, i.e., 4-MU, is sequestered within an inclusion complex as soon as it is released by the enzyme present in the sample droplet.

In yet another embodiment, surfactants may be used to retain 4-MU (or derivatives) within an aqueous phase (e.g., an aqueous phase droplet). The efficacy of different surfactants in containing 4-MU (or derivatives) within an aqueous phase may, for example, be evaluated and selected using a partitioning assay, such as the 4-MU partitioning assay described in reference to FIG. 13. In this example, parameters that may be varied in the assay for evaluation of surfactants in aqueous containment of 4-MU (or derivatives) include, but are not limited to, the pH of the aqueous phase solution (e.g. pH 2 to pH 10.5 range), and the critical micellar concentration of the surfactant.

An example of an assay format used for testing the effect of surfactants on contamination through 4-MU partitioning includes, but is not limited to, the following steps: Pipette an aliquot (20 μL) of an aqueous phase solution (e.g., pH range of pH 2 to pH 10.5) containing a selected concentration (e.g., 1.5× the surfactant's critical micellar concentration) of a surfactant in a well of a 96-well clear bottom microtiter plate (e.g., Costar® 3631). The aqueous phase solution also includes 4-MU (e.g., 1 mM). Add 130 μL of silicone oil (5 cSt, 0.1% Triton™ X-15) to each well that contains an aqueous phase droplet. Seal the plate with aluminum foil and shake using a bench top shaker (e.g., Thermofisher shaker at speed setting 5) for 30 min at room temperature. Carefully remove the aluminum foil and observe each well to note and record any defects in droplet quality (minimize light exposure during this step). Measure the fluorescence of each well using a bottom probe at, for example, a gain of 40. Transfer, without disturbing the aqueous droplet, 50 μL of the oil phase (FE oil) from each well into the respective well of a solid black microtiter plate that contains 50 μL of 200 mM NaHCO₃ pH 10.5 in each well. Seal the plate with aluminum foil and shake using, for example, a Thermofisher bench top shaker (e.g., speed setting 5) for 30 min at room temperature. Remove the aluminum foil and measure the fluorescence of each well using a top probe at gains 45, 50, 55, 60, 65, and 70.

FIG. 19 shows a data table 1900 of relative fluorescence readings for backward transfer partitioning (backward extraction; BE) of a 4-MU partitioning assay used to evaluate the effect of aqueous phase surfactants on 4-MU containment. In this example, surfactants were selected from an array of different surfactants available in the detergent testing kit HR2-408 from Hampton Research, Inc. The experiment was performed using 5 cSt silicone oil with 0.1% w/v Triton X-15 as the organic phase (oil phase). Each surfactant was used at 1.5 times the surfactant's critical micellar concentration (CMC). The identity of each surfactant is listed in Table 9. AS17 (ANAPOE®-20 or Tween® 20) was used as a reference signal (43,000-44,000 RFU) and reflects an example of the level of droplet cross-contamination that may be observed in a newborn testing assay performed on a droplet actuator. The data is presented in order of decreasing efficiency of the different surfactants in retaining 4-MU in an aqueous phase droplet.

TABLE 9

Aqueous surfactants (AS) in 4-MU retention assay of FIG. 19

| AS # | Surfactant |
|---|---|
| AS 93 | FOS-Choline ®-8 |
| AS 91 | ZWITTERGENT ® 3-10 |
| AS 1 | BAM |
| AS 90 | FOS-Choline ®-9 |
| AS 70 | n-Hexyl-β-D-glucopyranoside |
| AS 69 | CYMAL ®-2 |
| AS 66 | MEGA-8 |
| AS 68 | HEGA ®-8 |
| AS 89 | n-Decyl-N,N-dimethylglycine |
| AS 67 | HEGA ®-9 |
| AS 88 | FOS-Choline ®-10 |
| AS 83 | ZWITTERGENT ® 3-12 |
| AS 7 | Sodium cholate |
| AS 9 | ANAPOE ®-X-305 |
| AS 92 | CYCLOFOS ™-3 |
| AS 62 | CYMAL ®-3 |
| AS 86 | CHAPS |
| AS 94 | ZWITTERGENT ® 3-08 |
| AS 77 | NDSB-256 |
| AS 80 | FOS-Choline ®-12 |
| AS 58 | MEGA-9 |
| AS 87 | CHAPSO |
| AS 85 | FOS-MEA ®-10 |
| AS 78 | ZWITTERGENT ® 3-14 |
| AS 64 | HEGA ®-9 |
| AS 63 | C-HEGA ®-10 |
| AS 84 | DDMAB |
| AS 81 | FOS-Choline ®-8, fluorinated |
| AS 95 | LysoFos ™ Choline 12 |
| AS 2 | n-Dodecyl-β-iminodipropionic acid, monosodium salt |
| AS 79 | n-Dodecyl-N,N-dimethylglycine |
| AS 82 | n-Undecyl-N,N-Dimethlamine-oxide |
| AS 60 | n-Heptyl-β-D-thioglucopyranoside |
| AS 25 | ANAPOE ®-$C_{12}E_{10}$ |
| AS 54 | Pluronic ® F-68 |
| AS 53 | C-HEGA ®-11 |
| AS 55 | HECAMEG ® |
| AS 29 | ANAPOE ®-X-405 |
| AS 17 | ANAPOE ®-20 (Tween ® 20) |
| AS 56 | n-Octyl-β-D-glucoside |
| AS 96 | LysoFos ™ Choline 10 |
| AS 59 | 2,6-Dimethyl-4-heptyl-β-D-malto-pyranoside |
| AS 57 | n-Octanoylsucrose |
| AS 31 | ANAPOE ®-$C_{10}E_6$ |
| AS 74 | NDSB-201 |
| AS 12 | ANAPOE ®-58 |
| AS 34 | ANAPOE ®-$C_{10}E_9$ |
| AS 19 | ANAPOE ®-35 |

8.10.2 Modification of 4-MU and HMU Substrates for NBS

Droplet actuator-based lysosomal enzyme tests used in newborn testing assays (NBS) are fluorescent based tests which measure the release of 4-methylumbelliferone (4-MU) or 6-hexadecanoylamido-4-methylumbelliferone (HMU) after enzymatic hydrolysis of the substrates. The enzymatic assays of the invention may be performed in aqueous droplets within the oil filled gap of the droplet actuator. In one example, the oil filler fluid may be polydimethylsiloxane silicon oil (PDMS). The lysosomal enzyme tests are performed at acidic pH values ranging between pH 2.8 and pH 5.6. In some embodiments after incubation, the enzymatic reactions may be terminated by the addition of sodium bicarbonate, pH 10.1 which also dissociates the proton from the umbelliferone hydroxyl leading to a substantial increase in fluorescent signal. At the acid pH values used for testing lysosomal enzymes, the products of the assays, 4-MU and HMU, are protonated and may partition from the aqueous droplet into the PDMS filler fluid. Partitioning of 4-MU and HMU into the oil phase may result in a reduction in the assay signal and potential contamination of neighboring samples.

The invention provides methods to substantially reduce or eliminate the oil solubility of umbelliferyl derivatives (e.g., 4-MU and HMU) during fluorescent based assays (e.g., NBS samples, assays, glycosidase, protease, and immunoassays) on a droplet actuator. In one embodiment, chemical modification of 4-MU and HMU may be used to form derivatives with substantially reduced solubility in the oil filler fluid (e.g., PDMS). Examples of chemical modifications that may be used to reduce the oil solubility of umbelliferyl derivatives may include addition of amino groups, carbon chain length, tethering 4-MU or HMU with molecules such as cellulose or polylysine. Chemical modification(s) may be selected such that activity and/or specificity of the enzymatic reaction (e.g., various lysosomal enzyme assays) are not substantially altered (disrupted). Chemical modification(s) may also be selected such that the fluorescent signal of 4-MU or HMU is not eliminated. Preferably, retaining enough fluorescent signal of 4-MU or HMU to distinguish a positive or negative in the test. Chemical modification(s) may also be selected such that the umbelliferyl derivatives are compatible with downstream synthetic reactions used to prepare individual assay substrates. Chemical modification(s) may also be selected such that the umbelliferyl derivatives have sufficient water solubility suitable for specific NBS assays. In one example, the water solubility of umbelliferyl derivatives may be selected for assay conditions ranging between pH 3.5 and pH 6.0. Suitable umbelliferyl derivatives may, for example, be selected using the Log D values at pH 3.5 and pH 6.0.

In one example, the 4-methyl group of 4-MU and HMU may be modified with a chemical structure that increases the hydrophilicity of 4-MU and HMU. Because the 4-MU and HMU derivatives are hydrophilic, retention of the fluorescent derivatives in the aqueous phase reaction droplet is substantially increased. Examples of suitable chemical structures that may be used to modify 4-MU and HMU to increase their hydrophilicity include, but are not limited to, polymers including linear or branched polyalkalene glycols (PAG), such as polyethylene glycols (PEG), and/or polypropylene glycols (PPG), or combinations of PEG and PPG; sulfonic acids; and amino groups. The efficacy of chemical modification in promoting retention of 4-MU and HMU in the aqueous phase may, for example, be evaluated using an on-chip partitioning assay.

The compounds described herein are analogs of 4-methylumbilliferone (4-MU) and 6-hexadecanoyl-4-methylumbelliferone.

The 4-MU analogs have one of the following general formulas:

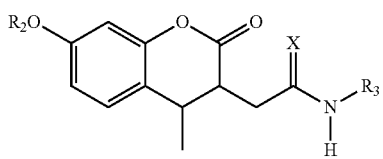

Formula 1

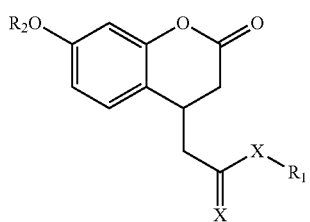

Formula 2

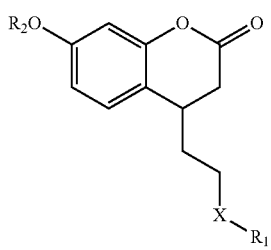

Formula 3

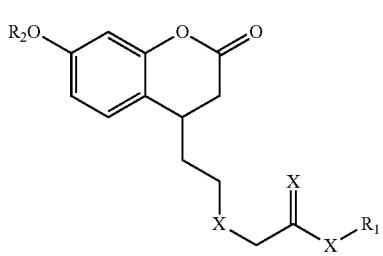

Formula 4

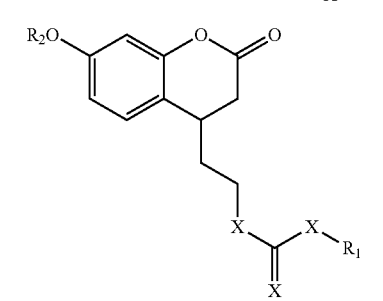

Formula 5 wherein:
X is, independently, selected from the group consisting of O, S, and NH,
$R_1$ is selected from the group consisting of H, $C_{1-15}$ oxyalkyl, —$C_{1-15}$ aminoalkyl, —$C_{1-15}$ alkylamino, —(CH$_2$CH$_2$O)$_n$—CH$_3$, —(CH$_2$CH$_2$O)$_n$—SO$_3$H, $C_{1-6}$-alkyl-C(O)NH$_2$, —(CH$_2$CH$_2$NH)$_n$—H, —SO$_3$H, —$C_{1-6}$-alkyl-C(O)OH, —SO$_3$Me, $C_{1-6}$-alkyl-heterocyclyl, monosaccharides, and disaccharides
$R_2$ is H, a monosaccharide, a disaccharide, or a polyhydric alcohol;
$R_3$ is a hydrophilic oligomer or polymer, which can be selected from the group consisting of polyalkylene glycols, such as polyethylene glycol, wherein the polyalkylene glycols can optionally further include NH or S moieties; polycationic polymers such as polylysine; carbohydrates, including mono-saccharides and disaccharides, $C_{1-15}$ oxyalkyl, —$C_{1-15}$ aminoalkyl, —$C_{1-15}$ alkylamino, —(CH$_2$CH$_2$O)$_n$—CH$_3$, —(CH$_2$CH$_2$O)$_n$—SO$_3$H, $C_{1-6}$-alkyl-C(O)NH$_2$, —(CH$_2$CH$_2$NH)$_n$—H, —SO$_3$H, —$C_{1-6}$-alkyl-C(O)OH, —SO$_3$Me, $C_{1-6}$-alkyl-heterocyclyl, monosaccharides, and disaccharides,
and n is an integer of from 1 to 100, or from 1 to 50, or from 1 to 25, or from 1 to 10.

The hydrophilic polymer or oligomer can be any of a variety of oligomers comprising a polyalkalene glycol moiety, as will be understood by those skilled in the art. Preferably, the polyalkalene glycol moiety of the oligomer has 1-100 polyalkalene glycol subunits. More preferably, the polyalkalene glycol moiety has 1-50 polyalkalene glycol subunits and, most preferably, the polyalkalene glycol moiety has 1-25 polyalkalene glycol subunits.

The hydrophilic polymer or oligomer can be any of a variety of oligomers comprising a polyethylene glycol moiety, as will be understood by those skilled in the art. Preferably, the polyethylene glycol moiety of the oligomer has 1-100 polyethylene glycol subunits. More preferably, the polyethylene glycol moiety has 1-50 polyethylene glycol subunits and, most preferably, the polyethylene glycol moiety has 1-25 polyethylene glycol subunits.

The hydrophilic polymer or oligomer can be any of a variety of oligomers comprising a polypropylene glycol moiety, as will be understood by those skilled in the art. Preferably, the polypropylene glycol moiety of the oligomer has 1-100 polypropylene glycol subunits. More preferably, the polypropylene glycol moiety has 1-50 polypropylene glycol subunits and, most preferably, the polypropylene glycol moiety has 1-25 polypropylene glycol subunits.

Additional hydrophilic oligomers and polymers include those containing polar or charged functional groups, rendering them soluble in water. For example, acrylics include acrylic acid, acrylamide, and maleic anhydride polymers and copolymers Amine-functional polymers include allylamine, ethyleneimine, oxazoline, and other polymers containing amine groups in their main- or side-chains, such as polylysine. These may be combined with PAGs.

The oligomer may comprise one or more other moieties as will be understood by those skilled in the art including, but not limited to, additional hydrophilic moieties, lipophilic moieties, spacer moieties, linker moieties, and terminating moieties. The various moieties in the oligomer are covalently coupled to one another by either hydrolyzable or non-hydrolyzable bonds.

The or more additional hydrophilic moieties (i.e., moieties in addition to the polyethylene glycol moiety) can include, but are not limited to, sugars, polyhydric alcohols, polyalkylene oxides, and polyamine/PEG copolymers. As polyethylene glycol is a polyalkylene oxide, the additional hydrophilic moiety may be a polyethylene glycol moiety. Adjacent polyethylene glycol moieties will be considered to be the same moiety if they are coupled by an ether bond. For example, the moiety —O—C$_2$H$_4$—O—C$_2$H$_4$—O—C$_2$H$_4$—O—C$_2$H$_4$—O—C$_2$H$_4$—O—C$_2$H$_4$— is a single polyethylene glycol moiety having six polyethylene glycol subunits. Adjacent polyethylene glycol moieties will be considered to be different moieties if they are coupled by a bond other than an ether bond.

The oligomer can further comprise one or more spacer moieties as will be understood by those skilled in the art.

Spacer moieties are preferably selected from the group consisting of sugar, cholesterol and glycerine moieties.

The oligomer can further comprise one or more terminating moieties at the one or more ends of the oligomer, which are not coupled to the 4-HU or 6HMU backbone. The terminating moiety is preferably an alkyl or alkoxy moiety, and is more preferably a lower alkyl or lower alkoxy moiety (where lower means $C_{1-6}$). Most preferably, the terminating moiety is methyl or methoxy. While the terminating moiety is preferably an alkyl or alkoxy moiety, it is to be understood that the terminating moiety may be various moieties as will be understood by those skilled in the art including, but not limited to, sugars, cholesterol, alcohols, and fatty acids. The oligomer or polymer may include one or more anionic or self-forming moietes, such as tertiary anion.

A subset of Formulas 1-5 is shown below, in which each $R_2$ is H.

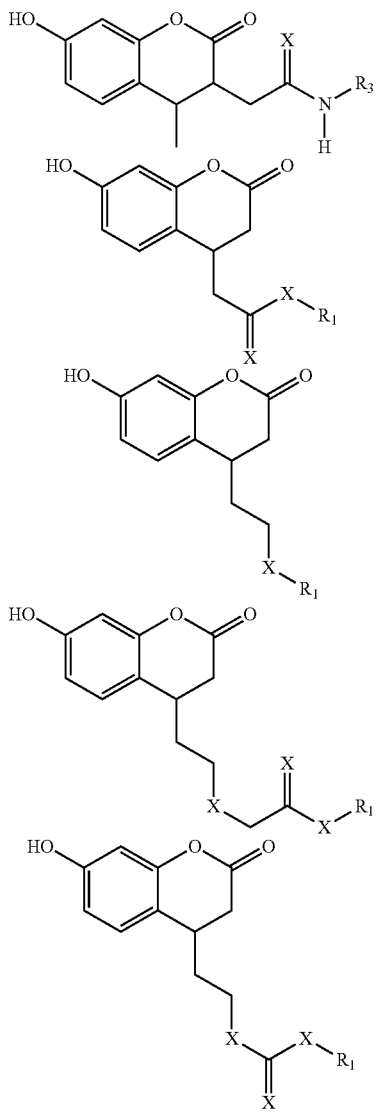

wherein:
$R_1$ is selected from the group consisting of H, $C_{1-15}$ oxyalkyl, —$C_{1-15}$ aminoalkyl, —$C_{1-15}$ alkylamino, —(CH$_2$CH$_2$O)$_n$—CH$_3$, —(CH$_2$CH$_2$O)$_n$—SO$_3$H, $C_{1-6}$-alkyl-C(O)NH$_2$, —(CH$_2$CH$_2$NH)$_n$—H, —SO$_3$H, —$C_{1-6}$-alkyl-C(O)OH, —SO$_3$Me, $C_{1-6}$-alkyl-heterocyclyl, monosaccharides, and disaccharides.

$R_3$ is a linear or branched hydrophilic oligomer or polymer, which can be selected from the group consisting of polyalkylene glycols, such as polyethylene glycol, wherein the polyalkylene glycols can optionally further include NH or S moieties; polycationic polymers such as polylysine; carbohydrates, including mono-saccharides and disaccharides, $C_{1-15}$ oxyalkyl, —$C_{1-15}$ aminoalkyl, —$C_{1-15}$ alkylamino, —(CH$_2$CH$_2$O)$_n$—CH$_3$, —(CH$_2$CH$_2$O)$_n$—SO$_3$H, $C_{1-6}$-alkyl-C(O)NH$_2$, —(CH$_2$CH$_2$NH)$_n$—H, —SO$_3$H, —$C_{1-6}$- alkyl-C(O)OH, —SO$_3$Me, $C_{1-6}$-alkyl-heterocyclyl, monosaccharides, and disaccharides.

X is, independently, selected from the group consisting of O, S, and NH, and n is an integer of from 1 to 100, or 1 to 50, or 1 to 25, or 1 to 10.

Representative sugar moieties that can be coupled to the 4-MU core structure at position $R_2$ include, but are not limited to:

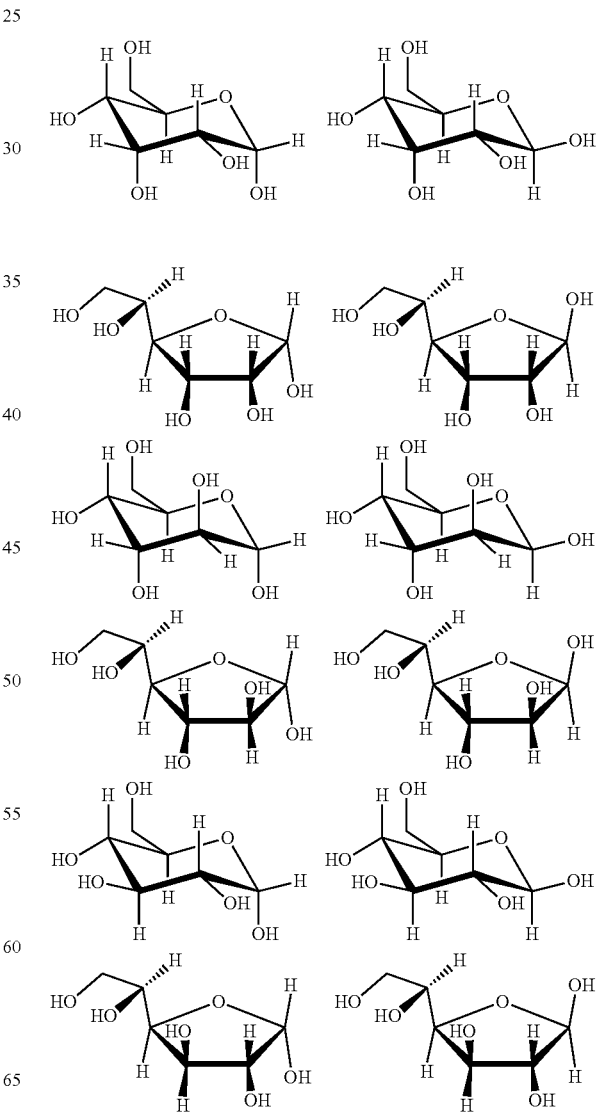

-continued

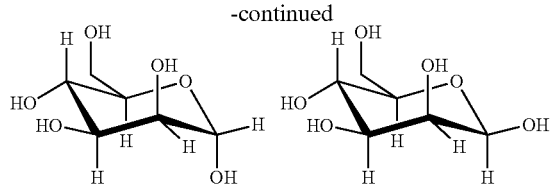
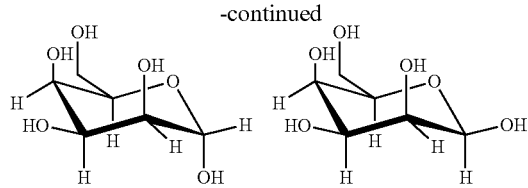

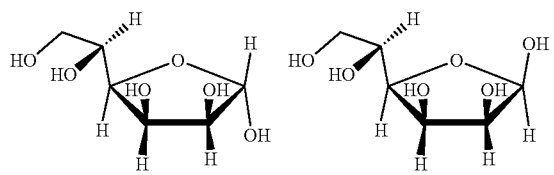
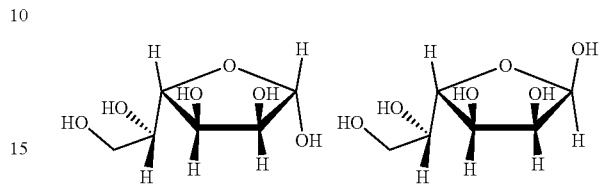

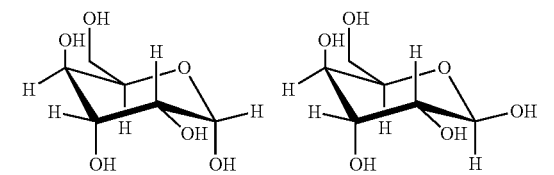

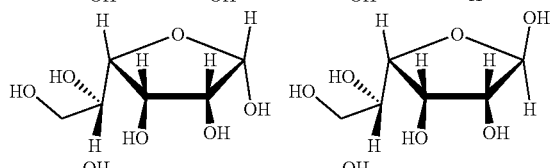

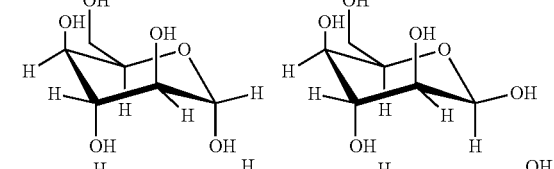

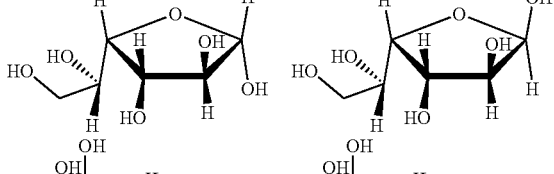

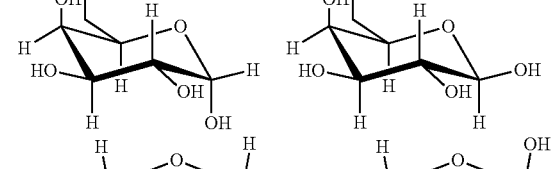

The sugar moieties shown are a-pyranose, b-pyranose, a-furanose, and b-furanose forms of allose, altrose, glucose, mannose, gulose, idose, galactose and talose, respectively. The sugar moeities can be attached to the phenol moiety to form an ether linkage using etherification techniques, ideally those in which the hydroxy groups not involved in the coupling chemistry are protected during the etherification step, and deprotected at a later time in the overall synthesis. Suitable protecting groups are described, for example, in Greene and Wuts, Protective Groups in Organic Synthesis, $3^{rd}$ Ed., John Wiley & Sons, 1999, the contents of which are hereby incorporated by reference.

Where glucose is the sugar, and reacts with the phenol at $R_2$, the resulting compound is known as a glucopyranoside. For formation of glucopyranosides is well known to those of skill in the art.

Ribose and deoxyribose sugars can also be coupled to the phenol at position $R_2$:

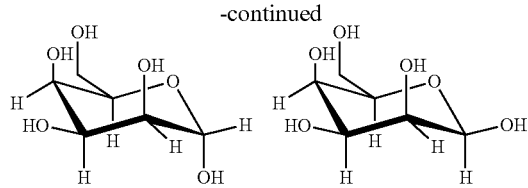

Representative polyhydric alcohols include glycol (2-carbon), glycerol (3-carbon), erythritol (4-carbon), threitol (4-carbon), arabitol (5-carbon), xylitol (5-carbon), ribitol (5-carbon), mannitol (6-carbon), sorbitol (6-carbon), dulcitol (6-carbon), iditol (6-carbon), isomalt (12-carbon), maltitol (12-carbon), lactitol (12-carbon), and polyglycitol.

Examples of individual 4-MU analogs include the following:

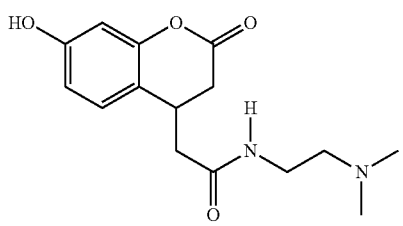
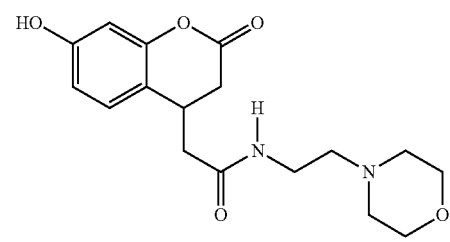

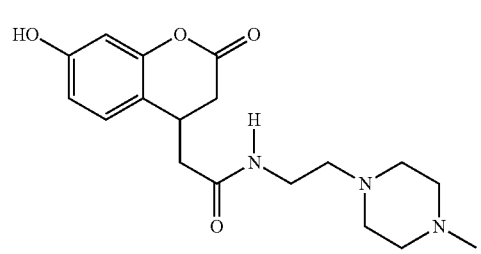
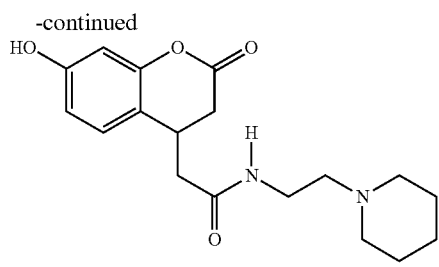
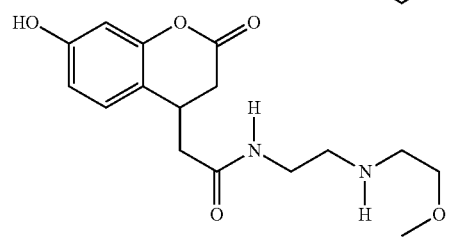
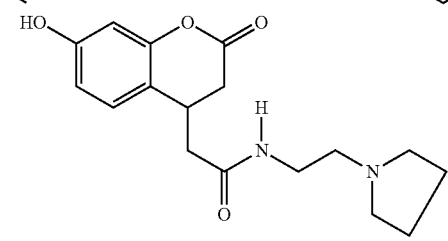
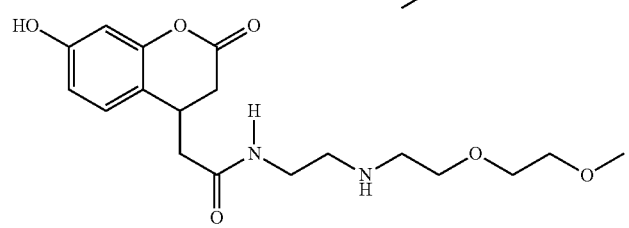
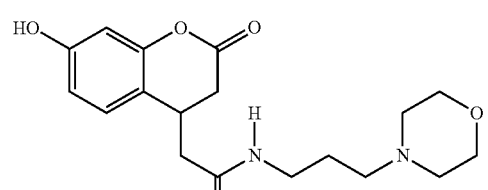
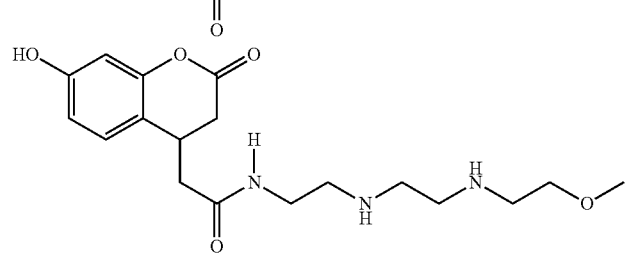
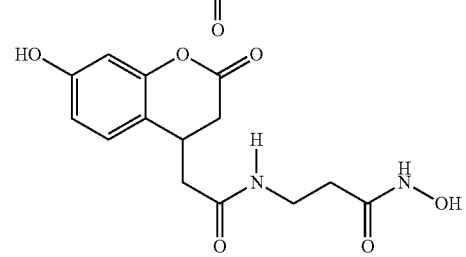
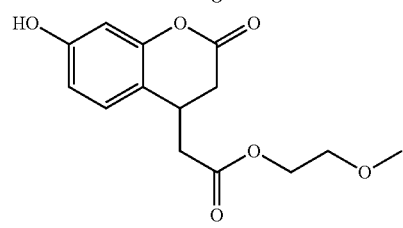
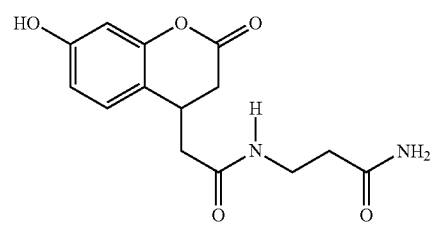
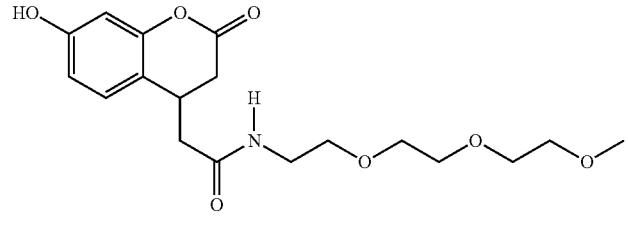
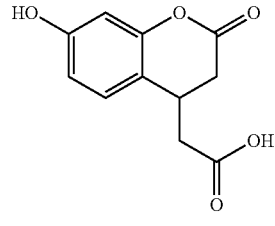
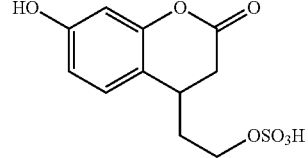
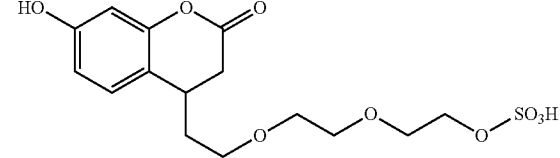

-continued
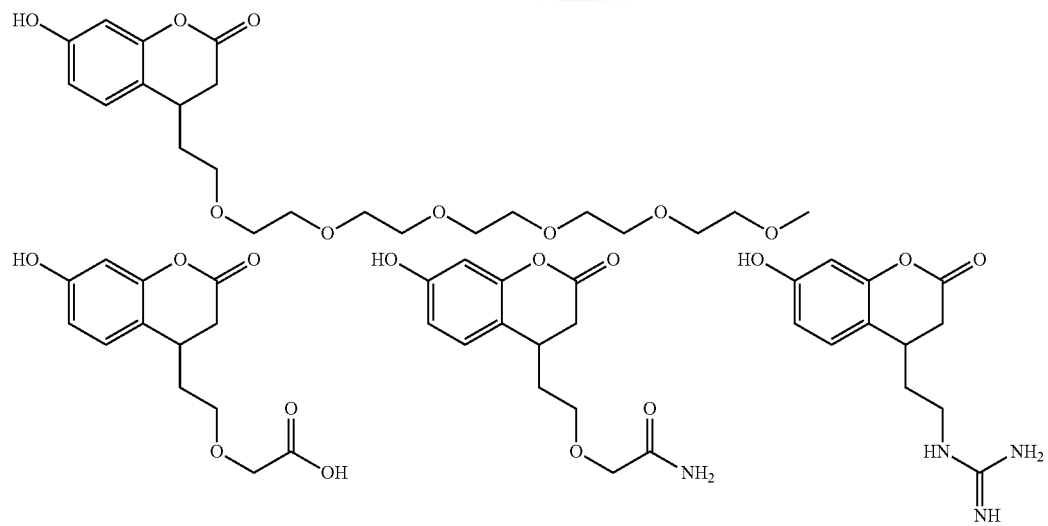
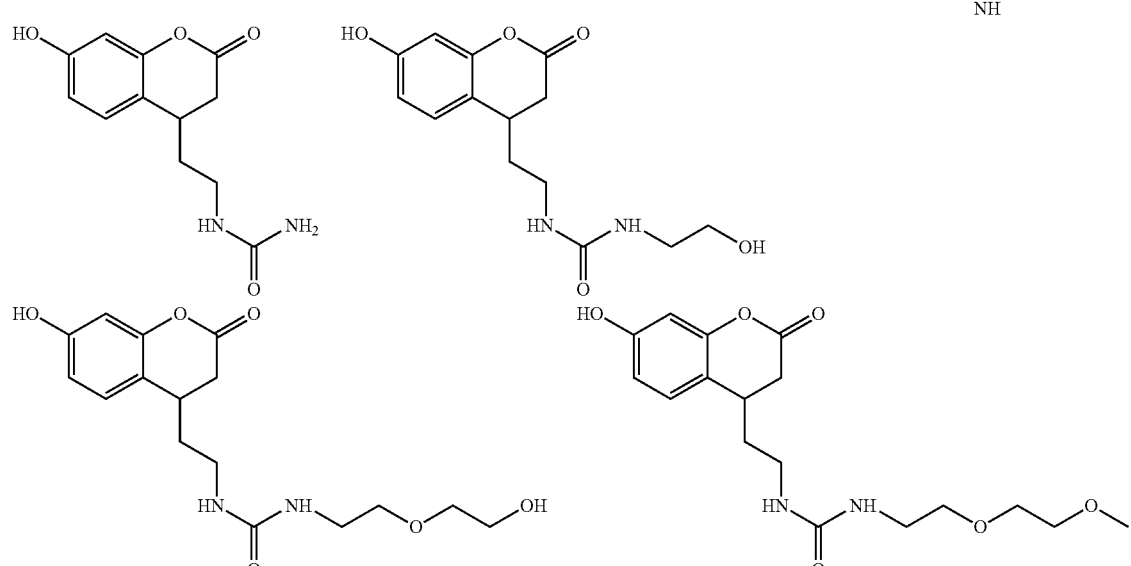
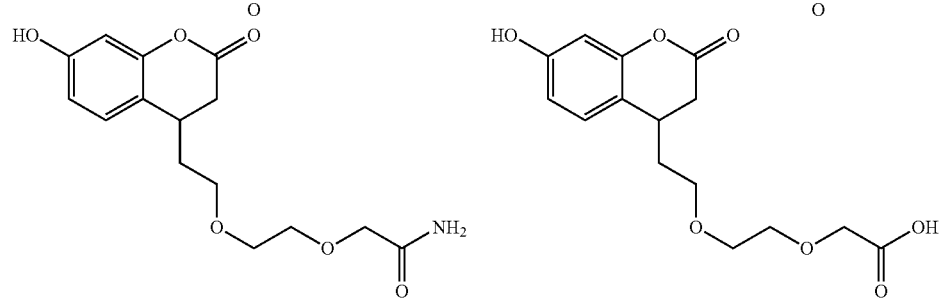
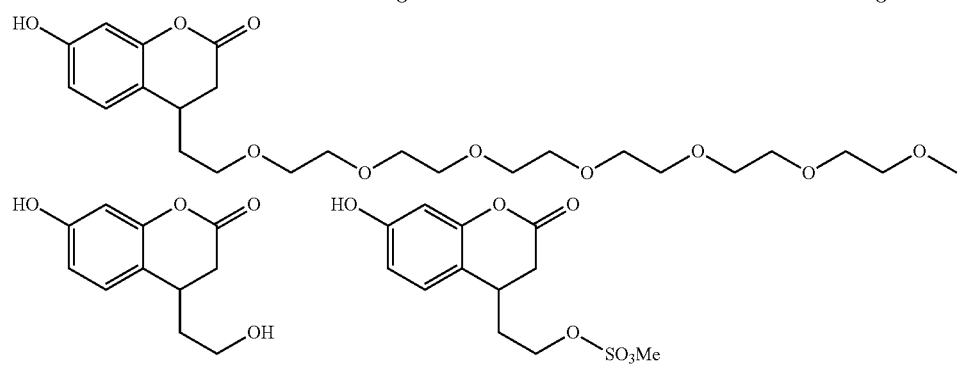

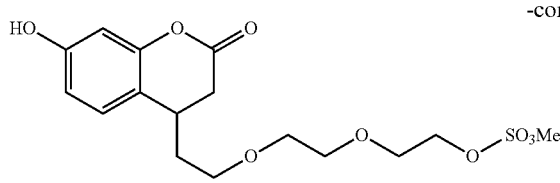

-continued

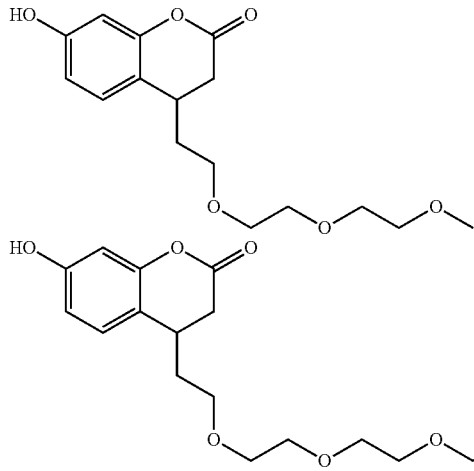

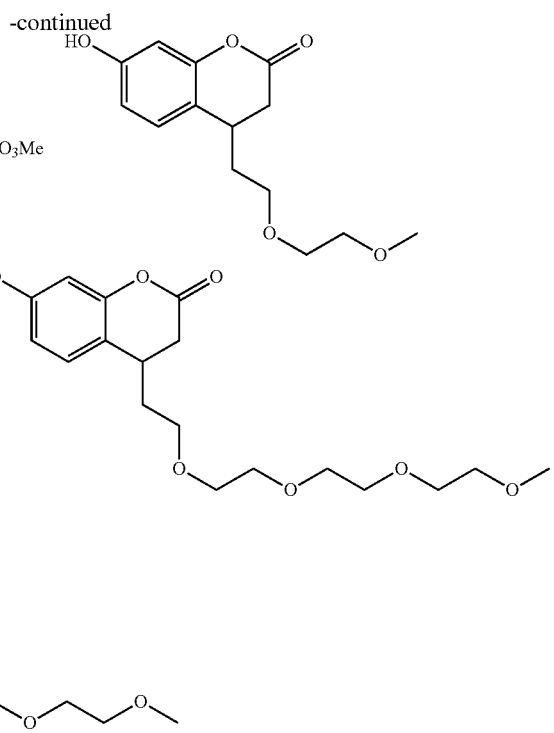

versions thereof in which one or more amines is quaternized to yield a quaternary ammonium salt, and salts thereof.

Examples of individual 4-HMU analogs that may be used in the methods for conducting enzymatic assays as described herein may include the structures as shown in FIGS. 35A-H.

The compounds of Formula 1 can be prepared according to the following general synthetic strategies:

Starting from 4-methylcoumarin-3-acetic acid, succinimidyl ester (AnaSpec, Catalog No. 81239):

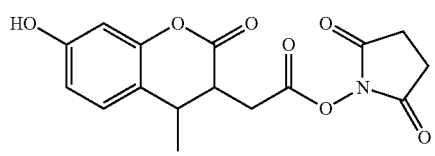 [SMILES: CC1c2ccc(O)cc2OC(=O)C1CC(=O)ON1C(=O)CCC1=O]

Reaction with a suitable amine-containing moiety ($R_3$—$NH_2$) displaces the succinimidyl (NHS) ester and forms an amide linkage:

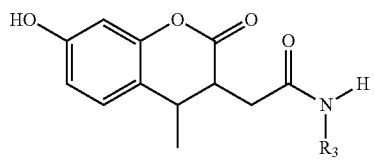

NHS-ester crosslinking reactions are most commonly performed in phosphate, bicarbonate/carbonate, HEPES or borate buffers at pH 7.2-8.5 for 0.5-4 hours at room temperature or 4° C. Primary amine buffers such as Tris (TBS) are not compatible because they compete for reaction; however, in some procedures, it is useful to add Tris or glycine buffer at the end of a conjugation procedure to quench (stop) the reaction.

To prepare compounds in which a thioamide or C(NH)—$NHR_3$ moiety is present, one can start with an analog in which the carbonyl in the succinimidyl ester is replaced with a C(S) or a C(NH) moiety.

To prepare compounds of Formula 2, one can use the following reactions:

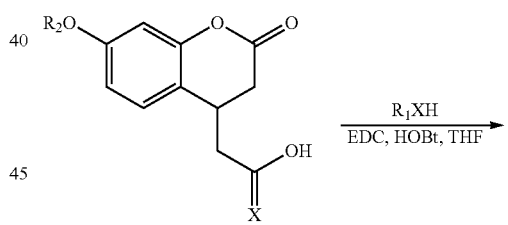

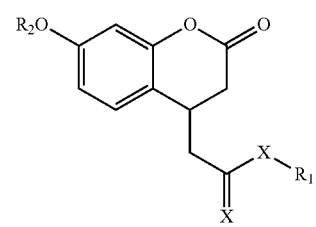

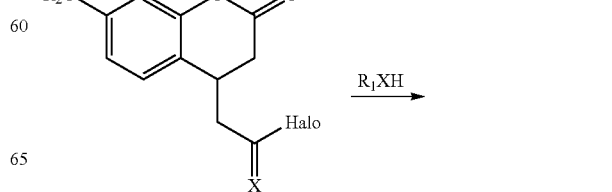

-continued

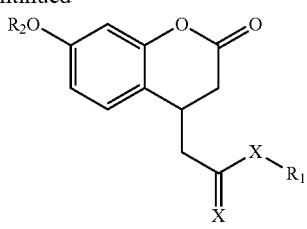

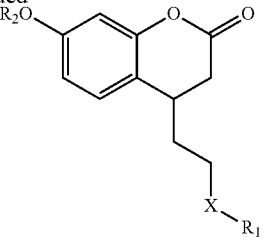

In these reactions, the phenol, if present at position $R_2$, should be protected until after the coupling chemistry is completed.

Suitable $C_{1-15}$ oxyalkyl, —$C_{1-15}$ aminoalkyl, —$C_{1-15}$ alkylamino, —$(CH_2CH_2O)_n$—$CH_3$, —$(CH_2CH_2O)_n$—$SO_3H$, $C_{1-6}$-alkyl-C(O)NH$_2$, —$(CH_2CH_2NH)_n$—H, —$SO_3H$, —$C_{1-6}$-alkyl-C(O)OH, —$SO_3Me$, $C_{1-6}$-alkyl-heterocyclyl, monosaccharides, disaccharides, and other moieties are well known to those of skill in the art, and can readily be prepared.

In the case of ester formation, one can reflux the desired alcohol with the carboxylic acid (where X is O) moiety and, using a Dean-Stark trap, remove water as it is formed to drive the equilibrium towards products.

To prepare compounds of Formula 3, one can use the following reactions:

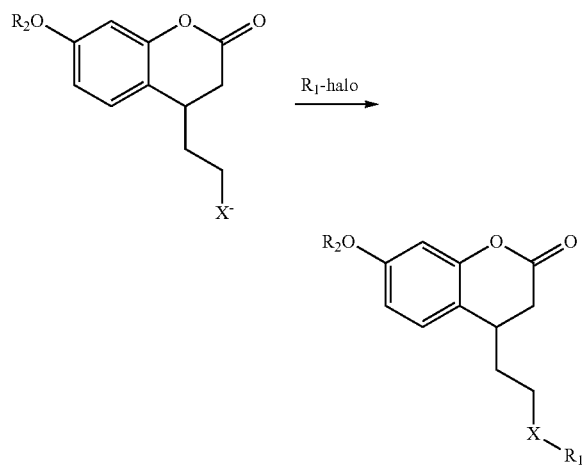

where the carbon on $R_1$ bonded to the halogen (preferably Cl, Br, or I), or, alternatively, another suitable leaving group, is a primary or secondary carbon.

In these reactions, the phenol, if present at position $R_2$, should be protected until after the coupling chemistry is completed.

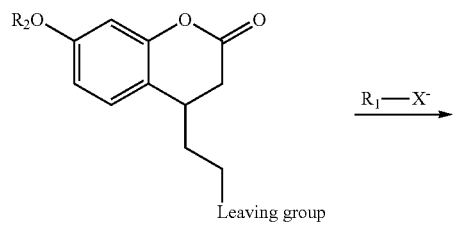

where X is an alkoxy or thioalkoxy moiety. When X is an amine, the amine can be used to displace the leaving group, without needing to deprotonate the amine (i.e., without needing to form $R_1$—$NH^-$).

To prepare compounds of Formula 4, one can use the following reaction:

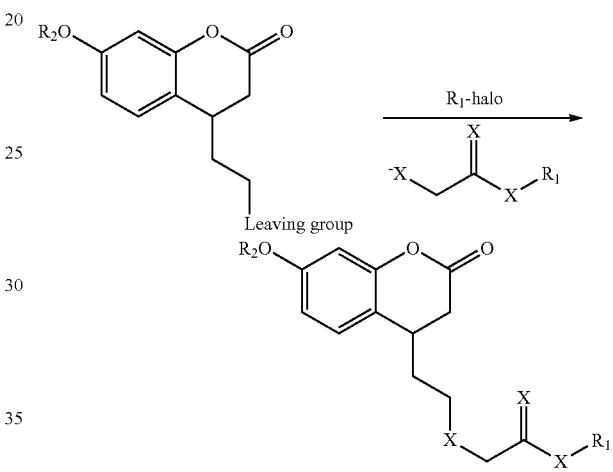

where X is an alkoxy or thioalkoxy moiety. When X is an amine, the amine can be used to displace the leaving group, without needing to deprotonate the amine (i.e., without needing to form $R_1$—$NH^-$).

Alternatively, the chemistry can be performed in a stepwise manner, where a moiety HX—CH$_2$—C(O)—XH is deprotonated, and the more basic X$^-$ anion (i.e., the one attached to the CH$_2$ moiety rather than the C(O) moiety) acts as a nucleophile to displace the leaving group. Then, the less basic X$^-$ anion can be protonated, and converted to a suitable leaving group (i.e., an acid halide, an anhydride, and the like), and an RAH moiety reacted with the leaving group to form the final product.

In these reactions, the phenol, if present at position $R_2$, should be protected until after the coupling chemistry is completed.

To prepare compounds of Formula 4, one can use the following reaction:

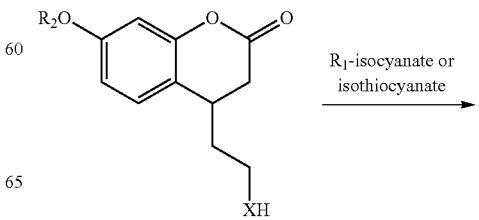

-continued

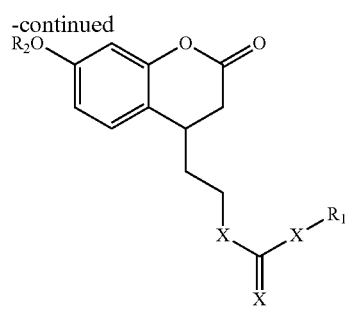

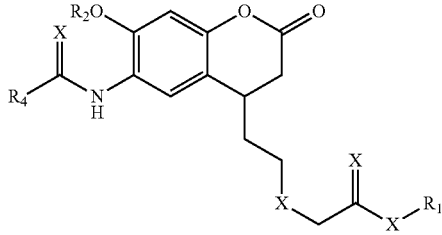

Formula 9

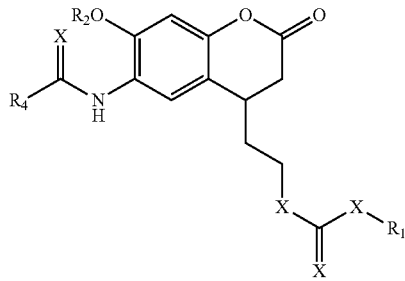

Formula 10

In this reaction, the phenol, if present at position $R_2$, should be protected until after the coupling chemistry is completed. Similarly, any functional groups on $R_1$ that would otherwise react with the isocyanate should be protected.

Examples of the 6-HMU analogs have the following general formulas:

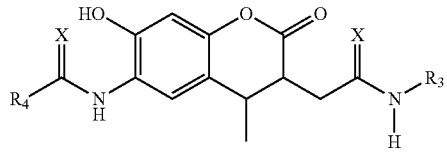

Formula 6

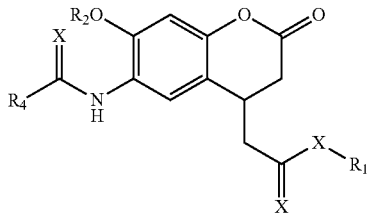

Formula 7

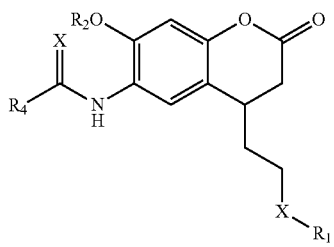

Formula 8 wherein:
X is, independently, selected from the group consisting of O, S, and NH,
$R_1$ is selected from the group consisting of H, $C_{1-15}$ oxyalkyl, —$C_{1-15}$ aminoalkyl, —$C_{1-15}$ alkylamino, —$(CH_2CH_2O)_n$—$CH_3$, —$(CH_2CH_2O)_n$—$SO_3H$, $C_{1-6}$-alkyl-C(O)NH$_2$, —$(CH_2CH_2NH)_n$—H, —$SO_3H$, —$C_{1-6}$-alkyl-C(O)OH, —$SO_3Me$, $C_{1-6}$-alkyl-heterocyclyl, monosaccharides, and disaccharides.
$R_2$ is H, a monosaccharide, a disaccharide, or a polyhydric alcohol;
$R_3$ is a hydrophilic oligomer or polymer, which can be selected from the group consisting of polyalkylene glycols, such as polyethylene glycol, wherein the polyalkylene glycols can optionally further include NH or S moieties; polycationic polymers such as polylysine; carbohydrates, including mono-saccharides and disaccharides, $C_{1-15}$ oxyalkyl, —$C_{1-15}$ aminoalkyl, —$C_{1-15}$ alkylamino, —$(CH_2CH_2O)_n$—$CH_3$, —$(CH_2CH_2O)_n$—$SO_3H$, $C_{1-6}$-alkyl-C(O)NH$_2$, —$(CH_2CH_2NH)_n$—H, —$SO_3H$, —$C_{1-6}$-alkyl-C(O)OH, —$SO_3Me$, $C_{1-6}$-alkyl-heterocyclyl, monosaccharides, and disaccharides.
$R_4$ is a $C_{5-16}$ alkyl, oxyalkyl, or amino-oxyalkyl, moiety, and n is an integer of from 1 to 100, or 1 to 50, or 1 to 25, or 1 to 10 and
Versions thereof in which one or more amines is quaternized to yield a quaternary ammonium salt, and salts thereof.
Examples of individual 6-HMU analogs include the following:

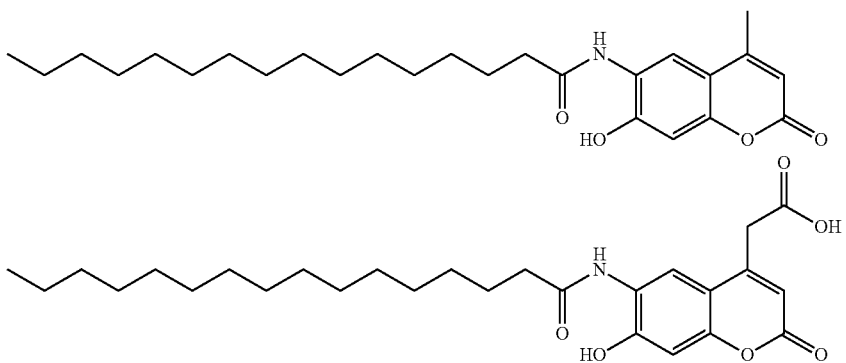

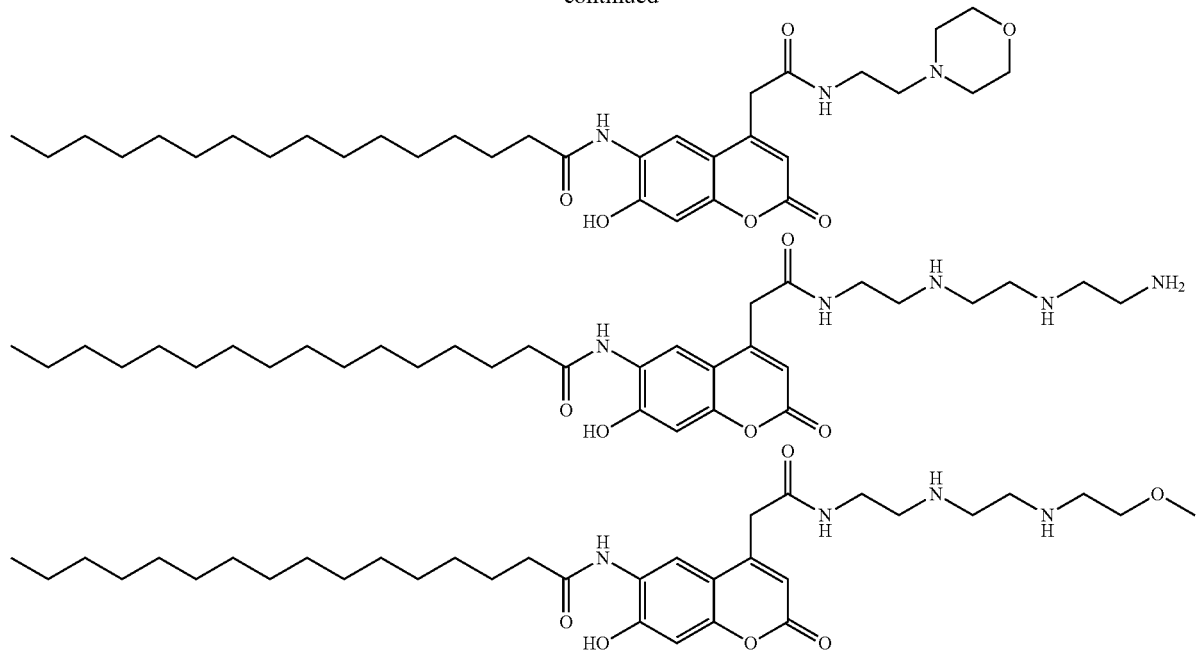

Examples of individual 6-HMU analogs may further include the structures as shown in FIGS. 36 A-H.

The compounds of Formulas 6-10 can be prepared using the same general reactions used to prepare the compounds of Formulas 1-5, except that the starting materials further include a —NH—C(X)—$R_4$ moiety. The amide, thioamide, or —C(NH)—NH— moiety is non-reactive under the coupling conditions used to prepare the compounds, so can be present at the time the coupling chemistry is performed. Alternatively, a protected aniline moiety (next to the phenol moiety) can be present, and can be deprotected at an appropriate time after the coupling chemistry is complete. From there, the aniline group can be reacted with a suitable acid chloride (i.e., $R_4$—C(O)-halo), or acid anhydride ($R_4$—C(O)—O—C(O)—$R_4$) to form an amine.

8.11 Enhanced Hydrolysis of Enzymatic Substrates

Fluorescent substrates used in enzymatic NBS assays may have varying degrees of hydrophobicity. Because the fluorescent substrates may be hydrophobic, their interaction with more hydrophilic enzymes, such as the enzymes in dried blood extracts, may be reduced. The invention provides methods to enhance the hydrolysis of enzymatic substrates such as fluorescent substrates used in NBS assays. In one embodiment, the hydrolysis of enzymatic substrates (e.g., 4-MU- or HMU-containing substrates) may be enhanced by formation of an inclusion complex that stabilizes the substrate within an aqueous environment. For example, cyclodextrins (e.g., hydroxypropyl-β-cyclodextrin, methyl-β-cyclodextrin) may be used to form an inclusion complex containing a hydrophobic substrate. Negatively charged cyclodextrins, may be used to further enhance substrate hydrolysis. The methods of the invention provide for improved separation between a lower signal and a higher signal in enzyme-substrate based bioassay such as NBS assays for Fabry, Gaucher, Pompe, Krabbe, and Niemann-Pick diseases.

To evaluate the efficacy of cyclodextrins in enhancing the hydrolysis of enzymatic substrates (4-MU substrates) used in NBS assays, DBS extracts were prepared from quality control (QC) dried blood spot samples (i.e., base pool (BP), low (L), medium (M) and high (H) activity samples). The QC samples were obtained from CDC, Atlanta Ga. The base pool (BP) QC sample was prepared from a pool of leukoreduced human red blood cells that was adjusted with serum to a hematocrit of 50%. The High (H) activity QC sample was prepared from pooled cord blood that was adjusted with serum to a hematocrit of 50%. The medium (M) activity QC sample was prepared by using 50% base pool (BP) and 50% high (H) activity sample. The low (L) activity QC sample was prepared by using 95% base pool (BP) and 5% high (H) activity sample. The BP sample is used as a control for hydrolysis non-specific to white blood cell lysosomal enzymes. The DBS extracts were analyzed using on-bench assay protocols for Fabry, Gaucher, Krabbe, and Pompe diseases. For each assay, on-chip reagent formulations were scaled up to bench volumes. Hydroxypropyl-β-cyclodextrin or methyl-β-cyclodextrin reagent stocks (300 mM) were prepared in appropriate assay buffers. For each reaction, 10 μL of the appropriate substrate was mixed with 10 μL of DBS extract. After an incubation period (20 hrs at 37° C.), 50 μL of stop buffer (0.2 M $NaCO_3$, pH 10.1) was added to the reaction. Fluorescence was read at 360/460 nm at a gain of 75. For each assay, QC samples (BP, L, M and H) were analyzed in duplicate.

Figure 20A:
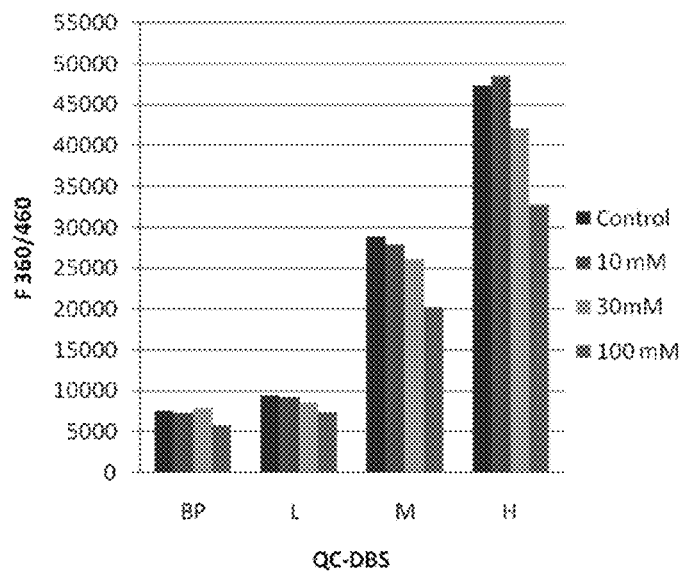
FIGS. 20A and 20B show bar graphs of the effect of hydroxypropyl-β-cyclodextrin and methyl-β-cyclodextrin, respectively, on substrate hydrolysis in a Fabry assay.
Figure 20B:
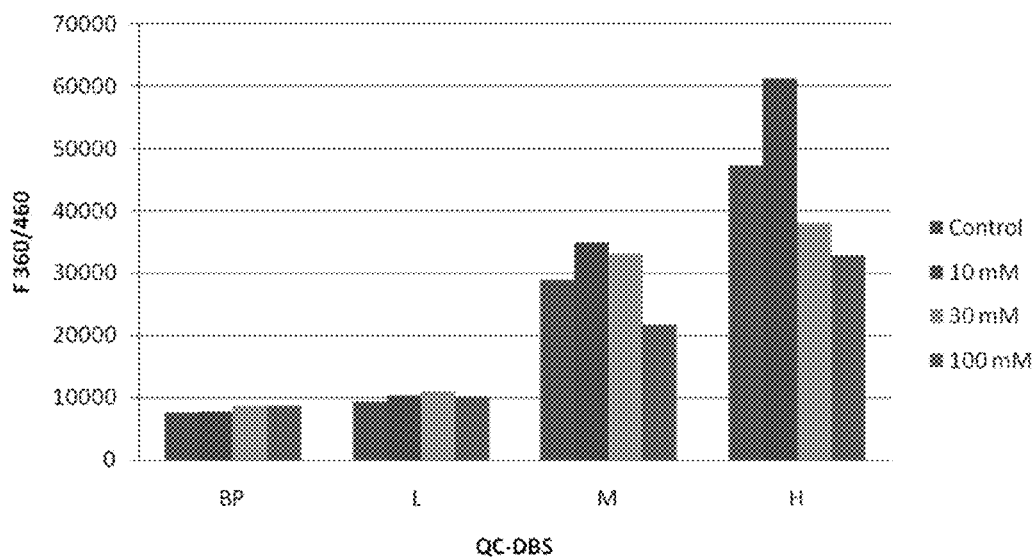

FIGS. 20A and 20B show bar graphs 2000 and 2050 of the effect of hydroxypropyl-β-cyclodextrin and methyl-β-cyclodextrin, respectively, on substrate hydrolysis in a Fabry assay. The 4-MU substrate in the Fabry assay was β-D-galactopyranoside. The concentrations of β-cyclodextrins in the reaction mixture (substrate+DBS extract) were 10 mM, 30 mM and 100 mM. The data show that low concentrations (10 mM) of methyl-β-cyclodextrin increase the hydrolysis of the 4-MU substrate in the Fabry assay and improve the separation between low, medium and high QC-dried blood spot samples. The effect of hydroxypropyl-β-cyclodextrin was less effective.

Figure 21A:
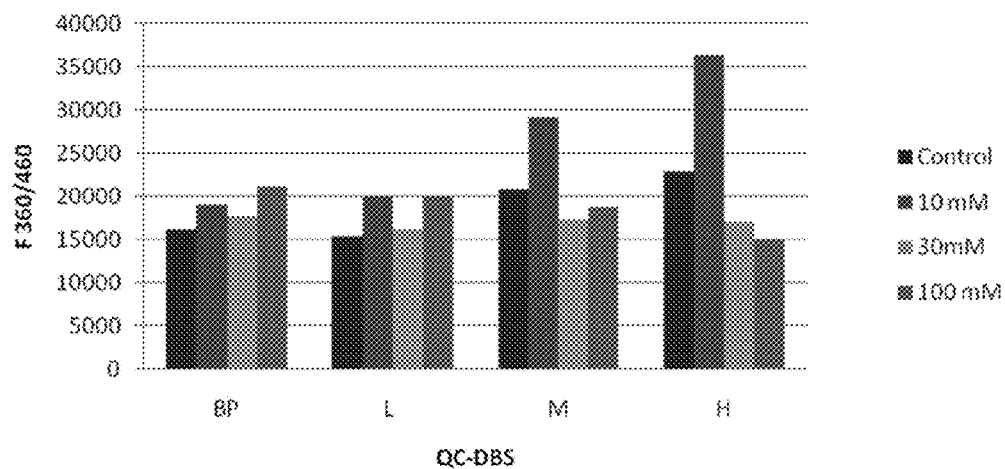
FIGS. 21A and 21B show bar graphs of the effect of hydroxypropyl-β-cyclodextrin and methyl-β-cyclodextrin, respectively, on substrate hydrolysis in a Gaucher assay.
Figure 21B:
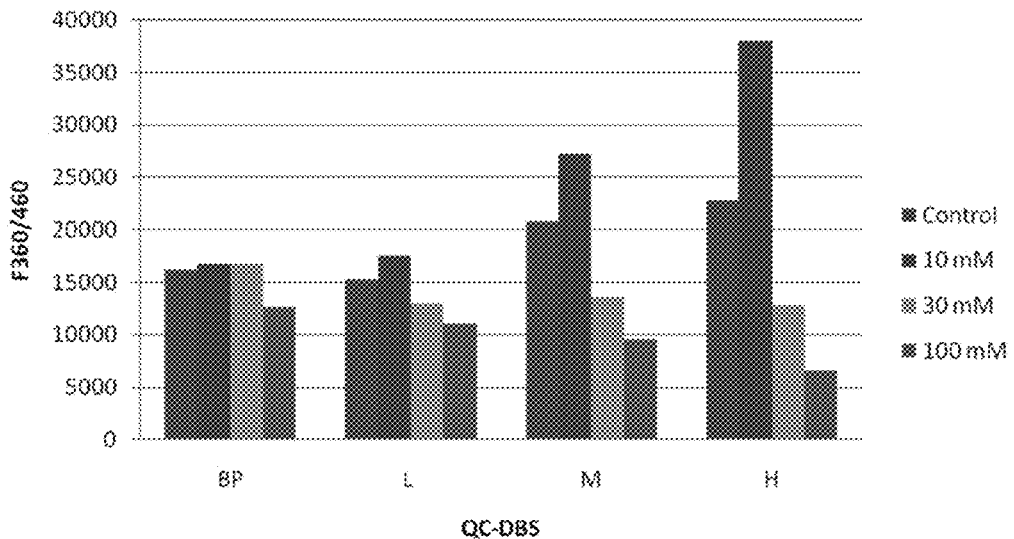

FIGS. 21A and 21B show bar graphs 2100 and 2150 of the effect of hydroxypropyl-β-cyclodextrin and methyl-β-cyclodextrin, respectively, on substrate hydrolysis in a Gaucher assay. The 4-MU substrate in the Gaucher assay was β-D- glucopyranoside. The concentrations of β-cyclodextrins in the reaction mixture (substrate+DBS extract) were 10 mM, 30 mM, and 100 mM. The data show that low concentrations (10 mM) of hydroxypropyl- and methyl-β-cyclodextrin increase the hydrolysis of the 4-MU substrate in the Gaucher assay and improve the separation between low, medium and high QC-dried blood spot samples.

Figure 22A:
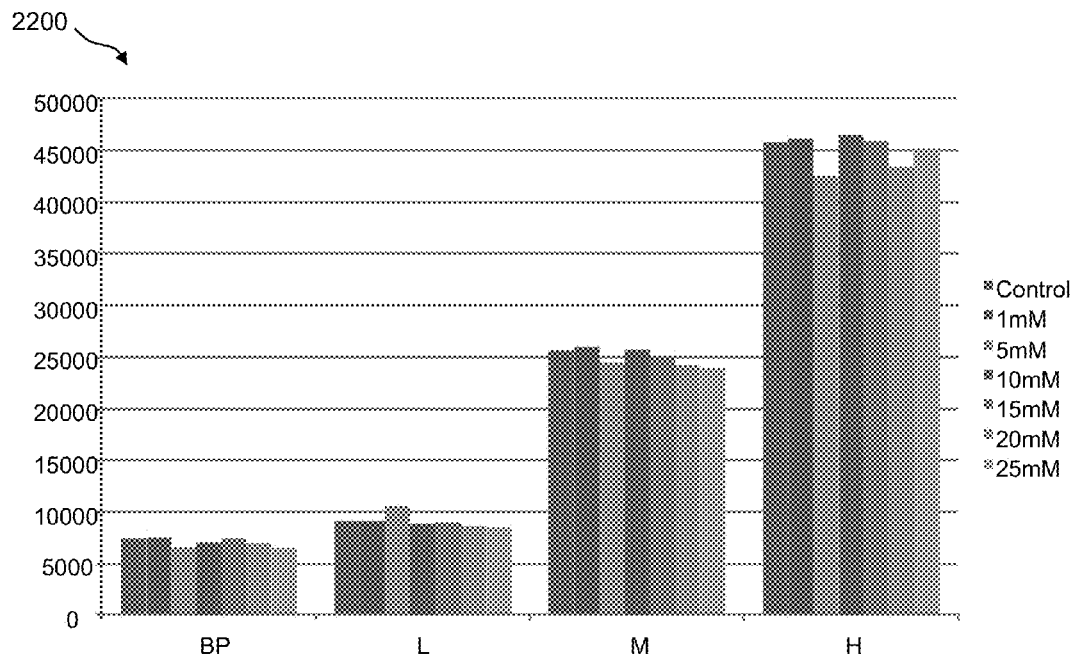
FIGS. 22A and 22B show bar graphs of the effect of lower concentrations of hydroxypropyl-β-cyclodextrin and methyl-β-cyclodextrin, respectively, on substrate hydrolysis in a Fabry assay.
Figure 22B:
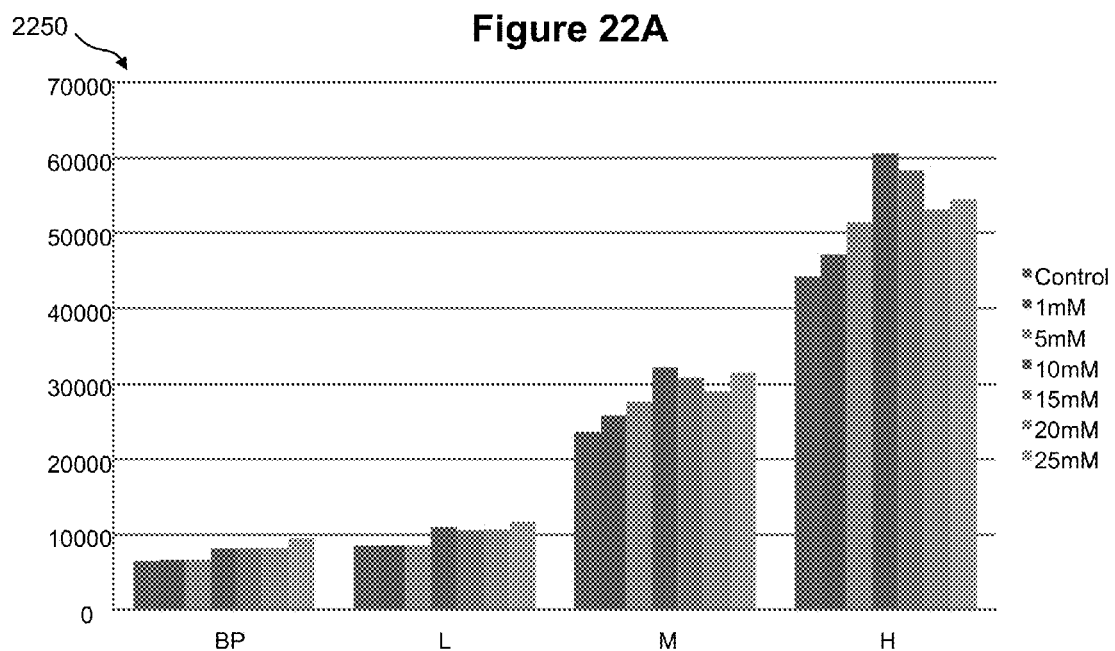

To further evaluate the efficacy of lower concentrations of cyclodextrins in enhancing the hydrolysis of 4-MU substrates, Fabry and Gaucher assays were repeated using cyclodextrins concentrations ranging from 1 mM to 25 mM. FIGS. 22A and 22B show bar graphs 2200 and 2250, respectively, of the effect of lower concentrations of hydroxypropyl-β-cyclodextrin and methyl-β-cyclodextrin, respectively, on substrate hydrolysis in a Fabry assay. The 4-MU substrate in the Fabry assay was β-D-galactopyranoside. The concentrations of β-cyclodextrins in the reaction mixture (substrate+DBS extract) were 1, 5, 10, 15, 20, and 25 mM. The data show that methyl-β-cyclodextrin (10 mM) has a positive effect on the Fabry assay increasing the QC-H signal by 37%. The preferred concentration of methyl-β-cyclodextrin is from about 1 mM to about 20 mM, or from about 5 mM to about 15 mM, or from about 7 mM to about 13 mM, or from about 9 mM to about 11 mM, or from about 9.5 mM to about 11.5 mM. The effect of hydroxypropyl-β-cyclodextrin on substrate hydrolysis in a Fabry assay was less effective.

Figure 23A:
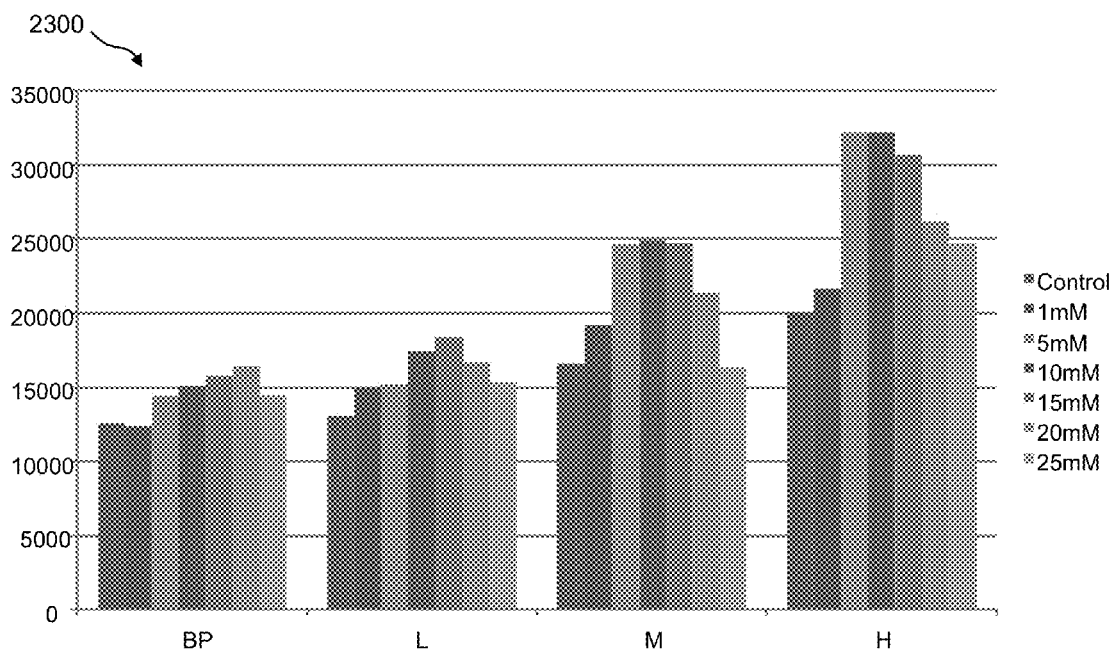
FIGS. 23A and 23B show bar graphs of the effect of lower concentrations of hydroxypropyl-β-cyclodextrin and methyl-β-cyclodextrin, respectively, on substrate hydrolysis in a Gaucher assay.
Figure 23B:
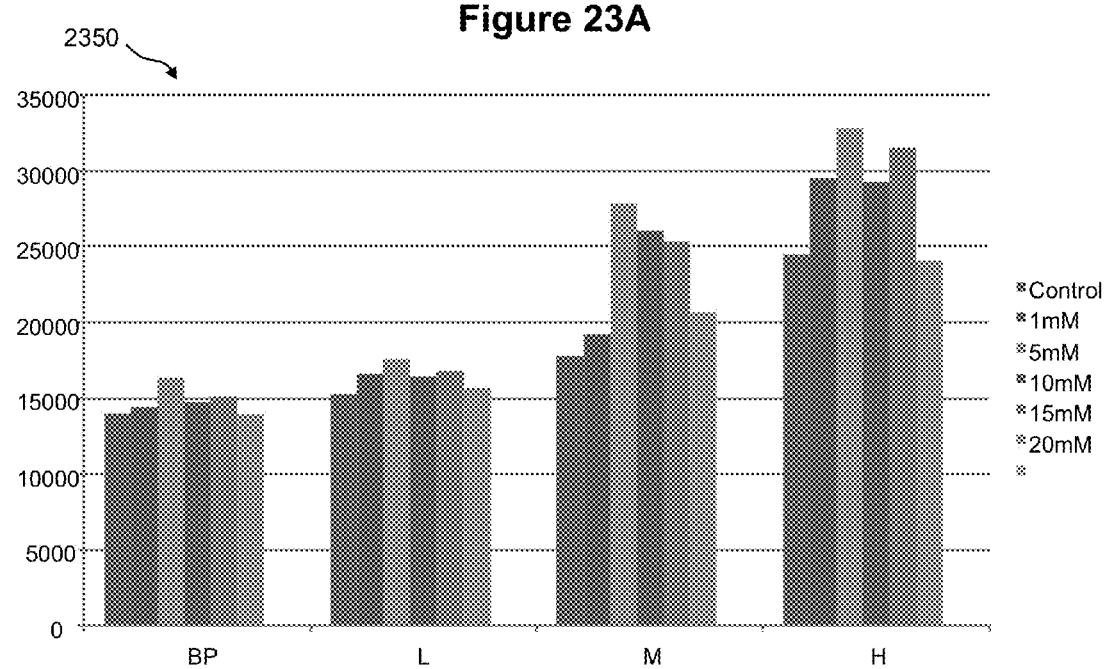

FIGS. 23A and 23B show bar graphs 2300 and 2350, respectively, of an experimental result of the effect of lower concentrations of hydroxypropyl-β-cyclodextrin and methyl-β-cyclodextrin, respectively, on substrate hydrolysis in a Gaucher assay. The 4-MU substrate in the Gaucher assay was β-D-glucopyranoside. The concentrations of β-cyclodextrins in the reaction mixture (substrate+DBS extract) were 1, 5, 10, 15, 20, and 25 mM. The data in one experiment suggested that both hydroxypropyl-β- and methyl-β-cyclodextrin may affect the fluorescence signal (in at least one case showing an increase), in the Gaucher assay. The β-cyclodextrin used may be hydroxypropyl-β-cyclodextrin at a concentration from about 5 mM to about 15 mM, or from about 7 mM to about 13 mM, or from about 9 mM to about 11 mM, or from about 9.5 mM to about 11.5 mM.

The effect of hydroxypropyl-β-cyclodextrin and methyl-β-cyclodextrin on substrate hydrolysis in a Pompe assay was less effective (data not shown). The effect of hydroxypropyl-β-cyclodextrin and methyl-β-cyclodextrin on substrate hydrolysis in a Krabbe assay was inhibitory (data not shown).

8.12 Clotting in Fabry Assay

The buffer system used to prepare substrate-inhibitor formulation for Fabry disease may include 0.1M sodium citrate, a pH from about 4-5, or from about 4.2-4.8, or from about 4.5-4.7, or about 4.6, containing 1% sodium taurocholate. Although this formulation produces statistically significant separation between the normal and Fabry affected dried blood spot extracts, the inventors have found that it results in clot formation within the droplets. This clotting may adversely affect the reproducibility of the assay because enzyme may be trapped within the clots where it is unavailable to the substrate. The clots seemed to appear very early in the assay (30 minutes from the inception). The inventors have found that a buffer system using 0.04M Sodium Citrate, a pH from about 4-5, or from about 4.2-4.8, or from about 4.5-4.7, or about 4.6, with 0.01% Tween® 20 does not affect the signal at all, and the clot formation was eliminated. In another example, 0.04M Sodium Acetate, pH 4.6 with 0.01% Tween® 20 was used in preparing substrate-inhibitor formulation which produced the same results as the Sodium citrate buffer. Thus, in one embodiment, the invention provides an enzymatic assay making use of blood, a blood component, or a reconstituted blood spot, and further makes use of a substrate inhibitor formulation at a pH from about 4-5, or from about 4.2-4.8, or from about 4.5-4.7, or about 4.6, but which lacks sodium taurocholate. In another embodiment, the invention provides an enzymatic assay making use of blood, a blood component, or a reconstituted blood spot, and further makes use of a substrate inhibitor formulation at a pH from about 4-5, or from about 4.2-4.8, or from about 4.5-4.7, or about 4.6, and comprises sodium citrate. In another embodiment, the invention provides an enzymatic assay making use of blood, a blood component, or a reconstituted blood spot, and further makes use of a substrate inhibitor formulation at a pH from about 4-5, or from about 4.2-4.8, or from about 4.5-4.7, or about 4.6, and comprises sodium acetate. In another embodiment, the invention provides an enzymatic assay making use of blood, a blood component, or a reconstituted blood spot, and further makes use of a substrate inhibitor formulation at a pH from about 4-5, or from about 4.2-4.8, or from about 4.5-4.7, or about 4.6, and comprises sodium citrate and lacks sodium acetate. In another embodiment, the invention provides an enzymatic assay making use of blood, a blood component, or a reconstituted blood spot, and further makes use of a substrate inhibitor formulation at a pH from about 4-5, or from about 4.2-4.8, or from about 4.5-4.7, or about 4.6, and comprises sodium acetate and lacks sodium acetate. In another embodiment, the invention provides an enzymatic assay making use of blood, a blood component, or a reconstituted blood spot, and further makes use of a substrate inhibitor formulation at a pH from about 4-5, or from about 4.2-4.8, or from about 4.5-4.7, or about 4.6, and comprises sodium citrate and a surfactant. In another embodiment, the invention provides an enzymatic assay making use of blood, a blood component, or a reconstituted blood spot, and further makes use of a substrate inhibitor formulation a pH from about 4-5, or from about 4.2-4.8, or from about 4.5-4.7, or about 4.6, and comprises sodium acetate and a surfactant.

8.13 Alternative Assay Protocols

In one embodiment, an assay in accordance with the invention involves the following: One set of dried blood spot extract droplets is combined using droplet operations with one set of substrate fluid droplets. The resulting set of 2× droplets is split using droplet operations to form two sets of 1× droplets. Each droplet in the first set of 1× droplets is combined using droplet operations with a stop buffer droplet. Endpoint fluorescence of the combined droplet measured. The second set of 1× reaction droplets is incubated for a predetermined time and then each reaction droplet is combined with a stop buffer droplet. Again, endpoint fluorescence is measured. The difference between time t–END hrs and t–0 hrs is reported. However, in some protocols there is no time t–0 measurement, which reduces the number of droplet handling operations by half.

In one embodiment, a droplet actuator of the invention is configured to perform 5-plex assays on 48 samples (240 assays) which means 240 2× droplets have to be stored for 20 hours in the limited real estate on the chip. Since 2× droplets cannot be stored on a 3 phase bus, the 2× droplets may be split using droplet operations, and 1× may be transported to waste while the remaining 1× droplet is incubated. In one embodiment, all the dispensing electrodes (reagent and sample) are smaller than the electrodes on the rest of the chip (900 microns or 750 microns; gap height 285 microns). In such a droplet actuator, a 2× droplet on the smaller electrodes would actually be close to a 1× droplet on the larger electrodes. This configuration would avoid the need for splitting the droplet, and would simplify droplet actuator design and work flow easier.

As already noted, a disadvantage performing detection at time t=0 and t=20 hours is the number of droplets that should be handled. Performing "m" plex assays on "n" number of samples, requires the total number of droplets to be "m*n*2", which limits the total number of samples that can be screened on a single droplet actuator. To fit as many samples as possible on a single cartridge, it is helpful to avoid the time t=0 measurement. The main reasons to perform a time t=0 measurement are to assess the quality of the substrates; to determine non-enzymatic hydrolysis; and to account for the effect of hemoglobin quench of fluorescence.

However, as already discussed, the inventors have surprisingly found that DBS quench on fluorescence is very minimal on chip due to the low path lengths. So it can safely be assumed that that hemoglobin does not affect fluorescence. By detecting the background fluorescence of all the substrates before the start of the actual assay, the QC of all the substrates can be obtained. A blank extract may be incubated with the substrate as a control for non-enzymatic hydrolysis. By taking these steps, the time t=0 measurement can be eliminated, thereby reducing the total number of droplets to handle by half. A droplet of known concentration of 4-MU sodium salt may be dispensed using droplet operations and its fluorescence may be detected to provide a calibrant. One droplet each of substrate may be dispensed and merged using droplet operations with a droplet of stop buffer. Endpoint fluorescence of this combination may be detected to assess the QC of the substrates and provide time t=0 measurement. Next, one droplet of each substrate may be merged with a corresponding droplet of DBS extract, yielding a set of reaction droplets. At the end of the incubation period, the reaction droplet may be combined with a stop buffer droplet, and endpoint fluorescence may be detected.

8.13.1 Hemoglobin Quench Normalization for NBS Assays

Dried blood spots (DBS) from newborns for testing of lysosomal storage disease (LSD) enzymes are inherently variable because of the variation in hematocrit between individuals and the irregular deposition of the blood across the filter paper. This variation leads to differences in the amount of hemoglobin in the final assay for a LSD target enzyme. In some cases, hemoglobin (or other quenching material) in the DBS sample may quench the fluorescence emitted from the reaction product (e.g., 4-MU or HMU). In the event of hemoglobin quench on fluorescence, enzyme activity in a sample may be underestimated.

The invention provides assay methods to measure fluorescence (e.g. 4-MU or HMU) quench in a reconstituted DBS sample in a droplet actuator-based NBS assay. In one example of a droplet actuator-based NBS assay, a droplet of known concentration of 4-MU (4-MU standard droplet) is combined using droplet operations with a droplet of reaction termination buffer (stop buffer) and fluorescence detected on-chip to provide a calibration value for the enzyme assays. This same 4-MU standard droplet may also be used to determine a quench coefficient for each DBS sample droplet to be tested. An example of an assay format for measuring fluorescence quench in a reconstituted DBS sample includes, but is not limited to, the following steps: At the start of an assay, a DBS sample droplet is dispensed and combined using droplet operations with a droplet of the 4-MU standard in termination buffer and the fluorescence read (no incubation period required). If no hemoglobin or quenching material is present in the DBS sample droplet, the fluorescence of the combined DBS sample/4-MU droplet will be equivalent to the fluorescence of the 4-MU standard droplet. The quench coefficient will be 1.0 or no quench observed. If hemoglobin or quenching material is present in the DBS sample droplet, a lower fluorescent signal will be detected in the combined DBS sample/4-MU droplet relative to the fluorescence of the 4-MU standard droplet. The fluorescence of the combined DBS sample/4-MU droplet divided by the fluorescence of the 4-MU standard droplet is a measure of the fluorescence quench (quench coefficient) in the sample. The fluorescence quench coefficient for each sample may be used to normalize all of the fluorescent output signals from all of the DBS assay samples and eliminate the differences in signal outputs because of differences in hemoglobin content (or other quench material) in each sample.

8.14 Multiplexed Pompe, Fabry and Hunter's Assays on a Droplet Actuator

The invention provides a droplet actuator device and methods for multiplexed testing (3-plex assay on 12 samples) for Pompe, Fabry and Hunter's lysosomal storage disorders (LSDs) on a single droplet actuator. In one embodiment, samples used for multiplexed testing for LSDs may be prepared from dried blood spots (DBS) using an on-bench protocol prior to loading on a droplet actuator. Reagent preparation (e.g., stop buffer, extraction buffer, substrate formulations and calibrant) may also be prepared using on-bench protocols prior to loading on a droplet actuator. In another embodiment reagent and/or samples may be prepared in reservoirs on the droplet actuator then flowed to different operations gaps, or prepared in the droplet operations gap.

8.14.1 Substrate Formulations and Reagent Preparation

All reagents and formulations required for Pompe, Fabry and Hunter's assays may be prepared on-bench and subsequently loaded into fluid dispensing reservoirs of a droplet actuator. Reagents common to all three assays include: stop buffer (STB; 0.2M Sodium bicarbonate pH 10.0 with 0.01% Tween® 20) and calibrant (CAL; 0.15 µM 4-Methyl umbelliferone prepared in stop buffer) used to calibrate fluorescence detection. Specific substrate formulations for Pompe, Fabry and Hunter's assays are summarized in Table 10. In another embodiment reagent and/or samples may be prepared in reservoirs on the droplet actuator then flowed to different operations gaps, or prepared in the droplet operations gap.

TABLE 10

Summary of substrate formulations

| Assay | Buffer (µL) | Inhibitor or Enzyme (µL) | Substrate (µL) | Total volume(µL) |
|---|---|---|---|---|
| PI-DIL | 197 (PB) | 3 (PI) | N/A | 200 |
| POM | 41.4 (PB) | 5.0 (PI-DIL) | 3.6 (PS) | 50.0 |
| FAB | 39.3 (FB) | 10.0 (FI) | 0.7 (FS) | 50.0 |
| HUN | N/A | 2.0 (HE) | 18.0 (HS) | 20.0 |

Reagents to prepare stock solutions and buffers for testing for lysosomal storage disorders (LSDs), such as Pompe, Fabry, Gaucher, Hurler and Hunter assays on a droplet actuator may include any one or more of the following: Fabry substrate (FS), e.g., 4-Methylumbelliferyl α-D-Galactopyranoside (4-MU-α Gal); Fabry inhibitor (FI), e.g., N-Acetyl-D-Galactosamine (GalNaC); Sodium Acetate (99% purity); Acetic Acid, 99.5% (17.4N); Pompe substrate (PS), e.g., 4-MU-α-D-glucopyranoside (4-MU-α-Gluc); Pompe Inhibitor (PI), e.g., Acarbose; Hunter Substrate (HS), e.g., 4-Methylumbelliferyl-α-L-Iduronide-2-Sulphate (4 MU-αIdoA-2S); Lead (II) Acetate Trihydrate, reagent grade; Molecular biology grade BSA; Recombinant Iduronidase from R&D Systems (HE), e.g., Recombinant α-L-Iduronidase supplied at 0.5 mg/mL (20 μL) in 0.05M Sodium Acetate pH 5.0 with 0.5M NaCl; Gaucher Substrate (GS), e.g., 4-Methyumbelliferyl β-D-Glucopyranoside (4-MU-β-Gluc); Hurler Substrate (MS), e.g., 4-Methylumbelliferyl-α-LIduronide Sodium Salt (4-MU-α-Idu); Hurler Inhibitor (MI), e.g., D-Saccharic acid 1,4-lactone monohydrate (D-Sac); Methyl-β-Cyclodextrin (MBCD); Dimethyl sulphoxide (DMSO); Molecular grade water; Tween® 20; Sodium bicarbonate; 4-Methyl Umbelliferone Sodium salt; Sodium chloride (NaCl), Molecular Biology Grade; Sodium Phosphate, monohydrate; Citric Acid, monohydrate; Taurocholic acid, sodium salt; Sodium Hydroxide (NaOH); Polydimethylysiloxane, Trimethlysiloxy Terminated (OIL); and Triton™ X15.

Stock solutions of Pompe substrate (PS; 70 mM 4-MU-α-D-glucopyranoside (4-MU gluc) in DMSO) and Pompe inhibitor (PI; 8 mM Acarbose prepared in 0.04 M Sodium Acetate, pH 3.8) may be prepared, aliquoted and stored at −80° C. until use.

Preparation of the substrate formulation for the Pompe assay includes the following steps:
1. Remove aliquots of PS and PI from the freezer and thaw at room temperature for 5 min in the dark (e.g., covered with aluminum foil);
2. Prepare a working stock of PI-DIL (120 μM Acarbose in 0.04 M Sodium Acetate, pH 3.8) by adding 3 μL of PI (8 mM Acarbose stock) to 197 μL of Pompe assay buffer (PB; 0.04 M Sodium Acetate, pH 3.8); and
3. Add 41.4 μL of PB (0.04 M Sodium Acetate pH 3.8), 5 μL of PI-DIL (120 μM Acarbose solution) and 3.6 μL of PS (70 mM substrate stock) in that order to yield 50 μL of reagent formulation. Vortex thoroughly. The final substrate concentration in the reagent formulation is 5 mM. The final Acarbose (inhibitor) concentration in the reagent formulation is 12 μM.

In an embodiment a method of preparing a stock solution of about 1800 μL Pompe substrate (PS), with a molecular weight of about 4-MU-α-Gluc-338.3 g/mol, at a concentration of about 70 mM), may include the following protocol. Weigh about 43 mg of 4-MU-α-Gluc and dissolve in about 1800 μL of DMSO; and vortex thoroughly until the substrate completely dissolves in the solution.

In an embodiment a method of preparing about 7.2 mLs Pompe Inhibitor (PI) with a molecular weight of Acarbose of about 645.6 g/mol, with a concentration of about 8 mM, may include the following protocol. Weigh about 37 mgs of Acarbose and dissolve in about 7.2 mL of 0.04M sodium acetate pH 3.8; vortex thoroughly until it dissolves substantially completely in the solution; and aliquote.

In an embodiment a method of preparing Pompe Buffer with about 21.5 mM Methyl-β-Cyclodextrin (PB) may include the following steps. Weigh about 0.656 g of Sodium Acetate and dissolve in about 200 mL of molecular grade water to result in about 0.04 M sodium acetate; vortex thoroughly until it is substantially completely dissolved; adjust the pH by titrating it with about 0.04M Acetic acid, measure the final pH using a pH meter until the final pH of the solution is about 3.8; place about 200 mL of the titrated buffer solution into about a 250-ml plastic bottle, add about 200 μL of 10% Tween® 20, cap and swirl for about 1 minute; in about a 250-mL plastic bottle, weigh about 2.537 g (+/−2%) of Methyl-β-Cyclodextrin; add about 90 mL of the buffer (0.04M Acetic acid pH 3.8, 0.01% Tween® 20); cap and swirl (if plastic bottle) or vortex (if centrifuge tube) until substantially complete dissolution of the solid is achieved; dispense appropriate aliquots in centrifuge tubes; and store at about 4° C.

Stock solutions of Fabry substrate (FS; 4-Methyumbelliferyl α-D-Galactopyranoside (4-MUGal)) and Fabry inhibitor (FI; 750 μM of N-Acetyl-D-Galactosamine (GalNaC)) may be prepared in molecular grade water, aliquoted and stored at −80° C. until use.

Preparation of the substrate formulation for the Fabry assay includes the following steps:
1. Remove aliquots of FS and FI from the freezer and thaw at room temperature for 5 min in the dark (e.g., covered with aluminum foil); and
2. Add 39.3 μL of Fabry buffer (FB; 0.04M Sodium Acetate pH 4.6 with 0.01% Tween® 20), 10 μL of FI (750 μM N-Acetyl Galactosamine) and 0.7 μL of FS (700 mM substrate stock) in that order to obtain 50 μL of reagent formulation. Vortex thoroughly. The final substrate concentration in the reagent formulation is 10 mM. The final inhibitor concentration in the reagent formulation is 150 μM.

In an embodiment a method of preparing a stock solution of about 1080 μL Fabry substrate (FS) of a molecular weight of 4-MU-α-Gal-338.3 g/mol, at a concentration of 0.7 mol/L (700 mM), with an aliquot size of about 3 μL (each aliquot enough for about 4 cartridges including some overage), may include the following protocol. Weighing 256 mg of 4-MU-α-Gal and dissolve in 1080 μL of DMSO; vortex thoroughly until the substrate is completely dissolved in the solution; and aliquote.

In an embodiment a method of preparing about 18 mLs of Fabry Inhibitor (FI) of a molecular weight of about GalNac 221.21 g/mol, with a concentration of about 750 μM, and an aliquot size of about 50 μL, may include the following protocol. Weighing about 10 mg of GalNac and dissolve in about 60.24 mL of molecular grade water; Vortex thoroughly until it is substantially completely dissolved in solution to obtain about 750 μM concentrated GalNac solution; aliquote; and store at about −80° C.

In an embodiment a method of preparing Tween® 20, 10% w/v (10% Tween20), may include the steps of weighing 1 g of Tween® 20 into about a 15-ml centrifuge tube; use molecular biology grade water and bring the volume up to 10 mL; and vortex (5×10 s).

In an embodiment a method of preparing a Fabry buffer with about 25.5 mM Methyl-β-Cyclodextrin (FB), may include the steps of: weighing about 0.656 g of sodium acetate and dissolve in about 200 mL of molecular grade water; vortex thoroughly until completely dissolved; prepare about 0.04 M acetic acid by measuring out about 0.46 mL about 17.4N acetic acid, then use molecular biology grade water and bring the solution to a final volume of about 200 mL; adjust the pH by titrating it with about 0.04 M Acetic acid; measure the final pH using a pH meter until the final pH of the solution is about 4.6; place about 200 mL of the titrated buffer solution into about a 250-ml plastic bottle; add about 200 μL of 10% Tween® 20; cap and swirl for about 1 minute; in about a 50-mL centrifuge tube, weigh 1.10+/−0.02 g (+/−2%) of Methyl-β-Cyclodextrin; add about 33.0 mL of the buffer; cap and swirl (if plastic bottle) or vortex (if centrifuge tube) until substantially complete dissolution of the solid is achieved; aliquote; and store at about 4° C.

Stock solutions of Hunter substrate (HS; 1.25 mM 4-Methylumbelliferyl-α-L-Iduronide-2-Sulfate prepared in 0.1 M Sodium Acetate pH 5.0 containing 10 mM Lead Acetate; 0.01% Tween® 20) and Recombinant Iduronidase (HE; 10 μg/mL of Iduronidase in Hunter assay buffer (HB; 0.05 M Sodium Acetate pH 5.0 with 0.01% Tween® 20 and 1 mg/mL BSA)) may be prepared, aliquoted (10 μL) and stored at −80° C. until use.

Preparation of the substrate formulation for the Hunter assay includes the following steps:
1. Remove aliquots of HS and HE from the freezer and thaw at room temperature for 5 minutes in the dark (e.g., covered with aluminum foil); and
2. Add 2 μL of HE (10 μg/mL Iduronidase) to 18 μL of HS (1.25 mM 4-MU-α-L-Iduronide-2-Sulfate). The final substrate concentration in the reagent formulation is 1.125 mM. The final Iduronidase concentration in the reagent formulation is 1.0 μg/mL.

In an embodiment a method of preparing 1 L of Hunter Substrate buffer with Methyl-β-Cyclodextrin (HSB) (0.1M Sodium Acetate/0.1M Acetic acid buffer containing 10 mM lead acetate, 0.01% Tween® 20, 22.2 mM Me-b-CD), may include the following. Tare a 2-L beaker containing about a 3" stirbar; weigh about 800 g of molecular biology grade water (max=about 994.25 g) into the beaker, and add about 5.75 mL of acetic acid (17.4 N) measured with a serological plastic pipette; stir for about 10 min with a magnetic stirrer at medium speed; bring the final volume to about 1 L with molecular biology grade water, this makes about 0.1M acetic acid. Then weigh about 8.2 g of sodium acetate in a weighing boat, and add the solid quantitatively to the beaker, (i.e. rinsing the boat out several times with molecular biology grade water and adding the rinses to the beaker); stir until all solids are substantially dissolved (~10 minutes); bring the final volume up to about 1 L with molecular biology grade water, this makes about 0.1M sodium acetate. Next weigh 0.285 g of lead II acetate (Pb(OAc)$_2$.3H$_2$O) into a weighing boat, and transfer quantitatively into a 250-ml plastic bottle fitted with about a 1"-1.5" magnetic stir bar; Add about 75 mL of the plain 0.1 M Sodium acetate buffer (pH about 5.0) to the bottle; Add about 75 uL of 10% Tween® 20 to the same bottle; Stir magnetically for about 10 min while avoiding the formation of excessive foam; In a about 50-mL centrifuge tube, weigh about 0.655 g (+/−2%) of Methyl-β-Cyclodextrin required for the total HSB preparation (prep is available in multiples of about 8.33 mL); Add about 22.5 mL of the buffer solution; cap and vortex until substantially complete dissolution of the solid is achieved; and store at 4° C.

In an embodiment a method of preparing 12 mLs of a Hunter Substrate (HS) with a molecular weight of about 4 MU-αIdoA-2S-477 g/mol and a concentration of about 1.25 mM, may include the following protocol. Add about 3 mL of substrate buffer (HSB) to a vial containing about 5 mg of 4 MU-αIdoA-2S, substantially dissolve the substrate and transfer the solution to about a 10 mL tube; rinse vial with about 3 mL substrate buffer (HSB) and add this solution to the 10 mL tube; add about 2.33 mL substrate buffer (HSB) to the 10 mL tube which now contains about 8.33 mL of 1.25 mM substrate solution (HS); repeat the process to produce about 8.33 mL of 1.25 mM substrate solution (HS) using another 5 mg vial; and aliquote.

In an embodiment a method of preparing Hunter Enzyme Buffer (HEB) may include the following. Preparing about 100 mg/mL BSA in molecular biology grade water, by adding about 1 mL molecular biology grade water to about 100 mg BSA; Preparing about 10 mL of HEB (=0.05 M sodium acetate, pH about 5.0; 0.01% Tween® 20, 1 mg/ml BSA), by placing about 5 ml of plain 0.1 M acetate buffer (pH about 5.0) (HB) in a about 15-mL centrifuge tube; Add about 5 mL molecular biology grade water; Add about 10 ul of 10% Tween® 20; Add about 100 ul of 100 mg/ml BSA in molecular biology grade water; cap and swirl for about 1 minute, trying to avoid foam formation; and store at about 4° C.

In an embodiment a method of preparing about 1.8 mLs of a Hunter Enzyme (HE) at a concentration of 10 μg/mL, may include the following protocol. Obtain about 10 μg vial of Iduronidase enzyme, measure the volume of enzyme in the vial, subtract the volume of enzyme from 1000 and add the difference of HEB to produce about 1000 μL of HE; vortex gently until it dissolves substantially completely in the solution, preferably avoiding creating foam; repeat the process using one more vial of Iduronidase enzyme to produce about 1000 μL (total volume=2000 μL); aliquote; and store at −80° C.

In an embodiment a method of preparing about 1080 μL Gaucher Substrate (GS) with a molecular weight of about 4-MU-β-Gluc-338.3 g/mol, and a concentration of about 0.7 mol/L (700 mM), may include the following protocol. Weigh 256 mg of 4-MU-β-Gluc and dissolve in about 1080 μL of DMSO; vortex thoroughly until the substrate is substantially completely dissolved in the solution; and aliquote.

In an embodiment a method of preparing a Gaucher Buffer (GB) may include the following steps. Tare an empty glass containing a magnetic stir bar and record the tare; in a tared weighing boat, weigh about 2.10 g (+/−0.05 g) of citric acid monohydrate and transfer quantitatively into the tared beaker containing the stirbar (rinse the boat into the bottle, using about 3×~5 mL of molecular biology grade water); in another tared weighing boat, weigh about 2.76 g (+/−0.05 g) of sodium phosphate monohydrate, and transfer quantitatively into the beaker, using about 3×5 mL to rinse the boat; Add about 50 mL of molecular biology grade water into the beaker. (total volume in bottle at this point preferably about 75-85 mL); magnetically stir until the solids are substantially completely dissolved (about 10 min); tare the beaker with its contents, and, while stirring, add NaOH (2M) until the pH reaches a value of about 5.20 (+/−0.05), as measured with a pH meter freshly calibrated between pH about 4.00 and 7.00; once the desired pH is reached, measure the weight of the beaker with its contents again, determine the weight of NaOH (2M) added, record this value in the batch traveler; to determine the total weight of chemicals added to the beaker, subtract the initial tare weight (=empty bottle+stirbar) from the final total weight, determine the difference between this weight and about 100 g, add this amount of molecular biology grade water to the beaker; stir for about 2 min, measure the final pH and record the value in the batch traveler (this constitutes plain citrate/phosphate buffer (about pH 5.2)); in about a tared 50-mL centrifuge tube, weigh directly about 0.540 g (+/−0.005 g) of sodium taurocholate, add about 36.0 g (+/−0.3 g) of plain citrate/phosphate buffer (pH 5.2); cap and vortex for about 4×10 s (this yields a final taurocholate concentration of about 1.5% w/v); measure the final pH with a pH meter calibrated between pH of about 4.00 and 7.00, record the final value in the batch traveler (it preferably is at a pH of about 5.20 (+/−0.05)); add about 100 μL of 10% Tween® 20 to the final solution and mix; and aliquote.

In an embodiment a method of preparing an extraction buffer (EXT) may include the steps of, obtaining about 5 mL of 10% Tween® 20 solution from a previous preparation; and mixing about 5 mL of 10% Tween® 20 solution into about 495 mL of molecular grade water to result in about 0.1% Tween® 20 solution (EXT).

In an embodiment a method of preparing a stop buffer (STB), may include the following steps. Tare about a 250-ml plastic bottle fitted with about a 1" magnetic stirbar; Weigh about 1.058 g of sodium bicarbonate (MW 84.01) into the bottle; bring the volume to about the 40-45 mL range by adding molecular biology grade water; magnetically stir thoroughly until the powder dissolves substantially completely; using a pH meter freshly calibrated between pH of about 7.00 and 10.00, measure the pH while adding NaOH (1 M) to the solution under agitation until the pH reaches about 10.00 (+/−0.05); bring the final volume of bottle contents to about 63.0 mL by adding molecular biology grade water; add about 63 µL of 10% Tween® 20 to the bottle, stir for about 5 minutes; measure the final pH, and record it (it should be at pH of about 10.00+/−0.05); and store at about room temperature.

In an embodiment a method of preparing a calibrant (CAL), may include the following steps. Dissolve about 60 mg of 4-MU sodium salt in about 10 mL of molecular grade DMSO; vortex thoroughly until it dissolves substantially completely into solution to obtain about 30 mM of 4-MU solution in DMSO; make a dilution by mixing about 100 µL of 30 mM stock solution with about 900 µL of DMSO, repeat this about 3 times resulting in about 30 µM 4-MU solution in STB; mix about 100 µL of 30 µM 4-MU solution with about 19.9 mL of STB to result in about 0.15 µM of 4-MU solution in STB which is used as the CAL; aliquote; and store at about −80° C.

8.14.2 Sample and QC DBS Preparation

Control DBS samples ("high" and "low" QC spots) may be obtained from U.S. Centers for Disease Control (CDC), Atlanta Ga. An on-bench protocol for preparation of DBS extracts from QC spots and patient DBS samples includes the following steps:
1. Punch a 3.2 mm punch from each DBS (e.g. 12 DBS samples) using a manual or automatic puncher and place each punch into a separate well of a round bottomed 96-well plate (e.g., Fisherbrand® 96-well plates);
2. Using a 20-200 µL multi-channel pipette, add 100 µL of extraction buffer (EXT; Molecular grade water with 0.1% Tween® 20) to each well that contains a DBS punch;
3. Cover the wells with a clear adhesive foil; and
4. Incubate the DBS punches for 30 minutes on a plate shaker at room temperature to extract the DBS samples.

During extraction of the DBS samples, the droplet actuator and instrument may be prepared to run the multiplexed assay.

8.14.3 Droplet Actuator

Figure 24:
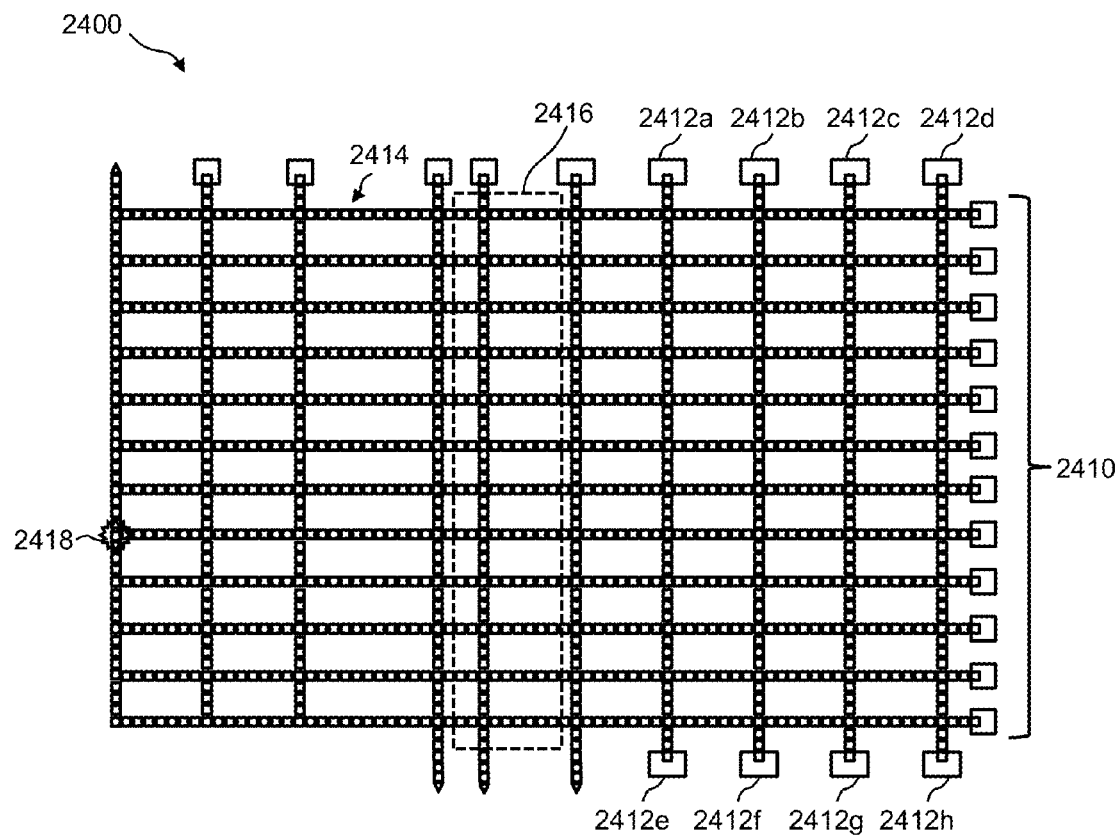
FIG. 24 illustrates a top view of an example of an electrode arrangement of a droplet actuator configured for performing multiplexed Pompe, Fabry and Hunter's assays.

FIG. 24 illustrates a top view of an example of an electrode arrangement 2400 of a droplet actuator configured for performing multiplexed Pompe, Fabry and Hunter's assays. The droplet actuator may include a bottom substrate (not shown) and a top substrate (not shown) that are separated by a gap. Electrode arrangement 2400 may be disposed on the bottom substrate. The gap is filled with a filler fluid, such as silicone oil or hexadecane filler fluid. In one example, the filler fluid is 5 cSt Silicone oil with 0.1% Triton X15. A spacer (not shown) is provided between the bottom substrate and top substrate to determine the height of the gap therebetween and define fluid dispensing reservoirs. Openings in the top substrate (not shown) are provided for introduction of oil filler fluid into the cartridge and dispensing reagent and sample fluids into each on-chip dispensing reservoir. The fluid dispensing reservoirs are aligned with a dispensing electrode and may be used to deliver a liquid through a fluid path into the gap of the droplet actuator and into each on-chip dispensing reservoir electrode.

Electrode arrangement 2400 includes multiple fluid dispensing reservoirs electrodes, which may, for example, be allocated as sample dispensing reservoirs electrodes 2410 (e.g., 12 sample dispensing reservoirs electrodes 2410) for dispensing sample fluids (e.g., dried blood spot extracts) and reagent dispensing reservoirs electrodes 2412 (e.g., 8 reagent dispensing reservoirs 2412a through 2412h) for dispensing reagent fluids. In one example, reagent dispensing reservoir electrode 2412a may be used to dispense a substrate formulation for a Pompe assay (POM); reagent dispensing reservoir electrode 2412b may be used to dispense a substrate formulation for a Fabry assay (FAB); reagent dispensing reservoir electrode 2412c may be used to dispense a substrate formulation for a Hunter assay (HUN); reagent dispensing reservoir electrode 2412d may be used to dispense extraction buffer; reagent dispensing reservoir electrodes 2412e through 2412g may be used to dispense reaction stop buffer; and reagent dispensing reservoir electrode 2412h may be used to dispense a calibration fluid for instrument calibration. A summary of reservoir allocation with reference to FIG. 24 is shown in Table 11.

TABLE 11

Reservoir allocation with reference to FIG. 24

| SAMPLE RESERVOIR (reservoirs 2410) | SAMPLE | REAGENT RESERVOIR | REAGENT |
|---|---|---|---|
| S1 | QC-H | R1 (reservoir 2412a) | POM |
| S2 | N1 | R2 (reservoir 2412b) | FAB |
| S3 | N2 | R3 (reservoir 2412c) | HUN |
| S4 | N3 | R4 (reservoir 2412d) | EXT |
| S5 | N4 | R5 (reservoir 2412e) | STB |
| S6 | N5 | R6 (reservoir 2412f) | STB |
| S7 | N6 | R7 (reservoir 2412g) | STB |
| S8 | N7 | R8 (reservoir 2412h) | CAL |
| S9 | N8 | | |
| S10 | N9 | | |
| S11 | N10 | | |
| S12 | QC-L | | |

Sample dispensing reservoir electrodes 2410 and reagent dispensing reservoir electrodes 2412 are interconnected through an arrangement, such as a path or array, of droplet operations electrodes 2414 (e.g., electrowetting electrodes). Droplet operations are conducted atop droplet operations electrodes 2414 on a droplet operations surface. Electrode arrangement 2400 includes a reaction zone 2416. Electrode arrangement 2400 also includes a detection spot 2418.

The droplet actuator that includes electrode arrangement 2400 is designed to fit onto an instrument deck that houses extra-droplet actuator features such as one or more thermal controllers (heater assemblies) for controlling the temperature within certain processing zones, and a fluorimeter for fluorescence detection. In one example, the droplet actuator is designed to fit into an NBS-LSD100 analyzer instrument that is connected to a desktop computer with SpotLogic software installed. The droplet actuator may be provided and stored in a vacuum sealed aluminum pouch prior to use.

8.14.4 Assay Protocol

A high level overview of an example of the steps used to prepare a droplet actuator and run a digital microfluidic protocol for multiplexed Pompe, Fabry and Hunter's assays is shown in Table 12 below. In this example, the instrument is an NBS-LSD100 analyzer that is connected to a desktop computer with SpotLogic software installed.

TABLE 12

Overview of multiplexed Pompe, Fabry and Hunter assay protocol

| SNo. | Step | Description |
|---|---|---|
| 0 | Initialization | Hardware components initialized. Thermal control set to heat the cartridge to 37° C. Wait for setpoint to be reached. Read and verify actual voltage and temperature. |
| 1 | Oil loading | Add 1.9 mL of OIL into the cartridge. |

TABLE 12-continued

Overview of multiplexed Pompe, Fabry and Hunter assay protocol

| SNo. | Step | Description |
|---|---|---|
| 2 | Sample and reagent loading | Add 3.4 μL of sample and 6.6 μL of reagents |
| 3 | Calibration Low | Detect background fluorescence of stop buffer |
| 4 | Calibration High | Detect background fluorescence of 0.15 μM of CAL |
| 5 | Substrate QC | Detect fluorescence of (EXT + POM/FAB/HUN + STB) to determine quality of substrate formulations |
| 6 | Set up reactions | Merge unit droplet of each DBS extract with unit droplet of POM/FAB/HUN |
| 7 | Incubate | Incubate the reaction droplets for 1 hours at 37° C. |
| 8 | Detection of Pompe assay droplets | Merge each Pompe assay droplet with unit droplet of STB and detect end point fluorescence |
| 9 | Detection of Fabry assay droplets | Merge each Fabry assay droplet with unit droplet of STB and detect end point fluorescence |
| 10 | Detection of Hunter assay droplets | Merge each Hunter assay droplet with unit droplet of STB and detect end point fluorescence |

Initialization of the instrument (referring to Step 0 of Table 12) includes the following steps:
1. Prior to starting each run, insert a "test cartridge" provided with the instrument into the instrument deck as specified in the instrument manual;
2. Engage the test cartridge to the voltage I/O pins by lowering the blue lever on the NBS-LSD 1000 instrument; and
3. Open the SpotLogic™ software application and click "Test" to test for the electrowetting effector, fluorimeter and the thermal controller.

Loading filler fluid in the droplet actuator (referring to Step 1 of Table 12) includes the following steps:
1. Remove a droplet actuator from its vacuum sealed aluminum pouch and place it flat on a bench surface;
2. Using a 1000 μL pipette (e.g., Fisherbrand® aerosol pipette tip) dispense 930 μL of filler fluid (e.g., 5 cSt Silicone oil with 0.1% Triton® X15) into the droplet actuator through the 2 mm oil-input opening in the top substrate. Proceed slowly in order to avoid formation of air bubbles. This process is repeated twice so that the total volume of oil in the cartridge is 1.86 mL;
3. Remove any air bubbles that are formed in the reservoirs by carefully sucking out air and some oil from the reservoirs using a 20 μL pipette;
4. Top the remaining 2 mm openings with 30-50 μL of oil so that there is excess oil in all the openings. The oil-filled cartridge is left flat on the bench surface for 3 minutes to test for any oil leaks through the bond line between the top substrate and the bottom substrate (e.g., a PCB). If oil is leaking from the bond line between the top substrate and bottom substrate, reject the droplet actuator and discard it into a biohazard bag. Obtain a new droplet actuator and load the filler fluid; and
5. After loading the filler fluid in the droplet actuator and testing all the main components of the NBS-LSD100 analyzer (Step 0 of Table 12), select the instrument serial number in the software where intend to perform the testing and click "Start". Follow the prompts on the software and install the droplet actuator in the instrument deck by lifting the blue lever. Stop when the software prompts "Load Samples".

Loading reagents and sample fluids in the droplet actuator (referring to Step 2 of Table 12) includes the following steps:
1. Following the instructions on the software, load the samples and reagents into the designated reservoirs using a 20 μL pipette. Reservoir allocation as set-up in SpotLogic™ software is described in reference to FIG. 24 and Table 11.
2. Load 3.4 μL of DBS extracts in the sample reservoirs as defined in the template in the SpotLogic™ software;
3. Load 6.6 μL of reagent fluids (POM, FAB, HUN, EXT, CAL, and STB) into their respective reagent dispensing reservoirs as specified by the SpotLogic™ software. Referring to Table 11, the order of reagent loading is STB in reservoirs R5, R6 and R7, CAL in reservoir R8, EXT in reservoir R4, POM in reservoir R1, FAB in reservoir R2 and HUN in reservoir R3;
4. A loading check (e.g., presence of air bubbles, volume) is performed visually during the loading of each reservoir. During reagent and sample loading, filler fluid (oil) may seep out of the reservoir openings in the top substrate. Seepage of oil may cause the formation of air bubbles in the reservoirs. To maintain the level of filler fluid and avoid the formation of air bubbles, about 30 μL to 50 μL of oil may be added to all reservoir openings. Expertise in fluid loading and visual inspection may be acquired and assessed, for example, during a training session on the instrumentation and NBS assay protocol;
5. After loading all the samples and reagents in their respective reservoirs, check the oil level again and confirm that all information that was entered is correct; and
6. Start the assay by clicking the "Start" button in the software.

Running the assay (referring to Steps 3 through 10 of Table 12) includes the following steps:
1. The initial steps of the assay, calibration (Steps 3 and 4) and substrate QC (Step 5) are monitored to identify any "flags". A flag may be generated due to malfunctioning of either the droplet actuator or the instrument. If any flags are observed, stop the assay, remove the cartridge and initiate a new run;
2. If no flags are observed, close the instrument lid and allow about 2.5 hours to obtain 36 data points (3-plex assays on 12 samples); and
3. After completion of the run, lift the blue lever to disengage the droplet actuator from the I/O connector pins and carefully remove the droplet actuator from the instrument deck. Discard the droplet actuator into a biohazard bag for disposal.

8.15 Hunter's Assay Using DBS Samples on a Droplet Actuator

The invention provides a digital microfluidic platform and assay methods using dried blood spot (DBS) samples for detection of the lysosomal storage disorder Hunter's syndrome (mucopolysaccharidosis II). Hunter's syndrome is caused by deficient activity of the lysosomal enzyme iduronate-2-sulfate sulphatase (IDS). The substrate fluid for IDS in an enzymatic assay may, for example, be the fluorogenic substrate 4-methylumbelliferyl-α-L-iduronide-2-sulfate (MU-αIdoA-2S). The use of MU-αIdoA-2S as a fluorescent substrate to measure the activity of IDS requires the sequential action of a second enzyme, α-L iduronidase, to convert the product of the sulphatase, 4-methylumbeliferyl-α-L-iduronic acid, into iduronic acid and 4-MU as described in reference to FIG. 1. The microfluidic protocol is a single-step homogenous assay using purified recombinant iduronidase that is performed at a single pH (i.e., pH from about 4.5-5.5, or from about 4.8-5.2, or from about 4.9-5.1, or about 5.0), with a time to result of 8 hours or less. In a preferred embodiment, the microfluidic protocol is performed with a time to result (from extraction of DBS to result) of about 2 hours or about 90 minutes or less. Other embodiments may make use of the alternative substrates described herein.

The digital microfluidics platform may, for example, include a disposable, self-contained droplet actuator in which the enzymatic reaction is performed in aqueous droplets within an oil filled gap of the droplet actuator. Samples and assay reagents (e.g., substrate, stop buffer) are manipulated as discrete droplets upon an electrode array (digital electrowetting). The electrode array may, for example, be fabricated on a printed-circuit-board (PCB) and enclosed in an oil (e.g., polydimethylsiloxane 2 cst, Gelest, Inc.) filled droplet actuator. The droplet actuator may be designed to fit into the deck of, or otherwise electronically coupled to, an instrument that incorporates all control and detection capabilities. The interface between the droplet actuator and instrument device may, for example, be provided by spring loaded connector pins between the device and contact pads on the droplet actuator. Samples and reagents are introduced into the droplet actuator through fluid loading ports and on-chip reservoirs. The droplet actuator may be inserted into the device which automatically performs all assay manipulations including dispensing required volumes of samples and reagents, mixing, incubation, reaction termination and detection. A droplet may be selectively dispensed from any reservoir, transported, combined with other droplets and divided thereby replicating all of the required liquid manipulations to perform an enzymatic assay. The volume of a single droplet on the droplet actuator may, for example, be 300 mL. Detection of the fluorescent sodium umbelliferone product (4-MU; 360 nm excitation, 460 nm emission) may, for example, be achieved using a fluorimeter module in an epi-illumination configuration mounted directly above a droplet actuator detection electrode. Filtered excitation light from an ultraviolet LED is directed at the sample and collected back along the same optical path. Fluorescent light greater than 427 nm wavelength passes through a dichroic beam splitter and an emission filter to a photodiode. The LED excitation and collection electronics may be in a lock-in configuration to reduce background noise. Specifically, the LED oscillates at 1 kHz and the photodiode signal is sampled at 32 kHz for one second. The reported fluorescent signal is obtained by examining the magnitude of the collected signal at 1 kHz using a fast Fourier transform.

Figure 25:
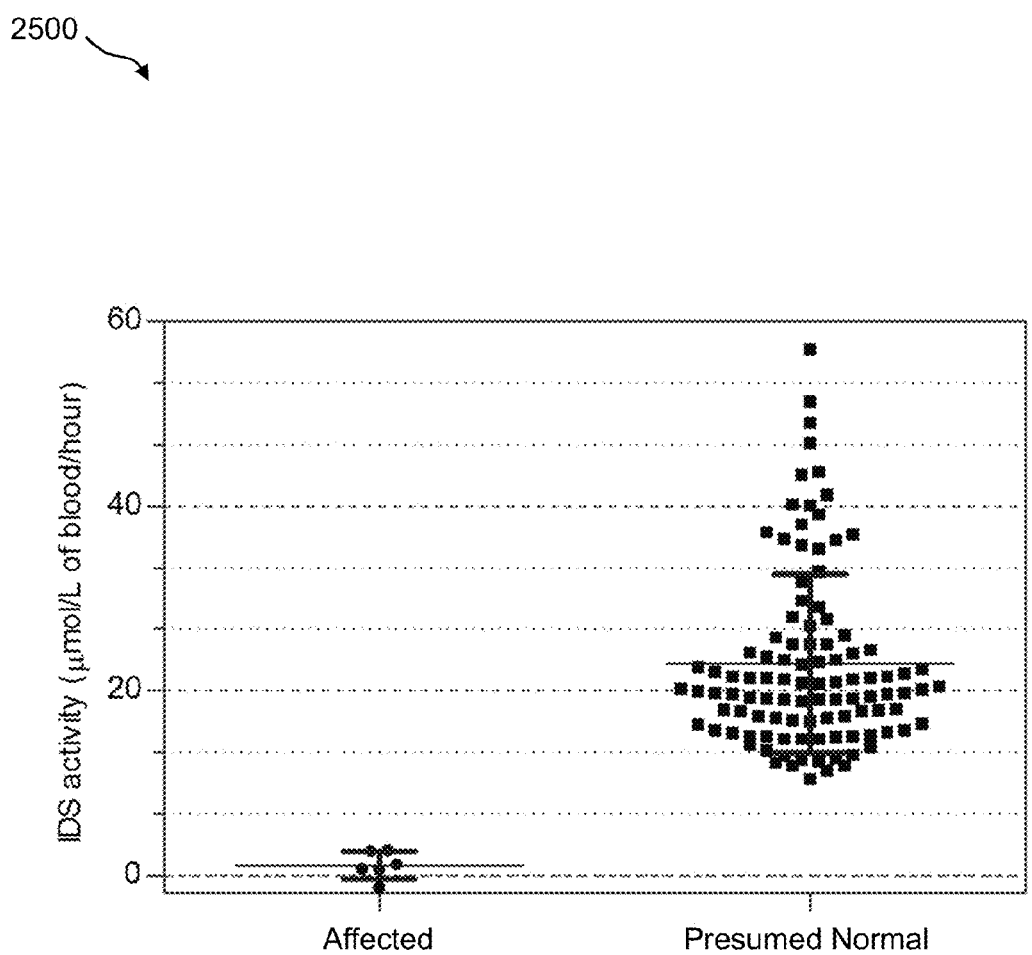
FIG. 25 shows a plot of IDS activity in a Hunter's assay performed on the digital microfluidic platform using extracts from DBS samples.

FIG. 25 shows a plot 2500 of IDS activity in a Hunter's assay performed on the digital microfluidic platform using extracts from DBS samples. A stock solution of recombinant human α-L-iduronidase (>7.5 nmoles/min/µg; 10 µg/ml iduronidase in 0.05 M sodium acetate, 0.5 M sodium chloride, 1 mg/ml BSA, 0.01% Tween® 20, pH 5.0 buffer) was prepared and stored in 10 µL aliquots at −80° C. Iduronidase-2-sulfate sulfatase (IDS) assay solution was prepared fresh by thawing an aliquot of iduronidase. Unused iduronidase was discarded and not refrozen. Dried blood spots (3 mm punches) from presumed normal individuals and from Hunter affected individuals were reconstituted on-bench by gentle mixing in 100 µL 0.1% Tween® 20 in microfuge tubes for 30 minutes at room temperature. Prepared reagents and DBS samples were loaded onto fluid dispensing reservoirs of a droplet actuator.

The digital microfluidic protocol for measuring IDS activity included the following steps: One droplet of reconstituted DBS extract was combined using droplet operations with one droplet of assay solution (1.125 mM 4-methylumbelliferyl-α-L-iduronate-2-sulfate, 1 µg/ml recombinant human α-L-iduronidase, 0.1 M sodium acetate, and 0.01 M lead acetate, pH 5.0) to yield a 2× reaction droplet. The 2× reaction droplet was split using droplet operations to yield two 1× reaction droplets. One 1× reaction droplet was immediately combined using droplet operations with one 1× droplet of termination buffer (0.2 M sodium bicarbonate, 0.01% Tween® 20, pH 10.0) and transported to the detector electrode to measure the fluorescent signal at zero time. The second 1× reaction droplet was incubated on the droplet actuator for one hour at 37° C. After the incubation period, the 1× reaction droplet was combined with a 1× droplet of termination buffer and transported to the detector electrode to measure the fluorescent signal at time t=1 hour. The activity of IDS is expressed in micromoles product formed per hour per liter blood. The IDS activity was calculated based on a 3 mm DBS punch containing 3.1 µL of blood. Assay calibration was performed on the droplet actuator using sodium 4-methylumbelliferone in 0.2 M sodium bicarbonate, 0.01% Tween® 20, pH 10.0 termination buffer as a standard.

In this example, an iduronidase concentration of 1 µg/ml in the IDS assay was sufficient to liberate 4-methylumbelliferone (4-MU) from 4-methylumbelliferyl-α-L-iduronic acid after IDS removal of the sulfate moiety from 4-methylumbelliferyl-α-L-iduronide-2-sulfate (data not shown). Dilution (31-fold) of blood during extraction of the DBS and the presence of 10 mM lead acetate in the substrate buffer as in section 7.14.1 was sufficient to substantially prevent inhibition of iduronidase-2-sulfate sulfatase activity by anions such as chloride, phosphate and sulfate in the reaction droplet.

The IDS activity in extracts of DBS from random newborns (n=105 random newborn DBS samples) and Hunter patients (n=6 affected DBS samples) was measured by two operators using two different instruments and droplet actuators. The data show the IDS activity in the Hunter patients (range, 0-2.7; mean, 1.1; median, 1.0 µmol/h/L blood with a standard deviation of 1.48) was well below and clearly separated from the IDS activity found in presumed normal newborns (range, 10.4-56.9; mean, 22.9; median 20.2 µmole/h/L blood with a standard deviation of 9.7). It is not known if any of the DBS from the random newborn pool were from carriers of the Hunter trait.

8.16 Single-Step Assay for Hunter's Syndrome

The invention provides an enzymatic assay for Hunter's Syndrome. The microfluidic protocol is a single-step homogenous assay using purified recombinant iduronidase that is performed at a single pH (i.e., pH 5.0) with a time to result of 8 hours or less. In one embodiment, on-chip reaction volumes i.e., 2 µL Hunter enzyme and 18 µL Hunter substrate may be scaled to on-bench volumes, i.e., 10 µL Hunter enzyme and 90 µL of Hunter substrate. The incubation time for sufficient enzymatic hydrolysis of substrate and time to result may be selected for applications. The assay may, for example, use extracts prepared from dried blood spot (DBS) samples to test for Hunter's disease. A stock solution of Hunter substrate (HS; 4-methylumbelliferyl-α-L-iduronide-2sulfate $Na_2$; Moscerdam Substrates) may be prepared in Hunter substrate buffer (HSB; 0.1 M Sodium Acetate, 10 mM lead (II) acetate (Sigma Aldrich), 0.01% (w/v) Tween® 20). The pH of the Hunter substrate buffer (HSB) may from about 4 to about 6, preferably from about 4.5 to about 5.5, ideally about 5. A stock solution of Hunter enzyme formulation (HE; recombinant human α-L-iduronidase; 10 µg/20 µL; R&D Systems) may be prepared in Hunter enzyme buffer (HEB; 0.05 M Sodium Acetate, 0.01% (w/v) Tween® 20, 1 mg/mL bovine serum albumin (BSA); Sigma Aldrich). The pH of the Hunter enzyme buffer (HEB) may from about 4 to about 6, preferably from about 4.5 to about 5.5, ideally about 5. Stock solutions may be prepared, aliquoted, and stored at −80° C. until use.

Preparation of the Hunter substrate formulation (HS) for an on-bench Hunter assay includes the following steps:
1. Add 3 mL of Hunter substrate buffer (HSB; 0.1 M Sodium Acetate, pH 5.0, 10 mM lead (II) acetate (Sigma Aldrich), 0.01% (w/v) Tween® 20) to a 5 mg vial of 4-methylumbelliferyl-α-L-iduronide-2sulfate $Na_z$. Dissolve and transfer the solution to a 10 mL conical, polystyrene tube wrapped in foil;
2. Rinse the vial by adding a second 3 mL of HSB to the vial and mix vigorously. Transfer this solution to the same 10 mL conical tube;
3. Add 2.33 mL of HSB to the same 10 mL conical tube to yield a total volume of 8.33 mL.
4. Aliquot 105 μL of the solution to individual microfuge tubes; and
5. Store at −80° C. protected from light.

Preparation of the Hunter enzyme (HE) formulation for the Hunter assay includes the following steps:
1. Add 20 μL of Iduronidase to 980 μL of Hunter enzyme buffer (HEB; 0.05 M Sodium Acetate, pH 5.0, 0.01% (w/v) Tween® 20, 1 mg/mL bovine serum albumin (BSA; Sigma Aldrich));
2. Gently vortex until completely dissolved;
3. Aliquot 13 μL of the solution to individual microfuge tubes; and
4. Store at −80° C.

An assay protocol for Hunter's syndrome includes, but is not limited to, the following steps:
1. Extract one 3 mm DBS sample punch in 100 μL of extraction buffer (0.1% w/v Tween® 20 in molecular grade water) for 30 min at room temperature on a shaking platform at 1400 rpm;
2. At the end of the extraction, transfer the liquid to a 1.5 mL microfuge tube;
3. Test each sample in duplicate. Each aliquot of HS and HE is sufficient for testing 5 samples in duplicate, 10 reactions total;
4. Prepare Hunter working substrate solution (HWSS) by combining 99 μL of HS with 11 μL of HE. Mix well and protect from light;
5. In a Costar black, half-area microtiter plate, combine 10 μL of DBS extract and 10 μL HWSS. Avoid using the wells on the edge of the plate (i.e., rows A and H and columns 1 and 12);
6. Seal the plate with adhesive plate sealer and wrap the plate in aluminum foil;
7. Incubate the reactions at 37° C. for 20 hrs;
8. At the end of the incubation period, stop the reaction with 50 μL of stop buffer (0.2 M sodium bicarbonate, pH 10.1) and mix well; and
9. Read fluorescence at 360/460 excitation/emission at a gain of 60.

Figure 26:
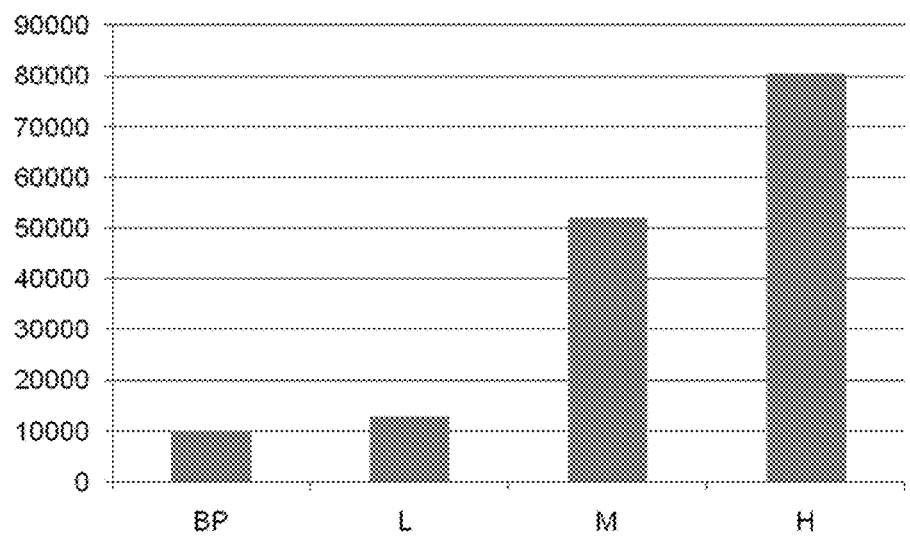
FIG. 26 shows a bar graph of fluorescence data of a single-step on bench assay for Hunter's syndrome.

FIG. 26 shows a bar graph 2600 of fluorescence data of a single-step on-bench assay for Hunter's syndrome. DBS extracts were prepared from quality control (QC) samples, i.e., base pool (BP), low (L), medium (M) and high (H) activity samples. The base pool (BP) QC sample was prepared from a pool of leukoreduced human red blood cells that was adjusted with heat-treated serum to a hematocrit of 50%. The High (H) activity QC sample was prepared from pooled cord blood that was adjusted with heat-treated serum to a hematocrit of 50%. The medium (M) activity QC sample was prepared by using 50% base pool (BP) and 50% high (H) activity sample. The low (L) activity QC sample was prepared by using 95% base pool (BP) and 5% high (H) activity sample. The BP sample is used as a control for hydrolysis non-specific to white blood cell lysosomal enzymes. The data show a strong signal and clear separation between L, M and H samples.

Figure 27:
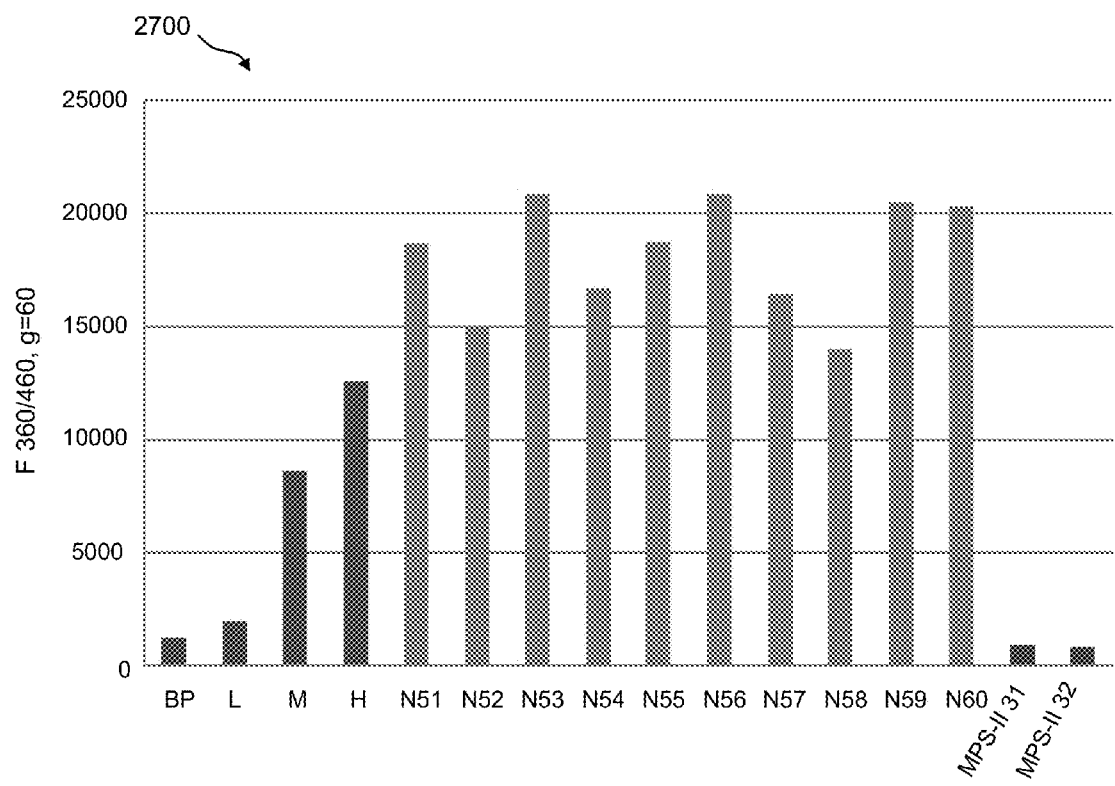
FIG. 27 shows a bar graph of another example of fluorescence data of a single-step assay for Hunter's syndrome.

FIG. 27 shows a bar graph 2700 of another example of fluorescence data of a single-step on-bench assay for Hunter's syndrome. In this example, DBS extracts were prepared from BP, L, M, and H QC samples, 10 normal (N; unaffected) DBS samples and 2 Hunter's (MPS-II; affected) DBS samples. The data show a strong signal and clear separation between normal and affected (MPS-II) samples. Higher levels of enzyme activity in the normal samples relative to QC samples may be due to the presence of enzyme activity in the non-heat treated normal samples. The level of enzyme activity in the non-heated treated Hunter's samples is essentially reduced to BP levels.

8.17 Assay for Fabry Disease

The invention provides an enzymatic assay for Fabry disease (described in reference to Tables 10 and 12 and FIG. 24) may be adapted to an on-bench protocol. In one embodiment, the assay uses extracts prepared from dried blood spot (DBS) samples to test for Fabry disease. Stock solutions for Fabry substrate, 4-Methylumbelliferyl α-D-galactopyranoside (40 MUGal; MW=338.3 g/mol; Sigma) may be prepared in Dimethly Sulfoxide (DMSO, 99.9%) at a concentration of 700 mM. Stock solutions of Fabry inhibitor (750 μM of N-Acetyl-D-Galactosamine; Sigma) may be prepared in molecular biology grade water. Fabry substrate and inhibitor stock solutions may be prepared, aliquoted and stored at −80° C. until use. The on-bench assay may, for example, be performed in multi-well microtiter plates (e.g., Costar black half-area plates). A microtiter plate reader (e.g., Biotek KC4 plate reader) may be used for fluorescence detection.

An on-bench assay protocol for Fabry disease includes, but is not limited to, the following steps:
1. Extract one 3 mm DBS sample punch in 100 μL of extraction buffer (0.1% w/v Tween® 20 in molecular grade water) for 30 min at room temperature on a shaking platform at 1400 rpm;
2. At the end of the extraction, transfer the liquid to a 1.5 mL microfuge tube;
3. Prepare a Fabry working substrate solution (FWS) by combining 78.6 μL Fabry enzyme buffer (0.04 M Sodium Acetate with 0.01% (w/v) Tween® 20, pH4.6) with 20 μL Fabry inhibitor stock solution and 1.4 μL Fabry substrate stock solution;
4. In a Costar black, half-area microtiter plate, combine 10 μL of DBS extract and 10 μL Fabry working substrate solution (FWS). Run each sample in duplicate;
5. Seal the microtiter plate with adhesive plate sealer and wrap the plate in aluminum foil;
6. Incubate the reactions at 37° C. for 20 hrs;
7. At the end of the incubation period, stop the reaction with 50 μL of stop buffer (0.2 M sodium bicarbonate, pH 10.1) and mix well; and
8. Read fluorescence at 360/460 excitation/emission at a gain of 75.

8.18 Enzyme-Mediated Release of Nucleic Acids from DBS

The use of dried blood spots (DBS) collected on filter paper for nucleic acid-based testing of infectious diseases, newborn testing and SCIDS is widespread in the public health community. In nucleic acid-based testing protocols, such as PCR, the entire DBS sample is inserted into a PCR tube and amplified. For nucleic acid testing on a droplet actuator, the DBS sample may be extracted from the filter paper prior to analysis. However, the release of nucleic acids (e.g., DNA and RNA) from the DBS samples is difficult and inefficient when using chemical extraction methods and may result in gross underestimations of target nucleic acid concentrations by up to several orders of magnitude. The inefficiency of nucleic acid extraction from DBS samples has been attributed to the physical interaction (e.g., intertwined) of the nucleic acid molecules with the fibers of the filter paper.

The use of DBS collected on filter paper for enzyme-based testing of infectious diseases, newborn testing and SCIDS is widespread in the public health community. For enzyme-based testing on a droplet actuator, the DBS sample may be extracted from the filter paper prior to analysis. However, the release of enzymes from the DBS samples is difficult and inefficient when using chemical extraction methods and may result in gross underestimations of target enzyme acid concentrations by up to several orders of magnitude. The inefficiency of enzyme extraction from DBS samples has been attributed to the physical interaction (e.g., intertwined) of the enzyme molecules with the fibers of the filter paper.

The present invention provides methods for using enzymes to release nucleic acids in DBS samples collected on filter paper. In one embodiment, a cellulose degrading enzyme, such as cellulase, may used to partially or totally solubilize the filter paper matrix to release substantially all of the nucleic acid in the sample into an extraction buffer. In one example, the cellulase complex from *Trichoderma reesei* (formerly *T. viride*) may be used to release nucleic acids in DBS samples collected on filter paper. The cellulase complex from *T. reesei* quantitatively converts cellulose to glucose. An example of an on-bench protocol to release nucleic acids from a DBS collected on filter paper may include the following: The DBS sample may be washed (e.g., two or three times) with an aqueous buffer to remove soluble PCR inhibitory components from the DBS. The washed DBS sample may be incubated with a cellulose degrading enzyme, such as cellulase from *T. reesei*, to release nucleic acids in the DBS. Nucleic acids in the sample may be concentrated using a magnetic bead-based protocol to reduce the sample volume prior to loading the extracted blood sample onto a droplet actuator. The concentrated DBS extract may be loaded onto a sample dispensing reservoir of a droplet actuator and dispensed for quantitative PCR analysis using a digital microfluidic protocol.

The method may be used for the enzymatic assays described herein. In one embodiment, a cellulose degrading enzyme, such as cellulase, may used to partially or totally solubilize the filter paper matrix to release substantially all of the enzyme in the sample into an extraction buffer.

8.19 Digital Microfluidic Platform for Bilirubin, G6PD and CH Newborn Testing

The present invention provides a digital microfluidic platform and assay methods for multiplexed testing of newborns. The digital microfluidic platform includes a multi-well droplet actuator that may be configured for one or more molecular assays for newborn testing. Because of the software programmability of digital microfluidics, most of the parameters varied between and within protocols, such as incubation times, sequences of reagent additions, and thermal programs, may be readily adapted to different assay protocols.

In one embodiment, the digital microfluidic platform may be configured for multiplexed testing of newborns that are at risk for hyperbilirubinemia and its most common underlying pathological causes, glucose-6-phosphate dehydrogenase (G6PD) deficiency, and congenital hypothyroidism (CH). On-bench assays for determination of total bilirubin, G6PD activity and CH (i.e., TSH assay) may be described and implemented on a droplet actuator as discrete step-by-step droplet-based protocols. Assay protocol parameters may, for example, be selected for linearity, increased sensitivity (limit of detection), specificity, droplet carryover, and rapid time-to-result.

The droplet actuator may be designed to fit into, or otherwise be electrically coupled to, an instrument deck that that houses other components that are external to the droplet actuator. Examples of external components include, but are not limited to, one or more magnets for immobilization of magnetically responsive beads, one or more heater assemblies for controlling the temperature within certain processing zones, and a detection system.

8.19.1 Total Bilirubin Assay

Assays for determination of total bilirubin (serum or plasma) levels may be adapted for use on a droplet actuator. In one example, the total bilirubin assay kit (B576-480) available from Teco Diagnostics may be adapted for use on a droplet actuator. The total bilirubin assay is a colorimetric assay based on the reaction between bilirubin and diazotized sufanilic acid to produce azobilirubin which has an absorbance maximum at 560 nm wavelength in the presence of dimethylsulfoxide (DMSO) solvent. The kit includes the following reagents: Total Bilirubin Reagent (sulfanilic acid 32 mM, hydrochloric acid 165 mM, DMSO 7 M (55% w/v)); and Bilirubin Nitrite Reagent (sodium nitrite 60 mM); Bilirubin Calibrator (20 mg/dL N-1-naphthylethylenediamine dihydrochloride salt). Working reagents and calibration solutions were prepared on-bench as follows: Total bilirubin working reagent was prepared on-bench before each experiment by adding 50 µL of sodium nitrite reagent to 1.0 mL of total bilirubin reagent. Bilirubin calibrator solutions were prepared on-bench at 3, 7, 10, 14, and 20 mg/dL by diluting the 20 mg/dL calibrator stock using deionized water.

Figure 28A:
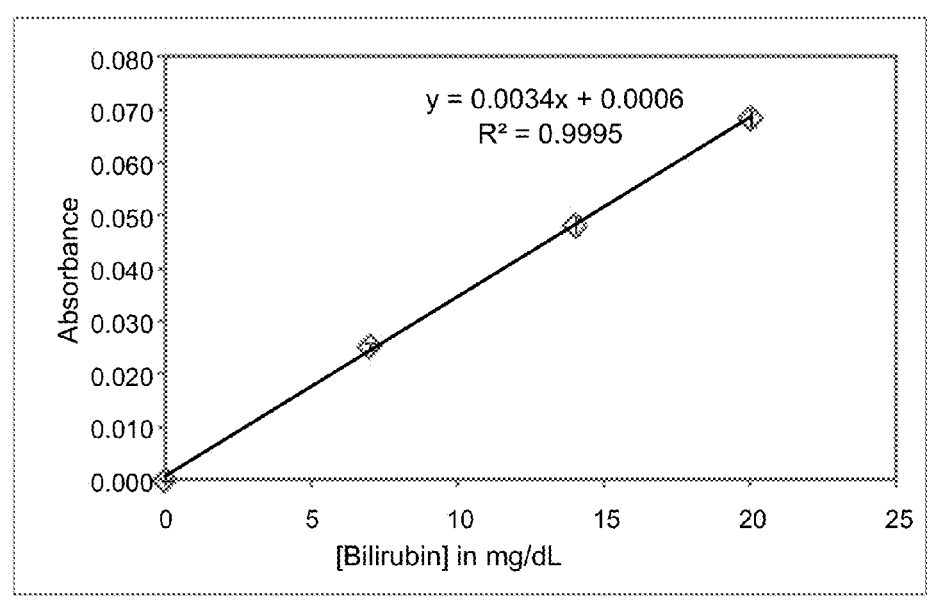
FIGS. 28A and 28B show plots of bilirubin calibration curves obtained on-chip and a scatter plot of values, respectively.
Figure 28B:
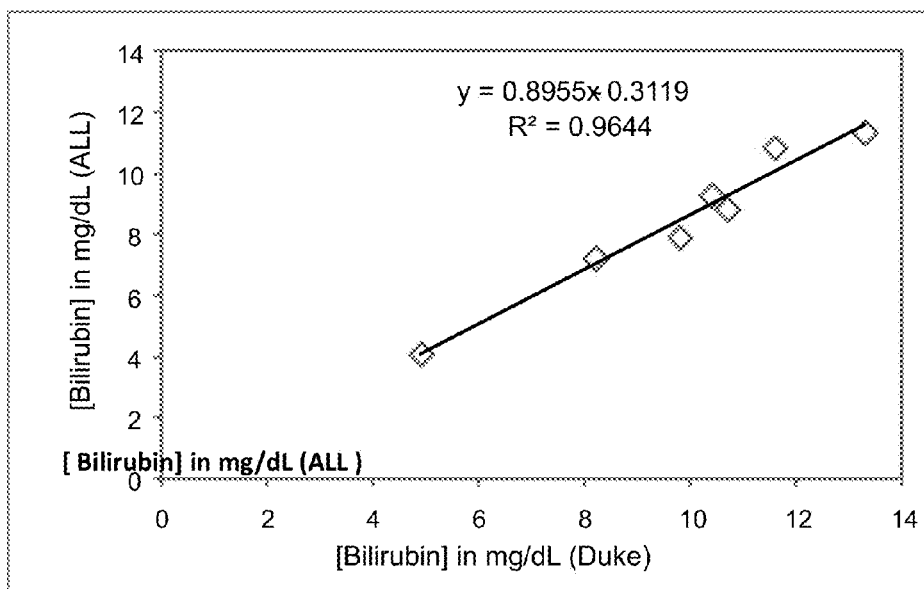

FIGS. 28A and 28B show plots 2800 and 2850 of bilirubin calibration curves obtained on-chip and a scatter plot of on-bench values, respectively. Discarded and deidentified pediatric serum samples were obtained from Duke University (Durham, N.C.) along with the total bilirubin values. The on-bench reference assay (Duke Method) was performed before (e.g., a day before) the on-chip assay. Prepared reagents, calibrators and serum samples were loaded onto fluid dispensing reservoirs of a droplet actuator. The on-chip assay protocol included the following steps: For calibration, a 1× droplet of calibrator was combined using droplet operations with two 1× droplets of working reagent to yield a 3× droplet. The 3× droplet was split using droplet operations into a 1× droplet and a 2× droplet. The 1× droplet was combined with two 1× droplets of working reagent. For serum blank, a 1× droplet of serum was combined using droplet operations with two 1× droplets of total bilirubin reagent to yield a 3× droplet. The 3× droplet was split using droplet operations into a 1× droplet and a 2× droplet. The 1× droplet was combined with two 1× droplets of total bilirubin reagent. For unknown serum bilirubin, a 1× droplet of serum was combined using droplet operations with two 1× droplets of working reagent to yield a 3× droplet. The combined droplet was incubated at 37° C. for 5 minutes. The 3× droplet was split using droplet operations into a 1× droplet and a 2× droplet. The 1× droplet was combined with two 1× droplets of working reagent. The combined droplet was incubated at about 37° C. for about 5 minutes. Absorbance was read at 560 nm wavelength using a LED-photodiode colorimeter. All experiments were performed in triplicate on three different droplet actuators. For both the on-bench and on-chip experiments, the calibration curve was obtained by linear regression analysis in Microsoft Excel®. The absorbance of the serum blank is subtracted from serum absorbance. The blank corrected serum absorbance value is used to obtain the unknown bilirubin value using the regression equation. The experiments were performed using electrowetting mediated droplet operations in silicon oil.

The data shows the calibration curve is linear up to 20 mg/dL. Examination of the scatter plot indicates that there is a small proportional bias in the assay on cartridge when compared to the on-bench reference assay. This may be expected while using diazo methods for bilirubin assay. The correlation is good and is may be improved by performing the reference assay and the on-chip assay at the same time. In this example, there was about a one day delay between the reference test and on-chip assay. Bilirubin is a very labile analyte and the method comparison should ideally be performed at the same time. In another example, a direct bilirubin test as a marker for hyperbilirubinemia may be adapted for use on a droplet actuator.

8.19.2 G6PD Assay

Neonatal testing test kits for glucose-6-phosphate dehydrogenase (G6PD) deficiency are commercially available and may be adapted for use on a droplet actuator. In one example, the G6PD deficiency neonatal testing test kit available from Interscientific Inc. may be adapted for use on a droplet actuator. The assay is based on the oxidation of glucose-6-phosphate to 6-phosphogluconate, and reduction of NADP to NADPH, in the presence of glucose-6-phosphate-dehydrogenase. The NADPH produced reduces tetrazolium dye (MTT) in the presence of phenazine methosulfate to produce a colored product with an absorbance peak at 565 nm. The kit includes the following reagents: R1 (Elution/Lysis Buffer), R2 (Work Reagent), R3 (Color Reagent), R4 (CRB; Color Reagent Buffer). To prepare the Working Color Reagent, 1 part of CRB (R4) and 10 parts of Color Reagent (R3) are mixed together on-bench. The kit also includes assay controls representing normal, intermediate and deficient G6PD values.

Figure 29:
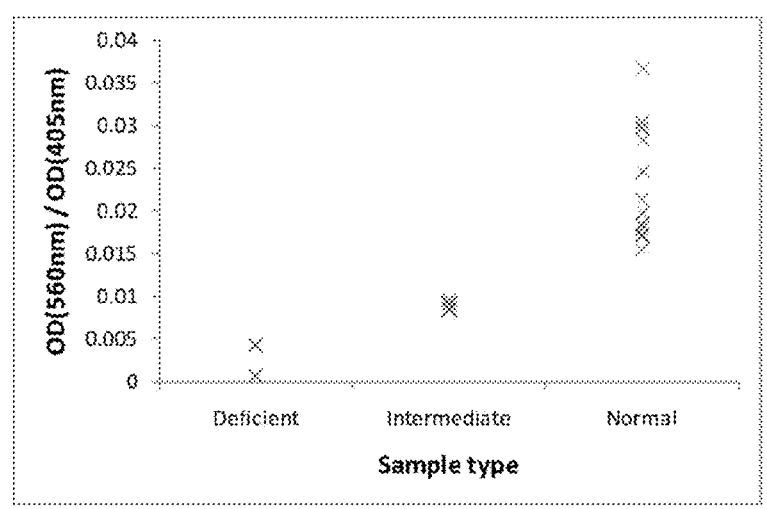
FIG. 29 shows a plot of the G6PD assay performed on-chip.

FIG. 29 shows a plot 2900 of the G6PD assay performed on-chip. Pediatric whole blood samples (n=8 presumed normal samples) were obtained from Duke University. Prepared reagents, assay controls (normal, intermediate and deficient) and whole blood samples (n=8 presumed normal) were loaded onto fluid dispensing reservoirs of a droplet actuator. The on-chip assay protocol for whole blood samples and controls included the following steps: A 1× droplet of whole blood (or control) was combined using droplet operations with three 1× droplets of elution/lysis buffer (R1) and incubated for 1 minute. The combined 4× droplet was split using droplet operations to yield a 1× droplet and a 3× droplet. The 1× droplet was combined using droplet operations with a 1× droplet of work reagent (R2) and incubated for 30 seconds. The combined 2× droplet was split using droplet operations to yield two 1× droplets. One 1× droplet was combined using droplet operations with two 1× droplets of work reagent (R2) and incubated for 30 seconds. The combined 3× droplet was split using droplet operations into a 1× droplet and a 2× droplet. The 2× droplet was transported using droplet operations to a detection spot and absorbance read at 405 nm wavelength for hemoglobin normalization. The remaining 1× droplet was combined using droplet operations with a 1× working color reagent droplet and absorbance read at 560 nm wavelength in kinetic mode. Sample concentration may be expressed using the following formula:

$$\text{Sample } (U/gm\ Hb) = \frac{\Delta OD_{SAMPLE\ 560\ nm}/\Delta OD_{CONTROL\ 560\ nm}}{\Delta OD_{SAMPLE\ 405\ nm}/\Delta OD_{CONTROL\ 405\ nm}} \times [\text{Control}]$$

The data shows good separation between deficient, intermediate and normal samples in the on-chip G6PD assay.

8.19.3 Congenital Hypothyroidism (CH) Assay

Congenital hypothyroidism (CH) is currently screened for in some newborn testing programs using a primary thyroid stimulating hormone (TSH) assay. Assays for determination of TSH levels may be adapted for use on a droplet actuator. In one example, the Access HYPERsensitive hTSH kit (Cat #33820) available from Beckman Coulter may be adapted for use on a droplet actuator. The assay is a paramagnetic particle, chemiluminescent assay for the quantitative determination of human thyroid-stimulating hormone (hTSH). The kit includes the following reagents: paramagnetic beads coated with primary capture antibody, blocking solution and alkaline phosphatase (ALP) labeled secondary antibody. Attoglow (Michigan Diagnostics) may be used as the chemiluminescent substrate.

Figure 30:
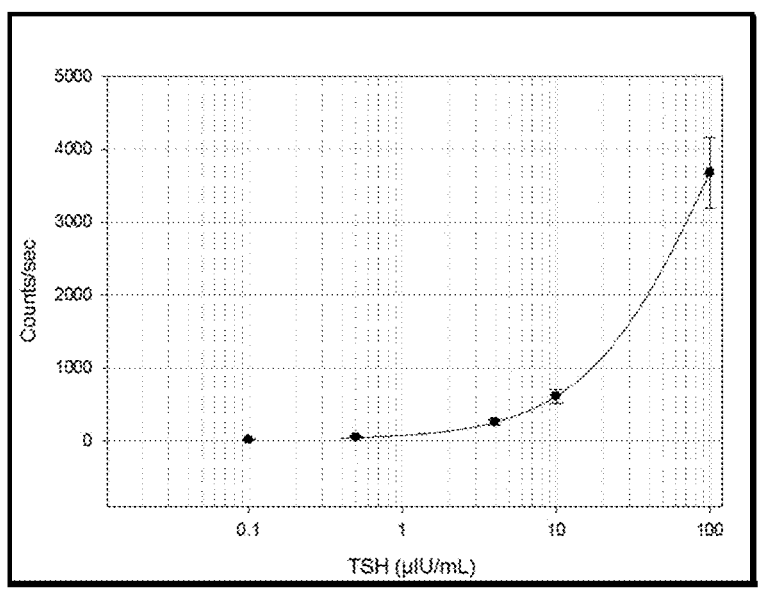
FIG. 30 shows a plot of a TSH calibration curve generated on-chip.

FIG. 30 shows a plot 3000 of a TSH calibration curve generated on-chip. A reagent mixture was prepared on-bench by mixing equal volumes of primary antibody bound to magnetically responsive beads, blocking solution and secondary antibody labeled with ALP. Prepared reagent mixture, TSH standards (at different concentrations), wash buffer and chemiluminescent substrate were loaded onto fluid dispensing reservoirs of a droplet actuator. The on-chip assay protocol included the following steps: A 1× droplet (300 mL) of reagent mixture was combined using droplet operations with two 1× droplets of a TSH standard and incubated for 4 minutes at room temperature. After the incubation period, the magnetically responsive beads were washed to remove any unbound secondary antibody by immobilizing the beads to the edge of the 4× reaction droplet using an external permanent magnet and removing the excess unbound material by activating the adjacent electrodes and deactivating the intermediate electrode. One 1× droplet of chemiluminescent substrate was combined with the bead containing droplet. After 2 minute incubation, end point chemiluminscence was measured using a photon counting photomultiplier tube. A 4-parameter logistic fit was used to fit the data. The error bars represent standard deviation from four different assays. Cut-off concentration for TSH that is used by most testing laboratories (US) is 20 μL U/mL.

In another example, the chemiluminescent TSH assay may be adapted for use on a droplet actuator as a colorimetric assay. In this example, an alkaline phosphatase (ALP) labeled secondary antibody may be used with a colorimetric substrate, such as p-nitrophenol phosphate (detection wavelength 405 nm), for detection of ALP. Assay parameters may be selected for increased sensitivity in the colorimetric assay. For example, the sample volume that is incubated with the primary capture beads may be increased from about 0.3 μL to about 25 μL. The detection reaction time may, for example, be increased from about 2 minutes to about 15 minutes. The assay temperature may, for example, be increased from room temperature to 37° C. The path length at the detection window may, for example, be increased from about 0.3 mm to about 1 mm.

8.19.4 Multiplexed Bilirubin, G6PD and TSH Assays on a Droplet Actuator

Figure 31:
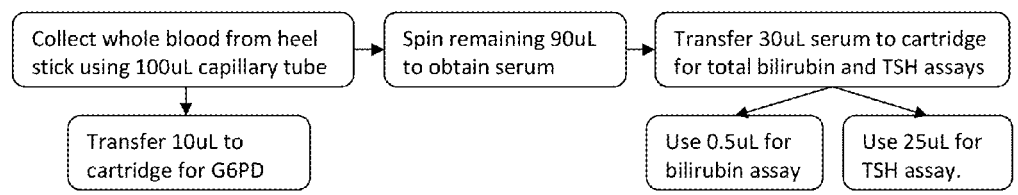
FIG. 31 illustrates a flow diagram of an example of a protocol for multiplexed newborn testing for total bilirubin, G6PD and TSH on a droplet actuator.

FIG. 31 illustrates a flow diagram of an example of a protocol 3100 for multiplexed newborn testing for total bilirubin, G6PD and TSH on a droplet actuator. Protocol 3100 may include, but is not limited to, the following steps: In one step, a sample of whole blood (e.g., about 100 μL) is collected from a heel stick using a 100 μL capillary blood collection tube (e.g., SAFE-T-FILL® collection tubes from Ram Scientific). In another step, an aliquot of the whole blood (e.g., about 10 μL) is transferred to a fluid reservoir of a droplet actuator for the G6PD assay. In another step, the remaining whole blood sample (e.g., about 90 μL) is centrifuged to obtain serum. In one embodiment, a bench-top centrifuge may be used to separate serum from whole blood. In another embodiment, an on-chip separation method (e.g., lateral flow filters) may be used to prepare serum from whole blood. In another step, an aliquot of the serum (e.g., about 30 μL) is transferred to another fluid reservoir of the droplet actuator for dispensing for total bilirubin and TSH assays. For the bilirubin assay, about 0.5 μL of serum is used. For the TSH assay, about 25 μL of serum is used.

Figure 32:
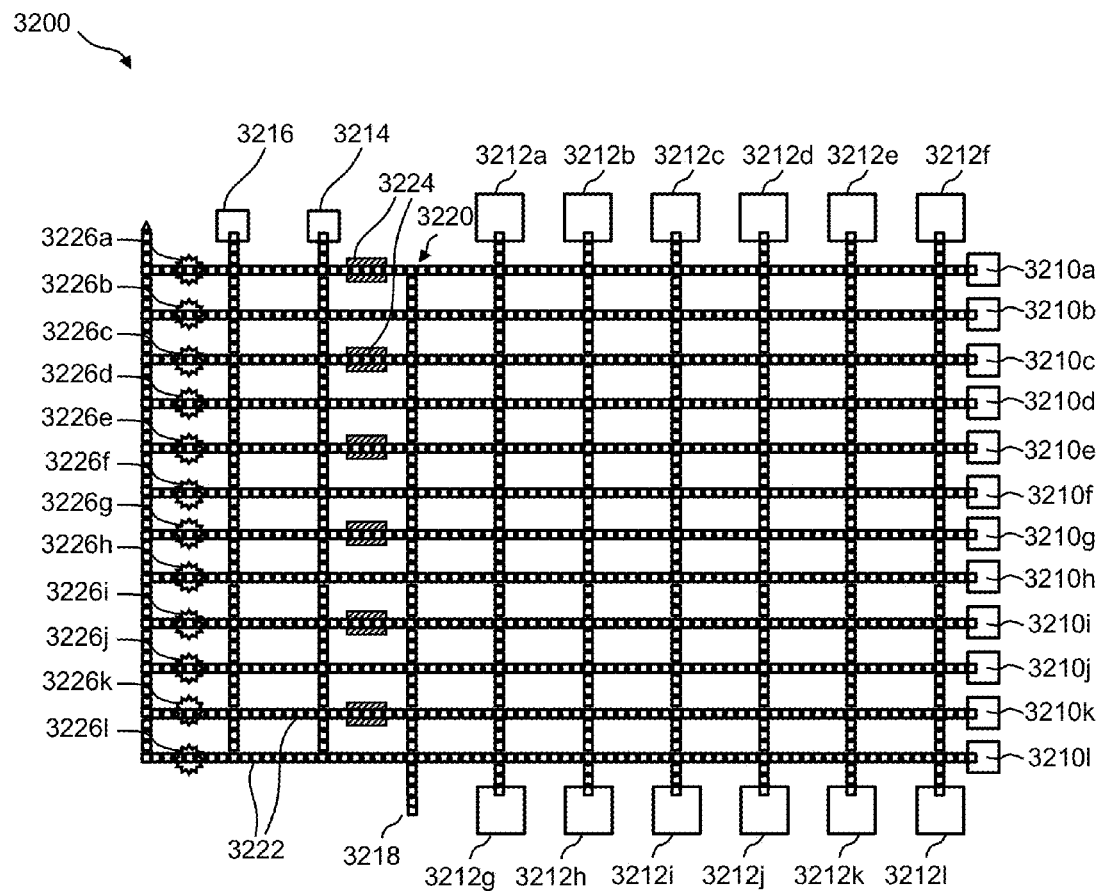
FIG. 32 shows a top view of an example of an electrode arrangement of a droplet actuator configured for performing multiplexed total bilirubin, G6PD and TSH assays on a droplet actuator.

FIG. 32 shows a top view of an example of an electrode arrangement 3200 of a droplet actuator configured for performing multiplexed total bilirubin, G6PD and TSH assays on a droplet actuator. In this example, the droplet actuator is configured for performing a 3-plex assay on 6 samples. The droplet actuator may include a bottom substrate (not shown) and a top substrate (not shown) that are separated by a gap. The bottom substrate may, for example, be a printed circuit board (PCB). Electrode arrangement 3200 may be disposed on the bottom substrate. The gap is filled with a filler fluid, such as silicone oil. Openings in the top substrate (not shown) are provided for introduction of oil filler fluid into the cartridge and dispensing reagent and sample fluids into each on-chip dispensing reservoir. The fluid dispensing reservoirs are aligned with a dispensing electrode and may be used to deliver a liquid through a fluid path into the gap of the droplet actuator and into each on-chip dispensing reservoir electrode. In one embodiment, bulk liquid reagents including filler fluid (e.g., oil) may be provided in dropper bottles to facilitate reagent loading and minimize pipetting steps, which may be done robotically. Because precision aliquoting of reagents is performed inside the droplet actuator using electrowetting-based droplet operations, variations in fluid input volume are readily tolerated. Dry reagents may be provided in metered containers in which they can be reconstituted and frozen if necessary.

Electrode arrangement 3200 includes multiple fluid dispensing reservoirs electrodes, which may, for example, be allocated as sample dispensing reservoirs electrodes 3210 (e.g., 12 sample dispensing reservoirs electrodes 3210*a* through 3210*l*) for dispensing sample fluids (e.g., whole blood, plasma or serum), reagent dispensing reservoirs electrodes 3212 (e.g., 12 reagent dispensing reservoirs 3212*a* through 3212*l*) for dispensing reagent fluids, a wash buffer dispensing reservoir 3214, a substrate dispensing reservoir 3216, and a waste collection site 3218. In one example, reagent dispensing reservoir electrodes 3212*a* through 3212*c* may be used to dispense reagents for the TSH assay (e.g., primary and secondary antibodies, calibration adjustor); reagent dispensing reservoir electrodes 3212*d* through 3212*f* may be used do dispense reagents for the total bilirubin assay (e.g., reagents and calibrator); reagent dispensing reservoir electrodes 3212*g* and 3212*h* may be used dispense dilution buffer; reagent dispensing reservoir electrodes 3212*i* through 3212*l* may be used to dispense reagents for the G6PD assay (e.g., lysis buffer, reagents, standard). Sample dispensing reservoirs 3210 may be used to dispense plasma and whole blood samples from six different sample sets. For example, sample dispensing reservoir electrodes 3210*a* and 3210*b* may be used to dispense plasma and whole blood, respectively, from a first sample; sample dispensing reservoir electrodes 3210*c* and 3210*d* may be used to dispense plasma and whole blood, respectively, from a second sample; sample dispensing reservoir electrodes 3210*e* and 3210*f* may be used to dispense plasma and whole blood, respectively, from a third sample; sample dispensing reservoir electrodes 3210*g* and 3210*h* may be used to dispense plasma and whole blood, respectively, from a fourth sample; sample dispensing reservoir electrodes 3210*i* and 3210*j* may be used to dispense plasma and whole blood, respectively, from a fifth sample; sample dispensing reservoir electrodes 3210*k* and 3210*l* may be used to dispense plasma and whole blood, respectively, from a sixth sample.

Sample dispensing reservoir electrodes 3210, reagent dispensing reservoir electrodes 3212, wash buffer dispensing reservoir electrode 3214, substrate dispensing reservoir electrode 3214 and waste collection site 3218 are interconnected through an arrangement, such as a path or array, of droplet operations electrodes 3220 (e.g., electrowetting electrodes). Droplet operations are conducted atop droplet operations electrodes 3220 on a droplet operations surface. A path of droplet operations electrodes 3220 extending from each sample dispensing electrode forms dedicated electrode lanes 3222, i.e., 12 dedicated electrode lanes 3222*a* through 3222*l*. Dedicated electrode lanes 3222 prove individual reaction zones for processing different samples and sample types (i.e., plasma and whole blood). The use of dedicated lanes for sample droplets minimizes cross-contamination among samples.

One or more magnets 3224 (e.g., six magnets 3224*a* through 3224*f*) may be positioned in proximity to certain droplet operations electrodes 3220 for retaining a quantity of magnetically responsive beads. Each magnet 3224 may, for example, be a permanent magnet or an electromagnet. Each magnet 3224 is positioned in a manner which ensures spatial immobilization of magnetically responsive beads during washing steps. Mixing and incubations may be performed on certain droplet operations electrodes 3220 away from the magnet.

Electrode arrangement 3200 includes multiple detection electrodes 3226 (e.g., 12 detection electrodes 3226*a* through 3226*l*). Detection electrodes 3226 are positioned in proximity to certain droplet operations electrodes in each dedicated electrode lanes 3222. The use of independent detection electrodes for sample droplets minimizes cross-contamination among samples. Detection electrodes 3226 may be fabricated as optically transparent electrodes as described in reference to FIG. 33. Detection electrodes 3226 may be aligned with certain optical detection channels (e.g., 560 nm channel or 405 nm channel) as described in reference to FIG. 34.

Because of the flexibility and programmability of a droplet actuator, the architecture of the droplet actuator may be readily configured to accommodate fewer or more samples.

For total bilirubin and G6PD assays, a single point calibration curve may be generated on-chip as the assays are substantially linear over the required range. For the TSH assay, a master calibration curve for every droplet actuator lot number or reagent batch may be generated. A calibration adjustor may be run on-chip to make adjustments to the calibration curve. This approach is commonly used in immunoassay analyzers. Positive and negative controls may be run to identify systematic errors such as a defective droplet actuator or bad reagent lot. A detailed Design Failure Modes and Effects Analysis (FMEA) may be conducted to identify both external and internal quality control needs.

Figure 33:
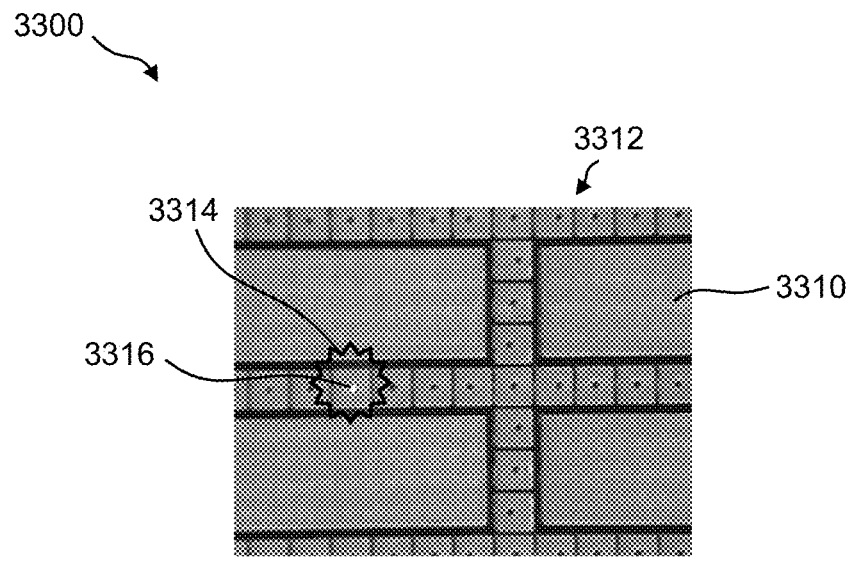
FIG. 33 illustrates a top view of a portion of a droplet actuator that includes optically transparent detection electrodes suitable for detection of colorimetric reaction products.

FIG. 33 illustrates a top view of a portion of a droplet actuator 3300 that includes optically transparent detection electrodes suitable for detection of colorimetric reaction products. Droplet actuator 3300 may include a bottom substrate 3310. Bottom substrate 3310 may, for example, be a PCB. An arrangement, such as a path or array, of droplet operations electrodes 3312 (e.g., electrowetting electrodes) may be disposed on the bottom substrate 3310. Droplet operations are conducted atop droplet operations electrodes 3312 on a droplet operations surface. Droplet actuator 3300 may include a detection electrode 3314. A plated through hole 3316 may be fabricated in detection electrode 3314. Plated through hole 3316 may, for example, be fabricated as unfilled via holes. Plated through hole 3316 may, for example, be about 250 μm in diameter. Plated through hole 3316 provides for transmission of light (e.g., from an LED) through bottom substrate 3310. Because plated through hole 3316 is sufficiently small relative to the size of detection electrode 3314 (e.g., about 1000 μm), electrowetting performance is substantially unaffected.

8.19.5 Instrument Platform

In one embodiment the invention provides an instrument platform that is suitable for use in limited resource settings. In one embodiment, the instrument may be a small, bench-top instrument that is light weight and portable. In another embodiment, the instrument may be a small handheld device (e.g., about 10"×5"×5") that is battery powered (e.g., 8 AA batteries). The instrument houses components that are external to the droplet actuator. Examples of external components include, but are not limited to, one or more magnets for immobilization of magnetically responsive beads, one or more heater assemblies for controlling the temperature within certain processing zones, and a detection system. A droplet actuator positioned in the instrument deck may be controlled using an electrical controller, which, for example, has a microprocessor and switching circuitry to control 108 high-voltage electrical I/Os. The electrical interface may, for example, use spring-loaded connector pins to make electrical contact with the droplet actuator. In this example, controllers and software provide switching of 108 high voltage channels independently. A high level user-friendly software package with varying levels of control for the switching circuitry may be selected to meet requirements of the end user.

One or more flexible heater circuits and passive cooling within the instrument may be used to control the temperature within certain processing zones on the droplet actuator. Because only certain processing zones are heated, power consumption during instrument use is substantially reduced. The relationship between heater temperature, heater power, and droplet temperature may depend on the thermal contact between the heater assembly(s) and the droplet actuator. Heater assembly materials may be selected to provide reproducible, low-thermal-resistance contact at the heater assembly/droplet actuator interface. For example, thermally conductive elastomers may be used to facilitate conformation of foil heaters to droplet actuator features. In another example, the thermal subsystem may be provided on the droplet actuator. For example, heating elements may be fabricated (e.g., screen printed) directly on the droplet actuator. Because the heating elements are provided on the droplet actuator, power consumptions during instrument use may be further reduced.

Figure 34:
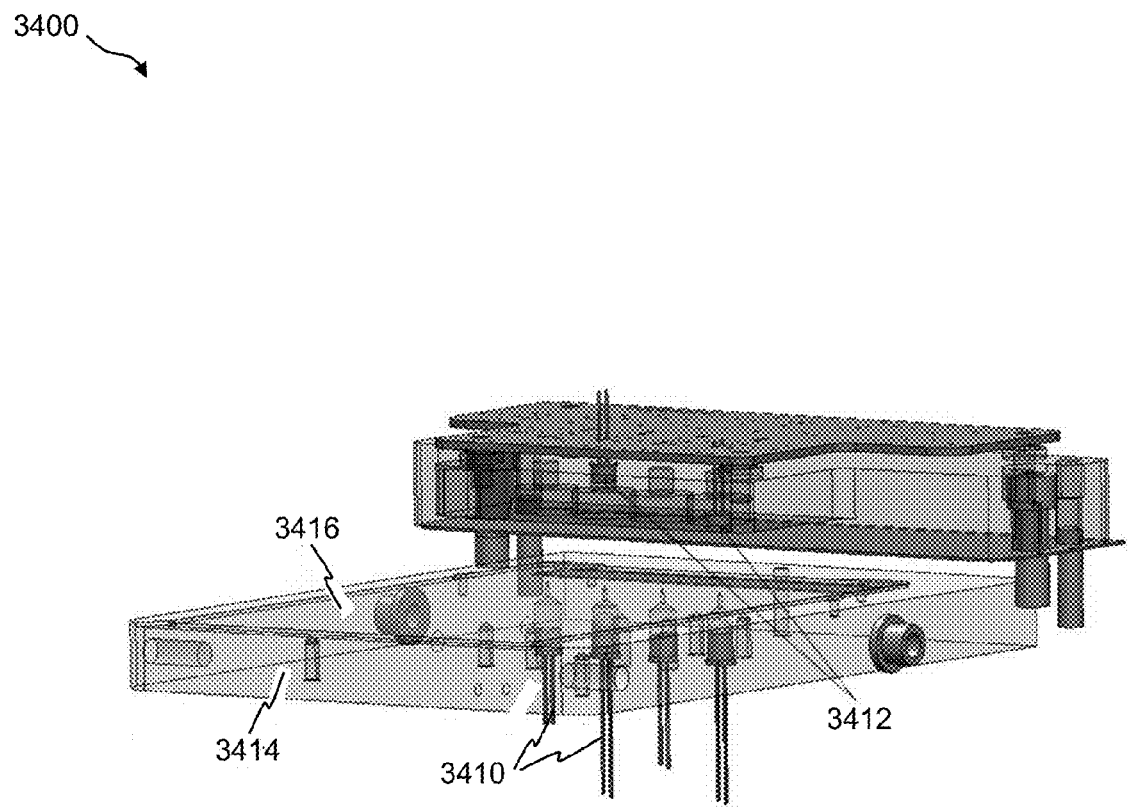
FIG. 34 illustrates a perspective view of an example of a detection system for detection of colorimetric reaction products.
Figure 35A:
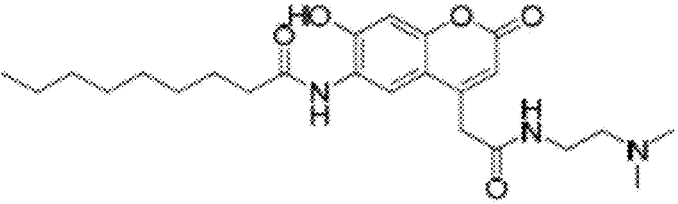
Figure 35B:
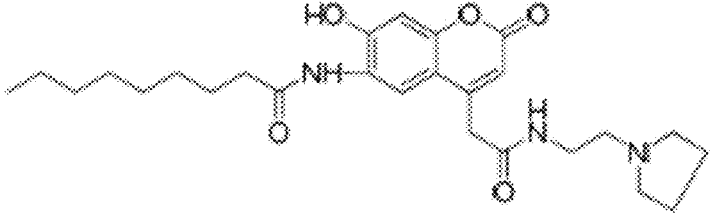
Figure 35B:
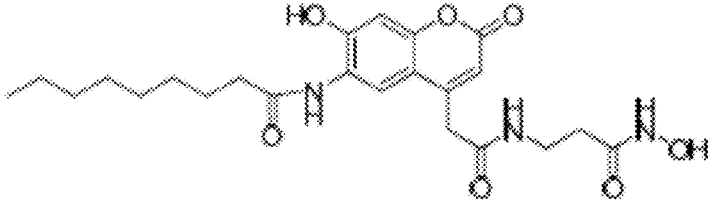
Figure 35B:
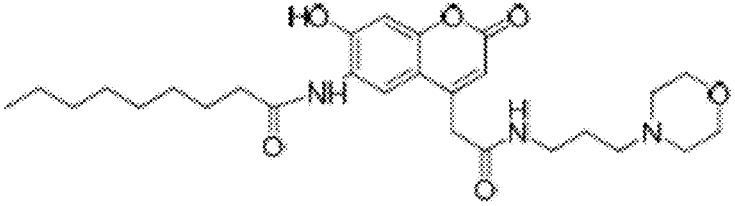
Figure 35B:
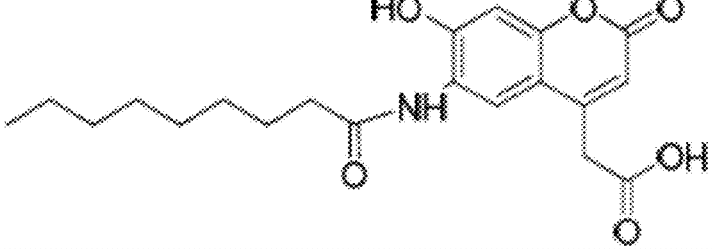
Figure 35B:
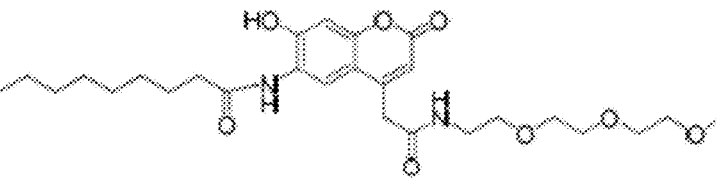
Figure 35B:
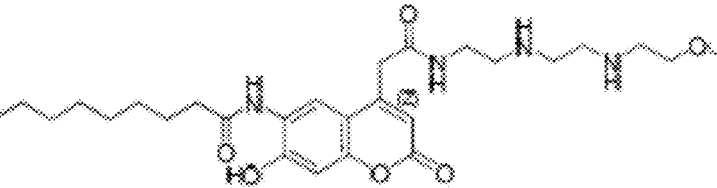
Figure 35D:
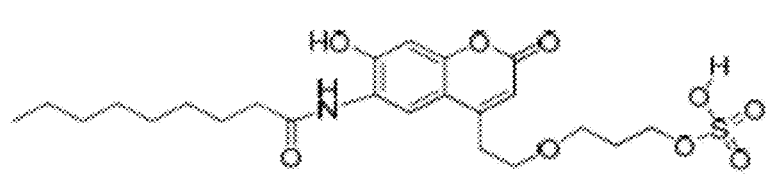
Figure 35D:
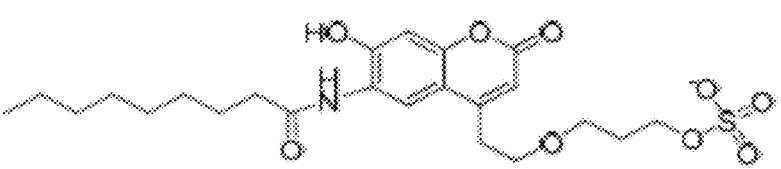
Figure 35D:
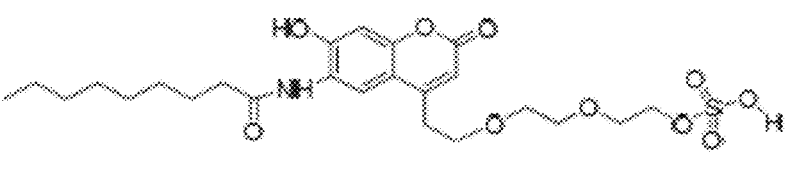
Figure 35D:
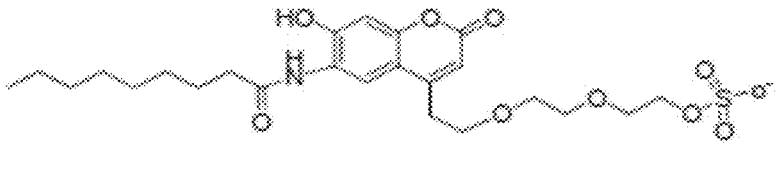
Figure 35D:
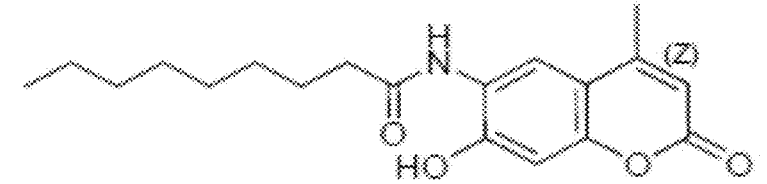
Figure 35D:
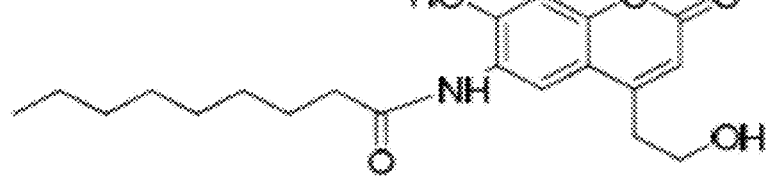
Figure 35E:
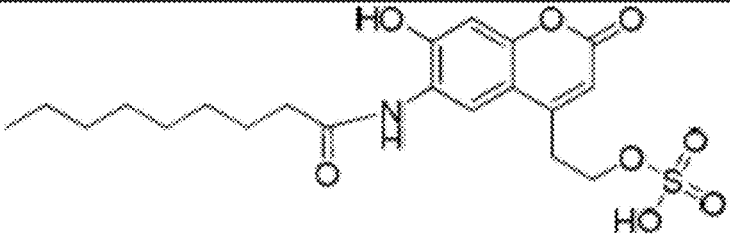
Figure 35G:
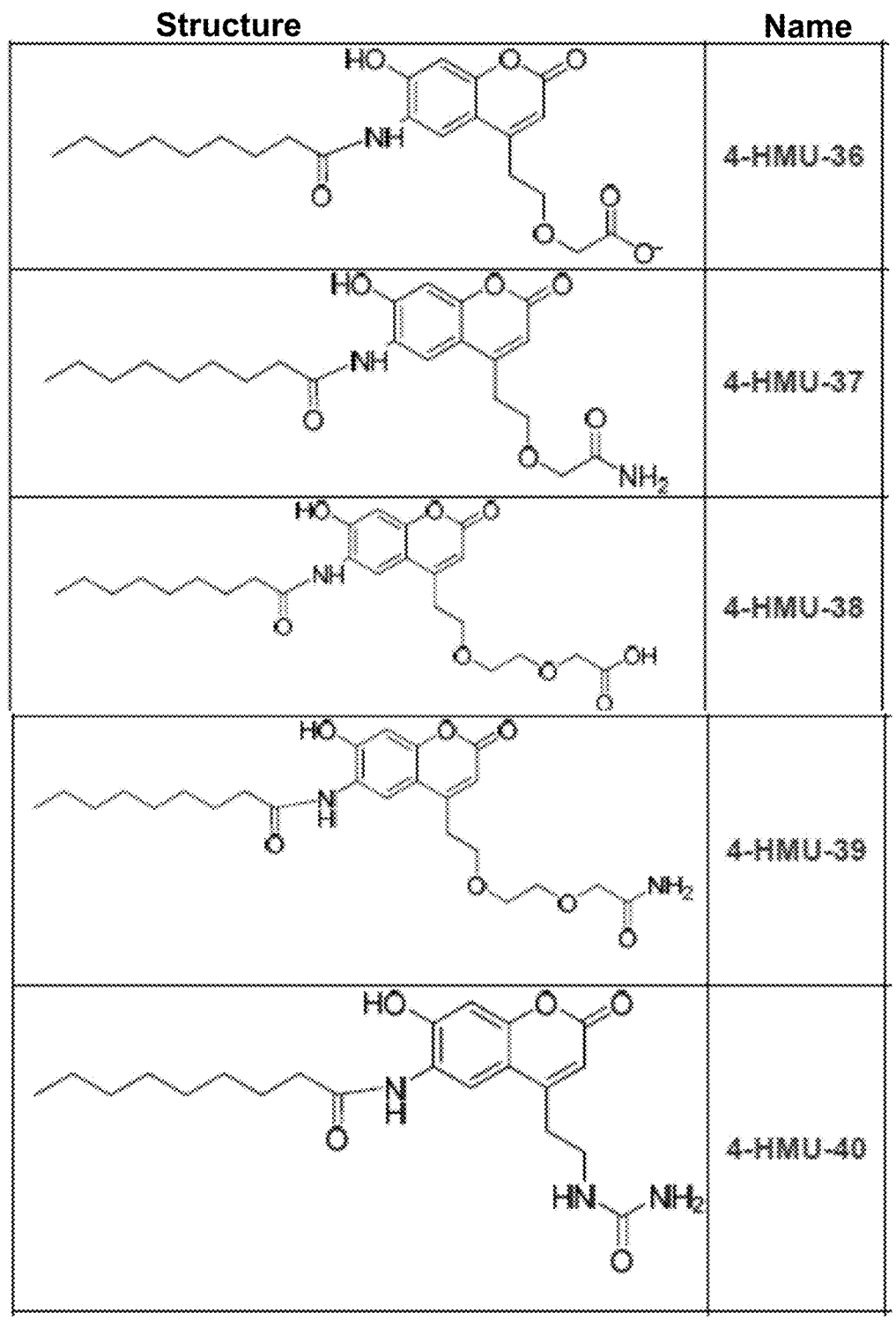
Figure 36A:
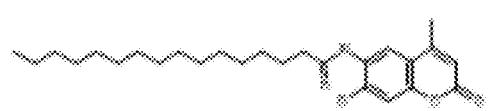
Figure 36A:
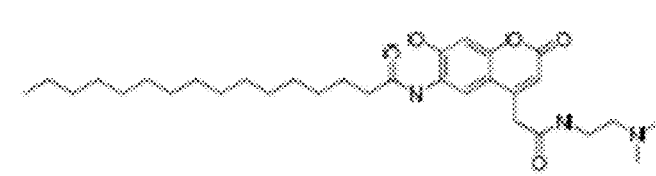
Figure 36A:
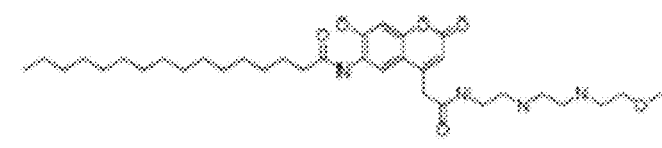
Figure 36A:
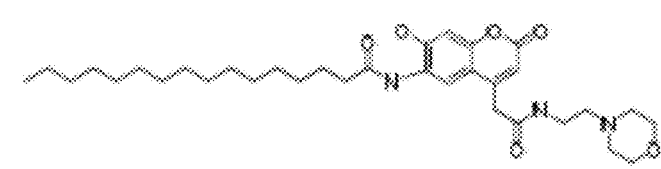
Figure 36A:
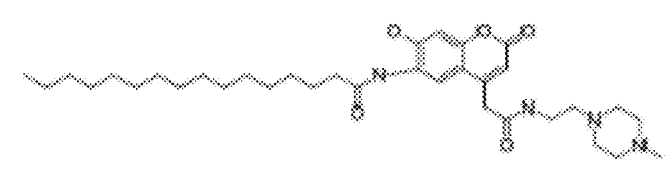
Figure 36A:
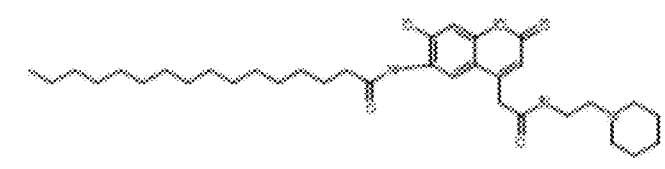
Figure 36C:
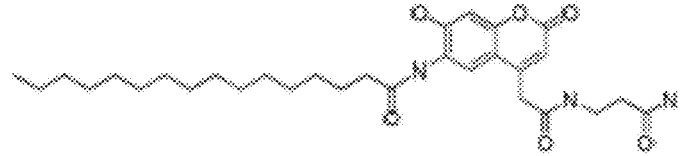
Figure 36C:
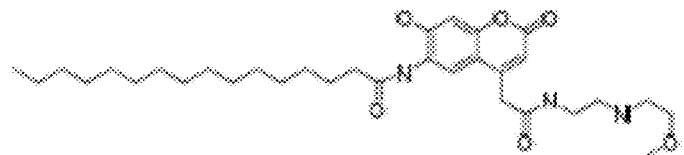
Figure 36C:
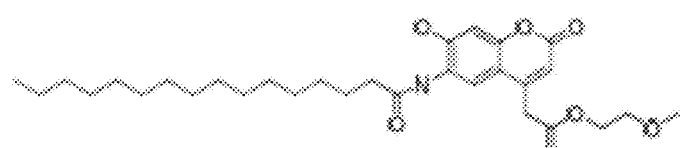
Figure 36C:
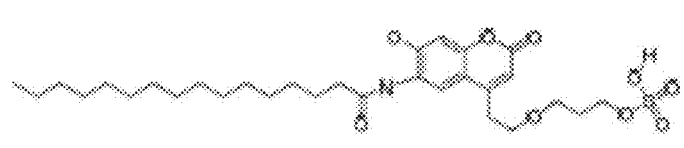
Figure 36C:
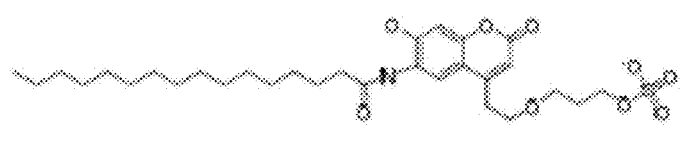
Figure 36D:
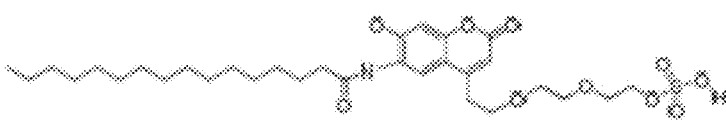
Figure 36D:
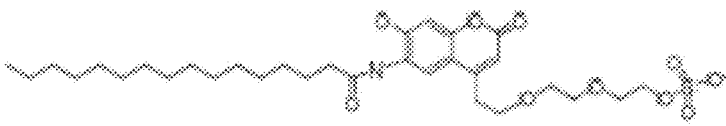
Figure 36D:
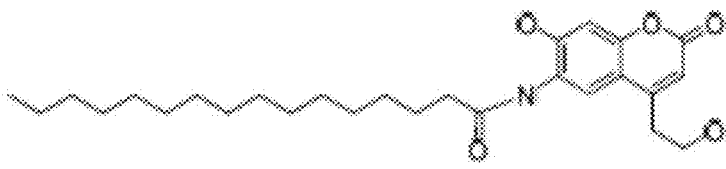
Figure 36D:
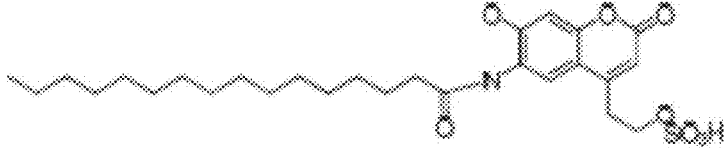
Figure 36D:
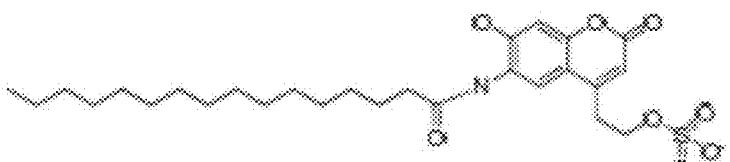
Figure 36E:
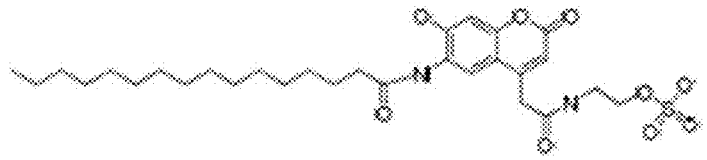
Figure 36E:
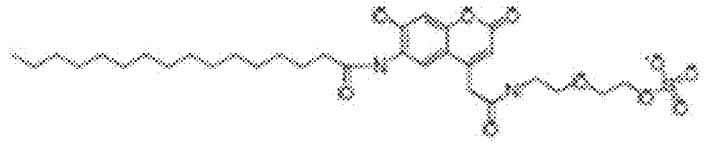
Figure 36E:
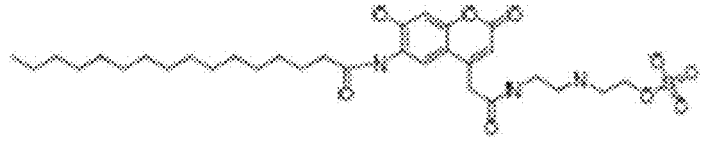
Figure 36E:
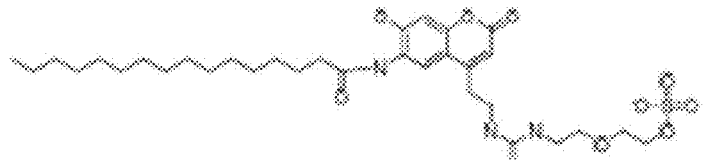
Figure 36F:
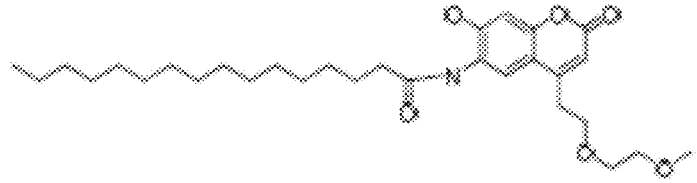
Figure 36F:
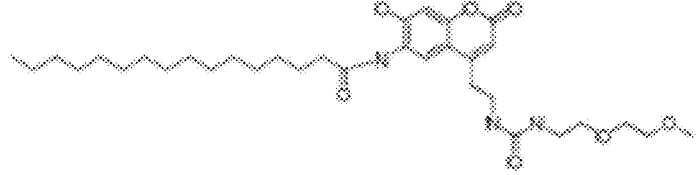
Figure 36F:
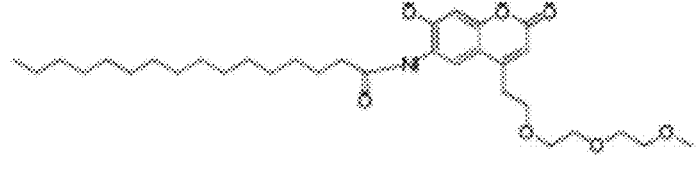
Figure 36F:
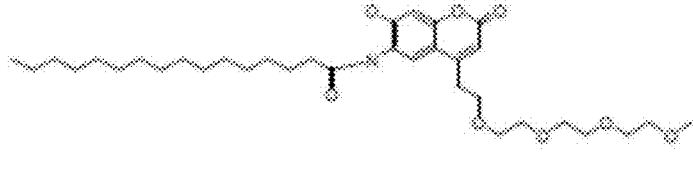
Figure 36F:
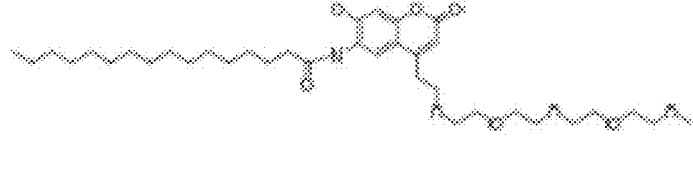
Figure 36G:
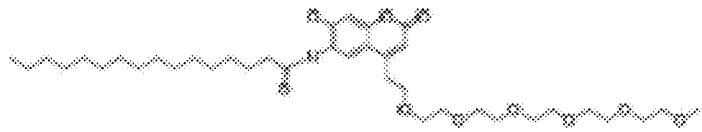
Figure 36G:
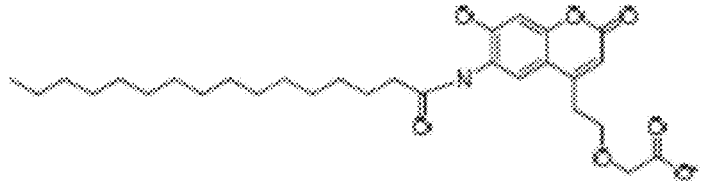
Figure 36G:
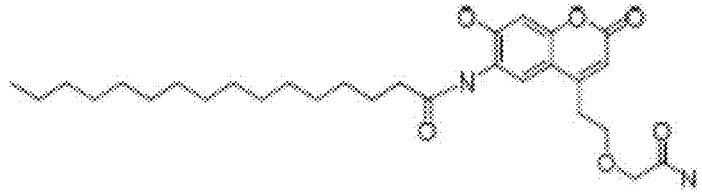
Figure 36G:
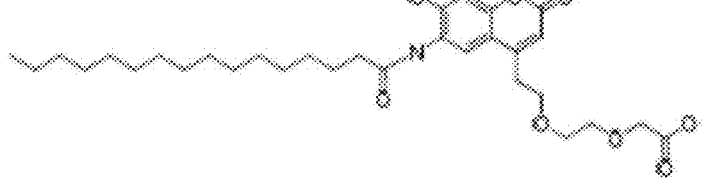
Figure 36H:
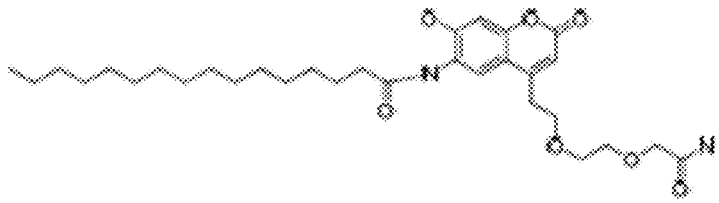
Figure 36H:
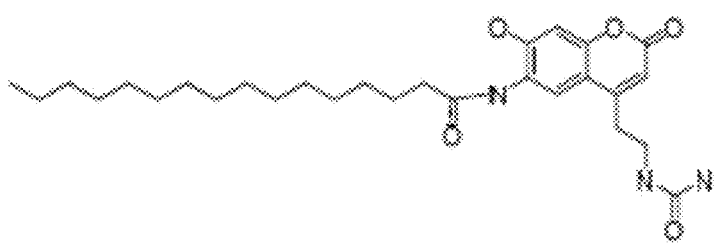
Figure 36H:
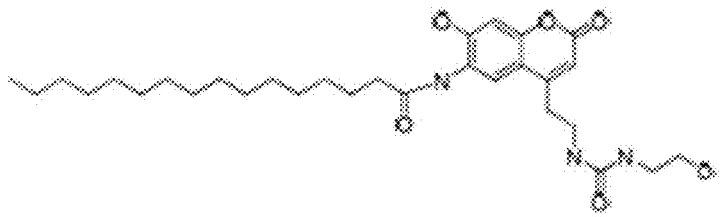
Figure 36H:
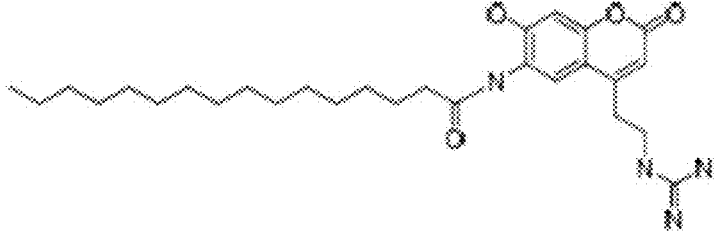

FIG. 34 illustrates a perspective view of an example of a detection system 3400 for detection of colorimetric reaction products. Detection system 3400 may include multiple excitation LEDs 3410 that are aligned with multiple detectors 3412. Detectors 3412 may, for example, be photodiodes. In one example, LEDs 3410 are positioned below an instrument deck 3414 and aligned with detectors 3412 positioned atop instrument deck 3414. By way of example, detection system 3400 may include four LEDs (e.g., LEDs 3410*a* through 3410*d*) that are aligned with four detectors 3412 (e.g., detectors 3412*a* through 3412*d*). LEDs 3410 and detectors 3412 may be selected to provide optical channels for one or more wavelengths of light. For example, LEDs 3410 and detectors 3412 may be selected to provide optical channels for the 560 nm wavelength required for bilirubin and G6PD newborn testing assays and for the 405 nm wavelength for hemoglobin measurements and TSH assay.

A droplet actuator 3416 may be positioned in instrument deck 3414 in proximity to imaging system 3400. In particular, droplet actuator 3416 may be positioned such that one or more detection electrodes (e.g., 4 detection electrodes; not shown) on droplet actuator 3416 are substantially aligned with detection system 3400.

The newborn testing instrument platform of the present invention is a low cost, portable and low maintenance instrument. The instrument platform is suitable for use in limited resource settings (e.g., developing countries such as China and India) and newborn testing environments such as a maternity hospital or birthing center laboratory.

8.20 Enzyme Assays for Sanfilippo A (MPS IIIA) and B (MPS IIIB) Syndromes on a Droplet Actuator The invention provides assay methods for detection of Sanfilippo A (MPS IIIA) and B (MPS IIIB) syndromes on a droplet actuator. Sanfilippo A syndrome and Sanfilippo B syndrome are caused by deficient activity of the lysosomal enzymes heparan sulfate sulfamidase (SGSH) and alpha-N-acetylglucosaminidase (NAGLU), respectively. In one embodiment, the invention provides methods for a droplet-based enzymatic assay for heparan sulfate sulfamidase activity in a biological sample. The sample for the enzymatic assay may, for example, be a dried blood extract droplet. The droplet-based enzymatic assay for heparan sulfate sulfamidase activity may, for example, be performed at a pH of about 6. The substrate fluid for heparan sulfate sulfamidase in the enzymatic assay may, for example, be the fluorogenic substrate 4-methylumbelliferyl-α-N-sulpho-D-glucosaminide (MU-αGlcNS; Moscerdam Substrates). Generation of a fluorescent signal from the MU-αGlcNS substrate requires the activity of two enzymes, heparan sulfate sulfamidase and a supplemented second enzyme α-N-acetylglucosaminidase. In this assay, heparan sulfate sulfamidase first acts on the MU-αGlcNS substrate fluid to yield a 4-MU-αGlcNH$_2$ intermediate. The second enzyme α-N-acetylglucosaminidase acts on the 4-MU-αGlcNH$_2$ intermediate to release 4-methylumbelliferyl (4-MU) generating a fluorescent signal. In the absence of heparan sulfate sulfamidase, the 4-MU-αGlcNH$_2$ intermediate is not formed and no fluorescent signal is produced. In one example, the supplemented α-N-acetylglucosaminidase activity may be provided by using yeast α-glucosidase. In another example, the supplemented α-N-acetylglucosaminidase activity may be provided by using recombinant α-N-acetylglucosaminidase.

In another embodiment, the invention provides methods for a droplet-based one-step enzymatic assay for alpha-N-acetylglucosaminidase (NAGLU) activity in a biological sample. The sample for the enzymatic assay may, for example, be a dried blood extract droplet. The substrate fluid for alpha-N-acetylglucosaminidase in the enzymatic assay may, for example, be the fluorogenic substrate 4-methylumbelliferyl-α-D-N-acetylglucosamine (Moscerdam Substrates).

Other embodiments may make use of the modified umbelliferyl substrates described herein.

8.21 Enzyme Assays for Metachromatic Leukodystrophy (MLD) and Maroteaux-Lamy Syndrome (MPS VI) on a Droplet Actuator The invention provides assay methods for detection of metachromatic leukodystrophy (MLD) and Maroteaux-Lamy syndrome on a droplet actuator. MLD and MPS VI are caused by deficient activity of the lysosomal enzymes arylsulfatase A and arylsulfatase B, respectively. Current bench-based assays for determination of arylsulfatase A and arylsulfatase B activities may be described and implemented on a droplet actuator as discrete step-by-step droplet-based protocols. In one embodiment, protocols that use the colorimetric substrate p-nitrocatechol sulfate (PNCS; Sigma) may be adapted for use on a droplet actuator. In one example, a bench-based protocol that uses PNCS for detection of arylsulfatase A activity may be adapted for use on a droplet actuator. In the bench-based assay, the assay buffer is 50 mM NaOAc, 0.5 M NaCl, pH 4.5. At a reaction temperature of 37° C., PNCS may be used as a substrate for detection of both arylsulfatase A and arylsulfatase B activities. For specific detection of arylsulfatase A activity (i.e., MLD), the enzymatic assay is performed at 0° C. Absorbance is read at 516 nm. Translation of the bench-based protocol to a droplet-based protocol may, for example, include modifications in reaction components (e.g., assay buffer, pH, and reaction volumes) and incubation time. The droplet actuator may, for example, be configured for absorbance (colorimetric) detection. The droplet actuator may be designed to fit onto an instrument deck that houses extra-droplet actuator features such as a cooling assembly (e.g., 0° C.) for performing arylsulfatase A-specific reactions (i.e., MLD) and a detection system for detection of colorimetric reaction products.

In another example, a bench-based protocol that uses PNCS for detection of arylsulfatase B activity may be adapted for use on a droplet actuator. In the bench-based assay, the assay buffer is 50 mM MES, pH 6.5. Absorbance is read at 516 nm. Translation of the bench-based protocol to a droplet-based protocol may, for example, include modifications in reaction components (e.g., assay buffer, pH, and reaction volumes) and incubation time. The droplet actuator may, for example, be configured for absorbance (colorimetric) detection. The droplet actuator may be designed to fit onto an instrument deck that houses extra-droplet actuator features such as a detection system for detection of colorimetric reaction products.

In another embodiment, a fluorogenic substrate such as 3-O-sulfate-β-D-galactosyl-4-methylumbelliferyl may be used for detection of arylsulfatase A activity (i.e., MLD). Generation of a fluorescent signal from the 3-O-sulfate-β-D-galactosyl-4-methylumbelliferyl substrate requires the activity of two enzymes, arylsulfatase A and a supplemented second enzyme β-galactosidase. In this assay, arylsulfatase A first acts on the 3-O-sulfate-β-D-galactosyl-4-methylumbelliferyl substrate fluid to yield a 4-methylumbelliferyl-β-D-galactose intermediate. The second enzyme β-galactosidase acts on 4-methylumbelliferyl-β-D-galactose to release 4-methylumbelliferyl (4-MU) generating a fluorescent signal. In the absence of arylsulfatase A, the 4-methylumbelliferyl-β-D-galactose intermediate is not formed and no fluorescent signal is produced. Supplemental β-galactosidase may be selected such that the enzyme has substantially no activity on 3-O-sulfate-β-D-galactosyl-4-methylumbelliferyl. In one example, the supplemented β-galactosidase activity may be provided by using bovine testis β-galactosidase. In another example, the supplemented β-galactosidase activity may be provided by using human galactocerebrosidase.

8.22 Sample

The enzyme assays of the invention make use of sample droplets and substrate droplets. Sample droplets are blood or blood-derived samples, such as plasma, serum, tissue, cell fractions, and treated, fractionated, concentrated and/or diluted forms of the foregoing. For example, diagnosis for Pompe disease is performed on fibroblasts. Other biological fluids may be used as samples; nonlimiting examples include tears, semen, urine, saliva, amniotic liquid and cerebrospinal fluid. For example, in the testing to diagnose Fabry disease, tears may be used as the input sample droplet. Still other examples of biological fluids are listed hereinbelow. Biological fluids may be treated as necessary to prepare them for being subjected to the protocols of the invention. For example, samples may be diluted or buffered, heated or cooled; pH may be adjusted; and/or blood samples may be treated with one or more anticoagulants. Samples may be loaded into a reservoir associated with a droplet actuator, and may be dispensed into one or more subsamples. In some cases, the subsamples are unit-sized subsamples. The subsamples may be in contact with or surrounded with one or more filler fluids.

In one embodiment, the sample includes a reconstituted dried blood spot. Typically the subject's skin is pricked using a sterile puncture device, such as a lancet. Droplets of blood are spotted onto filter paper and allowed to dry. The filter paper may, for example, be a Whatman Neonatal Screening Card, such as the Whatman 903 Neonatal Blood Collection Card (available from GE Healthcare, Inc.). To reconstitute the dried blood spots, a small disc is punched from the filter paper and placed in solution to yield a solution of reconstituted blood. The disc typically has a diameter of about 3.2 mm, though other sizes may be used. The reconstituted blood solution may be loaded onto a droplet actuator where it is subject to droplet operations for conducting one or more assays.

In some embodiments, the disc may be punched directly into a droplet actuator reservoir, such as a reservoir situated in a droplet operations gap and/or a reservoir which is external to the droplet operations gap. The external reservoir may be associated with a fluid passage suitable for flowing reconstituted blood sample into the droplet operations gap. Fluid input reservoirs may be sized to accommodate a punch and reconstitution solution. In one embodiment, the well-to-well pitch is 4.5 mm which is sufficient to fit a 3 mm DBS punch. Reservoirs may thus be arranged to permit use of existing punchers, such as the Perkin-Elmer DBS Puncher™. Since the inner surfaces of the droplet operations gap are hydrophobic, the reconstitution solution, when added in to the reservoir, will remain in the reservoir. Liquid from the reservoir containing the punch can be pulled into the droplet actuator through electric field to form droplets for subsequent enzymatic assays. Reservoirs may be associated with agitators or sonicators to effect mixing of the reconstituted samples. Any tendency of reconstituted sample to flow into the droplet operations gap, e.g., during moving or shaking of the droplet actuator, may be reduced or minimized by lowering the pressure of the liquid by configuring the reservoir to reduce the height of the liquid column in the reservoir.

In some embodiments, a disc having a diameter of less than about 8 mm is reconstituted in less than about 1000 μL of solution, the sample is dispensed into at least 10 sub-droplets, and each sub-droplet is used to conduct a different enzyme assay. In other embodiments, a disc having a diameter of less than about 4 mm is reconstituted in less than about 1000 μL of solution, the sample is dispensed into at least 10 sub-droplets, and each sub-droplet is used to conduct a different enzyme assay. In some embodiments, a disc having a diameter of less than about 8 mm is reconstituted in less than about 500 μL of solution, the sample is dispensed into at least 10 sub-droplets, and each sub-droplet is used to conduct a different enzyme assay. In some embodiments, a disc having a diameter of less than about 4 mm is reconstituted in less than about 500 μL of solution, the sample is dispensed into at least 10 sub-droplets, and each sub-droplet is used to conduct a different enzyme assay. In other embodiments, a disc having a diameter of less than about 8 mm is reconstituted in less than about 1000 µL of solution, the sample is dispensed into at least 20 sub-droplets, and each sub-droplet is used to conduct a different enzyme assay. In other embodiments, a disc having a diameter of less than about 4 mm is reconstituted in less than about 1000 µL of solution, the sample is dispensed into at least 20 sub-droplets, and each sub-droplet is used to conduct a different enzyme assay. In some embodiments, a disc having a diameter of less than about 8 mm is reconstituted in less than about 500 µL of solution, the sample is dispensed into at least 20 sub-droplets, and each sub-droplet is used to conduct a different enzyme assay. In some embodiments, a disc having a diameter of less than about 4 mm is reconstituted in less than about 500 µL of solution, the sample is dispensed into at least 20 sub-droplets, and each sub-droplet is used to conduct a different enzyme assay. In some embodiments, a disc having a diameter of less than about 8 mm is reconstituted in less than about 1000 µL of solution, the sample is dispensed into at least 100 sub-droplets, and each sub-droplet is used to conduct a different enzyme assay. In other embodiments, a disc having a diameter of less than about 4 mm is reconstituted in less than about 1000 µL of solution, the sample is dispensed into at least 100 sub-droplets, and each sub-droplet is used to conduct a different enzyme assay. In some embodiments, a disc having a diameter of less than about 8 mm is reconstituted in less than about 500 µL of solution, the sample is dispensed into at least 100 sub-droplets, and each sub-droplet is used to conduct a different enzyme assay. In some embodiments, a disc having a diameter of less than about 4 mm is reconstituted in less than about 500 µL of solution, the sample is dispensed into at least 100 sub-droplets, and each sub-droplet is used to conduct a different enzyme assay. In some embodiments, a disc having a diameter of less than about 8 mm is reconstituted in less than about 100 µL of solution, the sample is dispensed into at least 20 sub-droplets, and each sub-droplet is used to conduct a different enzyme assay. In some embodiments, a disc having a diameter of less than about 4 mm is reconstituted in less than about 100 µL of solution, the sample is dispensed into at least 20 sub-droplets, and each sub-droplet is used to conduct a different enzyme assay. In some embodiments, a disc having a diameter of less than about 8 mm is reconstituted in less than about 100 µL of solution, the sample is dispensed into at least 100 sub-droplets, and each sub-droplet is used to conduct a different enzyme assay. In some embodiments, a disc having a diameter of less than about 4 mm is reconstituted in less than about 100 µL of solution, the sample is dispensed into at least 100 sub-droplets, and each sub-droplet is used to conduct a different enzyme assay.

In some cases, the droplet including an enzyme of interest is prepared by reconstituting a dried blood spot disc having a diameter of less than about 3 mm in less than about 200 µL of solution. The sample may, for example, be dispensed into at least 10 sample droplets, and each sample droplet is used to conduct a different enzyme assay. In another embodiment, the disc has a diameter of less than about 3 mm; the disk is reconstituted in less than about 200 µL of solution; the sample is dispensed into at least 5 sub-droplets; and at least 5 sub-droplets are each used to conduct a different enzyme assay. In another embodiment, the disc has a diameter of less than about 6 mm; the disc is reconstituted in less than about 800 µL of solution; the sample is dispensed into at least 5 sub-droplets; and at least 5 sub-droplets are each used to conduct a different enzyme assay. In another embodiment, the disc has a diameter of less than about 6 mm; the disc is reconstituted in less than about 800 µL of solution; the sample is dispensed into at least 5 sub-droplets; and at least 5 sub-droplets are each used to conduct a different enzyme assay. In another embodiment, the disc has a diameter of less than about 3 mm; the disk is reconstituted in less than about 200 µL of solution; the sample is dispensed into at least 10 sub-droplets; and at least 10 sub-droplets are each used to conduct a different enzyme assay. In another embodiment, the disc has a diameter of less than about 6 mm; the disc is reconstituted in less than about 800 µL of solution; the sample is dispensed into at least 10 sub-droplets; and at least 10 sub-droplets are each used to conduct a different enzyme assay. In another embodiment, the disc has a diameter of less than about 6 mm; the disc is reconstituted in less than about 800 µL of solution; the sample is dispensed into at least 10 sub-droplets; and at least 10 sub-droplets are each used to conduct a different enzyme assay. In another embodiment, the disc has a diameter ranging from about 1 mm to about 6 mm; the disc is reconstituted in solution ranging from about 22 µL to about 800 µL; the sample is dispensed into at least 5 sub-droplets; and at least 5 sub-droplets are each used to conduct a different enzyme assay.

In some cases, the volume of each of the sample and substrate droplets used to conduct the enzyme assays of the invention may range from about 1 nL to about 1000 µL; or about 1 nL to about 1000 nL; or about 1 nL to about 500 nL; or about 1 nL to about 250 nL. Where a dried blood spot is used, the sample droplet is prepared by reconstituting a dried blood spot disc. In some cases, the disc has a diameter of less than about 10 mm and is reconstituted in less than about 1000 µL of solution; or less than about 750 µL of solution; or less than about 500 µL of solution; or less than about 250 µL of solution; or ranging from about 25 µL to about 750 µL; or ranging from about 25 µL to about 500 µL; or ranging from about 25 µL to about 250 µL; or ranging from about 25 µL to about 150 µL. In some cases, the sample is dispensed into at least 5 sample droplets; or at least 10 sample droplets; or at least 25 sample droplets; or at least 40 sample droplets. In some cases, the dried blood spot disc has a diameter ranging from about 1 mm to about 10 mm; or from about 1 mm to about 8 mm; or from about 1 mm to about 6 mm; or from about 1 mm to about 4 mm.

In another aspect of the invention, fresh blood from a subject is used to conduct the assays of the invention. In one aspect, less than about 1.0 mL of blood is removed from a newborn. In another aspect, less than about 0.1 mL of blood is removed from a newborn. In another aspect, less than about 0.05 mL of blood is removed from a newborn. In another aspect, less than about 0.01 mL of blood is removed from a newborn. The removed blood may be deposited into a reservoir on a droplet actuator. In some cases a diluents and/or buffer droplet may be combined with the fresh blood sample. In some cases a droplet comprising an anticoagulant may be combined with the fresh blood sample or an anticoagulant may be mixed with the sample droplet.

8.23 Systems

Fluorescence and absorbance detection may be performed on a single droplet actuator, such as the droplet actuator device described in reference to FIG. 11. The path lengths for fluorescence detection and/or, in some embodiments, absorbance detection, on a droplet actuator may, for example, be about 300 µm. Because of the small path lengths, it may be useful to reduce interference of hemoglobin in the DBS extract. For example, in an LSD testing assay, hemoglobin in a DBS extract does not substantially affect fluorescence at 365 nm. The droplet actuator device may be further adapted for increased detection sensitivity. In one example, filler fluids may be selected to substantially minimize partitioning of reaction products into the filler fluid. In another example, substrate coatings on bottom and/or top substrates of the droplet actuator may be selected to substantially minimize background fluorescence. In addition, appropriate filters in a photomultiplier-based detection system may be used to increase detection sensitivity. In yet another example, because the assays are enzymatic, the substrate fluid may be added in excess to yield a better signal over a more prolonged period of time. In yet another example, additives such as DMSO and other ionic surfactants may be added to increase the solubility of the reaction products within the aqueous droplet.

The various aspects of the invention may be embodied as a method, system, computer readable medium, and/or computer program product. Aspects of the invention may take the form of hardware embodiments, software embodiments (including firmware, resident software, micro-code, etc.), or embodiments combining software and hardware aspects that may all generally be referred to herein as a "circuit," "module" or "system." Furthermore, the methods of the invention may take the form of a computer program product on a computer-usable storage medium having computer-usable program code embodied in the medium.

Any suitable computer useable medium may be utilized for software aspects of the invention. The computer-usable or computer-readable medium may be, for example but not limited to, an electronic, magnetic, optical, electromagnetic, infrared, or semiconductor system, apparatus, device, or propagation medium. The computer readable medium may include transitory and/or non-transitory embodiments. More specific examples (a non-exhaustive list) of the computer-readable medium would include some or all of the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission medium such as those supporting the Internet or an intranet, or a magnetic storage device. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device.

Program code for carrying out operations of the invention may be written in an object oriented programming language such as Java, Smalltalk, C++ or the like. However, the program code for carrying out operations of the invention may also be written in procedural programming languages, such as the "C" programming language or similar programming languages. The program code may be executed by a processor, application specific integrated circuit (ASIC), or other component that executes the program code. The program code may be simply referred to as a software application that is stored in memory (such as the computer readable medium discussed above). The program code may cause the processor (or any processor-controlled device) to produce a graphical user interface ("GUI"). The graphical user interface may be visually produced on a display device, yet the graphical user interface may also have audible features. The program code, however, may operate in any processor-controlled device, such as a computer, server, personal digital assistant, phone, television, or any processor-controlled device utilizing the processor and/or a digital signal processor.

The program code may locally and/or remotely execute. The program code, for example, may be entirely or partially stored in local memory of the processor-controlled device. The program code, however, may also be at least partially remotely stored, accessed, and downloaded to the processor-controlled device. A user's computer, for example, may entirely execute the program code or only partly execute the program code. The program code may be a stand-alone software package that is at least partly on the user's computer and/or partly executed on a remote computer or entirely on a remote computer or server. In the latter scenario, the remote computer may be connected to the user's computer through a communications network.

The invention may be applied regardless of networking environment. The communications network may be a cable network operating in the radio-frequency domain and/or the Internet Protocol (IP) domain. The communications network, however, may also include a distributed computing network, such as the Internet (sometimes alternatively known as the "World Wide Web"), an intranet, a local-area network (LAN), and/or a wide-area network (WAN). The communications network may include coaxial cables, copper wires, fiber optic lines, and/or hybrid-coaxial lines. The communications network may even include wireless portions utilizing any portion of the electromagnetic spectrum and any signaling standard (such as the IEEE 802 family of standards, GSM/CDMA/TDMA or any cellular standard, and/or the ISM band). The communications network may even include powerline portions, in which signals are communicated via electrical wiring. The invention may be applied to any wireless/wireline communications network, regardless of physical componentry, physical configuration, or communications standard(s).

Certain aspects of invention are described with reference to various methods and method steps. It will be understood that each method step can be implemented by the program code and/or by machine instructions. The program code and/or the machine instructions may create means for implementing the functions/acts specified in the methods.

The program code may also be stored in a computer-readable memory that can direct the processor, computer, or other programmable data processing apparatus to function in a particular manner, such that the program code stored in the computer-readable memory produce or transform an article of manufacture including instruction means which implement various aspects of the method steps.

The program code may also be loaded onto a computer or other programmable data processing apparatus to cause a series of operational steps to be performed to produce a processor/computer implemented process such that the program code provides steps for implementing various functions/acts specified in the methods of the invention.

9 CONCLUDING REMARKS

The foregoing detailed description of embodiments refers to the accompanying drawings, which illustrate specific embodiments of the invention. Other embodiments having different structures and operations do not depart from the scope of the present invention. The term "the invention" or the like is used with reference to certain specific examples of the many alternative aspects or embodiments of the applicants' invention set forth in this specification, and neither its use nor its absence is intended to limit the scope of the applicants' invention or the scope of the claims. This specification is divided into sections for the convenience of the reader only.

Headings should not be construed as limiting of the scope of the invention. The definitions are intended as a part of the description of the invention. It will be understood that various details of the present invention may be changed without departing from the scope of the present invention. Furthermore, the foregoing description is for the purpose of illustration only, and not for the purpose of limitation.

I claim:

1. A method of conducting an assay comprising:
   (I) combining a sample droplet with a droplet comprising an umbelliferyl derivative to yield an assay droplet wherein:
      (a) the sample potentially comprises an enzyme capable of cleaving the umbelliferyl derivative; and
      (b) the umbelliferyl derivative is a modified version of an umbelliferyl parent compound comprising an umbelliferyl core modified with one or more modifying moieties, said one or more modifying moieties:
         (i) selected to increase hydrophilicity of the derivative relative to the parent compound without eliminating the fluorescence of the umbelliferyl core upon cleavage by the enzyme; and
         (ii) coupled to the umbelliferyl core at a site that remains with the umbelliferyl core following cleavage by the compound; and
   (II) detecting a signal from the assay droplet which is indicative of the presence of an enzyme capable of cleaving the umbelliferyl derivative.

2. The method of claim 1, wherein the droplets are in oil.

3. The method of claim 1, wherein the droplets are surrounded by oil.

4. The method of claim 1, wherein the combining is conducted using droplet operations mediated by electrodes on a droplet actuator.

5. The method of claim 1, wherein the umbelliferyl derivatives comprise an umbelliferyl core coupled to a hydrophilic polymer or oligomer group.

6. The method of claim 5 wherein the hydrophilic polymer or oligomer group comprises a salt moiety.

7. The method of claim 1, wherein the umbelliferyl derivatives comprise an umbelliferyl core coupled to a moiety comprising a polyalkalene glycol group.

8. The method of any of claim 1 and following, wherein the umbelliferyl derivatives comprise an umbelliferyl core coupled to a moiety comprising a polyethylene glycol group.

9. The method of claim 1, wherein the umbelliferyl derivatives comprise an umbelliferyl core coupled to a moiety comprising a polypropylene glycol group.

10. The method of claim 1, wherein the umbelliferyl derivatives comprise an umbelliferyl core coupled to a sulfonic acid.

11. The method of claim 1, wherein the umbelliferyl derivatives comprise an umbelliferyl core coupled to an amino group.

* * * * *